US009885085B2

(12) United States Patent
Hoidal et al.

(10) Patent No.: US 9,885,085 B2
(45) Date of Patent: Feb. 6, 2018

(54) APPARATUS, COMPOSITIONS, AND METHODS FOR ASSESSMENT OF CHRONIC OBSTRUCTIVE PULMONARY DISEASE PROGRESSION AMONG RAPID AND SLOW DECLINE CONDITIONS

(75) Inventors: John Hoidal, Salt Lake City, UT (US); Mary Beth Scholand, Salt Lake City, UT (US); Mark F. Leppert, Salt Lake City, UT (US); Michael S. Paul, Salt Lake City, UT (US); Robert Mark Gritz, Fairfax, VA (US); Joel Gardner Pounds, Richland, WA (US); Richard Dale Smith, Richland, WA (US)

(73) Assignees: University of Utah Research Foundation, Salt Lake City, UT (US); Lineagen, Inc., Salt Lake City, UT (US)

( * ) Notice: Subject to any disclaimer, the term of this patent is extended or adjusted under 35 U.S.C. 154(b) by 172 days.

(21) Appl. No.: 11/770,074

(22) Filed: Jun. 28, 2007

(65) Prior Publication Data
US 2008/0026949 A1 Jan. 31, 2008

Related U.S. Application Data

(60) Provisional application No. 60/817,316, filed on Jun. 28, 2006.

(51) Int. Cl.
*C12Q 1/68* (2006.01)
*G01N 33/68* (2006.01)
*G06F 19/18* (2011.01)

(52) U.S. Cl.
CPC ....... *C12Q 1/6883* (2013.01); *G01N 33/6848* (2013.01); *G01N 2800/122* (2013.01); *G06F 19/18* (2013.01)

(58) Field of Classification Search
CPC ............ C12Q 1/6883; G01N 33/6848; G01N 2800/122; G06F 19/18
(Continued)

(56) References Cited

U.S. PATENT DOCUMENTS 7,604,948 B2 * 10/2009 Amaral et al. ................. 435/7.1
8,389,222 B2 * 3/2013 Breyer et al. .................. 435/7.1
(Continued)

OTHER PUBLICATIONS

Sandford (Feb. 2001) American Journal of Respiratory and Critical Care Medicine vol. 163 p. 469.*
(Continued)

*Primary Examiner* — Jeremy C Flinders
(74) *Attorney, Agent, or Firm* — Perkins Coie LLP

(57) ABSTRACT

Methods are disclosed for generating and isolating an informative content repository of respiratory related biomarkers to accurately determine whether an individual has normal or abnormal pulmonary function. Specifically, methods are directed to determination of whether individuals have chronic obstructive pulmonary disease, and if so, whether the affected individuals experience rapid long decline or slow lung decline as a result of COPD. Also disclosed is an informative content repository of chronic obstructive pulmonary disease biomarkers, which when linked with other informative content provides a powerful tool for diagnosis, study, therapeutic discovery and development, condition management, health maintenance, and linking chronic obstructive pulmonary disease through pattern of life style, environmental exposure, and genetic susceptibility and inheritance. Disclosed herein is a chronic obstructive pulmonary disease biomarker informative content repository comprising at least one COPD biomarker, apparatus and methods to diagnose, assess, address, and ameliorate related conditions.

27 Claims, 6 Drawing Sheets

(58) Field of Classification Search
USPC .......... 702/19; 435/7.1, 7.2, 68.1, 70.1, 183; 530/300, 350, 387.1; 422/50, 420, 68.1, 422/69, 500
See application file for complete search history.

(56) References Cited

U.S. PATENT DOCUMENTS

| | | | |
|---|---|---|---|
| 2002/0091687 A1 | 7/2002 | Eglington | |
| 2004/0249677 A1 | 12/2004 | Datta | |
| 2005/0137253 A1 | 6/2005 | Phinney | |
| 2005/0255494 A1 | 11/2005 | Aerssens | |
| 2006/0009410 A1* | 1/2006 | Crooke et al. | 514/44 |
| 2011/0218116 A1* | 9/2011 | Cook et al. | 506/9 |

OTHER PUBLICATIONS

Basili (Nov. 8, 1999) Atherosclerosis vol. 147 p. 249.*
NCBI web site, 4502153 searched (downloaded Jan. 5, 2010 from http://www.ncbi.nlm.nih.gov/gquery/?term=4502153).*
NCBI Entrez Protein web site, 4502153 searched (downloaded Jan. 5, 2010 from http://www.ncbi.nlm.nih.gov/protein/4502153) apolipoprotein B precursor [Homo sapiens].*
NCBI Entrez SNP web site, 4502153 searched (downloaded Jan. 5, 2010 from http://www.ncbi.nlm.nih.gov/sites/entrez?db=snp &cmd=search&term=4502153) rs4502153 [Homo sapiens].*
NCBI Entrez web site (downloaded Jan. 6, 2010 from http://www.ncbi.nlm.nih.gov/Genbank/index.html) GenBank Overview.*
International Search Report from Korean Intellectual Property Office, dated Feb. 1, 2008.
Belov, M.E et al., An Automated High Performance Capillary Liquide Chromatography-Fourier Transform Ion cyclotron Resonance Mass Spectrometer for High-Throughput Proteomics, 2004. J. Am Soc. Mass Spectrom. 15, 212-232.
Bolstad, B.M. et al, A comparison of normalization methods for high density oligonucleotide array data based on variance and bias. Bioinformatics, 2003, 19(2), pp. 185-193.
Efron, B., Large-Scale Simultaneous Hypothesis Testing: The Choice of a Null Hypothesis, 2004, J. Am. Stat. Assoc., 99(465), pp. 96-104.
Eng, J.K. et al., An Approach to Correlate Tandem Mass Spectral Data of Peptides with Amino Acid Sequences in a Protein Database, 1994, Am Soc. Mass Spectrom. 5: 976-989.
Kiebel, G.R. et al, PRISM: A data management system for high-throughput proteomics, Proteomics, 2006 6:1783-1790. 2006.
Link, A.J. et al, Direct Analysis of Protein Complexes Using Mass Spectrometry, Jul. 1999. Nat. Biotechnologyl. 17: 676-682.
Smith, R.D. et al, An accurate mass tag strategy for quantitative and high-throughput proteome measurements, 2002. Proteomics 2, 513-523.
Tang, H. et al, Use of relaxation-edited one-dimensional and two dimensional nuclear magnetic resonance spectroscopy to improve detection of small metabolites in blood plasma, Analytical Biochemistry, 2003, 325:260-272.
Washburn, M.P. et al, Large-scale analysis of the yeast proteome by multidimensional protein identification technology, Mar. 2001. Nat. Biotechnology, 19: 242-247.
Wei-Jun Qia et al, Comparative Proteome Analyses of Human Plasma Following in vivo Lipopolysaccharide Administration Using Multidimensional Separations Coupled with Tandem Mass Spectrometry, 2005. Proteomics 5:572-584.
Donaldson et al., "Airway and Systemic Inflammation and Decline in Lung Function in Patients with COPD," *Chest*, 128(4), pp. 1995-2004, Oct. 2005 (Oct. 2005).
Marko-Varga et al., "Discovery of Biomarker Candidates Within Disease by Protein Profiling: Principles and Concepts," *J Proteome Res*, 4, pp. 1200-1212, Jul. 20, 2005 (Jul. 20, 2005).
Merkel et al., "Proteomic Study of Human Bronchoalveolar Lavage Fluids from Smokers with Chronic Obstructive Pulmonary Disease by Combining Surface-enhanced Laser Desorption/Ionization-Mass Spectrometry Profiling with Mass Spectrometric Protein Identification," *Proteomics*, 5(11), pp. 2972-2980, Jul. 2005 (Jul. 2005).

* cited by examiner

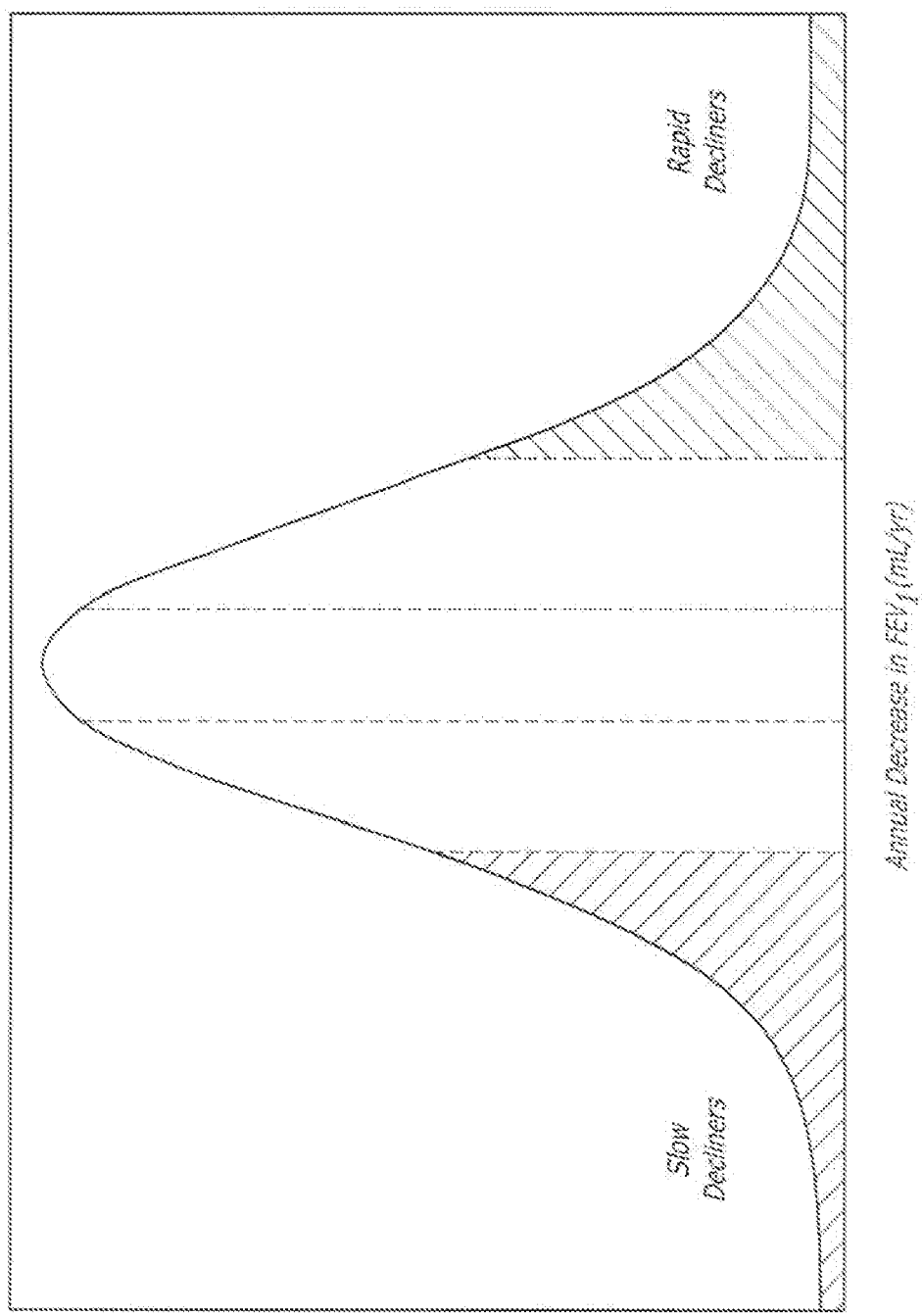

SEQUENCE LISTING

<160> NUMBER OF SEQ ID NOS: 343

<210> SEQ ID NO 1
<211> LENGTH: 22
<212> TYPE: PRT
<213> ORGANISM: Homo sapiens

<400> SEQUENCE: 1

Arg Asn Pro Phe Val Phe Ala Pro Thr Leu Leu Thr Val Ala Val His
1               5                   10                  15

Phe Glu Glu Val Ala Lys
            20

<210> SEQ ID NO 2
<211> LENGTH: 8
<212> TYPE: PRT
<213> ORGANISM: Homo sapiens

<400> SEQUENCE: 2

Asp Asp Asn Pro Asn Leu Pro Arg
1               5

<210> SEQ ID NO 3
<211> LENGTH: 7
<212> TYPE: PRT
<213> ORGANISM: Homo sapiens

<400> SEQUENCE: 3

Glu Phe Ala Glu Val Ser Lys
1               5

<210> SEQ ID NO 4
<211> LENGTH: 9
<212> TYPE: PRT
<213> ORGANISM: Homo sapiens

<400> SEQUENCE: 4

Lys Asp Leu Gly Glu Glu Asn Phe Lys
1               5

<210> SEQ ID NO 5
<211> LENGTH: 7
<212> TYPE: PRT
<213> ORGANISM: Homo sapiens

<400> SEQUENCE: 5

Leu Ser Gln Arg Phe Pro Lys
1               5

<210> SEQ ID NO 6
<211> LENGTH: 11
<212> TYPE: PRT
<213> ORGANISM: Homo sapiens

<400> SEQUENCE: 6

Leu Val Ala Ala Ser Gln Ala Ala Leu Gly Leu
1               5                   10

<210> SEQ ID NO 7
<211> LENGTH: 10
<212> TYPE: PRT
<213> ORGANISM: Homo sapiens

<400> SEQUENCE: 7

```
Leu Val Asn Glu Val Thr Glu Phe Ala Lys
1               5                   10
```

<210> SEQ ID NO 8
<211> LENGTH: 19
<212> TYPE: PRT
<213> ORGANISM: Homo sapiens

<400> SEQUENCE: 8

```
Asn Tyr Ala Glu Ala Lys Asp Val Phe Leu Gly Met Phe Leu Tyr Glu
1               5                   10                  15

Tyr Ala Arg
```

<210> SEQ ID NO 9
<211> LENGTH: 8
<212> TYPE: PRT
<213> ORGANISM: Homo sapiens

<400> SEQUENCE: 9

```
Thr Tyr Glu Thr Thr Leu Glu Lys
1               5
```

<210> SEQ ID NO 10
<211> LENGTH: 20
<212> TYPE: PRT
<213> ORGANISM: Homo sapiens

<400> SEQUENCE: 10

```
Gly Ala Ala Ala Asn Leu Glu Leu Ile Phe Val Gly Pro Gln His Ala
1               5                   10                  15

Gly Asn Tyr Arg
            20
```

<210> SEQ ID NO 11
<211> LENGTH: 9
<212> TYPE: PRT
<213> ORGANISM: Homo sapiens

<400> SEQUENCE: 11

```
Gly Glu Lys Glu Leu Leu Val Pro Arg
1               5
```

<210> SEQ ID NO 12
<211> LENGTH: 37
<212> TYPE: PRT
<213> ORGANISM: Homo sapiens

<400> SEQUENCE: 12

```
Leu His Asp Asn Gln Asn Gly Trp Ser Gly Asp Ser Ala Pro Val Glu
1               5                   10                  15

Leu Ile Leu Ser Asp Glu Thr Leu Pro Ala Pro Glu Phe Ser Pro Glu
            20                  25                  30

Pro Glu Ser Gly Arg
            35
```

<210> SEQ ID NO 13
<211> LENGTH: 12
<212> TYPE: PRT
<213> ORGANISM: Homo sapiens

<400> SEQUENCE: 13

```
Ser Gly Leu Ser Thr Gly Trp Thr Gln Leu Ser Lys
1               5                   10
```

```
<210> SEQ ID NO 14
<211> LENGTH: 20
<212> TYPE: PRT
<213> ORGANISM: Homo sapiens

<400> SEQUENCE: 14

Ser Leu Pro Ala Pro Trp Leu Ser Met Ala Pro Val Ser Trp Ile Thr
1               5                   10                  15

Pro Gly Leu Lys
            20

<210> SEQ ID NO 15
<211> LENGTH: 17
<212> TYPE: PRT
<213> ORGANISM: Homo sapiens

<400> SEQUENCE: 15

Val Thr Leu Thr Cys Val Ala Pro Leu Ser Gly Val Asp Phe Gln Leu
1               5                   10                  15

Arg

<210> SEQ ID NO 16
<211> LENGTH: 18
<212> TYPE: PRT
<213> ORGANISM: Homo sapiens

<400> SEQUENCE: 16

Leu Tyr Gly Ser Glu Ala Phe Ala Thr Asp Phe Gln Asp Ser Ala Ala
1               5                   10                  15

Ala Lys

<210> SEQ ID NO 17
<211> LENGTH: 14
<212> TYPE: PRT
<213> ORGANISM: Homo sapiens

<400> SEQUENCE: 17

Trp Glu Met Pro Phe Asp Pro Gln Asp Thr His Gln Ser Arg
1               5                   10

<210> SEQ ID NO 18
<211> LENGTH: 19
<212> TYPE: PRT
<213> ORGANISM: Homo sapiens

<400> SEQUENCE: 18

Ala Ser Val Ser Val Leu Gly Asp Ile Leu Gly Ser Ala Met Gln Asn
1               5                   10                  15

Thr Gln Asn

<210> SEQ ID NO 19
<211> LENGTH: 30
<212> TYPE: PRT
<213> ORGANISM: Homo sapiens

<400> SEQUENCE: 19

Gly Gly Val Glu Asp Glu Val Thr Leu Ser Ala Tyr Ile Thr Ile Ala
1               5                   10                  15

Leu Leu Glu Ile Pro Leu Thr Val Thr His Pro Val Val Arg
            20                  25                  30
```

<210> SEQ ID NO 20
<211> LENGTH: 8
<212> TYPE: PRT
<213> ORGANISM: Homo sapiens

<400> SEQUENCE: 20

Gly Pro Thr Gln Glu Phe Lys Lys
1               5

<210> SEQ ID NO 21
<211> LENGTH: 18
<212> TYPE: PRT
<213> ORGANISM: Homo sapiens

<400> SEQUENCE: 21

Leu Leu Leu Gln Gln Val Ser Leu Pro Glu Leu Pro Gly Glu Tyr Ser
1               5                   10                  15

Met Lys

<210> SEQ ID NO 22
<211> LENGTH: 12
<212> TYPE: PRT
<213> ORGANISM: Homo sapiens

<400> SEQUENCE: 22

Gln Glu Gly Asp His Gly Ser His Val Tyr Thr Lys
1               5                   10

<210> SEQ ID NO 23
<211> LENGTH: 11
<212> TYPE: PRT
<213> ORGANISM: Homo sapiens

<400> SEQUENCE: 23

Val Gly Phe Tyr Glu Ser Asp Val Met Gly Arg
1               5                   10

<210> SEQ ID NO 24
<211> LENGTH: 19
<212> TYPE: PRT
<213> ORGANISM: Homo sapiens

<400> SEQUENCE: 24

Asp Ser Phe His Leu Asp Glu Gln Phe Thr Val Pro Val Glu Met Met
1               5                   10                  15

Gln Ala Arg

<210> SEQ ID NO 25
<211> LENGTH: 33
<212> TYPE: PRT
<213> ORGANISM: Homo sapiens

<400> SEQUENCE: 25

Glu Ala Thr Glu Gly Lys Ile Gln Glu Phe Leu Ser Gly Leu Pro Glu
1               5                   10                  15

Asp Thr Val Leu Leu Leu Leu Asn Ala Ile His Phe Gln Gly Phe Trp
            20                  25                  30

Arg

<210> SEQ ID NO 26
<211> LENGTH: 23
<212> TYPE: PRT

```
<213> ORGANISM: Homo sapiens

<400> SEQUENCE: 26

Glu Leu Lys Glu Gln Gln Asp Ser Pro Gly Asn Lys Asp Phe Leu Gln
1               5                   10                  15

Ser Leu Lys Gly Phe Pro Arg
            20

<210> SEQ ID NO 27
<211> LENGTH: 39
<212> TYPE: PRT
<213> ORGANISM: Homo sapiens

<400> SEQUENCE: 27

Gly Phe Pro Ile Lys Glu Asp Phe Leu Glu Gln Ser Glu Gln Leu Phe
1               5                   10                  15

Gly Ala Lys Pro Val Ser Leu Thr Gly Lys Gln Glu Asp Asp Leu Ala
            20                  25                  30

Asn Ile Asn Gln Trp Val Lys
            35

<210> SEQ ID NO 28
<211> LENGTH: 27
<212> TYPE: PRT
<213> ORGANISM: Homo sapiens

<400> SEQUENCE: 28

Ile Gln Glu Phe Leu Ser Gly Leu Pro Glu Asp Thr Val Leu Leu Leu
1               5                   10                  15

Leu Asn Ala Ile His Phe Gln Gly Phe Trp Arg
            20                  25

<210> SEQ ID NO 29
<211> LENGTH: 8
<212> TYPE: PRT
<213> ORGANISM: Homo sapiens

<400> SEQUENCE: 29

Asn Pro Asn Pro Ser Ala Pro Arg
1               5

<210> SEQ ID NO 30
<211> LENGTH: 14
<212> TYPE: PRT
<213> ORGANISM: Homo sapiens

<400> SEQUENCE: 30

Pro Pro Met Glu Glu Asp Tyr Pro Gln Phe Gly Ser Pro Lys
1               5                   10

<210> SEQ ID NO 31
<211> LENGTH: 14
<212> TYPE: PRT
<213> ORGANISM: Homo sapiens

<400> SEQUENCE: 31

Pro Lys Asp Pro Thr Phe Ile Pro Ala Pro Ile Gln Ala Lys
1               5                   10

<210> SEQ ID NO 32
<211> LENGTH: 20
<212> TYPE: PRT
<213> ORGANISM: Homo sapiens
```

```
<400> SEQUENCE: 32

Gln Lys Leu His Glu Leu Gln Glu Lys Leu Ser Pro Leu Gly Glu Glu
1               5                   10                  15

Met Arg Asp Arg
            20

<210> SEQ ID NO 33
<211> LENGTH: 16
<212> TYPE: PRT
<213> ORGANISM: Homo sapiens

<400> SEQUENCE: 33

Ser Gly Arg Asp Tyr Val Ser Gln Phe Glu Gly Ser Ala Leu Gly Lys
1               5                   10                  15

<210> SEQ ID NO 34
<211> LENGTH: 21
<212> TYPE: PRT
<213> ORGANISM: Homo sapiens

<400> SEQUENCE: 34

Ala Gly Thr Glu Leu Val Asn Phe Leu Ser Tyr Phe Val Glu Leu Gly
1               5                   10                  15

Thr Gln Pro Ala Thr
            20

<210> SEQ ID NO 35
<211> LENGTH: 22
<212> TYPE: PRT
<213> ORGANISM: Homo sapiens

<400> SEQUENCE: 35

Ala Gly Thr Glu Leu Val Asn Phe Leu Ser Tyr Phe Val Glu Leu Gly
1               5                   10                  15

Thr Gln Pro Ala Thr Gln
            20

<210> SEQ ID NO 36
<211> LENGTH: 11
<212> TYPE: PRT
<213> ORGANISM: Homo sapiens

<400> SEQUENCE: 36

Ile Asp Gln Asn Val Glu Glu Leu Lys Gly Arg
1               5                   10

<210> SEQ ID NO 37
<211> LENGTH: 12
<212> TYPE: PRT
<213> ORGANISM: Homo sapiens

<400> SEQUENCE: 37

Lys Leu Val Pro Phe Ala Thr Glu Leu His Glu Arg
1               5                   10

<210> SEQ ID NO 38
<211> LENGTH: 21
<212> TYPE: PRT
<213> ORGANISM: Homo sapiens

<400> SEQUENCE: 38

Leu Thr Pro Tyr Ala Asp Glu Phe Lys Val Lys Ile Asp Gln Thr Val
```

```
                1               5              10              15

Glu Glu Leu Arg Arg
            20

<210> SEQ ID NO 39
<211> LENGTH: 9
<212> TYPE: PRT
<213> ORGANISM: Homo sapiens

<400> SEQUENCE: 39

Pro Phe Ala Thr Glu Leu His Glu Arg
1               5

<210> SEQ ID NO 40
<211> LENGTH: 7
<212> TYPE: PRT
<213> ORGANISM: Homo sapiens

<400> SEQUENCE: 40

Pro Tyr Ala Asp Glu Phe Lys
1               5

<210> SEQ ID NO 41
<211> LENGTH: 17
<212> TYPE: PRT
<213> ORGANISM: Homo sapiens

<400> SEQUENCE: 41

Ser Leu Ala Glu Leu Gly Gly His Leu Asp Gln Gln Val Glu Glu Phe
1               5                  10                  15

Arg

<210> SEQ ID NO 42
<211> LENGTH: 18
<212> TYPE: PRT
<213> ORGANISM: Homo sapiens

<400> SEQUENCE: 42

Ser Leu Ala Glu Leu Gly Gly His Leu Asp Gln Gln Val Glu Glu Phe
1               5                  10                  15

Arg Arg

<210> SEQ ID NO 43
<211> LENGTH: 15
<212> TYPE: PRT
<213> ORGANISM: Homo sapiens

<400> SEQUENCE: 43

Ala Leu Tyr Trp Val Asn Gly Gln Val Pro Asp Gly Val Ser Lys
1               5                  10                  15

<210> SEQ ID NO 44
<211> LENGTH: 11
<212> TYPE: PRT
<213> ORGANISM: Homo sapiens

<400> SEQUENCE: 44

Asp Leu Lys Val Glu Asp Ile Pro Leu Ala Arg
1               5                  10

<210> SEQ ID NO 45
<211> LENGTH: 11
<212> TYPE: PRT
```

<213> ORGANISM: Homo sapiens

<400> SEQUENCE: 45

Glu Phe Gln Val Pro Thr Phe Thr Ile Pro Lys
1               5                   10

<210> SEQ ID NO 46
<211> LENGTH: 7
<212> TYPE: PRT
<213> ORGANISM: Homo sapiens

<400> SEQUENCE: 46

Phe Ile Ile Pro Ser Pro Lys
1               5

<210> SEQ ID NO 47
<211> LENGTH: 13
<212> TYPE: PRT
<213> ORGANISM: Homo sapiens

<400> SEQUENCE: 47

Phe Leu Asp Ser Asn Ile Lys Phe Ser His Val Glu Lys
1               5                   10

<210> SEQ ID NO 48
<211> LENGTH: 18
<212> TYPE: PRT
<213> ORGANISM: Homo sapiens

<400> SEQUENCE: 48

Phe Ser Val Pro Ala Gly Ile Val Ile Pro Ser Phe Gln Ala Leu Thr
1               5                   10                  15

Ala Arg

<210> SEQ ID NO 49
<211> LENGTH: 13
<212> TYPE: PRT
<213> ORGANISM: Homo sapiens

<400> SEQUENCE: 49

Ile Ala Glu Leu Ser Ala Thr Ala Gln Glu Ile Ile Lys
1               5                   10

<210> SEQ ID NO 50
<211> LENGTH: 10
<212> TYPE: PRT
<213> ORGANISM: Homo sapiens

<400> SEQUENCE: 50

Ile Glu Ile Pro Leu Pro Phe Gly Gly Lys
1               5                   10

<210> SEQ ID NO 51
<211> LENGTH: 18
<212> TYPE: PRT
<213> ORGANISM: Homo sapiens

<400> SEQUENCE: 51

Ile His Ser Gly Ser Phe Gln Ser Gln Val Glu Leu Ser Asn Asp Gln
1               5                   10                  15

Glu Lys

<210> SEQ ID NO 52

```
<211> LENGTH: 20
<212> TYPE: PRT
<213> ORGANISM: Homo sapiens

<400> SEQUENCE: 52

Ile Thr Glu Asn Asp Ile Gln Ile Ala Leu Asp Asp Ala Lys Ile Asn
1               5                   10                  15

Phe Asn Glu Lys
            20

<210> SEQ ID NO 53
<211> LENGTH: 19
<212> TYPE: PRT
<213> ORGANISM: Homo sapiens

<400> SEQUENCE: 53

Leu Leu Leu Gln Met Asp Ser Ser Ala Thr Ala Tyr Gly Ser Thr Val
1               5                   10                  15

Ser Lys Arg

<210> SEQ ID NO 54
<211> LENGTH: 9
<212> TYPE: PRT
<213> ORGANISM: Homo sapiens

<400> SEQUENCE: 54

Leu Thr Ile Phe Lys Thr Glu Leu Arg
1               5

<210> SEQ ID NO 55
<211> LENGTH: 8
<212> TYPE: PRT
<213> ORGANISM: Homo sapiens

<400> SEQUENCE: 55

Leu Thr Leu Asp Ile Gln Asn Lys
1               5

<210> SEQ ID NO 56
<211> LENGTH: 12
<212> TYPE: PRT
<213> ORGANISM: Homo sapiens

<400> SEQUENCE: 56

Met Asn Phe Lys Gln Glu Leu Asn Gly Asn Thr Lys
1               5                   10

<210> SEQ ID NO 57
<211> LENGTH: 15
<212> TYPE: PRT
<213> ORGANISM: Homo sapiens

<400> SEQUENCE: 57

Asn Leu Gln Asn Asn Ala Glu Trp Val Tyr Gln Gly Ala Ile Arg
1               5                   10                  15

<210> SEQ ID NO 58
<211> LENGTH: 23
<212> TYPE: PRT
<213> ORGANISM: Homo sapiens

<400> SEQUENCE: 58

Asn Ser Leu Phe Phe Ser Ala Gln Pro Phe Glu Ile Thr Ala Ser Thr
1               5                   10                  15
```

Asn Asn Glu Gly Asn Leu Lys
            20

<210> SEQ ID NO 59
<211> LENGTH: 10
<212> TYPE: PRT
<213> ORGANISM: Homo sapiens

<400> SEQUENCE: 59

Gln Gly Phe Phe Pro Asp Ser Val Asn Lys
1               5                   10

<210> SEQ ID NO 60
<211> LENGTH: 19
<212> TYPE: PRT
<213> ORGANISM: Homo sapiens

<400> SEQUENCE: 60

Gln Val Phe Leu Tyr Pro Glu Lys Asp Glu Pro Thr Tyr Ile Leu Asn
1               5                   10                  15

Ile Lys Arg

<210> SEQ ID NO 61
<211> LENGTH: 16
<212> TYPE: PRT
<213> ORGANISM: Homo sapiens

<400> SEQUENCE: 61

Arg Asn Leu Gln Asn Asn Ala Glu Trp Val Tyr Gln Gly Ala Ile Arg
1               5                   10                  15

<210> SEQ ID NO 62
<211> LENGTH: 7
<212> TYPE: PRT
<213> ORGANISM: Homo sapiens

<400> SEQUENCE: 62

Ser Gln Ala Ile Ala Thr Lys
1               5

<210> SEQ ID NO 63
<211> LENGTH: 13
<212> TYPE: PRT
<213> ORGANISM: Homo sapiens

<400> SEQUENCE: 63

Ser Val Ser Leu Pro Ser Leu Asp Pro Ala Ser Ala Lys
1               5                   10

<210> SEQ ID NO 64
<211> LENGTH: 13
<212> TYPE: PRT
<213> ORGANISM: Homo sapiens

<400> SEQUENCE: 64

Thr Lys Asn Ser Glu Glu Phe Ala Ala Ala Met Ser Arg
1               5                   10

<210> SEQ ID NO 65
<211> LENGTH: 14
<212> TYPE: PRT
<213> ORGANISM: Homo sapiens

<400> SEQUENCE: 65

```
Val Leu Leu Asp Gln Leu Gly Thr Thr Ile Ser Phe Glu Arg
1               5                   10

<210> SEQ ID NO 66
<211> LENGTH: 11
<212> TYPE: PRT
<213> ORGANISM: Homo sapiens

<400> SEQUENCE: 66

Val Arg Glu Ser Asp Glu Glu Thr Gln Ile Lys
1               5                   10

<210> SEQ ID NO 67
<211> LENGTH: 9
<212> TYPE: PRT
<213> ORGANISM: Homo sapiens

<400> SEQUENCE: 67

Val Ser Thr Ala Phe Val Tyr Thr Lys
1               5

<210> SEQ ID NO 68
<211> LENGTH: 21
<212> TYPE: PRT
<213> ORGANISM: Homo sapiens

<400> SEQUENCE: 68

Asp Val Ser Ser Ala Leu Asp Lys Leu Lys Glu Phe Gly Asn Thr Leu
1               5                   10                  15

Glu Asp Lys Ala Arg
            20

<210> SEQ ID NO 69
<211> LENGTH: 9
<212> TYPE: PRT
<213> ORGANISM: Homo sapiens

<400> SEQUENCE: 69

Leu Gln Ala Glu Ala Phe Gln Ala Arg
1               5

<210> SEQ ID NO 70
<211> LENGTH: 10
<212> TYPE: PRT
<213> ORGANISM: Homo sapiens

<400> SEQUENCE: 70

Lys Ala Thr Val Val Tyr Gln Gly Glu Arg
1               5                   10

<210> SEQ ID NO 71
<211> LENGTH: 17
<212> TYPE: PRT
<213> ORGANISM: Homo sapiens

<400> SEQUENCE: 71

Thr Ser Ile Tyr Pro Phe Leu Asp Phe Met Pro Ser Pro Gln Val Val
1               5                   10                  15

Arg

<210> SEQ ID NO 72
<211> LENGTH: 10
<212> TYPE: PRT
```

```
<213> ORGANISM: Homo sapiens

<400> SEQUENCE: 72

Val Gly Glu Ala Asn Pro Lys Leu Gln Lys
1               5                   10

<210> SEQ ID NO 73
<211> LENGTH: 15
<212> TYPE: PRT
<213> ORGANISM: Homo sapiens

<400> SEQUENCE: 73

Glu Ala Leu Ile Gln Phe Leu Glu Gln Val His Gln Gly Ile Lys
1               5                   10                  15

<210> SEQ ID NO 74
<211> LENGTH: 22
<212> TYPE: PRT
<213> ORGANISM: Homo sapiens

<400> SEQUENCE: 74

His Leu Tyr Val Leu Glu Phe Ser Asp His Pro Gly Ile His Glu Pro
1               5                   10                  15

Leu Glu Pro Glu Val Lys
            20

<210> SEQ ID NO 75
<211> LENGTH: 20
<212> TYPE: PRT
<213> ORGANISM: Homo sapiens

<400> SEQUENCE: 75

Lys Leu Ile Ser Val Asp Thr Glu His Ser Asn Ile Tyr Leu Gln Asn
1               5                   10                  15

Gly Pro Asp Arg
            20

<210> SEQ ID NO 76
<211> LENGTH: 42
<212> TYPE: PRT
<213> ORGANISM: Homo sapiens

<400> SEQUENCE: 76

Met Phe Gly Asn Leu Gln Gly Leu Thr Met His Val Gly Asp Glu Val
1               5                   10                  15

Asn Trp Tyr Leu Met Gly Met Gly Asn Glu Ile Asp Leu His Thr Val
                20                  25                  30

His Phe His Gly His Ser Phe Gln Tyr Lys
            35                  40

<210> SEQ ID NO 77
<211> LENGTH: 21
<212> TYPE: PRT
<213> ORGANISM: Homo sapiens

<400> SEQUENCE: 77

Met Tyr Tyr Ser Ala Val Asp Pro Thr Lys Asp Ile Phe Thr Gly Leu
1               5                   10                  15

Ile Gly Pro Met Lys
            20

<210> SEQ ID NO 78
```

```
<211> LENGTH: 10
<212> TYPE: PRT
<213> ORGANISM: Homo sapiens

<400> SEQUENCE: 78

Pro Leu Ser Ile Glu Pro Ile Gly Val Arg
1               5                   10

<210> SEQ ID NO 79
<211> LENGTH: 13
<212> TYPE: PRT
<213> ORGANISM: Homo sapiens

<400> SEQUENCE: 79

Gln Tyr Thr Asp Ser Thr Phe Arg Val Pro Val Glu Arg
1               5                   10

<210> SEQ ID NO 80
<211> LENGTH: 17
<212> TYPE: PRT
<213> ORGANISM: Homo sapiens

<400> SEQUENCE: 80

Thr Thr Ile Glu Lys Pro Val Trp Leu Gly Phe Leu Gly Pro Ile Ile
1               5                   10                  15

Lys

<210> SEQ ID NO 81
<211> LENGTH: 10
<212> TYPE: PRT
<213> ORGANISM: Homo sapiens

<400> SEQUENCE: 81

Thr Leu Leu Ser Asn Leu Glu Glu Ala Lys
1               5                   10

<210> SEQ ID NO 82
<211> LENGTH: 20
<212> TYPE: PRT
<213> ORGANISM: Homo sapiens

<400> SEQUENCE: 82

Ile Val Glu Gly Ser Asp Ala Glu Ile Gly Met Ser Pro Trp Gln Val
1               5                   10                  15

Met Leu Phe Arg
            20

<210> SEQ ID NO 83
<211> LENGTH: 13
<212> TYPE: PRT
<213> ORGANISM: Homo sapiens

<400> SEQUENCE: 83

Thr Ala Thr Ser Glu Tyr Gln Thr Phe Phe Asn Pro Arg
1               5                   10

<210> SEQ ID NO 84
<211> LENGTH: 17
<212> TYPE: PRT
<213> ORGANISM: Homo sapiens

<400> SEQUENCE: 84

Val Thr Gly Trp Gly Asn Leu Lys Glu Thr Trp Thr Ala Asn Val Gly
1               5                   10                  15
```

Lys

<210> SEQ ID NO 85
<211> LENGTH: 11
<212> TYPE: PRT
<213> ORGANISM: Homo sapiens

<400> SEQUENCE: 85

Trp Ile Gln Lys Val Ile Asp Gln Phe Gly Glu
1               5                   10

<210> SEQ ID NO 86
<211> LENGTH: 9
<212> TYPE: PRT
<213> ORGANISM: Homo sapiens

<400> SEQUENCE: 86

Thr Gly Ile Val Ser Gly Phe Gly Arg
1               5

<210> SEQ ID NO 87
<211> LENGTH: 10
<212> TYPE: PRT
<213> ORGANISM: Homo sapiens

<400> SEQUENCE: 87

Phe Gln Pro Thr Leu Leu Thr Leu Pro Arg
1               5                   10

<210> SEQ ID NO 88
<211> LENGTH: 8
<212> TYPE: PRT
<213> ORGANISM: Homo sapiens

<400> SEQUENCE: 88

Pro Thr Leu Leu Thr Leu Pro Arg
1               5

<210> SEQ ID NO 89
<211> LENGTH: 15
<212> TYPE: PRT
<213> ORGANISM: Homo sapiens

<400> SEQUENCE: 89

Met Gly Asn Phe Pro Trp Gln Val Phe Thr Asn Ile His Gly Arg
1               5                   10                  15

<210> SEQ ID NO 90
<211> LENGTH: 40
<212> TYPE: PRT
<213> ORGANISM: Homo sapiens

<400> SEQUENCE: 90

Ser Val Leu Leu Ala Gln Glu Leu Pro Gln Gln Leu Thr Ser Pro Gly
1               5                   10                  15

Tyr Pro Glu Pro Tyr Gly Lys Gly Gln Glu Ser Ser Thr Asp Ile Lys
            20                  25                  30

Ala Pro Glu Gly Phe Ala Val Arg
            35                  40

<210> SEQ ID NO 91
<211> LENGTH: 19
<212> TYPE: PRT

```
<213> ORGANISM: Homo sapiens

<400> SEQUENCE: 91

Ser Ser Asn Asn Pro His Ser Pro Ile Val Glu Glu Phe Gln Val Pro
1               5                   10                  15

Tyr Asn Lys

<210> SEQ ID NO 92
<211> LENGTH: 14
<212> TYPE: PRT
<213> ORGANISM: Homo sapiens

<400> SEQUENCE: 92

Ala Leu His Gln Val Phe Glu His Met Leu Asp Val Ser Lys
1               5                   10

<210> SEQ ID NO 93
<211> LENGTH: 12
<212> TYPE: PRT
<213> ORGANISM: Homo sapiens

<400> SEQUENCE: 93

Gln His Leu Gly Asp Val Leu Asn Phe Leu Pro Leu
1               5                   10

<210> SEQ ID NO 94
<211> LENGTH: 14
<212> TYPE: PRT
<213> ORGANISM: Homo sapiens

<400> SEQUENCE: 94

Ala Gly Asp Phe Leu Glu Ala Asn Tyr Met Asn Leu Gln Arg
1               5                   10

<210> SEQ ID NO 95
<211> LENGTH: 7
<212> TYPE: PRT
<213> ORGANISM: Homo sapiens

<400> SEQUENCE: 95

Ala Val Leu Tyr Asn Tyr Arg
1               5

<210> SEQ ID NO 96
<211> LENGTH: 18
<212> TYPE: PRT
<213> ORGANISM: Homo sapiens

<400> SEQUENCE: 96

Ala Tyr Tyr Glu Asn Ser Pro Gln Gln Val Phe Ser Thr Glu Phe Glu
1               5                   10                  15

Val Lys

<210> SEQ ID NO 97
<211> LENGTH: 32
<212> TYPE: PRT
<213> ORGANISM: Homo sapiens

<400> SEQUENCE: 97

His Gln Gln Thr Val Thr Ile Pro Pro Lys Ser Ser Leu Ser Val Pro
1               5                   10                  15

Tyr Val Ile Val Pro Leu Lys Thr Gly Leu Gln Glu Val Glu Val Lys
                20                  25                  30
```

```
<210> SEQ ID NO 98
<211> LENGTH: 14
<212> TYPE: PRT
<213> ORGANISM: Homo sapiens

<400> SEQUENCE: 98

Ile Pro Ile Glu Asp Gly Ser Gly Glu Val Val Leu Ser Arg
1               5                   10

<210> SEQ ID NO 99
<211> LENGTH: 7
<212> TYPE: PRT
<213> ORGANISM: Homo sapiens

<400> SEQUENCE: 99

Leu Met Asn Ile Phe Leu Lys
1               5

<210> SEQ ID NO 100
<211> LENGTH: 24
<212> TYPE: PRT
<213> ORGANISM: Homo sapiens

<400> SEQUENCE: 100

Leu Met Asn Ile Phe Leu Lys Asp Ser Ile Thr Thr Trp Glu Ile Leu
1               5                   10                  15

Ala Val Ser Met Ser Asp Lys Lys
            20

<210> SEQ ID NO 101
<211> LENGTH: 8
<212> TYPE: PRT
<213> ORGANISM: Homo sapiens

<400> SEQUENCE: 101

Pro Gly Gln Gln Met Thr Leu Lys
1               5

<210> SEQ ID NO 102
<211> LENGTH: 16
<212> TYPE: PRT
<213> ORGANISM: Homo sapiens

<400> SEQUENCE: 102

Pro Leu Ser Trp Asp Ile Pro Glu Leu Val Asn Met Gly Gln Trp Lys
1               5                   10                  15

<210> SEQ ID NO 103
<211> LENGTH: 11
<212> TYPE: PRT
<213> ORGANISM: Homo sapiens

<400> SEQUENCE: 103

Gln Glu Leu Ser Glu Ala Glu Gln Ala Thr Arg
1               5                   10

<210> SEQ ID NO 104
<211> LENGTH: 8
<212> TYPE: PRT
<213> ORGANISM: Homo sapiens

<400> SEQUENCE: 104

Gln Gly Ala Leu Glu Leu Ile Lys
```

-continued

<210> SEQ ID NO 105
<211> LENGTH: 23
<212> TYPE: PRT
<213> ORGANISM: Homo sapiens

<400> SEQUENCE: 105

Gln Lys Pro Asp Gly Val Phe Gln Glu Asp Ala Pro Val Ile His Gln
1               5                   10                  15

Glu Met Ile Gly Gly Leu Arg
            20

<210> SEQ ID NO 106
<211> LENGTH: 29
<212> TYPE: PRT
<213> ORGANISM: Homo sapiens

<400> SEQUENCE: 106

Gln Leu Tyr Asn Val Glu Ala Thr Ser Tyr Ala Leu Leu Ala Leu Leu
1               5                   10                  15

Gln Leu Lys Asp Phe Asp Phe Val Pro Pro Val Val Arg
            20                  25

<210> SEQ ID NO 107
<211> LENGTH: 10
<212> TYPE: PRT
<213> ORGANISM: Homo sapiens

<400> SEQUENCE: 107

Ser Asp Asp Lys Val Thr Leu Glu Glu Arg
1               5                   10

<210> SEQ ID NO 108
<211> LENGTH: 13
<212> TYPE: PRT
<213> ORGANISM: Homo sapiens

<400> SEQUENCE: 108

Ser Asp Asp Lys Val Thr Leu Glu Glu Arg Leu Asp Lys
1               5                   10

<210> SEQ ID NO 109
<211> LENGTH: 18
<212> TYPE: PRT
<213> ORGANISM: Homo sapiens

<400> SEQUENCE: 109

Ser Gly Gln Ser Glu Asp Arg Gln Pro Val Pro Gly Gln Gln Met Thr
1               5                   10                  15

Leu Lys

<210> SEQ ID NO 110
<211> LENGTH: 10
<212> TYPE: PRT
<213> ORGANISM: Homo sapiens

<400> SEQUENCE: 110

Ser Leu Lys Val Val Pro Glu Gly Ile Arg
1               5                   10

<210> SEQ ID NO 111
<211> LENGTH: 16

```
<212> TYPE: PRT
<213> ORGANISM: Homo sapiens

<400> SEQUENCE: 111

Ser Asn Leu Asp Glu Asp Ile Ile Ala Glu Glu Asn Ile Val Ser Arg
1               5                   10                  15

<210> SEQ ID NO 112
<211> LENGTH: 13
<212> TYPE: PRT
<213> ORGANISM: Homo sapiens

<400> SEQUENCE: 112

Ser Pro Met Tyr Ser Ile Ile Thr Pro Asn Ile Leu Arg
1               5                   10

<210> SEQ ID NO 113
<211> LENGTH: 16
<212> TYPE: PRT
<213> ORGANISM: Homo sapiens

<400> SEQUENCE: 113

Ser Tyr Thr Val Ala Ile Ala Gly Tyr Ala Leu Ala Gln Met Gly Arg
1               5                   10                  15

<210> SEQ ID NO 114
<211> LENGTH: 16
<212> TYPE: PRT
<213> ORGANISM: Homo sapiens

<400> SEQUENCE: 114

Val His Gln Tyr Phe Asn Val Glu Leu Ile Gln Pro Gly Ala Val Lys
1               5                   10                  15

<210> SEQ ID NO 115
<211> LENGTH: 10
<212> TYPE: PRT
<213> ORGANISM: Homo sapiens

<400> SEQUENCE: 115

Leu Asn Asn Gly Glu Ile Thr Gln His Arg
1               5                   10

<210> SEQ ID NO 116
<211> LENGTH: 9
<212> TYPE: PRT
<213> ORGANISM: Homo sapiens

<400> SEQUENCE: 116

Asp His Ala Val Asp Leu Ile Gln Lys
1               5

<210> SEQ ID NO 117
<211> LENGTH: 10
<212> TYPE: PRT
<213> ORGANISM: Homo sapiens

<400> SEQUENCE: 117

Phe Gly Leu Leu Asp Glu Asp Gly Lys Lys
1               5                   10

<210> SEQ ID NO 118
<211> LENGTH: 38
<212> TYPE: PRT
<213> ORGANISM: Homo sapiens
```

<400> SEQUENCE: 118

Gly Ser Phe Glu Phe Pro Val Gly Asp Ala Val Ser Lys Val Leu Gln
1               5                   10                  15

Ile Glu Lys Glu Gly Ala Ile His Arg Glu Glu Leu Val Tyr Glu Leu
            20                  25                  30

Asn Pro Leu Asp His Arg
            35

<210> SEQ ID NO 119
<211> LENGTH: 27
<212> TYPE: PRT
<213> ORGANISM: Homo sapiens

<400> SEQUENCE: 119

Lys Lys Glu Val Tyr Met Pro Ser Ser Ile Phe Gln Asp Asp Phe Val
1               5                   10                  15

Ile Pro Asp Ile Ser Glu Pro Gly Thr Trp Lys
            20                  25

<210> SEQ ID NO 120
<211> LENGTH: 36
<212> TYPE: PRT
<213> ORGANISM: Homo sapiens

<400> SEQUENCE: 120

Leu Tyr Val Ala Ala Ile Ile Glu Ser Pro Gly Gly Glu Met Glu
1               5                   10                  15

Glu Ala Glu Leu Thr Ser Trp Tyr Phe Val Ser Ser Pro Phe Ser Leu
            20                  25                  30

Asp Leu Ser Lys
        35

<210> SEQ ID NO 121
<211> LENGTH: 41
<212> TYPE: PRT
<213> ORGANISM: Homo sapiens

<400> SEQUENCE: 121

Ser Met Gln Gly Gly Leu Val Gly Asn Asp Glu Thr Val Ala Leu Thr
1               5                   10                  15

Ala Phe Val Thr Ile Ala Leu His His Gly Leu Ala Val Phe Gln Asp
            20                  25                  30

Glu Gly Ala Glu Pro Leu Lys Gln Arg
        35                  40

<210> SEQ ID NO 122
<211> LENGTH: 23
<212> TYPE: PRT
<213> ORGANISM: Homo sapiens

<400> SEQUENCE: 122

Thr Leu Glu Ile Pro Gly Asn Ser Asp Pro Asn Met Ile Pro Asp Gly
1               5                   10                  15

Asp Phe Asn Ser Tyr Val Arg
            20

<210> SEQ ID NO 123
<211> LENGTH: 10
<212> TYPE: PRT
<213> ORGANISM: Homo sapiens

```
<400> SEQUENCE: 123

Val Gly Asp Thr Leu Asn Leu Asn Leu Arg
1               5                   10

<210> SEQ ID NO 124
<211> LENGTH: 25
<212> TYPE: PRT
<213> ORGANISM: Homo sapiens

<400> SEQUENCE: 124

Val Leu Gln Ile Glu Lys Glu Gly Ala Ile His Arg Glu Glu Leu Val
1               5                   10                  15

Tyr Glu Leu Asn Pro Leu Asp His Arg
            20                  25

<210> SEQ ID NO 125
<211> LENGTH: 26
<212> TYPE: PRT
<213> ORGANISM: Homo sapiens

<400> SEQUENCE: 125

Val Thr Ala Ser Asp Pro Leu Asp Thr Leu Gly Ser Glu Gly Ala Leu
1               5                   10                  15

Ser Pro Gly Gly Val Ala Ser Leu Leu Arg
            20                  25

<210> SEQ ID NO 126
<211> LENGTH: 9
<212> TYPE: PRT
<213> ORGANISM: Homo sapiens

<400> SEQUENCE: 126

Tyr Arg Val Phe Ala Leu Asp Gln Lys
1               5

<210> SEQ ID NO 127
<211> LENGTH: 9
<212> TYPE: PRT
<213> ORGANISM: Homo sapiens

<400> SEQUENCE: 127

Tyr Val Leu Pro Asn Phe Glu Val Lys
1               5

<210> SEQ ID NO 128
<211> LENGTH: 24
<212> TYPE: PRT
<213> ORGANISM: Homo sapiens

<400> SEQUENCE: 128

Glu Lys Phe Ser Asp Ala Ser Tyr Gln Ser Ile Asn Ile Pro Val Thr
1               5                   10                  15

Gln Asn Met Val Pro Ser Ser Arg
            20

<210> SEQ ID NO 129
<211> LENGTH: 22
<212> TYPE: PRT
<213> ORGANISM: Homo sapiens

<400> SEQUENCE: 129

Phe Ser Asp Ala Ser Tyr Gln Ser Ile Asn Ile Pro Val Thr Gln Asn
```

```
1               5                   10                  15
Met Val Pro Ser Ser Arg
            20
```

<210> SEQ ID NO 130
<211> LENGTH: 14
<212> TYPE: PRT
<213> ORGANISM: Homo sapiens

<400> SEQUENCE: 130

```
Lys Gln Thr Ala Cys Lys Pro Glu Ile Ala Tyr Ala Tyr Lys
1               5                   10
```

<210> SEQ ID NO 131
<211> LENGTH: 11
<212> TYPE: PRT
<213> ORGANISM: Homo sapiens

<400> SEQUENCE: 131

```
Thr Leu Leu Pro Val Ser Lys Pro Glu Ile Arg
1               5                   10
```

<210> SEQ ID NO 132
<211> LENGTH: 12
<212> TYPE: PRT
<213> ORGANISM: Homo sapiens

<400> SEQUENCE: 132

```
Ala Lys Asp Leu His Leu Ser Asp Val Phe Leu Lys
1               5                   10
```

<210> SEQ ID NO 133
<211> LENGTH: 15
<212> TYPE: PRT
<213> ORGANISM: Homo sapiens

<400> SEQUENCE: 133

```
Leu Ser Glu Lys His Glu Gly Ser Phe Ile Gln Gly Ala Glu Lys
1               5                   10                  15
```

<210> SEQ ID NO 134
<211> LENGTH: 28
<212> TYPE: PRT
<213> ORGANISM: Homo sapiens

<400> SEQUENCE: 134

```
Thr Phe Ser Glu Trp Leu Glu Ser Val Lys Glu Asn Pro Ala Val Ile
1               5                   10                  15
Asp Phe Glu Leu Ala Pro Ile Val Asp Leu Val Arg
            20                  25
```

<210> SEQ ID NO 135
<211> LENGTH: 14
<212> TYPE: PRT
<213> ORGANISM: Homo sapiens

<400> SEQUENCE: 135

```
Ser Arg Glu Cys Asn Asn Pro Pro Pro Ser Gly Gly Gly Arg
1               5                   10
```

<210> SEQ ID NO 136
<211> LENGTH: 16
<212> TYPE: PRT
<213> ORGANISM: Homo sapiens

<400> SEQUENCE: 136

Tyr Ser Ala Trp Ala Glu Ser Val Thr Asn Leu Pro Gln Val Ile Lys
1               5                   10                  15

<210> SEQ ID NO 137
<211> LENGTH: 10
<212> TYPE: PRT
<213> ORGANISM: Homo sapiens

<400> SEQUENCE: 137

Ala Met Ala Val Glu Asp Ile Ile Ser Arg
1               5                   10

<210> SEQ ID NO 138
<211> LENGTH: 15
<212> TYPE: PRT
<213> ORGANISM: Homo sapiens

<400> SEQUENCE: 138

Gln Lys Ile Ser Glu Gly Leu Pro Ala Leu Glu Phe Pro Asn Glu
1               5                   10                  15

<210> SEQ ID NO 139
<211> LENGTH: 8
<212> TYPE: PRT
<213> ORGANISM: Homo sapiens

<400> SEQUENCE: 139

Tyr Ala Phe Glu Leu Lys Glu Lys
1               5

<210> SEQ ID NO 140
<211> LENGTH: 10
<212> TYPE: PRT
<213> ORGANISM: Homo sapiens

<400> SEQUENCE: 140

Ala Leu Phe Val Ser Glu Glu Glu Lys Lys
1               5                   10

<210> SEQ ID NO 141
<211> LENGTH: 9
<212> TYPE: PRT
<213> ORGANISM: Homo sapiens

<400> SEQUENCE: 141

Asp Ile Ser Glu Val Val Thr Pro Arg
1               5

<210> SEQ ID NO 142
<211> LENGTH: 11
<212> TYPE: PRT
<213> ORGANISM: Homo sapiens

<400> SEQUENCE: 142

Glu Lys Leu Gln Asp Glu Asp Leu Gly Phe Leu
1               5                   10

<210> SEQ ID NO 143
<211> LENGTH: 32
<212> TYPE: PRT
<213> ORGANISM: Homo sapiens

<400> SEQUENCE: 143

```
His Val Ile Ile Leu Met Thr Asp Gly Leu His Asn Met Gly Gly Asp
1               5                   10                  15

Pro Ile Thr Val Ile Asp Glu Ile Arg Asp Leu Leu Tyr Ile Gly Lys
            20                  25                  30
```

<210> SEQ ID NO 144
<211> LENGTH: 14
<212> TYPE: PRT
<213> ORGANISM: Homo sapiens

<400> SEQUENCE: 144

```
Val Ser Glu Ala Asp Ser Ser Asn Ala Asp Trp Val Thr Lys
1               5                   10
```

<210> SEQ ID NO 145
<211> LENGTH: 34
<212> TYPE: PRT
<213> ORGANISM: Homo sapiens

<400> SEQUENCE: 145

```
Val Ser Glu Ala Asp Ser Ser Asn Ala Asp Trp Val Thr Lys Gln Leu
1               5                   10                  15

Asn Glu Ile Asn Tyr Glu Asp His Lys Leu Lys Ser Gly Thr Asn Thr
            20                  25                  30

Lys Lys
```

<210> SEQ ID NO 146
<211> LENGTH: 8
<212> TYPE: PRT
<213> ORGANISM: Homo sapiens

<400> SEQUENCE: 146

```
Val Ser Val Gly Gly Glu Lys Arg
1               5
```

<210> SEQ ID NO 147
<211> LENGTH: 9
<212> TYPE: PRT
<213> ORGANISM: Homo sapiens

<400> SEQUENCE: 147

```
Glu Phe Asp His Asn Ser Asn Ile Arg
1               5
```

<210> SEQ ID NO 148
<211> LENGTH: 9
<212> TYPE: PRT
<213> ORGANISM: Homo sapiens

<400> SEQUENCE: 148

```
Ile Asp Val His Leu Val Pro Asp Arg
1               5
```

<210> SEQ ID NO 149
<211> LENGTH: 7
<212> TYPE: PRT
<213> ORGANISM: Homo sapiens

<400> SEQUENCE: 149

```
Asn Asp Phe Thr Trp Phe Lys
1               5
```

```
<210> SEQ ID NO 150
<211> LENGTH: 19
<212> TYPE: PRT
<213> ORGANISM: Homo sapiens

<400> SEQUENCE: 150

Ala Asp Ser Gly Glu Gly Asp Phe Leu Ala Glu Gly Gly Gly Val Arg
1               5                   10                  15

Gly Pro Arg

<210> SEQ ID NO 151
<211> LENGTH: 20
<212> TYPE: PRT
<213> ORGANISM: Homo sapiens

<400> SEQUENCE: 151

Glu Val Asp Leu Lys Asp Tyr Glu Asp Gln Gln Lys Gln Leu Glu Gln
1               5                   10                  15

Val Ile Ala Lys
            20

<210> SEQ ID NO 152
<211> LENGTH: 16
<212> TYPE: PRT
<213> ORGANISM: Homo sapiens

<400> SEQUENCE: 152

Gly Leu Ile Asp Glu Val Asn Gln Asp Phe Thr Asn Arg Ile Asn Lys
1               5                   10                  15

<210> SEQ ID NO 153
<211> LENGTH: 13
<212> TYPE: PRT
<213> ORGANISM: Homo sapiens

<400> SEQUENCE: 153

Met Glu Leu Glu Arg Pro Gly Gly Asn Glu Ile Thr Arg
1               5                   10

<210> SEQ ID NO 154
<211> LENGTH: 13
<212> TYPE: PRT
<213> ORGANISM: Homo sapiens

<400> SEQUENCE: 154

Met Lys Pro Val Pro Asp Leu Val Pro Gly Asn Phe Lys
1               5                   10

<210> SEQ ID NO 155
<211> LENGTH: 11
<212> TYPE: PRT
<213> ORGANISM: Homo sapiens

<400> SEQUENCE: 155

Pro Val Pro Asp Leu Val Pro Gly Asn Phe Lys
1               5                   10

<210> SEQ ID NO 156
<211> LENGTH: 10
<212> TYPE: PRT
<213> ORGANISM: Homo sapiens

<400> SEQUENCE: 156

Val Thr Ser Gly Ser Thr Thr Thr Thr Arg
```

<210> SEQ ID NO 157
<211> LENGTH: 20
<212> TYPE: PRT
<213> ORGANISM: Homo sapiens

<400> SEQUENCE: 157

Gly Gly Glu Thr Ser Glu Met Tyr Leu Ile Gln Pro Asp Ser Val
1               5                   10                  15

Lys Pro Tyr Arg
            20

<210> SEQ ID NO 158
<211> LENGTH: 8
<212> TYPE: PRT
<213> ORGANISM: Homo sapiens

<400> SEQUENCE: 158

Ile Arg Pro Phe Phe Pro Gln Gln
1               5

<210> SEQ ID NO 159
<211> LENGTH: 21
<212> TYPE: PRT
<213> ORGANISM: Homo sapiens

<400> SEQUENCE: 159

Lys Gly Gly Glu Thr Ser Glu Met Tyr Leu Ile Gln Pro Asp Ser
1               5                   10                  15

Val Lys Pro Tyr Arg
            20

<210> SEQ ID NO 160
<211> LENGTH: 19
<212> TYPE: PRT
<213> ORGANISM: Homo sapiens

<400> SEQUENCE: 160

Lys Trp Asp Pro Tyr Lys Gln Gly Phe Gly Asn Val Ala Thr Asn
1               5                   10                  15

Asp Gly Lys

<210> SEQ ID NO 161
<211> LENGTH: 7
<212> TYPE: PRT
<213> ORGANISM: Homo sapiens

<400> SEQUENCE: 161

Ser Ile Leu Glu Asn Leu Arg
1               5

<210> SEQ ID NO 162
<211> LENGTH: 26
<212> TYPE: PRT
<213> ORGANISM: Homo sapiens

<400> SEQUENCE: 162

Thr Met Thr Ile His Asn Gly Met Phe Phe Ser Thr Tyr Asp Arg Asp
1               5                   10                  15

Asn Asp Gly Trp Leu Thr Ser Asp Pro Arg
            20                  25

<210> SEQ ID NO 163
<211> LENGTH: 27
<212> TYPE: PRT
<213> ORGANISM: Homo sapiens

<400> SEQUENCE: 163

Thr Met Thr Ile His Asn Gly Met Phe Phe Ser Tyr Asp Arg Asp
1               5                   10                  15

Asn Asp Gly Trp Leu Thr Ser Asp Pro Arg Lys
            20                  25

<210> SEQ ID NO 164
<211> LENGTH: 18
<212> TYPE: PRT
<213> ORGANISM: Homo sapiens

<400> SEQUENCE: 164

Trp Asp Pro Tyr Lys Gln Gly Phe Gly Asn Val Ala Thr Asn Thr Asp
1               5                   10                  15

Gly Lys

<210> SEQ ID NO 165
<211> LENGTH: 13
<212> TYPE: PRT
<213> ORGANISM: Homo sapiens

<400> SEQUENCE: 165

Tyr Tyr Trp Gly Gly Gln Tyr Thr Trp Asp Met Ala Lys
1               5                   10

<210> SEQ ID NO 166
<211> LENGTH: 15
<212> TYPE: PRT
<213> ORGANISM: Homo sapiens

<400> SEQUENCE: 166

Ile His Leu Ile Ser Thr Gln Ser Ala Ile Pro Tyr Ala Leu Arg
1               5                   10                  15

<210> SEQ ID NO 167
<211> LENGTH: 10
<212> TYPE: PRT
<213> ORGANISM: Homo sapiens

<400> SEQUENCE: 167

Pro Asn Met Ile Asp Ala Ala Thr Leu Lys
1               5                   10

<210> SEQ ID NO 168
<211> LENGTH: 8
<212> TYPE: PRT
<213> ORGANISM: Homo sapiens

<400> SEQUENCE: 168

Thr Ala Asp Tyr Ala Met Phe Lys
1               5

<210> SEQ ID NO 169
<211> LENGTH: 19
<212> TYPE: PRT
<213> ORGANISM: Homo sapiens

<400> SEQUENCE: 169

```
Thr Tyr Asn Pro Asp Glu Ser Ser Lys Pro Asn Met Ile Asp Ala Ala
1               5                   10                  15

Thr Leu Lys

<210> SEQ ID NO 170
<211> LENGTH: 18
<212> TYPE: PRT
<213> ORGANISM: Homo sapiens

<400> SEQUENCE: 170

Tyr Asn Pro Asp Glu Ser Ser Lys Pro Asn Met Ile Asp Ala Ala Thr
1               5                   10                  15

Leu Lys

<210> SEQ ID NO 171
<211> LENGTH: 16
<212> TYPE: PRT
<213> ORGANISM: Homo sapiens

<400> SEQUENCE: 171

Gly Ala Thr Tyr Asn Ile Ile Val Glu Ala Leu Lys Asp Gln Gln Arg
1               5                   10                  15

<210> SEQ ID NO 172
<211> LENGTH: 22
<212> TYPE: PRT
<213> ORGANISM: Homo sapiens

<400> SEQUENCE: 172

Thr Glu Ile Asp Lys Pro Ser Gln Met Gln Val Thr Asp Val Gln Asp
1               5                   10                  15

Asn Ser Ile Ser Val Lys
            20

<210> SEQ ID NO 173
<211> LENGTH: 40
<212> TYPE: PRT
<213> ORGANISM: Homo sapiens

<400> SEQUENCE: 173

Thr Pro Phe Val Thr His Pro Gly Tyr Asp Thr Gly Asn Gly Ile Gln
1               5                   10                  15

Leu Pro Gly Thr Ser Gly Gln Gln Pro Ser Val Gly Gln Gln Met Ile
            20                  25                  30

Phe Glu Glu His Gly Phe Arg Arg
        35                  40

<210> SEQ ID NO 174
<211> LENGTH: 13
<212> TYPE: PRT
<213> ORGANISM: Homo sapiens

<400> SEQUENCE: 174

Ala Gly Ala Leu Asn Ser Asn Asp Ala Phe Val Leu Lys
1               5                   10

<210> SEQ ID NO 175
<211> LENGTH: 22
<212> TYPE: PRT
<213> ORGANISM: Homo sapiens

<400> SEQUENCE: 175
```

Ala Gln Pro Val Gln Val Ala Glu Gly Ser Glu Pro Asp Gly Phe Trp
1               5                   10                  15

Glu Ala Leu Gly Gly Lys
            20

<210> SEQ ID NO 176
<211> LENGTH: 30
<212> TYPE: PRT
<213> ORGANISM: Homo sapiens

<400> SEQUENCE: 176

Ile Glu Gly Ser Asn Lys Val Pro Val Asp Pro Ala Thr Tyr Gly Gln
1               5                   10                  15

Phe Tyr Gly Gly Asp Ser Tyr Ile Ile Leu Tyr Asn Tyr Arg
            20                  25                  30

<210> SEQ ID NO 177
<211> LENGTH: 20
<212> TYPE: PRT
<213> ORGANISM: Homo sapiens

<400> SEQUENCE: 177

Pro Val Gln Val Ala Glu Gly Ser Glu Pro Asp Gly Phe Trp Glu Ala
1               5                   10                  15

Leu Gly Gly Lys
            20

<210> SEQ ID NO 178
<211> LENGTH: 17
<212> TYPE: PRT
<213> ORGANISM: Homo sapiens

<400> SEQUENCE: 178

Gln Thr Gln Val Ser Val Leu Pro Glu Gly Gly Glu Thr Pro Leu Phe
1               5                   10                  15

Lys

<210> SEQ ID NO 179
<211> LENGTH: 8
<212> TYPE: PRT
<213> ORGANISM: Homo sapiens

<400> SEQUENCE: 179

Arg Thr Pro Ile Thr Val Val Lys
1               5

<210> SEQ ID NO 180
<211> LENGTH: 8
<212> TYPE: PRT
<213> ORGANISM: Homo sapiens

<400> SEQUENCE: 180

Thr Ala Ser Asp Phe Ile Thr Lys
1               5

<210> SEQ ID NO 181
<211> LENGTH: 28
<212> TYPE: PRT
<213> ORGANISM: Homo sapiens

<400> SEQUENCE: 181

Cys Ser Pro His Leu Val Leu Ser Ala Leu Thr Ser Asp Asn His Gly
1               5                   10                  15

Ala Thr Tyr Ala Phe Ser Gly Thr His Tyr Trp Arg
            20                  25

<210> SEQ ID NO 182
<211> LENGTH: 12
<212> TYPE: PRT
<213> ORGANISM: Homo sapiens

<400> SEQUENCE: 182

Asp Val Arg Asp Tyr Phe Met Pro Cys Pro Gly Arg
1               5                   10

<210> SEQ ID NO 183
<211> LENGTH: 6
<212> TYPE: PRT
<213> ORGANISM: Homo sapiens

<400> SEQUENCE: 183

Glu Lys Gly Tyr Pro Lys
1               5

<210> SEQ ID NO 184
<211> LENGTH: 9
<212> TYPE: PRT
<213> ORGANISM: Homo sapiens

<400> SEQUENCE: 184

Val Trp Val Tyr Pro Pro Glu Lys Lys
1               5

<210> SEQ ID NO 185
<211> LENGTH: 15
<212> TYPE: PRT
<213> ORGANISM: Homo sapiens

<400> SEQUENCE: 185

Phe Thr Val Asp Arg Pro Phe Leu Phe Leu Ile Tyr Glu His Arg
1               5                   10                  15

<210> SEQ ID NO 186
<211> LENGTH: 7
<212> TYPE: PRT
<213> ORGANISM: Homo sapiens

<400> SEQUENCE: 186

Leu Asn Ile Leu Asn Ala Lys
1               5

<210> SEQ ID NO 187
<211> LENGTH: 8
<212> TYPE: PRT
<213> ORGANISM: Homo sapiens

<400> SEQUENCE: 187

Thr Arg Glu Val Leu Leu Pro Lys
1               5

<210> SEQ ID NO 188
<211> LENGTH: 10
<212> TYPE: PRT
<213> ORGANISM: Homo sapiens

<400> SEQUENCE: 188

Val Phe Ser Leu Gln Trp Gly Glu Val Lys

```
<210> SEQ ID NO 189
<211> LENGTH: 7
<212> TYPE: PRT
<213> ORGANISM: Homo sapiens

<400> SEQUENCE: 189

His Leu Ser Asp Leu Cys Lys
1               5

<210> SEQ ID NO 190
<211> LENGTH: 12
<212> TYPE: PRT
<213> ORGANISM: Homo sapiens

<400> SEQUENCE: 190

Ala Ala Ile Ser Gly Glu Asn Ala Gly Leu Val Arg
1               5                   10

<210> SEQ ID NO 191
<211> LENGTH: 18
<212> TYPE: PRT
<213> ORGANISM: Homo sapiens

<400> SEQUENCE: 191

Phe Ala His Tyr Val Val Thr Ser Gln Val Val Asn Thr Ala Asn Glu
1               5                   10                  15

Ala Arg

<210> SEQ ID NO 192
<211> LENGTH: 28
<212> TYPE: PRT
<213> ORGANISM: Homo sapiens

<400> SEQUENCE: 192

Gly Met Ala Asp Gln Asp Gly Leu Lys Pro Thr Ile Asp Lys Pro Ser
1               5                   10                  15

Glu Asp Ser Pro Pro Leu Glu Met Leu Gly Pro Arg
            20                  25

<210> SEQ ID NO 193
<211> LENGTH: 13
<212> TYPE: PRT
<213> ORGANISM: Homo sapiens

<400> SEQUENCE: 193

Lys Ala Ala Ile Ser Gly Glu Asn Ala Gly Leu Val Arg
1               5                   10

<210> SEQ ID NO 194
<211> LENGTH: 10
<212> TYPE: PRT
<213> ORGANISM: Homo sapiens

<400> SEQUENCE: 194

Leu Asp Ala Gln Ala Ser Phe Leu Pro Lys
1               5                   10

<210> SEQ ID NO 195
<211> LENGTH: 13
<212> TYPE: PRT
<213> ORGANISM: Homo sapiens
```

<400> SEQUENCE: 195

Gln Ala Val Asp Thr Ala Val Asp Gly Val Phe Ile Arg
1               5                   10

<210> SEQ ID NO 196
<211> LENGTH: 8
<212> TYPE: PRT
<213> ORGANISM: Homo sapiens

<400> SEQUENCE: 196

Ala Thr Thr Met Ile Gln Ser Lys
1               5

<210> SEQ ID NO 197
<211> LENGTH: 10
<212> TYPE: PRT
<213> ORGANISM: Homo sapiens

<400> SEQUENCE: 197

Asp Lys His Ala Asp Pro Asp Phe Thr Arg
1               5                   10

<210> SEQ ID NO 198
<211> LENGTH: 15
<212> TYPE: PRT
<213> ORGANISM: Homo sapiens

<400> SEQUENCE: 198

Ile Gln Pro Ser Gly Gly Thr Asn Ile Asn Glu Ala Leu Leu Arg
1               5                   10                  15

<210> SEQ ID NO 199
<211> LENGTH: 12
<212> TYPE: PRT
<213> ORGANISM: Homo sapiens

<400> SEQUENCE: 199

Ile Tyr Gly Asn Gln Asp Thr Ser Ser Gln Leu Lys
1               5                   10

<210> SEQ ID NO 200
<211> LENGTH: 13
<212> TYPE: PRT
<213> ORGANISM: Homo sapiens

<400> SEQUENCE: 200

Ile Tyr Gly Asn Gln Asp Thr Ser Ser Gln Leu Lys Lys
1               5                   10

<210> SEQ ID NO 201
<211> LENGTH: 7
<212> TYPE: PRT
<213> ORGANISM: Homo sapiens

<400> SEQUENCE: 201

Ile Tyr Leu Gln Pro Gly Arg
1               5

<210> SEQ ID NO 202
<211> LENGTH: 14
<212> TYPE: PRT
<213> ORGANISM: Homo sapiens

<400> SEQUENCE: 202

```
Leu Trp Ala Tyr Leu Thr Ile Asn Gln Leu Leu Ala Glu Arg
1               5                   10
```

<210> SEQ ID NO 203
<211> LENGTH: 9
<212> TYPE: PRT
<213> ORGANISM: Homo sapiens

<400> SEQUENCE: 203

```
Met Lys Gln Thr Val Glu Ala Met Lys
1               5
```

<210> SEQ ID NO 204
<211> LENGTH: 7
<212> TYPE: PRT
<213> ORGANISM: Homo sapiens

<400> SEQUENCE: 204

```
Gln Thr Val Glu Ala Met Lys
1               5
```

<210> SEQ ID NO 205
<211> LENGTH: 22
<212> TYPE: PRT
<213> ORGANISM: Homo sapiens

<400> SEQUENCE: 205

```
Thr Ile Leu Asp Asp Leu Arg Ala Glu Asp His Phe Ser Val Ile Asp
1               5                   10                  15

Phe Asn Gln Asn Ile Arg
            20
```

<210> SEQ ID NO 206
<211> LENGTH: 35
<212> TYPE: PRT
<213> ORGANISM: Homo sapiens

<400> SEQUENCE: 206

```
His Phe Glu Ile Glu Val Asp Ile Phe Glu Pro Gln Gly Ile Ser Met
1               5                   10                  15

Leu Asp Ala Glu Ala Ser Phe Ile Thr Asn Asp Leu Leu Gly Ser Ala
            20                  25                  30

Leu Thr Lys
        35
```

<210> SEQ ID NO 207
<211> LENGTH: 15
<212> TYPE: PRT
<213> ORGANISM: Homo sapiens

<400> SEQUENCE: 207

```
Ala Asn Thr Val Gln Glu Ala Thr Phe Gln Met Glu Leu Pro Lys
1               5                   10                  15
```

<210> SEQ ID NO 208
<211> LENGTH: 9
<212> TYPE: PRT
<213> ORGANISM: Homo sapiens

<400> SEQUENCE: 208

```
Leu Gly Val Tyr Glu Leu Leu Leu Lys
1               5
```

```
<210> SEQ ID NO 209
<211> LENGTH: 16
<212> TYPE: PRT
<213> ORGANISM: Homo sapiens

<400> SEQUENCE: 209

Leu Gln Asp Arg Gly Pro Asp Val Leu Thr Ala Thr Val Ser Gly Lys
1               5                   10                  15

<210> SEQ ID NO 210
<211> LENGTH: 16
<212> TYPE: PRT
<213> ORGANISM: Homo sapiens

<400> SEQUENCE: 210

Asn Met Glu Gln Phe Gln Val Ser Val Ser Val Ala Pro Asn Ala Lys
1               5                   10                  15

<210> SEQ ID NO 211
<211> LENGTH: 24
<212> TYPE: PRT
<213> ORGANISM: Homo sapiens

<400> SEQUENCE: 211

Gln Gly Pro Val Asn Leu Leu Ser Asp Pro Glu Gln Gly Val Glu Val
1               5                   10                  15

Thr Gly Gln Tyr Glu Arg Glu Lys
            20

<210> SEQ ID NO 212
<211> LENGTH: 20
<212> TYPE: PRT
<213> ORGANISM: Homo sapiens

<400> SEQUENCE: 212

Gln Leu Gly Leu Pro Gly Pro Pro Asp Val Pro Asp His Ala Ala Tyr
1               5                   10                  15

His Pro Phe Arg
            20

<210> SEQ ID NO 213
<211> LENGTH: 21
<212> TYPE: PRT
<213> ORGANISM: Homo sapiens

<400> SEQUENCE: 213

Gln Leu Gly Leu Pro Gly Pro Pro Asp Val Pro Asp His Ala Ala Tyr
1               5                   10                  15

His Pro Phe Arg Arg
            20

<210> SEQ ID NO 214
<211> LENGTH: 10
<212> TYPE: PRT
<213> ORGANISM: Homo sapiens

<400> SEQUENCE: 214

Arg Leu Gly Val Tyr Glu Leu Leu Leu Lys
1               5                   10

<210> SEQ ID NO 215
<211> LENGTH: 10
<212> TYPE: PRT
<213> ORGANISM: Homo sapiens
```

<400> SEQUENCE: 215

Val Gln Gly Asn Asp His Ser Ala Thr Arg
1               5                   10

<210> SEQ ID NO 216
<211> LENGTH: 9
<212> TYPE: PRT
<213> ORGANISM: Homo sapiens

<400> SEQUENCE: 216

Tyr Ile Phe His Asn Phe Met Glu Arg
1               5

<210> SEQ ID NO 217
<211> LENGTH: 7
<212> TYPE: PRT
<213> ORGANISM: Homo sapiens

<400> SEQUENCE: 217

Tyr Tyr Leu Gln Gly Ala Lys
1               5

<210> SEQ ID NO 218
<211> LENGTH: 11
<212> TYPE: PRT
<213> ORGANISM: Homo sapiens

<400> SEQUENCE: 218

Ala Val Glu Gln Val Lys Asn Ala Phe Asn Lys
1               5                   10

<210> SEQ ID NO 219
<211> LENGTH: 32
<212> TYPE: PRT
<213> ORGANISM: Homo sapiens

<400> SEQUENCE: 219

Asn Ala Phe Asn Lys Leu Gln Glu Lys Gly Ile Tyr Lys Ala Met Ser
1               5                   10                  15

Glu Phe Asp Ile Phe Ile Asn Tyr Ile Glu Ala Tyr Met Thr Met Lys
                20                  25                  30

<210> SEQ ID NO 220
<211> LENGTH: 9
<212> TYPE: PRT
<213> ORGANISM: Homo sapiens

<400> SEQUENCE: 220

Gln Val Val Ala Gly Leu Asn Phe Arg
1               5

<210> SEQ ID NO 221
<211> LENGTH: 7
<212> TYPE: PRT
<213> ORGANISM: Homo sapiens

<400> SEQUENCE: 221

Val Gln Val Val Ala Gly Lys
1               5

<210> SEQ ID NO 222
<211> LENGTH: 8
<212> TYPE: PRT

```
<213> ORGANISM: Homo sapiens

<400> SEQUENCE: 222

Phe Asn Ala Leu Gln Tyr Leu Arg
1               5

<210> SEQ ID NO 223
<211> LENGTH: 11
<212> TYPE: PRT
<213> ORGANISM: Homo sapiens

<400> SEQUENCE: 223

Leu Lys Glu Asp Ala Val Ser Ala Ala Phe Lys
1               5                   10

<210> SEQ ID NO 224
<211> LENGTH: 7
<212> TYPE: PRT
<213> ORGANISM: Homo sapiens

<400> SEQUENCE: 224

Ile Ala Leu Asp Phe Leu Lys
1               5

<210> SEQ ID NO 225
<211> LENGTH: 29
<212> TYPE: PRT
<213> ORGANISM: Homo sapiens

<400> SEQUENCE: 225

Gly Ile Glu Thr Gly Ser Glu Asp Leu Glu Ile Leu Pro Asn Gly Leu
1               5                   10                  15

Ala Phe Ile Ser Ser Gly Leu Lys Tyr Pro Gly Ile Lys
            20                  25

<210> SEQ ID NO 226
<211> LENGTH: 17
<212> TYPE: PRT
<213> ORGANISM: Homo sapiens

<400> SEQUENCE: 226

Pro Ser Leu Ser His Leu Leu Ser Gln Tyr Tyr Gly Ala Gly Val Ala
1               5                   10                  15

Arg

<210> SEQ ID NO 227
<211> LENGTH: 24
<212> TYPE: PRT
<213> ORGANISM: Homo sapiens

<400> SEQUENCE: 227

Ser Leu Pro Leu Leu Met Asp Ser Val Ile Gln Ala Leu Ala Glu Leu
1               5                   10                  15

Glu Gln Lys Val Pro Ala Ala Lys
            20

<210> SEQ ID NO 228
<211> LENGTH: 9
<212> TYPE: PRT
<213> ORGANISM: Homo sapiens

<400> SEQUENCE: 228

Glu Ile Ile Ile His Gln Asn Tyr Lys
```

-continued

```
<210> SEQ ID NO 229
<211> LENGTH: 19
<212> TYPE: PRT
<213> ORGANISM: Homo sapiens

<400> SEQUENCE: 229

Glu Pro Leu Asp Asp Tyr Val Asn Thr Gln Gly Ala Ser Leu Phe Ser
1               5                   10                  15

Val Thr Lys

<210> SEQ ID NO 230
<211> LENGTH: 10
<212> TYPE: PRT
<213> ORGANISM: Homo sapiens

<400> SEQUENCE: 230

Met Arg Asp Val Val Leu Phe Glu Lys Lys
1               5                   10

<210> SEQ ID NO 231
<211> LENGTH: 10
<212> TYPE: PRT
<213> ORGANISM: Homo sapiens

<400> SEQUENCE: 231

Ala Gly Ala Asn Val Leu Ala Lys Asn Lys
1               5                   10

<210> SEQ ID NO 232
<211> LENGTH: 6
<212> TYPE: PRT
<213> ORGANISM: Homo sapiens

<400> SEQUENCE: 232

Thr Val Ser Ile Pro Arg
1               5

<210> SEQ ID NO 233
<211> LENGTH: 17
<212> TYPE: PRT
<213> ORGANISM: Homo sapiens

<400> SEQUENCE: 233

Glu Gly Ile Phe Pro Ala Val Phe Val Arg Pro Cys Pro Ala Glu Ala
1               5                   10                  15

Lys

<210> SEQ ID NO 234
<211> LENGTH: 16
<212> TYPE: PRT
<213> ORGANISM: Homo sapiens

<400> SEQUENCE: 234

Leu Ser Asn Asn Ala Leu Ser Gly Leu Pro Gln Gly Val Phe Gly Lys
1               5                   10                  15

<210> SEQ ID NO 235
<211> LENGTH: 9
<212> TYPE: PRT
<213> ORGANISM: Homo sapiens

<400> SEQUENCE: 235
```

```
Asp Phe Thr Glu Ala Val Gly Ala Lys
1               5
```

<210> SEQ ID NO 236
<211> LENGTH: 15
<212> TYPE: PRT
<213> ORGANISM: Homo sapiens

<400> SEQUENCE: 236

```
Ser Gln Asp Thr His Gly Ala Val Gly Pro Phe Leu Phe Arg Lys
1               5                   10                  15
```

<210> SEQ ID NO 237
<211> LENGTH: 28
<212> TYPE: PRT
<213> ORGANISM: Homo sapiens

<400> SEQUENCE: 237

```
Ile Thr Thr Gly Gly Asp Val Ile Asn Asn Gly Leu Trp Asn Met Val
1               5                   10                  15

Ser Val Glu Glu Leu Glu His Ser Ile Ser Ile Lys
            20                  25
```

<210> SEQ ID NO 238
<211> LENGTH: 8
<212> TYPE: PRT
<213> ORGANISM: Homo sapiens

<400> SEQUENCE: 238

```
Val Tyr Phe Ala Gly Phe Pro Arg
1               5
```

<210> SEQ ID NO 239
<211> LENGTH: 19
<212> TYPE: PRT
<213> ORGANISM: Homo sapiens

<400> SEQUENCE: 239

```
Asn Asn Glu Glu Tyr Leu Ala Leu Ile Phe Glu Lys Gly Gly Ser Tyr
1               5                   10                  15

Leu Gly Arg
```

<210> SEQ ID NO 240
<211> LENGTH: 10
<212> TYPE: PRT
<213> ORGANISM: Homo sapiens

<400> SEQUENCE: 240

```
Gln Arg Gln Glu Glu Leu Cys Leu Ala Arg
1               5                   10
```

<210> SEQ ID NO 241
<211> LENGTH: 10
<212> TYPE: PRT
<213> ORGANISM: Homo sapiens

<400> SEQUENCE: 241

```
Leu Ser Ile Thr Gly Thr Tyr Asp Leu Lys
1               5                   10
```

<210> SEQ ID NO 242
<211> LENGTH: 9
<212> TYPE: PRT

```
<213> ORGANISM: Homo sapiens

<400> SEQUENCE: 242

Leu Ser Ser Trp Val Leu Leu Met Lys
1               5

<210> SEQ ID NO 243
<211> LENGTH: 10
<212> TYPE: PRT
<213> ORGANISM: Homo sapiens

<400> SEQUENCE: 243

Ser Val Leu Gly Gln Leu Gly Ile Thr Lys
1               5                   10

<210> SEQ ID NO 244
<211> LENGTH: 31
<212> TYPE: PRT
<213> ORGANISM: Homo sapiens

<400> SEQUENCE: 244

Ser Val Leu Gly Gln Leu Gly Ile Thr Lys Val Phe Ser Asn Gly Ala
1               5                   10                  15

Asp Leu Ser Gly Val Thr Glu Glu Ala Pro Leu Lys Leu Ser Lys
            20                  25                  30

<210> SEQ ID NO 245
<211> LENGTH: 7
<212> TYPE: PRT
<213> ORGANISM: Homo sapiens

<400> SEQUENCE: 245

Ser Ile Leu Phe Leu Gly Lys
1               5

<210> SEQ ID NO 246
<211> LENGTH: 12
<212> TYPE: PRT
<213> ORGANISM: Homo sapiens

<400> SEQUENCE: 246

Glu Val Pro Leu Asn Thr Ile Ile Phe Met Gly Arg
1               5                   10

<210> SEQ ID NO 247
<211> LENGTH: 34
<212> TYPE: PRT
<213> ORGANISM: Homo sapiens

<400> SEQUENCE: 247

Phe Ala Thr Thr Phe Tyr Gln His Leu Ala Asp Ser Lys Asn Asp Asn
1               5                   10                  15

Asp Asn Ile Phe Leu Ser Pro Leu Ser Ile Ser Thr Ala Phe Ala Met
            20                  25                  30

Thr Lys

<210> SEQ ID NO 248
<211> LENGTH: 12
<212> TYPE: PRT
<213> ORGANISM: Homo sapiens

<400> SEQUENCE: 248

Pro Leu Asp Phe Lys Glu Asn Ala Glu Gln Ser Arg
```

```
1               5                   10
```

<210> SEQ ID NO 249
<211> LENGTH: 29
<212> TYPE: PRT
<213> ORGANISM: Homo sapiens

<400> SEQUENCE: 249

```
Arg Val Ala Glu Gly Thr Gln Val Leu Glu Leu Pro Phe Lys Gly Asp
1               5                   10                  15

Asp Ile Thr Met Val Leu Ile Leu Pro Lys Pro Glu Lys
            20                  25
```

<210> SEQ ID NO 250
<211> LENGTH: 22
<212> TYPE: PRT
<213> ORGANISM: Homo sapiens

<400> SEQUENCE: 250

```
Ser Lys Leu Pro Gly Ile Val Ala Glu Gly Arg Asp Asp Leu Tyr Val
1               5                   10                  15

Ser Asp Ala Phe His Lys
            20
```

<210> SEQ ID NO 251
<211> LENGTH: 32
<212> TYPE: PRT
<213> ORGANISM: Homo sapiens

<400> SEQUENCE: 251

```
Ser Leu Ala Lys Val Glu Lys Glu Leu Thr Pro Glu Val Leu Gln Glu
1               5                   10                  15

Trp Leu Asp Glu Leu Glu Glu Met Met Leu Val Val His Met Pro Arg
            20                  25                  30
```

<210> SEQ ID NO 252
<211> LENGTH: 28
<212> TYPE: PRT
<213> ORGANISM: Homo sapiens

<400> SEQUENCE: 252

```
Val Ala Glu Gly Thr Gln Val Leu Glu Leu Pro Phe Lys Gly Asp Asp
1               5                   10                  15

Ile Thr Met Val Leu Ile Leu Pro Lys Pro Glu Lys
            20                  25
```

<210> SEQ ID NO 253
<211> LENGTH: 13
<212> TYPE: PRT
<213> ORGANISM: Homo sapiens

<400> SEQUENCE: 253

```
Lys Thr Ser Leu Glu Asp Phe Tyr Leu Asp Glu Glu Arg
1               5                   10
```

<210> SEQ ID NO 254
<211> LENGTH: 8
<212> TYPE: PRT
<213> ORGANISM: Homo sapiens

<400> SEQUENCE: 254

```
Val Pro Met Met Ser Asp Pro Lys
1               5
```

<210> SEQ ID NO 255
<211> LENGTH: 10
<212> TYPE: PRT
<213> ORGANISM: Homo sapiens

<400> SEQUENCE: 255

Asp Asn Glu Leu Leu Val Tyr Lys Glu Arg
1               5                   10

<210> SEQ ID NO 256
<211> LENGTH: 10
<212> TYPE: PRT
<213> ORGANISM: Homo sapiens

<400> SEQUENCE: 256

Val Gly Glu Tyr Ser Leu Tyr Ile Gly Arg
1               5                   10

<210> SEQ ID NO 257
<211> LENGTH: 24
<212> TYPE: PRT
<213> ORGANISM: Homo sapiens

<400> SEQUENCE: 257

Val Val Leu Ser Ser Gly Ser Gly Pro Gly Leu Asp Leu Pro Leu Val
1               5                   10                  15

Leu Gly Leu Pro Leu Gln Leu Lys
            20

<210> SEQ ID NO 258
<211> LENGTH: 9
<212> TYPE: PRT
<213> ORGANISM: Homo sapiens

<400> SEQUENCE: 258

Lys Ala Leu Gln Thr Glu Met Ala Arg
1               5

<210> SEQ ID NO 259
<211> LENGTH: 8
<212> TYPE: PRT
<213> ORGANISM: Homo sapiens

<400> SEQUENCE: 259

Asn Asp Leu Leu Ser Ala Thr Lys
1               5

<210> SEQ ID NO 260
<211> LENGTH: 18
<212> TYPE: PRT
<213> ORGANISM: Homo sapiens

<400> SEQUENCE: 260

Gly Ile Leu Gly Lys Asp Val Ser Gly Phe Ser Asp Pro Tyr Cys Leu
1               5                   10                  15

Leu Gly

<210> SEQ ID NO 261
<211> LENGTH: 8
<212> TYPE: PRT
<213> ORGANISM: Homo sapiens

<400> SEQUENCE: 261

Leu Pro Glu Val Phe Leu Ser Lys
1               5

<210> SEQ ID NO 262
<211> LENGTH: 11
<212> TYPE: PRT
<213> ORGANISM: Homo sapiens

<400> SEQUENCE: 262

Val Met Asp Lys Tyr Thr Phe Glu Leu Ser Arg
1               5                   10

<210> SEQ ID NO 263
<211> LENGTH: 16
<212> TYPE: PRT
<213> ORGANISM: Homo sapiens

<400> SEQUENCE: 263

Asp Trp His Gly Val Pro Gly Gln Val Asp Ala Ala Met Ala Gly Arg
1               5                   10                  15

<210> SEQ ID NO 264
<211> LENGTH: 11
<212> TYPE: PRT
<213> ORGANISM: Homo sapiens

<400> SEQUENCE: 264

Pro Gly Gln Val Asp Ala Ala Met Ala Gly Arg
1               5                   10

<210> SEQ ID NO 265
<211> LENGTH: 11
<212> TYPE: PRT
<213> ORGANISM: Homo sapiens

<400> SEQUENCE: 265

Arg Val Asp Thr Val Asp Pro Pro Tyr Pro Arg
1               5                   10

<210> SEQ ID NO 266
<211> LENGTH: 13
<212> TYPE: PRT
<213> ORGANISM: Homo sapiens

<400> SEQUENCE: 266

Thr Ser Ala Gly Thr Arg Gln Pro Gln Phe Ile Ser Arg
1               5                   10

<210> SEQ ID NO 267
<211> LENGTH: 599
<212> TYPE: PRT
<213> ORGANISM: Homo sapiens

<400> SEQUENCE: 267

Met Lys Leu Leu Lys Leu Thr Gly Phe Ile Phe Phe Leu Phe Phe Leu
1               5                   10                  15

Thr Glu Ser Leu Thr Leu Pro Thr Gln Pro Arg Asp Ile Glu Asn Phe
            20                  25                  30

Asn Ser Thr Gln Lys Phe Ile Glu Asp Asn Ile Glu Tyr Ile Thr Ile
        35                  40                  45

Ile Ala Phe Ala Gln Tyr Val Gln Glu Ala Thr Phe Glu Glu Met Glu
    50                  55                  60

```
Lys Leu Val Lys Asp Met Val Glu Tyr Lys Asp Arg Cys Met Ala Asp
 65                  70                  75                  80

Lys Thr Leu Pro Glu Cys Ser Lys Leu Pro Asn Asn Val Leu Gln Glu
                 85                  90                  95

Lys Ile Cys Ala Met Glu Gly Leu Pro Gln Lys His Asn Phe Ser His
            100                 105                 110

Cys Cys Ser Lys Val Asp Ala Gln Arg Arg Leu Cys Phe Phe Tyr Asn
        115                 120                 125

Lys Lys Ser Asp Val Gly Phe Leu Pro Pro Phe Thr Leu Asp Pro
130                 135                 140

Glu Glu Lys Cys Gln Ala Tyr Glu Ser Asn Arg Glu Ser Leu Leu Asn
145                 150                 155                 160

His Phe Leu Tyr Glu Val Ala Arg Arg Asn Pro Phe Val Phe Ala Pro
                165                 170                 175

Thr Leu Leu Thr Val Ala Val His Phe Glu Glu Val Ala Lys Ser Cys
            180                 185                 190

Cys Glu Glu Gln Asn Lys Val Asn Cys Leu Gln Thr Arg Ala Ile Pro
        195                 200                 205

Val Thr Gln Tyr Leu Lys Ala Phe Ser Ser Tyr Gln Lys His Val Cys
210                 215                 220

Gly Ala Leu Leu Lys Phe Gly Thr Lys Val Val His Phe Ile Tyr Ile
225                 230                 235                 240

Ala Ile Leu Ser Gln Lys Phe Pro Lys Ile Glu Phe Lys Glu Leu Ile
                245                 250                 255

Ser Leu Val Glu Asp Val Ser Ser Asn Tyr Asp Gly Cys Cys Glu Gly
            260                 265                 270

Asp Val Val Gln Cys Ile Arg Asp Thr Ser Lys Val Met Asn His Ile
        275                 280                 285

Cys Ser Lys Gln Asp Ser Ile Ser Ser Lys Ile Lys Glu Cys Cys Glu
        290                 295                 300

Lys Lys Ile Pro Glu Arg Gly Gln Cys Ile Ile Asn Ser Asn Lys Asp
305                 310                 315                 320

Asp Arg Pro Lys Asp Leu Ser Leu Arg Glu Gly Lys Phe Thr Asp Ser
                325                 330                 335

Glu Asn Val Cys Gln Glu Arg Asp Ala Asp Pro Asp Thr Phe Phe Ala
            340                 345                 350

Lys Phe Thr Phe Glu Tyr Ser Arg Arg His Pro Asp Leu Ser Ile Pro
        355                 360                 365

Glu Leu Leu Arg Ile Val Gln Ile Tyr Lys Asp Leu Leu Arg Asn Cys
370                 375                 380

Cys Asn Thr Glu Asn Pro Pro Gly Cys Tyr Arg Tyr Ala Glu Asp Lys
385                 390                 395                 400

Phe Asn Glu Thr Thr Glu Lys Ser Leu Lys Met Val Gln Gln Glu Cys
                405                 410                 415

Lys His Phe Gln Asn Leu Gly Lys Asp Gly Leu Lys Tyr His Tyr Leu
            420                 425                 430

Ile Arg Leu Thr Lys Ile Ala Pro Gln Leu Ser Thr Glu Glu Leu Val
        435                 440                 445

Ser Leu Gly Glu Lys Met Val Thr Ala Phe Thr Thr Cys Cys Thr Leu
450                 455                 460

Ser Glu Glu Phe Ala Cys Val Asp Asn Leu Ala Asp Leu Val Phe Gly
465                 470                 475                 480

Glu Leu Cys Gly Val Asn Glu Asn Arg Thr Ile Asn Pro Ala Val Asp
```

```
                    485                 490                 495
His Cys Cys Lys Thr Asn Phe Ala Phe Arg Arg Pro Cys Phe Glu Ser
                500                 505                 510

Leu Lys Ala Asp Lys Thr Tyr Val Pro Pro Phe Ser Gln Asp Leu
                515                 520                 525

Phe Thr Phe His Ala Asp Met Cys Gln Ser Gln Asn Glu Glu Leu Gln
                530                 535                 540

Arg Lys Thr Asp Arg Phe Leu Val Asn Leu Val Lys Leu Lys His Glu
545                 550                 555                 560

Leu Thr Asp Glu Glu Leu Gln Ser Leu Phe Thr Asn Phe Ala Asn Val
                565                 570                 575

Val Asp Lys Cys Cys Lys Ala Glu Ser Pro Glu Val Cys Phe Asn Glu
                580                 585                 590

Glu Ser Pro Lys Ile Gly Asn
                595

<210> SEQ ID NO 268
<211> LENGTH: 609
<212> TYPE: PRT
<213> ORGANISM: Homo sapiens

<400> SEQUENCE: 268

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
                35                  40                  45

Ile Ala Phe Ala Gln Tyr Leu Gln Gln Cys Pro Phe Glu Asp His Val
            50                  55                  60

Lys Leu Val Asn Glu Val Thr Glu Phe Ala Lys Thr Cys Val Ala Asp
65              70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
                100                 105                 110

Asp Cys Cys Ala Lys Gln Glu Pro Glu Arg Asn Glu Cys Phe Leu Gln
                115                 120                 125

His Lys Asp Asp Asn Pro Asn Leu Pro Arg Leu Val Arg Pro Glu Val
            130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
                180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255
```

```
Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 269
<211> LENGTH: 495
<212> TYPE: PRT
<213> ORGANISM: Homo sapiens

<400> SEQUENCE: 269

Met Ser Met Leu Val Val Phe Leu Leu Leu Trp Gly Val Thr Trp Gly
1               5                   10                  15
```

-continued

Pro Val Thr Glu Ala Ala Ile Phe Tyr Glu Thr Gln Pro Ser Leu Trp
         20                  25                  30
Ala Glu Ser Glu Ser Leu Leu Lys Pro Leu Ala Asn Val Thr Leu Thr
             35                  40                  45
Cys Gln Ala His Leu Glu Thr Pro Asp Phe Gln Leu Phe Lys Asn Gly
 50                  55                  60
Val Ala Gln Glu Pro Val His Leu Asp Ser Pro Ala Ile Lys His Gln
 65                  70                  75                  80
Phe Leu Leu Thr Gly Asp Thr Gln Gly Arg Tyr Arg Cys Arg Ser Gly
                 85                  90                  95
Leu Ser Thr Gly Trp Thr Gln Leu Ser Lys Leu Leu Glu Leu Thr Gly
                100                 105                 110
Pro Lys Ser Leu Pro Ala Pro Trp Leu Ser Met Ala Pro Val Ser Trp
            115                 120                 125
Ile Thr Pro Gly Leu Lys Thr Thr Ala Val Cys Arg Gly Val Leu Arg
        130                 135                 140
Gly Val Thr Phe Leu Leu Arg Arg Glu Gly Asp His Glu Phe Leu Glu
145                 150                 155                 160
Val Pro Glu Ala Gln Glu Asp Val Glu Ala Thr Phe Pro Val His Gln
                165                 170                 175
Pro Gly Asn Tyr Ser Cys Ser Tyr Arg Thr Asp Gly Glu Gly Ala Leu
            180                 185                 190
Ser Glu Pro Ser Ala Thr Val Thr Ile Glu Glu Leu Ala Ala Pro Pro
        195                 200                 205
Pro Pro Val Leu Met His His Gly Glu Ser Ser Gln Val Leu His Pro
210                 215                 220
Gly Asn Lys Val Thr Leu Thr Cys Val Ala Pro Leu Ser Gly Val Asp
225                 230                 235                 240
Phe Gln Leu Arg Arg Gly Glu Lys Glu Leu Leu Val Pro Arg Ser Ser
                245                 250                 255
Thr Ser Pro Asp Arg Ile Phe Phe His Leu Asn Ala Val Ala Leu Gly
            260                 265                 270
Asp Gly Gly His Tyr Thr Cys Arg Tyr Arg Leu His Asp Asn Gln Asn
        275                 280                 285
Gly Trp Ser Gly Asp Ser Ala Pro Val Glu Leu Ile Leu Ser Asp Glu
290                 295                 300
Thr Leu Pro Ala Pro Glu Phe Ser Pro Glu Pro Glu Ser Gly Arg Ala
305                 310                 315                 320
Leu Arg Leu Arg Cys Leu Ala Pro Leu Glu Gly Ala Arg Phe Ala Leu
                325                 330                 335
Val Arg Glu Asp Arg Gly Gly Arg Arg Val His Arg Phe Gln Ser Pro
            340                 345                 350
Ala Gly Thr Glu Ala Leu Phe Glu Leu His Asn Ile Ser Val Ala Asp
        355                 360                 365
Ser Ala Asn Tyr Ser Cys Val Tyr Val Asp Leu Lys Pro Pro Phe Gly
    370                 375                 380
Gly Ser Ala Pro Ser Glu Arg Leu Glu Leu His Val Asp Gly Pro Pro
385                 390                 395                 400
Pro Arg Pro Gln Leu Arg Ala Thr Trp Ser Gly Ala Val Leu Ala Gly
                405                 410                 415
Arg Asp Ala Val Leu Arg Cys Glu Gly Pro Ile Pro Asp Val Thr Phe
            420                 425                 430
Glu Leu Leu Arg Glu Gly Glu Thr Lys Ala Val Lys Thr Val Arg Thr

```
                     435                 440                 445
Pro Gly Ala Ala Ala Asn Leu Glu Leu Ile Phe Val Gly Pro Gln His
    450                 455                 460

Ala Gly Asn Tyr Arg Cys Arg Tyr Arg Ser Trp Val Pro His Thr Phe
465                 470                 475                 480

Glu Ser Glu Leu Ser Asp Pro Val Glu Leu Leu Val Ala Glu Ser
                485                 490                 495

<210> SEQ ID NO 270
<211> LENGTH: 433
<212> TYPE: PRT
<213> ORGANISM: Homo sapiens

<400> SEQUENCE: 270

Met Glu Arg Met Leu Pro Leu Ala Leu Gly Leu Leu Ala Ala Gly
1               5                   10                  15

Phe Cys Pro Ala Val Leu Cys His Pro Asn Ser Pro Leu Asp Glu Glu
                20                  25                  30

Asn Leu Thr Gln Glu Asn Gln Asp Arg Gly Thr His Val Asp Leu Gly
            35                  40                  45

Leu Ala Ser Ala Asn Val Asp Phe Ala Phe Ser Leu Tyr Lys Gln Leu
    50                  55                  60

Val Leu Lys Ala Leu Asp Lys Asn Val Ile Phe Ser Pro Leu Ser Ile
65                  70                  75                  80

Ser Thr Ala Leu Ala Phe Leu Ser Leu Gly Ala His Asn Thr Thr Leu
                85                  90                  95

Thr Glu Ile Leu Lys Ala Ser Ser Pro His Gly Asp Leu Leu Arg
                100                 105                 110

Gln Lys Phe Thr Gln Ser Phe Gln His Leu Arg Ala Pro Ser Ile Ser
        115                 120                 125

Ser Ser Asp Glu Leu Gln Leu Ser Met Gly Asn Ala Met Phe Val Lys
    130                 135                 140

Glu Gln Leu Ser Leu Leu Asp Arg Phe Thr Glu Asp Ala Lys Arg Leu
145                 150                 155                 160

Tyr Gly Ser Glu Ala Phe Ala Thr Asp Phe Gln Asp Ser Ala Ala Ala
                165                 170                 175

Lys Lys Leu Ile Asn Asp Tyr Val Lys Asn Gly Thr Arg Gly Lys Ile
            180                 185                 190

Thr Asp Leu Ile Lys Asp Pro Asp Ser Gln Thr Met Met Val Leu Val
        195                 200                 205

Asn Tyr Ile Phe Phe Lys Ala Lys Trp Glu Met Pro Phe Asp Pro Gln
    210                 215                 220

Asp Thr His Gln Ser Arg Phe Tyr Leu Ser Lys Lys Lys Trp Val Met
225                 230                 235                 240

Val Pro Met Met Ser Leu His His Leu Thr Ile Pro Tyr Phe Arg Asp
                245                 250                 255

Glu Glu Leu Ser Cys Thr Val Val Glu Leu Lys Tyr Thr Gly Asn Ala
            260                 265                 270

Ser Ala Leu Phe Ile Leu Pro Asp Gln Asp Lys Met Glu Glu Val Glu
        275                 280                 285

Ala Met Leu Leu Pro Glu Thr Leu Lys Arg Trp Arg Asp Ser Leu Glu
    290                 295                 300

Phe Arg Glu Ile Gly Glu Leu Tyr Leu Pro Lys Phe Ser Ile Ser Arg
305                 310                 315                 320
```

```
Asp Tyr Asn Leu Asn Asp Ile Leu Leu Gln Leu Gly Ile Glu Glu Ala
                325                 330                 335

Phe Thr Ser Lys Ala Asp Leu Ser Gly Ile Thr Gly Ala Arg Asn Leu
            340                 345                 350

Ala Val Ser Gln Val Val His Lys Val Val Ser Asp Val Phe Glu Glu
        355                 360                 365

Gly Thr Glu Ala Ser Ala Thr Ala Val Lys Ile Thr Leu Leu Ser
370                 375                 380

Ala Leu Val Glu Thr Arg Thr Ile Val Arg Phe Asn Arg Pro Phe Leu
385                 390                 395                 400

Met Ile Ile Val Pro Thr Asp Thr Gln Asn Ile Phe Phe Met Ser Lys
                405                 410                 415

Val Thr Asn Pro Ser Lys Pro Arg Ala Cys Ile Lys Gln Trp Gly Ser
                420                 425                 430

Gln

<210> SEQ ID NO 271
<211> LENGTH: 1474
<212> TYPE: PRT
<213> ORGANISM: Homo sapiens

<400> SEQUENCE: 271

Met Gly Lys Asn Lys Leu Leu His Pro Ser Leu Val Leu Leu Leu
1               5                   10                  15

Val Leu Leu Pro Thr Asp Ala Ser Val Ser Gly Lys Pro Gln Tyr Met
                20                  25                  30

Val Leu Val Pro Ser Leu Leu His Thr Glu Thr Thr Glu Lys Gly Cys
            35                  40                  45

Val Leu Leu Ser Tyr Leu Asn Glu Thr Val Thr Val Ser Ala Ser Leu
        50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
                100                 105                 110

Glu Phe Lys Lys Arg Thr Thr Val Met Val Lys Asn Glu Asp Ser Leu
            115                 120                 125

Val Phe Val Gln Thr Asp Lys Ser Ile Tyr Lys Pro Gly Gln Thr Val
        130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
                180                 185                 190

Pro Leu Ser Ser Glu Pro Phe Gln Gly Ser Tyr Lys Val Val Val Gln
            195                 200                 205

Lys Lys Ser Gly Gly Arg Thr Glu His Pro Phe Thr Val Glu Glu Phe
        210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255
```

```
Gly Lys Pro Val Pro Gly His Val Thr Val Ser Ile Cys Arg Lys Tyr
            260             265                 270

Ser Asp Ala Ser Asp Cys His Gly Glu Asp Ser Gln Ala Phe Cys Glu
        275                 280             285

Lys Phe Ser Gly Gln Leu Asn Ser His Gly Cys Phe Tyr Gln Gln Val
    290                 295             300

Lys Thr Lys Val Phe Gln Leu Lys Arg Lys Glu Tyr Glu Met Lys Leu
305             310                 315                 320

His Thr Glu Ala Gln Ile Gln Glu Gly Thr Val Val Glu Leu Thr
                325                 330                 335

Gly Arg Gln Ser Ser Glu Ile Thr Arg Thr Ile Thr Lys Leu Ser Phe
            340                 345                 350

Val Lys Val Asp Ser His Phe Arg Gln Gly Ile Pro Phe Phe Gly Gln
        355                 360             365

Val Arg Leu Val Asp Gly Lys Gly Val Pro Ile Pro Asn Lys Val Ile
        370             375             380

Phe Ile Arg Gly Asn Glu Ala Asn Tyr Tyr Ser Asn Ala Thr Thr Asp
385             390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
            420                 425                 430

Gly Tyr Gln Trp Val Ser Glu Glu His Glu Glu Ala His Thr Ala
            435                 440                 445

Tyr Leu Val Phe Ser Pro Ser Lys Ser Phe Val His Leu Glu Pro Met
450                 455                 460

Ser His Glu Leu Pro Cys Gly His Thr Gln Thr Val Gln Ala His Tyr
465             470                 475                 480

Ile Leu Asn Gly Gly Thr Leu Leu Gly Leu Lys Lys Leu Ser Phe Tyr
            485                 490                 495

Tyr Leu Ile Met Ala Lys Gly Gly Ile Val Arg Thr Gly Thr His Gly
            500                 505                 510

Leu Leu Val Lys Gln Glu Asp Met Lys Gly His Phe Ser Ile Ser Ile
            515                 520                 525

Pro Val Lys Ser Asp Ile Ala Pro Val Ala Arg Leu Leu Ile Tyr Ala
            530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
            565                 570                 575

Ser Leu Pro Ala Ser His Ala His Leu Arg Val Thr Ala Ala Pro Gln
            580                 585                 590

Ser Val Cys Ala Leu Arg Ala Val Asp Gln Ser Val Leu Leu Met Lys
        595                 600                 605

Pro Asp Ala Glu Leu Ser Ala Ser Ser Val Tyr Asn Leu Leu Pro Glu
            610                 615                 620

Lys Asp Leu Thr Gly Phe Pro Gly Pro Leu Asn Asp Gln Asp Asp Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
            660                 665                 670

Met Gly Leu Lys Ala Phe Thr Asn Ser Lys Ile Arg Lys Pro Lys Met
```

```
            675                 680                 685
Cys Pro Gln Leu Gln Gln Tyr Glu Met His Gly Pro Glu Gly Leu Arg
            690                 695                 700
Val Gly Phe Tyr Glu Ser Asp Val Met Gly Arg Gly His Ala Arg Leu
705                 710                 715                 720
Val His Val Glu Glu Pro His Thr Glu Thr Val Arg Lys Tyr Phe Pro
            725                 730                 735
Glu Thr Trp Ile Trp Asp Leu Val Val Asn Ser Ala Gly Val Ala
            740                 745                 750
Glu Val Gly Val Thr Val Pro Asp Thr Ile Thr Glu Trp Lys Ala Gly
            755                 760                 765
Ala Phe Cys Leu Ser Glu Asp Ala Gly Leu Gly Ile Ser Ser Thr Ala
770                 775                 780
Ser Leu Arg Ala Phe Gln Pro Phe Phe Val Leu Thr Met Pro Tyr
785                 790                 795                 800
Ser Val Ile Arg Gly Glu Ala Phe Thr Leu Lys Ala Thr Val Leu Asn
            805                 810                 815
Tyr Leu Pro Lys Cys Ile Arg Val Ser Val Gln Leu Glu Ala Ser Pro
            820                 825                 830
Ala Phe Leu Ala Val Pro Val Glu Lys Glu Gln Ala Pro His Cys Ile
            835                 840                 845
Cys Ala Asn Gly Arg Gln Thr Val Ser Trp Ala Val Thr Pro Lys Ser
850                 855                 860
Leu Gly Asn Val Asn Phe Thr Val Ser Ala Glu Ala Leu Glu Ser Gln
865                 870                 875                 880
Glu Leu Cys Gly Thr Glu Val Pro Ser Val Pro Glu His Gly Arg Lys
            885                 890                 895
Asp Thr Val Ile Lys Pro Leu Leu Val Glu Pro Glu Gly Leu Glu Lys
            900                 905                 910
Glu Thr Thr Phe Asn Ser Leu Leu Cys Pro Ser Gly Gly Glu Val Ser
            915                 920                 925
Glu Glu Leu Ser Leu Lys Leu Pro Pro Asn Val Val Glu Glu Ser Ala
930                 935                 940
Arg Ala Ser Val Ser Val Leu Gly Asp Ile Leu Gly Ser Ala Met Gln
945                 950                 955                 960
Asn Thr Gln Asn Leu Leu Gln Met Pro Tyr Gly Cys Gly Glu Gln Asn
            965                 970                 975
Met Val Leu Phe Ala Pro Asn Ile Tyr Val Leu Asp Tyr Leu Asn Glu
            980                 985                 990
Thr Gln Gln Leu Thr Pro Glu Val  Lys Ser Lys Ala Ile  Gly Tyr Leu
            995                 1000                1005
Asn Thr Gly Tyr Gln Arg Gln  Leu Asn Tyr Lys His  Tyr Asp Gly
            1010                1015                1020
Ser Tyr Ser Thr Phe Gly Glu  Arg Tyr Gly Arg Asn  Gln Gly Asn
            1025                1030                1035
Thr Trp Leu Thr Ala Phe Val  Leu Lys Thr Phe Ala  Gln Ala Arg
            1040                1045                1050
Ala Tyr Ile Phe Ile Asp Glu  Ala His Ile Thr Gln  Ala Leu Ile
            1055                1060                1065
Trp Leu Ser Gln Arg Gln Lys  Asp Asn Gly Cys Phe  Arg Ser Ser
            1070                1075                1080
Gly Ser Leu Leu Asn Asn Ala  Ile Lys Gly Gly Val  Glu Asp Glu
            1085                1090                1095
```

```
Val Thr Leu Ser Ala Tyr Ile Thr Ile Ala Leu Leu Glu Ile Pro
1100                1105            1110

Leu Thr Val Thr His Pro Val Arg Asn Ala Leu Phe Cys Leu
1115                1120            1125

Glu Ser Ala Trp Lys Thr Ala Gln Glu Gly Asp His Gly Ser His
1130                1135            1140

Val Tyr Thr Lys Ala Leu Leu Ala Tyr Ala Phe Ala Leu Ala Gly
1145                1150            1155

Asn Gln Asp Lys Arg Lys Glu Val Leu Lys Ser Leu Asn Glu Glu
1160                1165            1170

Ala Val Lys Lys Asp Asn Ser Val His Trp Glu Arg Pro Gln Lys
1175                1180            1185

Pro Lys Ala Pro Val Gly His Phe Tyr Glu Pro Gln Ala Pro Ser
1190                1195            1200

Ala Glu Val Glu Met Thr Ser Tyr Val Leu Leu Ala Tyr Leu Thr
1205                1210            1215

Ala Gln Pro Ala Pro Thr Ser Glu Asp Leu Thr Ser Ala Thr Asn
1220                1225            1230

Ile Val Lys Trp Ile Thr Lys Gln Gln Asn Ala Gln Gly Gly Phe
1235                1240            1245

Ser Ser Thr Gln Asp Thr Val Val Ala Leu His Ala Leu Ser Lys
1250                1255            1260

Tyr Gly Ala Ala Thr Phe Thr Arg Thr Gly Lys Ala Ala Gln Val
1265                1270            1275

Thr Ile Gln Ser Ser Gly Thr Phe Ser Ser Lys Phe Gln Val Asp
1280                1285            1290

Asn Asn Asn Arg Leu Leu Leu Gln Gln Val Ser Leu Pro Glu Leu
1295                1300            1305

Pro Gly Glu Tyr Ser Met Lys Val Thr Gly Glu Gly Cys Val Tyr
1310                1315            1320

Leu Gln Thr Ser Leu Lys Tyr Asn Ile Leu Pro Glu Lys Glu Glu
1325                1330            1335

Phe Pro Phe Ala Leu Gly Val Gln Thr Leu Pro Gln Thr Cys Asp
1340                1345            1350

Glu Pro Lys Ala His Thr Ser Phe Gln Ile Ser Leu Ser Val Ser
1355                1360            1365

Tyr Thr Gly Ser Arg Ser Ala Ser Asn Met Ala Ile Val Asp Val
1370                1375            1380

Lys Met Val Ser Gly Phe Ile Pro Leu Lys Pro Thr Val Lys Met
1385                1390            1395

Leu Glu Arg Ser Asn His Val Ser Arg Thr Glu Val Ser Ser Asn
1400                1405            1410

His Val Leu Ile Tyr Leu Asp Lys Val Ser Asn Gln Thr Leu Ser
1415                1420            1425

Leu Phe Phe Thr Val Leu Gln Asp Val Pro Val Arg Asp Leu Lys
1430                1435            1440

Pro Ala Ile Val Lys Val Tyr Asp Tyr Tyr Glu Thr Asp Glu Phe
1445                1450            1455

Ala Ile Ala Glu Tyr Asn Ala Pro Cys Ser Lys Asp Leu Gly Asn
1460                1465            1470

Ala
```

<210> SEQ ID NO 272
<211> LENGTH: 491
<212> TYPE: PRT
<213> ORGANISM: Homo sapiens

<400> SEQUENCE: 272

```
Met Ala Leu Leu Trp Gly Leu Leu Val Leu Ser Trp Ser Cys Leu Gln
1               5                   10                  15

Gly Pro Cys Ser Val Phe Ser Pro Val Ser Ala Met Glu Pro Leu Gly
            20                  25                  30

Trp Gln Leu Thr Ser Gly Pro Asn Gln Glu Gln Val Ser Pro Leu Thr
        35                  40                  45

Leu Leu Lys Leu Gly Asn Gln Glu Pro Gly Gly Gln Thr Ala Leu Lys
    50                  55                  60

Ser Pro Pro Gly Val Cys Ser Arg Asp Pro Thr Pro Glu Gln Thr His
65                  70                  75                  80

Arg Leu Ala Arg Ala Met Met Ala Phe Thr Ala Asp Leu Phe Ser Leu
                85                  90                  95

Val Ala Gln Thr Ser Thr Cys Pro Asn Leu Ile Leu Ser Pro Leu Ser
            100                 105                 110

Val Ala Leu Ala Leu Ser His Leu Ala Leu Gly Ala Gln Asn His Thr
        115                 120                 125

Leu Gln Arg Leu Gln Gln Val Leu His Ala Gly Ser Gly Pro Cys Leu
    130                 135                 140

Pro His Leu Leu Ser Arg Leu Cys Gln Asp Leu Gly Pro Gly Ala Phe
145                 150                 155                 160

Arg Leu Ala Ala Arg Met Tyr Leu Gln Lys Gly Phe Pro Ile Lys Glu
                165                 170                 175

Asp Phe Leu Glu Gln Ser Glu Gln Leu Phe Gly Ala Lys Pro Val Ser
            180                 185                 190

Leu Thr Gly Lys Gln Glu Asp Asp Leu Ala Asn Ile Asn Gln Trp Val
        195                 200                 205

Lys Glu Ala Thr Glu Gly Lys Ile Gln Glu Phe Leu Ser Gly Leu Pro
    210                 215                 220

Glu Asp Thr Val Leu Leu Leu Asn Ala Ile His Phe Gln Gly Phe
225                 230                 235                 240

Trp Arg Asn Lys Phe Asp Pro Ser Leu Thr Gln Arg Asp Ser Phe His
                245                 250                 255

Leu Asp Glu Gln Phe Thr Val Pro Val Glu Met Met Gln Ala Arg Thr
            260                 265                 270

Tyr Pro Leu Arg Trp Phe Leu Leu Glu Gln Pro Glu Ile Gln Val Ala
        275                 280                 285

His Phe Pro Phe Lys Asn Asn Met Ser Phe Val Val Leu Val Pro Thr
    290                 295                 300

His Phe Glu Trp Asn Val Ser Gln Val Leu Ala Asn Leu Ser Trp Asp
305                 310                 315                 320

Thr Leu His Pro Pro Leu Val Trp Glu Arg Pro Thr Lys Val Arg Leu
                325                 330                 335

Pro Lys Leu Tyr Leu Lys His Gln Met Asp Leu Val Ala Thr Leu Ser
            340                 345                 350

Gln Leu Gly Leu Gln Glu Leu Phe Gln Ala Pro Asp Leu Arg Gly Ile
        355                 360                 365

Ser Glu Gln Ser Leu Val Val Ser Gly Val Gln His Gln Ser Thr Leu
    370                 375                 380
```

-continued

```
Glu Leu Ser Glu Val Gly Val Glu Ala Ala Ala Thr Ser Ile Ala
385                 390                 395                 400

Met Ser Arg Met Ser Leu Ser Ser Phe Ser Val Asn Arg Pro Phe Leu
                405                 410                 415

Phe Phe Ile Phe Glu Asp Thr Thr Gly Leu Pro Leu Phe Val Gly Ser
            420                 425                 430

Val Arg Asn Pro Asn Pro Ser Ala Pro Arg Glu Leu Lys Glu Gln Gln
        435                 440                 445

Asp Ser Pro Gly Asn Lys Asp Phe Leu Gln Ser Leu Lys Gly Phe Pro
    450                 455                 460

Arg Gly Asp Lys Leu Phe Gly Pro Asp Leu Lys Leu Val Pro Pro Met
465                 470                 475                 480

Glu Glu Asp Tyr Pro Gln Phe Gly Ser Pro Lys
                485                 490

<210> SEQ ID NO 273
<211> LENGTH: 485
<212> TYPE: PRT
<213> ORGANISM: Homo sapiens

<400> SEQUENCE: 273

Met Arg Lys Arg Ala Pro Gln Ser Glu Met Ala Pro Ala Gly Val Ser
1               5                   10                  15

Leu Arg Ala Thr Ile Leu Cys Leu Leu Ala Trp Ala Gly Leu Ala Ala
                20                  25                  30

Gly Asp Arg Val Tyr Ile His Pro Phe His Leu Val Ile His Asn Glu
            35                  40                  45

Ser Thr Cys Glu Gln Leu Ala Lys Ala Asn Ala Gly Lys Pro Lys Asp
    50                  55                  60

Pro Thr Phe Ile Pro Ala Pro Ile Gln Ala Lys Thr Ser Pro Val Asp
65                  70                  75                  80

Glu Lys Ala Leu Gln Asp Gln Leu Val Leu Val Ala Ala Lys Leu Asp
                85                  90                  95

Thr Glu Asp Lys Leu Arg Ala Ala Met Val Gly Met Leu Ala Asn Phe
                100                 105                 110

Leu Gly Phe Arg Ile Tyr Gly Met His Ser Glu Leu Trp Gly Val Val
            115                 120                 125

His Gly Ala Thr Val Leu Ser Pro Thr Ala Val Phe Gly Thr Leu Ala
    130                 135                 140

Ser Leu Tyr Leu Gly Ala Leu Asp His Thr Ala Asp Arg Leu Gln Ala
145                 150                 155                 160

Ile Leu Gly Val Pro Trp Lys Asp Lys Asn Cys Thr Ser Arg Leu Asp
                165                 170                 175

Ala His Lys Val Leu Ser Ala Leu Gln Ala Val Gln Gly Leu Leu Val
            180                 185                 190

Ala Gln Gly Arg Ala Asp Ser Gln Ala Gln Leu Leu Leu Ser Thr Val
        195                 200                 205

Val Gly Val Phe Thr Ala Pro Gly Leu His Leu Lys Gln Pro Phe Val
    210                 215                 220

Gln Gly Leu Ala Leu Tyr Thr Pro Val Val Leu Pro Arg Ser Leu Asp
225                 230                 235                 240

Phe Thr Glu Leu Asp Val Ala Ala Glu Lys Ile Asp Arg Phe Met Gln
                245                 250                 255

Ala Val Thr Gly Trp Lys Thr Gly Cys Ser Leu Met Gly Ala Ser Val
            260                 265                 270
```

```
Asp Ser Thr Leu Ala Phe Asn Thr Tyr Val His Phe Gln Gly Lys Met
        275                 280                 285

Lys Gly Phe Ser Leu Leu Ala Glu Pro Gln Glu Phe Trp Val Asp Asn
    290                 295                 300

Ser Thr Ser Val Ser Val Pro Met Leu Ser Gly Met Gly Thr Phe Gln
305                 310                 315                 320

His Trp Ser Asp Ile Gln Asp Asn Phe Ser Val Thr Gln Val Pro Phe
                325                 330                 335

Thr Glu Ser Ala Cys Leu Leu Ile Gln Pro His Tyr Ala Ser Asp
                340                 345                 350

Leu Asp Lys Val Glu Gly Leu Thr Phe Gln Gln Asn Ser Leu Asn Trp
            355                 360                 365

Met Lys Lys Leu Ser Pro Arg Thr Ile His Leu Thr Met Pro Gln Leu
        370                 375                 380

Val Leu Gln Gly Ser Tyr Asp Leu Gln Asp Leu Leu Ala Gln Ala Glu
385                 390                 395                 400

Leu Pro Ala Ile Leu His Thr Glu Leu Asn Leu Gln Lys Leu Ser Asn
                405                 410                 415

Asp Arg Ile Arg Val Gly Glu Val Leu Asn Ser Ile Phe Phe Glu Leu
            420                 425                 430

Glu Ala Asp Glu Arg Glu Pro Thr Glu Ser Thr Gln Leu Asn Lys
        435                 440                 445

Pro Glu Val Leu Glu Val Thr Leu Asn Arg Pro Phe Leu Phe Ala Val
    450                 455                 460

Tyr Asp Gln Ser Ala Thr Ala Leu His Phe Leu Gly Arg Val Ala Asn
465                 470                 475                 480

Pro Leu Ser Thr Ala
                485

<210> SEQ ID NO 274
<211> LENGTH: 267
<212> TYPE: PRT
<213> ORGANISM: Homo sapiens

<400> SEQUENCE: 274

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
```

-continued

```
                145                 150                 155                 160
Leu Gln Glu Lys Leu Ser Pro Leu Gly Glu Glu Met Arg Asp Arg Ala
                    165                 170                 175
Arg Ala His Val Asp Ala Leu Arg Thr His Leu Ala Pro Tyr Ser Asp
                180                 185                 190
Glu Leu Arg Gln Arg Leu Ala Ala Arg Leu Glu Ala Leu Lys Glu Asn
            195                 200                 205
Gly Gly Ala Arg Leu Ala Glu Tyr His Ala Lys Ala Thr Glu His Leu
        210                 215                 220
Ser Thr Leu Ser Glu Lys Ala Lys Pro Ala Leu Glu Asp Leu Arg Gln
225                 230                 235                 240
Gly Leu Leu Pro Val Leu Glu Ser Phe Lys Val Ser Phe Leu Ser Ala
                    245                 250                 255
Leu Glu Glu Tyr Thr Lys Lys Leu Asn Thr Gln
                260                 265

<210> SEQ ID NO 275
<211> LENGTH: 100
<212> TYPE: PRT
<213> ORGANISM: Homo sapiens

<400> SEQUENCE: 275

Met Lys Leu Leu Ala Ala Thr Val Leu Leu Thr Ile Cys Ser Leu
1               5                   10                  15
Glu Gly Ala Leu Val Arg Arg Gln Ala Lys Glu Pro Cys Val Glu Ser
                    20                  25                  30
Leu Val Ser Gln Tyr Phe Gln Thr Val Thr Asp Tyr Gly Lys Asp Leu
                35                  40                  45
Met Glu Lys Val Lys Ser Pro Glu Leu Gln Ala Glu Ala Lys Ser Tyr
            50                  55                  60
Phe Glu Lys Ser Lys Glu Gln Leu Thr Pro Leu Ile Lys Lys Ala Gly
65                  70                  75                  80
Thr Glu Leu Val Asn Phe Leu Ser Tyr Phe Val Glu Leu Gly Thr Gln
                    85                  90                  95
Pro Ala Thr Gln
            100

<210> SEQ ID NO 276
<211> LENGTH: 396
<212> TYPE: PRT
<213> ORGANISM: Homo sapiens

<400> SEQUENCE: 276

Met Phe Leu Lys Ala Val Val Leu Thr Leu Ala Leu Val Ala Val Ala
1               5                   10                  15
Gly Ala Arg Ala Glu Val Ser Ala Asp Gln Val Ala Thr Val Met Trp
                    20                  25                  30
Asp Tyr Phe Ser Gln Leu Ser Asn Asn Ala Lys Glu Ala Val Glu His
                35                  40                  45
Leu Gln Lys Ser Glu Leu Thr Gln Gln Leu Asn Ala Leu Phe Gln Asp
            50                  55                  60
Lys Leu Gly Glu Val Asn Thr Tyr Ala Gly Asp Leu Gln Lys Lys Leu
65                  70                  75                  80
Val Pro Phe Ala Thr Glu Leu His Glu Arg Leu Ala Lys Asp Ser Glu
                    85                  90                  95
Lys Leu Lys Glu Glu Ile Gly Lys Glu Leu Glu Glu Leu Arg Ala Arg
```

```
            100                 105                 110
Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Arg Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Thr Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 277
<211> LENGTH: 4563
<212> TYPE: PRT
<213> ORGANISM: Homo sapiens

<400> SEQUENCE: 277

Met Asp Pro Pro Arg Pro Ala Leu Leu Ala Leu Leu Ala Leu Pro Ala
1               5                   10                  15

Leu Leu Leu Leu Leu Leu Ala Gly Ala Arg Ala Glu Glu Glu Met Leu
            20                  25                  30

Glu Asn Val Ser Leu Val Cys Pro Lys Asp Ala Thr Arg Phe Lys His
        35                  40                  45

Leu Arg Lys Tyr Thr Tyr Asn Tyr Glu Ala Glu Ser Ser Ser Gly Val
    50                  55                  60

Pro Gly Thr Ala Asp Ser Arg Ser Ala Thr Arg Ile Asn Cys Lys Val
65                  70                  75                  80
```

-continued

```
Glu Leu Glu Val Pro Gln Leu Cys Ser Phe Ile Leu Lys Thr Ser Gln
             85                  90                  95

Cys Thr Leu Lys Glu Val Tyr Gly Phe Asn Pro Glu Gly Lys Ala Leu
        100                 105                 110

Leu Lys Lys Thr Lys Asn Ser Glu Glu Phe Ala Ala Ala Met Ser Arg
        115                 120                 125

Tyr Glu Leu Lys Leu Ala Ile Pro Glu Gly Lys Gln Val Phe Leu Tyr
        130                 135                 140

Pro Glu Lys Asp Glu Pro Thr Tyr Ile Leu Asn Ile Lys Arg Gly Ile
145                 150                 155                 160

Ile Ser Ala Leu Leu Val Pro Pro Glu Thr Glu Glu Ala Lys Gln Val
                165                 170                 175

Leu Phe Leu Asp Thr Val Tyr Gly Asn Cys Ser Thr His Phe Thr Val
                180                 185                 190

Lys Thr Arg Lys Gly Asn Val Ala Thr Glu Ile Ser Thr Glu Arg Asp
        195                 200                 205

Leu Gly Gln Cys Asp Arg Phe Lys Pro Ile Arg Thr Gly Ile Ser Pro
        210                 215                 220

Leu Ala Leu Ile Lys Gly Met Thr Arg Pro Leu Ser Thr Leu Ile Ser
225                 230                 235                 240

Ser Ser Gln Ser Cys Gln Tyr Thr Leu Asp Ala Lys Arg Lys His Val
                245                 250                 255

Ala Glu Ala Ile Cys Lys Glu Gln His Leu Phe Leu Pro Phe Ser Tyr
                260                 265                 270

Asn Asn Lys Tyr Gly Met Val Ala Gln Val Thr Gln Thr Leu Lys Leu
        275                 280                 285

Glu Asp Thr Pro Lys Ile Asn Ser Arg Phe Phe Gly Glu Gly Thr Lys
        290                 295                 300

Lys Met Gly Leu Ala Phe Glu Ser Thr Lys Ser Thr Ser Pro Pro Lys
305                 310                 315                 320

Gln Ala Glu Ala Val Leu Lys Thr Leu Gln Glu Leu Lys Lys Leu Thr
                325                 330                 335

Ile Ser Glu Gln Asn Ile Gln Arg Ala Asn Leu Phe Asn Lys Leu Val
                340                 345                 350

Thr Glu Leu Arg Gly Leu Ser Asp Glu Ala Val Thr Ser Leu Leu Pro
        355                 360                 365

Gln Leu Ile Glu Val Ser Ser Pro Ile Thr Leu Gln Ala Leu Val Gln
        370                 375                 380

Cys Gly Gln Pro Gln Cys Ser Thr His Ile Leu Gln Trp Leu Lys Arg
385                 390                 395                 400

Val His Ala Asn Pro Leu Leu Ile Asp Val Val Thr Tyr Leu Val Ala
                405                 410                 415

Leu Ile Pro Glu Pro Ser Ala Gln Gln Leu Arg Glu Ile Phe Asn Met
                420                 425                 430

Ala Arg Asp Gln Arg Ser Arg Ala Thr Leu Tyr Ala Leu Ser His Ala
        435                 440                 445

Val Asn Asn Tyr His Lys Thr Asn Pro Thr Gly Thr Gln Glu Leu Leu
        450                 455                 460

Asp Ile Ala Asn Tyr Leu Met Glu Gln Ile Gln Asp Asp Cys Thr Gly
465                 470                 475                 480

Asp Glu Asp Tyr Thr Tyr Leu Ile Leu Arg Val Ile Gly Asn Met Gly
                485                 490                 495

Gln Thr Met Glu Gln Leu Thr Pro Glu Leu Lys Ser Ser Ile Leu Lys
```

```
            500                 505                 510
Cys Val Gln Ser Thr Lys Pro Ser Leu Met Ile Gln Lys Ala Ala Ile
            515                 520                 525
Gln Ala Leu Arg Lys Met Glu Pro Lys Asp Lys Asp Gln Glu Val Leu
            530                 535                 540
Leu Gln Thr Phe Leu Asp Asp Ala Ser Pro Gly Asp Lys Arg Leu Ala
545                 550                 555                 560
Ala Tyr Leu Met Leu Met Arg Ser Pro Ser Gln Ala Asp Ile Asn Lys
            565                 570                 575
Ile Val Gln Ile Leu Pro Trp Glu Gln Asn Glu Gln Val Lys Asn Phe
            580                 585                 590
Val Ala Ser His Ile Ala Asn Ile Leu Asn Ser Glu Glu Leu Asp Ile
            595                 600                 605
Gln Asp Leu Lys Lys Leu Val Lys Glu Ala Leu Lys Glu Ser Gln Leu
            610                 615                 620
Pro Thr Val Met Asp Phe Arg Lys Phe Ser Arg Asn Tyr Gln Leu Tyr
625                 630                 635                 640
Lys Ser Val Ser Leu Pro Ser Leu Asp Pro Ala Ser Ala Lys Ile Glu
            645                 650                 655
Gly Asn Leu Ile Phe Asp Pro Asn Asn Tyr Leu Pro Lys Glu Ser Met
            660                 665                 670
Leu Lys Thr Thr Leu Thr Ala Phe Gly Phe Ala Ser Ala Asp Leu Ile
            675                 680                 685
Glu Ile Gly Leu Glu Gly Lys Gly Phe Glu Pro Thr Leu Glu Ala Leu
            690                 695                 700
Phe Gly Lys Gln Gly Phe Phe Pro Asp Ser Val Asn Lys Ala Leu Tyr
705                 710                 715                 720
Trp Val Asn Gly Gln Val Pro Asp Gly Val Ser Lys Val Leu Val Asp
            725                 730                 735
His Phe Gly Tyr Thr Lys Asp Asp Lys His Glu Gln Asp Met Val Asn
            740                 745                 750
Gly Ile Met Leu Ser Val Glu Lys Leu Ile Lys Asp Leu Lys Ser Lys
            755                 760                 765
Glu Val Pro Glu Ala Arg Ala Tyr Leu Arg Ile Leu Gly Glu Glu Leu
            770                 775                 780
Gly Phe Ala Ser Leu His Asp Leu Gln Leu Leu Gly Lys Leu Leu Leu
785                 790                 795                 800
Met Gly Ala Arg Thr Leu Gln Gly Ile Pro Gln Met Ile Gly Glu Val
            805                 810                 815
Ile Arg Lys Gly Ser Lys Asn Asp Phe Phe Leu His Tyr Ile Phe Met
            820                 825                 830
Glu Asn Ala Phe Glu Leu Pro Thr Gly Ala Gly Leu Gln Leu Gln Ile
            835                 840                 845
Ser Ser Ser Gly Val Ile Ala Pro Gly Ala Lys Ala Gly Val Lys Leu
            850                 855                 860
Glu Val Ala Asn Met Gln Ala Glu Leu Val Ala Lys Pro Ser Val Ser
865                 870                 875                 880
Val Glu Phe Val Thr Asn Met Gly Ile Ile Pro Asp Phe Ala Arg
            885                 890                 895
Ser Gly Val Gln Met Asn Thr Asn Phe Phe His Glu Ser Gly Leu Glu
            900                 905                 910
Ala His Val Ala Leu Lys Ala Gly Lys Leu Lys Phe Ile Ile Pro Ser
            915                 920                 925
```

-continued

```
Pro Lys Arg Pro Val Lys Leu Leu Ser Gly Gly Asn Thr Leu His Leu
    930                 935                 940

Val Ser Thr Thr Lys Thr Glu Val Ile Pro Leu Ile Glu Asn Arg
945                 950                 955                 960

Gln Ser Trp Ser Val Cys Lys Gln Val Phe Pro Gly Leu Asn Tyr Cys
                965                 970                 975

Thr Ser Gly Ala Tyr Ser Asn Ala Ser Ser Thr Asp Ser Ala Ser Tyr
            980                 985                 990

Tyr Pro Leu Thr Gly Asp Thr Arg Leu Glu Leu Glu Leu Arg Pro Thr
        995                 1000                1005

Gly Glu Ile Glu Gln Tyr Ser Val Ser Ala Thr Tyr Glu Leu Gln
    1010                1015                1020

Arg Glu Asp Arg Ala Leu Val Asp Thr Leu Lys Phe Val Thr Gln
    1025                1030                1035

Ala Glu Gly Ala Lys Gln Thr Glu Ala Thr Met Thr Phe Lys Tyr
    1040                1045                1050

Asn Arg Gln Ser Met Thr Leu Ser Ser Glu Val Gln Ile Pro Asp
    1055                1060                1065

Phe Asp Val Asp Leu Gly Thr Ile Leu Arg Val Asn Asp Glu Ser
    1070                1075                1080

Thr Glu Gly Lys Thr Ser Tyr Arg Leu Thr Leu Asp Ile Gln Asn
    1085                1090                1095

Lys Lys Ile Thr Glu Val Ala Leu Met Gly His Leu Ser Cys Asp
    1100                1105                1110

Thr Lys Glu Glu Arg Lys Ile Lys Gly Val Ile Ser Ile Pro Arg
    1115                1120                1125

Leu Gln Ala Glu Ala Arg Ser Glu Ile Leu Ala His Trp Ser Pro
    1130                1135                1140

Ala Lys Leu Leu Leu Gln Met Asp Ser Ser Ala Thr Ala Tyr Gly
    1145                1150                1155

Ser Thr Val Ser Lys Arg Val Ala Trp His Tyr Asp Glu Glu Lys
    1160                1165                1170

Ile Glu Phe Glu Trp Asn Thr Gly Thr Asn Val Asp Thr Lys Lys
    1175                1180                1185

Met Thr Ser Asn Phe Pro Val Asp Leu Ser Asp Tyr Pro Lys Ser
    1190                1195                1200

Leu His Met Tyr Ala Asn Arg Leu Leu Asp His Arg Val Pro Glu
    1205                1210                1215

Thr Asp Met Thr Phe Arg His Val Gly Ser Lys Leu Ile Val Ala
    1220                1225                1230

Met Ser Ser Trp Leu Gln Lys Ala Ser Gly Ser Leu Pro Tyr Thr
    1235                1240                1245

Gln Thr Leu Gln Asp His Leu Asn Ser Leu Lys Glu Phe Asn Leu
    1250                1255                1260

Gln Asn Met Gly Leu Pro Asp Phe His Ile Pro Glu Asn Leu Phe
    1265                1270                1275

Leu Lys Ser Asp Gly Arg Val Lys Tyr Thr Leu Asn Lys Asn Ser
    1280                1285                1290

Leu Lys Ile Glu Ile Pro Leu Pro Phe Gly Gly Lys Ser Ser Arg
    1295                1300                1305

Asp Leu Lys Met Leu Glu Thr Val Arg Thr Pro Ala Leu His Phe
    1310                1315                1320
```

```
Lys Ser Val Gly Phe His Leu Pro Ser Arg Glu Phe Gln Val Pro
    1325                1330                1335

Thr Phe Thr Ile Pro Lys Leu Tyr Gln Leu Gln Val Pro Leu Leu
    1340                1345                1350

Gly Val Leu Asp Leu Ser Thr Asn Val Tyr Ser Asn Leu Tyr Asn
    1355                1360                1365

Trp Ser Ala Ser Tyr Ser Gly Gly Asn Thr Ser Thr Asp His Phe
    1370                1375                1380

Ser Leu Arg Ala Arg Tyr His Met Lys Ala Asp Ser Val Val Asp
    1385                1390                1395

Leu Leu Ser Tyr Asn Val Gln Gly Ser Gly Glu Thr Thr Tyr Asp
    1400                1405                1410

His Lys Asn Thr Phe Thr Leu Ser Cys Asp Gly Ser Leu Arg His
    1415                1420                1425

Lys Phe Leu Asp Ser Asn Ile Lys Phe Ser His Val Glu Lys Leu
    1430                1435                1440

Gly Asn Asn Pro Val Ser Lys Gly Leu Leu Ile Phe Asp Ala Ser
    1445                1450                1455

Ser Ser Trp Gly Pro Gln Met Ser Ala Ser Val His Leu Asp Ser
    1460                1465                1470

Lys Lys Lys Gln His Leu Phe Val Lys Glu Val Lys Ile Asp Gly
    1475                1480                1485

Gln Phe Arg Val Ser Ser Phe Tyr Ala Lys Gly Thr Tyr Gly Leu
    1490                1495                1500

Ser Cys Gln Arg Asp Pro Asn Thr Gly Arg Leu Asn Gly Glu Ser
    1505                1510                1515

Asn Leu Arg Phe Asn Ser Ser Tyr Leu Gln Gly Thr Asn Gln Ile
    1520                1525                1530

Thr Gly Arg Tyr Glu Asp Gly Thr Leu Ser Leu Thr Ser Thr Ser
    1535                1540                1545

Asp Leu Gln Ser Gly Ile Ile Lys Asn Thr Ala Ser Leu Lys Tyr
    1550                1555                1560

Glu Asn Tyr Glu Leu Thr Leu Lys Ser Asp Thr Asn Gly Lys Tyr
    1565                1570                1575

Lys Asn Phe Ala Thr Ser Asn Lys Met Asp Met Thr Phe Ser Lys
    1580                1585                1590

Gln Asn Ala Leu Leu Arg Ser Glu Tyr Gln Ala Asp Tyr Glu Ser
    1595                1600                1605

Leu Arg Phe Phe Ser Leu Leu Ser Gly Ser Leu Asn Ser His Gly
    1610                1615                1620

Leu Glu Leu Asn Ala Asp Ile Leu Gly Thr Asp Lys Ile Asn Ser
    1625                1630                1635

Gly Ala His Lys Ala Thr Leu Arg Ile Gly Gln Asp Gly Ile Ser
    1640                1645                1650

Thr Ser Ala Thr Thr Asn Leu Lys Cys Ser Leu Leu Val Leu Glu
    1655                1660                1665

Asn Glu Leu Asn Ala Glu Leu Gly Leu Ser Gly Ala Ser Met Lys
    1670                1675                1680

Leu Thr Thr Asn Gly Arg Phe Arg Glu His Asn Ala Lys Phe Ser
    1685                1690                1695

Leu Asp Gly Lys Ala Ala Leu Thr Glu Leu Ser Leu Gly Ser Ala
    1700                1705                1710

Tyr Gln Ala Met Ile Leu Gly Val Asp Ser Lys Asn Ile Phe Asn
```

```
            1715                1720                1725
Phe Lys Val Ser Gln Glu Gly Leu Lys Leu Ser Asn Asp Met Met
        1730                1735                1740
Gly Ser Tyr Ala Glu Met Lys Phe Asp His Thr Asn Ser Leu Asn
        1745                1750                1755
Ile Ala Gly Leu Ser Leu Asp Phe Ser Ser Lys Leu Asp Asn Ile
        1760                1765                1770
Tyr Ser Ser Asp Lys Phe Tyr Lys Gln Thr Val Asn Leu Gln Leu
        1775                1780                1785
Gln Pro Tyr Ser Leu Val Thr Thr Leu Asn Ser Asp Leu Lys Tyr
        1790                1795                1800
Asn Ala Leu Asp Leu Thr Asn Asn Gly Lys Leu Arg Leu Glu Pro
        1805                1810                1815
Leu Lys Leu His Val Ala Gly Asn Leu Lys Gly Ala Tyr Gln Asn
        1820                1825                1830
Asn Glu Ile Lys His Ile Tyr Ala Ile Ser Ser Ala Ala Leu Ser
        1835                1840                1845
Ala Ser Tyr Lys Ala Asp Thr Val Ala Lys Val Gln Gly Val Glu
        1850                1855                1860
Phe Ser His Arg Leu Asn Thr Asp Ile Ala Gly Leu Ala Ser Ala
        1865                1870                1875
Ile Asp Met Ser Thr Asn Tyr Asn Ser Asp Ser Leu His Phe Ser
        1880                1885                1890
Asn Val Phe Arg Ser Val Met Ala Pro Phe Thr Met Thr Ile Asp
        1895                1900                1905
Ala His Thr Asn Gly Asn Gly Lys Leu Ala Leu Trp Gly Glu His
        1910                1915                1920
Thr Gly Gln Leu Tyr Ser Lys Phe Leu Leu Lys Ala Glu Pro Leu
        1925                1930                1935
Ala Phe Thr Phe Ser His Asp Tyr Lys Gly Ser Thr Ser His His
        1940                1945                1950
Leu Val Ser Arg Lys Ser Ile Ser Ala Ala Leu Glu His Lys Val
        1955                1960                1965
Ser Ala Leu Leu Thr Pro Ala Glu Gln Thr Gly Thr Trp Lys Leu
        1970                1975                1980
Lys Thr Gln Phe Asn Asn Asn Glu Tyr Ser Gln Asp Leu Asp Ala
        1985                1990                1995
Tyr Asn Thr Lys Asp Lys Ile Gly Val Glu Leu Thr Gly Arg Thr
        2000                2005                2010
Leu Ala Asp Leu Thr Leu Leu Asp Ser Pro Ile Lys Val Pro Leu
        2015                2020                2025
Leu Leu Ser Glu Pro Ile Asn Ile Ile Asp Ala Leu Glu Met Arg
        2030                2035                2040
Asp Ala Val Glu Lys Pro Gln Glu Phe Thr Ile Val Ala Phe Val
        2045                2050                2055
Lys Tyr Asp Lys Asn Gln Asp Val His Ser Ile Asn Leu Pro Phe
        2060                2065                2070
Phe Glu Thr Leu Gln Glu Tyr Phe Glu Arg Asn Arg Gln Thr Ile
        2075                2080                2085
Ile Val Val Val Glu Asn Val Gln Arg Asn Leu Lys His Ile Asn
        2090                2095                2100
Ile Asp Gln Phe Val Arg Lys Tyr Arg Ala Ala Leu Gly Lys Leu
        2105                2110                2115
```

```
Pro Gln Gln Ala Asn Asp Tyr Leu Asn Ser Phe Asn Trp Glu Arg
    2120                2125                2130

Gln Val Ser His Ala Lys Glu Lys Leu Thr Ala Leu Thr Lys Lys
    2135                2140                2145

Tyr Arg Ile Thr Glu Asn Asp Ile Gln Ile Ala Leu Asp Asp Ala
    2150                2155                2160

Lys Ile Asn Phe Asn Glu Lys Leu Ser Gln Leu Gln Thr Tyr Met
    2165                2170                2175

Ile Gln Phe Asp Gln Tyr Ile Lys Asp Ser Tyr Asp Leu His Asp
    2180                2185                2190

Leu Lys Ile Ala Ile Ala Asn Ile Ile Asp Glu Ile Ile Glu Lys
    2195                2200                2205

Leu Lys Ser Leu Asp Glu His Tyr His Ile Arg Val Asn Leu Val
    2210                2215                2220

Lys Thr Ile His Asp Leu His Leu Phe Ile Glu Asn Ile Asp Phe
    2225                2230                2235

Asn Lys Ser Gly Ser Ser Thr Ala Ser Trp Ile Gln Asn Val Asp
    2240                2245                2250

Thr Lys Tyr Gln Ile Arg Ile Gln Ile Gln Glu Lys Leu Gln Gln
    2255                2260                2265

Leu Lys Arg His Ile Gln Asn Ile Asp Ile Gln His Leu Ala Gly
    2270                2275                2280

Lys Leu Lys Gln His Ile Glu Ala Ile Asp Val Arg Val Leu Leu
    2285                2290                2295

Asp Gln Leu Gly Thr Thr Ile Ser Phe Glu Arg Ile Asn Asp Val
    2300                2305                2310

Leu Glu His Val Lys His Phe Val Ile Asn Leu Ile Gly Asp Phe
    2315                2320                2325

Glu Val Ala Glu Lys Ile Asn Ala Phe Arg Ala Lys Val His Glu
    2330                2335                2340

Leu Ile Glu Arg Tyr Glu Val Asp Gln Gln Ile Gln Val Leu Met
    2345                2350                2355

Asp Lys Leu Val Glu Leu Thr His Gln Tyr Lys Leu Lys Glu Thr
    2360                2365                2370

Ile Gln Lys Leu Ser Asn Val Leu Gln Gln Val Lys Ile Lys Asp
    2375                2380                2385

Tyr Phe Glu Lys Leu Val Gly Phe Ile Asp Asp Ala Val Lys Lys
    2390                2395                2400

Leu Asn Glu Leu Ser Phe Lys Thr Phe Ile Glu Asp Val Asn Lys
    2405                2410                2415

Phe Leu Asp Met Leu Ile Lys Lys Leu Lys Ser Phe Asp Tyr His
    2420                2425                2430

Gln Phe Val Asp Glu Thr Asn Asp Lys Ile Arg Glu Val Thr Gln
    2435                2440                2445

Arg Leu Asn Gly Glu Ile Gln Ala Leu Glu Leu Pro Gln Lys Ala
    2450                2455                2460

Glu Ala Leu Lys Leu Phe Leu Glu Glu Thr Lys Ala Thr Val Ala
    2465                2470                2475

Val Tyr Leu Glu Ser Leu Gln Asp Thr Lys Ile Thr Leu Ile Ile
    2480                2485                2490

Asn Trp Leu Gln Glu Ala Leu Ser Ser Ala Ser Leu Ala His Met
    2495                2500                2505
```

```
Lys Ala Lys Phe Arg Glu Thr Leu Glu Asp Thr Arg Asp Arg Met
2510                2515                2520

Tyr Gln Met Asp Ile Gln Gln Glu Leu Gln Arg Tyr Leu Ser Leu
    2525                2530                2535

Val Gly Gln Val Tyr Ser Thr Leu Val Thr Tyr Ile Ser Asp Trp
2540                2545                2550

Trp Thr Leu Ala Ala Lys Asn Leu Thr Asp Phe Ala Glu Gln Tyr
2555                2560                2565

Ser Ile Gln Asp Trp Ala Lys Arg Met Lys Ala Leu Val Glu Gln
2570                2575                2580

Gly Phe Thr Val Pro Glu Ile Lys Thr Ile Leu Gly Thr Met Pro
2585                2590                2595

Ala Phe Glu Val Ser Leu Gln Ala Leu Gln Lys Ala Thr Phe Gln
2600                2605                2610

Thr Pro Asp Phe Ile Val Pro Leu Thr Asp Leu Arg Ile Pro Ser
2615                2620                2625

Val Gln Ile Asn Phe Lys Asp Leu Lys Asn Ile Lys Ile Pro Ser
2630                2635                2640

Arg Phe Ser Thr Pro Glu Phe Thr Ile Leu Asn Thr Phe His Ile
2645                2650                2655

Pro Ser Phe Thr Ile Asp Phe Val Glu Met Lys Val Lys Ile Ile
2660                2665                2670

Arg Thr Ile Asp Gln Met Gln Asn Ser Glu Leu Gln Trp Pro Val
2675                2680                2685

Pro Asp Ile Tyr Leu Arg Asp Leu Lys Val Glu Asp Ile Pro Leu
2690                2695                2700

Ala Arg Ile Thr Leu Pro Asp Phe Arg Leu Pro Glu Ile Ala Ile
2705                2710                2715

Pro Glu Phe Ile Ile Pro Thr Leu Asn Leu Asn Asp Phe Gln Val
2720                2725                2730

Pro Asp Leu His Ile Pro Glu Phe Gln Leu Pro His Ile Ser His
2735                2740                2745

Thr Ile Glu Val Pro Thr Phe Gly Lys Leu Tyr Ser Ile Leu Lys
2750                2755                2760

Ile Gln Ser Pro Leu Phe Thr Leu Asp Ala Asn Ala Asp Ile Gly
2765                2770                2775

Asn Gly Thr Thr Ser Ala Asn Glu Ala Gly Ile Ala Ala Ser Ile
2780                2785                2790

Thr Ala Lys Gly Glu Ser Lys Leu Glu Val Leu Asn Phe Asp Phe
2795                2800                2805

Gln Ala Asn Ala Gln Leu Ser Asn Pro Lys Ile Asn Pro Leu Ala
2810                2815                2820

Leu Lys Glu Ser Val Lys Phe Ser Ser Lys Tyr Leu Arg Thr Glu
2825                2830                2835

His Gly Ser Glu Met Leu Phe Phe Gly Asn Ala Ile Glu Gly Lys
2840                2845                2850

Ser Asn Thr Val Ala Ser Leu His Thr Glu Lys Asn Thr Leu Glu
2855                2860                2865

Leu Ser Asn Gly Val Ile Val Lys Ile Asn Asn Gln Leu Thr Leu
2870                2875                2880

Asp Ser Asn Thr Lys Tyr Phe His Lys Leu Asn Ile Pro Lys Leu
2885                2890                2895

Asp Phe Ser Ser Gln Ala Asp Leu Arg Asn Glu Ile Lys Thr Leu
```

```
            2900               2905                2910
Leu Lys Ala Gly His Ile Ala Trp Thr Ser Ser Gly Lys Gly Ser
    2915               2920                2925

Trp Lys Trp Ala Cys Pro Arg Phe Ser Asp Glu Gly Thr His Glu
    2930               2935                2940

Ser Gln Ile Ser Phe Thr Ile Glu Gly Pro Leu Thr Ser Phe Gly
    2945               2950                2955

Leu Ser Asn Lys Ile Asn Ser Lys His Leu Arg Val Asn Gln Asn
    2960               2965                2970

Leu Val Tyr Glu Ser Gly Ser Leu Asn Phe Ser Lys Leu Glu Ile
    2975               2980                2985

Gln Ser Gln Val Asp Ser Gln His Val Gly His Ser Val Leu Thr
    2990               2995                3000

Ala Lys Gly Met Ala Leu Phe Gly Glu Gly Lys Ala Glu Phe Thr
    3005               3010                3015

Gly Arg His Asp Ala His Leu Asn Gly Lys Val Ile Gly Thr Leu
    3020               3025                3030

Lys Asn Ser Leu Phe Phe Ser Ala Gln Pro Phe Glu Ile Thr Ala
    3035               3040                3045

Ser Thr Asn Asn Glu Gly Asn Leu Lys Val Arg Phe Pro Leu Arg
    3050               3055                3060

Leu Thr Gly Lys Ile Asp Phe Leu Asn Asn Tyr Ala Leu Phe Leu
    3065               3070                3075

Ser Pro Ser Ala Gln Gln Ala Ser Trp Gln Val Ser Ala Arg Phe
    3080               3085                3090

Asn Gln Tyr Lys Tyr Asn Gln Asn Phe Ser Ala Gly Asn Asn Glu
    3095               3100                3105

Asn Ile Met Glu Ala His Val Gly Ile Asn Gly Glu Ala Asn Leu
    3110               3115                3120

Asp Phe Leu Asn Ile Pro Leu Thr Ile Pro Glu Met Arg Leu Pro
    3125               3130                3135

Tyr Thr Ile Ile Thr Thr Pro Pro Leu Lys Asp Phe Ser Leu Trp
    3140               3145                3150

Glu Lys Thr Gly Leu Lys Glu Phe Leu Lys Thr Thr Lys Gln Ser
    3155               3160                3165

Phe Asp Leu Ser Val Lys Ala Gln Tyr Lys Lys Asn Lys His Arg
    3170               3175                3180

His Ser Ile Thr Asn Pro Leu Ala Val Leu Cys Glu Phe Ile Ser
    3185               3190                3195

Gln Ser Ile Lys Ser Phe Asp Arg His Phe Glu Lys Asn Arg Asn
    3200               3205                3210

Asn Ala Leu Asp Phe Val Thr Lys Ser Tyr Asn Glu Thr Lys Ile
    3215               3220                3225

Lys Phe Asp Lys Tyr Lys Ala Glu Lys Ser His Asp Glu Leu Pro
    3230               3235                3240

Arg Thr Phe Gln Ile Pro Gly Tyr Thr Val Pro Val Val Asn Val
    3245               3250                3255

Glu Val Ser Pro Phe Thr Ile Glu Met Ser Ala Phe Gly Tyr Val
    3260               3265                3270

Phe Pro Lys Ala Val Ser Met Pro Ser Phe Ser Ile Leu Gly Ser
    3275               3280                3285

Asp Val Arg Val Pro Ser Tyr Thr Leu Ile Leu Pro Ser Leu Glu
    3290               3295                3300
```

```
Leu Pro Val Leu His Val Pro Arg Asn Leu Lys Leu Ser Leu Pro
3305                3310                3315

His Phe Lys Glu Leu Cys Thr Ile Ser His Ile Phe Ile Pro Ala
3320                3325                3330

Met Gly Asn Ile Thr Tyr Asp Phe Ser Phe Lys Ser Ser Val Ile
3335                3340                3345

Thr Leu Asn Thr Asn Ala Glu Leu Phe Asn Gln Ser Asp Ile Val
3350                3355                3360

Ala His Leu Leu Ser Ser Ser Ser Val Ile Asp Ala Leu Gln
3365                3370                3375

Tyr Lys Leu Glu Gly Thr Thr Arg Leu Thr Arg Lys Arg Gly Leu
3380                3385                3390

Lys Leu Ala Thr Ala Leu Ser Leu Ser Asn Lys Phe Val Glu Gly
3395                3400                3405

Ser His Asn Ser Thr Val Ser Leu Thr Thr Lys Asn Met Glu Val
3410                3415                3420

Ser Val Ala Lys Thr Thr Lys Ala Glu Ile Pro Ile Leu Arg Met
3425                3430                3435

Asn Phe Lys Gln Glu Leu Asn Gly Asn Thr Lys Ser Lys Pro Thr
3440                3445                3450

Val Ser Ser Ser Met Glu Phe Lys Tyr Asp Phe Asn Ser Ser Met
3455                3460                3465

Leu Tyr Ser Thr Ala Lys Gly Ala Val Asp His Lys Leu Ser Leu
3470                3475                3480

Glu Ser Leu Thr Ser Tyr Phe Ser Ile Glu Ser Ser Thr Lys Gly
3485                3490                3495

Asp Val Lys Gly Ser Val Leu Ser Arg Glu Tyr Ser Gly Thr Ile
3500                3505                3510

Ala Ser Glu Ala Asn Thr Tyr Leu Asn Ser Lys Ser Thr Arg Ser
3515                3520                3525

Ser Val Lys Leu Gln Gly Thr Ser Lys Ile Asp Asp Ile Trp Asn
3530                3535                3540

Leu Glu Val Lys Glu Asn Phe Ala Gly Glu Ala Thr Leu Gln Arg
3545                3550                3555

Ile Tyr Ser Leu Trp Glu His Ser Thr Lys Asn His Leu Gln Leu
3560                3565                3570

Glu Gly Leu Phe Phe Thr Asn Gly Glu His Thr Ser Lys Ala Thr
3575                3580                3585

Leu Glu Leu Ser Pro Trp Gln Met Ser Ala Leu Val Gln Val His
3590                3595                3600

Ala Ser Gln Pro Ser Ser Phe His Asp Phe Pro Asp Leu Gly Gln
3605                3610                3615

Glu Val Ala Leu Asn Ala Asn Thr Lys Asn Gln Lys Ile Arg Trp
3620                3625                3630

Lys Asn Glu Val Arg Ile His Ser Gly Ser Phe Gln Ser Gln Val
3635                3640                3645

Glu Leu Ser Asn Asp Gln Glu Lys Ala His Leu Asp Ile Ala Gly
3650                3655                3660

Ser Leu Glu Gly His Leu Arg Phe Leu Lys Asn Ile Ile Leu Pro
3665                3670                3675

Val Tyr Asp Lys Ser Leu Trp Asp Phe Leu Lys Leu Asp Val Thr
3680                3685                3690
```

```
Thr Ser Ile Gly Arg Arg Gln His Leu Arg Val Ser Thr Ala Phe
    3695                3700                3705

Val Tyr Thr Lys Asn Pro Asn Gly Tyr Ser Phe Ser Ile Pro Val
3710                3715                3720

Lys Val Leu Ala Asp Lys Phe Ile Thr Pro Gly Leu Lys Leu Asn
3725                3730                3735

Asp Leu Asn Ser Val Leu Val Met Pro Thr Phe His Val Pro Phe
3740                3745                3750

Thr Asp Leu Gln Val Pro Ser Cys Lys Leu Asp Phe Arg Glu Ile
3755                3760                3765

Gln Ile Tyr Lys Lys Leu Arg Thr Ser Ser Phe Ala Leu Asn Leu
3770                3775                3780

Pro Thr Leu Pro Glu Val Lys Phe Pro Glu Val Asp Val Leu Thr
3785                3790                3795

Lys Tyr Ser Gln Pro Glu Asp Ser Leu Ile Pro Phe Phe Glu Ile
3800                3805                3810

Thr Val Pro Glu Ser Gln Leu Thr Val Ser Gln Phe Thr Leu Pro
3815                3820                3825

Lys Ser Val Ser Asp Gly Ile Ala Ala Leu Asp Leu Asn Ala Val
3830                3835                3840

Ala Asn Lys Ile Ala Asp Phe Glu Leu Pro Thr Ile Ile Val Pro
3845                3850                3855

Glu Gln Thr Ile Glu Ile Pro Ser Ile Lys Phe Ser Val Pro Ala
3860                3865                3870

Gly Ile Val Ile Pro Ser Phe Gln Ala Leu Thr Ala Arg Phe Glu
3875                3880                3885

Val Asp Ser Pro Val Tyr Asn Ala Thr Trp Ser Ala Ser Leu Lys
3890                3895                3900

Asn Lys Ala Asp Tyr Val Glu Thr Val Leu Asp Ser Thr Cys Ser
3905                3910                3915

Ser Thr Val Gln Phe Leu Glu Tyr Glu Leu Asn Val Leu Gly Thr
3920                3925                3930

His Lys Ile Glu Asp Gly Thr Leu Ala Ser Lys Thr Lys Gly Thr
3935                3940                3945

Leu Ala His Arg Asp Phe Ser Ala Glu Tyr Glu Glu Asp Gly Lys
3950                3955                3960

Phe Glu Gly Leu Gln Glu Trp Glu Gly Lys Ala His Leu Asn Ile
3965                3970                3975

Lys Ser Pro Ala Phe Thr Asp Leu His Leu Arg Tyr Gln Lys Asp
3980                3985                3990

Lys Lys Gly Ile Ser Thr Ser Ala Ala Ser Pro Ala Val Gly Thr
3995                4000                4005

Val Gly Met Asp Met Asp Glu Asp Asp Asp Phe Ser Lys Trp Asn
4010                4015                4020

Phe Tyr Tyr Ser Pro Gln Ser Ser Pro Asp Lys Lys Leu Thr Ile
4025                4030                4035

Phe Lys Thr Glu Leu Arg Val Arg Glu Ser Asp Glu Glu Thr Gln
4040                4045                4050

Ile Lys Val Asn Trp Glu Glu Glu Ala Ala Ser Gly Leu Leu Thr
4055                4060                4065

Ser Leu Lys Asp Asn Val Pro Lys Ala Thr Gly Val Leu Tyr Asp
4070                4075                4080

Tyr Val Asn Lys Tyr His Trp Glu His Thr Gly Leu Thr Leu Arg
```

-continued

```
              4085                4090                4095
Glu Val Ser Ser Lys Leu Arg Arg Asn Leu Gln Asn Asn Ala Glu
         4100                4105                4110
Trp Val Tyr Gln Gly Ala Ile Arg Gln Ile Asp Asp Ile Asp Val
         4115                4120                4125
Arg Phe Gln Lys Ala Ala Ser Gly Thr Thr Gly Thr Tyr Gln Glu
         4130                4135                4140
Trp Lys Asp Lys Ala Gln Asn Leu Tyr Gln Glu Leu Leu Thr Gln
         4145                4150                4155
Glu Gly Gln Ala Ser Phe Gln Gly Leu Lys Asp Asn Val Phe Asp
         4160                4165                4170
Gly Leu Val Arg Val Thr Gln Lys Phe His Met Lys Val Lys His
         4175                4180                4185
Leu Ile Asp Ser Leu Ile Asp Phe Leu Asn Phe Pro Arg Phe Gln
         4190                4195                4200
Phe Pro Gly Lys Pro Gly Ile Tyr Thr Arg Glu Glu Leu Cys Thr
         4205                4210                4215
Met Phe Ile Arg Glu Val Gly Thr Val Leu Ser Gln Val Tyr Ser
         4220                4225                4230
Lys Val His Asn Gly Ser Glu Ile Leu Phe Ser Tyr Phe Gln Asp
         4235                4240                4245
Leu Val Ile Thr Leu Pro Phe Glu Leu Arg Lys His Lys Leu Ile
         4250                4255                4260
Asp Val Ile Ser Met Tyr Arg Glu Leu Leu Lys Asp Leu Ser Lys
         4265                4270                4275
Glu Ala Gln Glu Val Phe Lys Ala Ile Gln Ser Leu Lys Thr Thr
         4280                4285                4290
Glu Val Leu Arg Asn Leu Gln Asp Leu Leu Gln Phe Ile Phe Gln
         4295                4300                4305
Leu Ile Glu Asp Asn Ile Lys Gln Leu Lys Glu Met Lys Phe Thr
         4310                4315                4320
Tyr Leu Ile Asn Tyr Ile Gln Asp Glu Ile Asn Thr Ile Phe Asn
         4325                4330                4335
Asp Tyr Ile Pro Tyr Val Phe Lys Leu Leu Lys Glu Asn Leu Cys
         4340                4345                4350
Leu Asn Leu His Lys Phe Asn Glu Phe Ile Gln Asn Glu Leu Gln
         4355                4360                4365
Glu Ala Ser Gln Glu Leu Gln Gln Ile His Gln Tyr Ile Met Ala
         4370                4375                4380
Leu Arg Glu Glu Tyr Phe Asp Pro Ser Ile Val Gly Trp Thr Val
         4385                4390                4395
Lys Tyr Tyr Glu Leu Glu Glu Lys Ile Val Ser Leu Ile Lys Asn
         4400                4405                4410
Leu Leu Val Ala Leu Lys Asp Phe His Ser Glu Tyr Ile Val Ser
         4415                4420                4425
Ala Ser Asn Phe Thr Ser Gln Leu Ser Ser Gln Val Glu Gln Phe
         4430                4435                4440
Leu His Arg Asn Ile Gln Glu Tyr Leu Ser Ile Leu Thr Asp Pro
         4445                4450                4455
Asp Gly Lys Gly Lys Glu Lys Ile Ala Glu Leu Ser Ala Thr Ala
         4460                4465                4470
Gln Glu Ile Ile Lys Ser Gln Ala Ile Ala Thr Lys Lys Ile Ile
         4475                4480                4485
```

```
Ser Asp Tyr His Gln Gln Phe Arg Tyr Lys Leu Gln Asp Phe Ser
    4490                4495                4500

Asp Gln Leu Ser Asp Tyr Tyr Glu Lys Phe Ile Ala Glu Ser Lys
    4505                4510                4515

Arg Leu Ile Asp Leu Ser Ile Gln Asn Tyr His Thr Phe Leu Ile
    4520                4525                4530

Tyr Ile Thr Glu Leu Leu Lys Lys Leu Gln Ser Thr Thr Val Met
    4535                4540                4545

Asn Pro Tyr Met Lys Leu Ala Pro Gly Glu Leu Thr Ile Ile Leu
    4550                4555                4560

<210> SEQ ID NO 278
<211> LENGTH: 83
<212> TYPE: PRT
<213> ORGANISM: Homo sapiens

<400> SEQUENCE: 278

Met Arg Leu Phe Leu Ser Leu Pro Val Leu Val Val Val Leu Ser Ile
1               5                   10                  15

Val Leu Glu Gly Pro Ala Pro Ala Gln Gly Thr Pro Asp Val Ser Ser
                20                  25                  30

Ala Leu Asp Lys Leu Lys Glu Phe Gly Asn Thr Leu Glu Asp Lys Ala
            35                  40                  45

Arg Glu Leu Ile Ser Arg Ile Lys Gln Ser Glu Leu Ser Ala Lys Met
        50                  55                  60

Arg Glu Trp Phe Ser Glu Thr Phe Gln Lys Val Lys Glu Lys Leu Lys
65                  70                  75                  80

Ile Asp Ser

<210> SEQ ID NO 279
<211> LENGTH: 317
<212> TYPE: PRT
<213> ORGANISM: Homo sapiens

<400> SEQUENCE: 279

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
                20                  25                  30

Arg Gln Gln Thr Glu Trp Gln Ser Gly Gln Arg Trp Glu Leu Ala Leu
            35                  40                  45

Gly Arg Phe Trp Asp Tyr Leu Arg Trp Val Gln Thr Leu Ser Glu Gln
        50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
                100                 105                 110

Lys Glu Leu Gln Ala Ala Gln Ala Arg Leu Gly Ala Asp Met Glu Asp
            115                 120                 125

Val Cys Gly Arg Leu Val Gln Tyr Arg Gly Glu Val Gln Ala Met Leu
        130                 135                 140

Gly Gln Ser Thr Glu Glu Leu Arg Val Arg Leu Ala Ser His Leu Arg
145                 150                 155                 160
```

-continued

```
Lys Leu Arg Lys Arg Leu Leu Arg Asp Ala Asp Leu Gln Lys Arg
            165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
            195                 200                 205

Arg Ala Ala Thr Val Gly Ser Leu Ala Gly Gln Pro Leu Gln Glu Arg
            210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
            245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
            290                 295                 300

Val Gly Thr Ser Ala Ala Pro Val Pro Ser Asp Asn His
305                 310                 315

<210> SEQ ID NO 280
<211> LENGTH: 345
<212> TYPE: PRT
<213> ORGANISM: Homo sapiens

<400> SEQUENCE: 280

Met Ile Ser Pro Val Leu Ile Leu Phe Ser Ser Phe Leu Cys His Val
1               5                   10                  15

Ala Ile Ala Gly Arg Thr Cys Pro Lys Pro Asp Asp Leu Pro Phe Ser
            20                  25                  30

Thr Val Val Pro Leu Lys Thr Phe Tyr Glu Pro Gly Glu Glu Ile Thr
            35                  40                  45

Tyr Ser Cys Lys Pro Gly Tyr Val Ser Arg Gly Gly Met Arg Lys Phe
        50                  55                  60

Ile Cys Pro Leu Thr Gly Leu Trp Pro Ile Asn Thr Leu Lys Cys Thr
65                  70                  75                  80

Pro Arg Val Cys Pro Phe Ala Gly Ile Leu Glu Asn Gly Ala Val Arg
                85                  90                  95

Tyr Thr Thr Phe Glu Tyr Pro Asn Thr Ile Ser Phe Ser Cys Asn Thr
            100                 105                 110

Gly Phe Tyr Leu Asn Gly Ala Asp Ser Ala Lys Cys Thr Glu Glu Gly
        115                 120                 125

Lys Trp Ser Pro Glu Leu Pro Val Cys Ala Pro Ile Ile Cys Pro Pro
130                 135                 140

Pro Ser Ile Pro Thr Phe Ala Thr Leu Arg Val Tyr Lys Pro Ser Ala
145                 150                 155                 160

Gly Asn Asn Ser Leu Tyr Arg Asp Thr Ala Val Phe Glu Cys Leu Pro
                165                 170                 175

Gln His Ala Met Phe Gly Asn Asp Thr Ile Thr Cys Thr Thr His Gly
            180                 185                 190

Asn Trp Thr Lys Leu Pro Glu Cys Arg Glu Val Lys Cys Pro Phe Pro
            195                 200                 205

Ser Arg Pro Asp Asn Gly Phe Val Asn Tyr Pro Ala Lys Pro Thr Leu
        210                 215                 220
```

```
Tyr Tyr Lys Asp Lys Ala Thr Phe Gly Cys His Asp Gly Tyr Ser Leu
225                 230                 235                 240

Asp Gly Pro Glu Glu Ile Glu Cys Thr Lys Leu Gly Asn Trp Ser Ala
            245                 250                 255

Met Pro Ser Cys Lys Ala Ser Cys Lys Leu Pro Val Lys Lys Ala Thr
        260                 265                 270

Val Val Tyr Gln Gly Glu Arg Val Lys Ile Gln Glu Lys Phe Lys Asn
            275                 280                 285

Gly Met Leu His Gly Asp Lys Val Ser Phe Phe Cys Lys Asn Lys Glu
        290                 295                 300

Lys Lys Cys Ser Tyr Thr Glu Asp Ala Gln Cys Ile Asp Gly Thr Ile
305                 310                 315                 320

Glu Val Pro Lys Cys Phe Lys Glu His Ser Ser Leu Ala Phe Trp Lys
            325                 330                 335

Thr Asp Ala Ser Asp Val Lys Pro Cys
            340                 345

<210> SEQ ID NO 281
<211> LENGTH: 543
<212> TYPE: PRT
<213> ORGANISM: Homo sapiens

<400> SEQUENCE: 281

Met Ala His Ala His Ile Gln Gly Gly Arg Arg Ala Lys Ser Arg Phe
1               5                   10                  15

Val Val Cys Ile Met Ser Gly Ala Arg Ser Lys Leu Ala Leu Phe Leu
            20                  25                  30

Cys Gly Cys Tyr Val Val Ala Leu Gly Ala His Thr Gly Glu Glu Ser
        35                  40                  45

Val Ala Asp His His Glu Ala Glu Tyr Tyr Val Ala Val Tyr Glu
    50                  55                  60

His Pro Ser Ile Leu Ser Leu Asn Pro Leu Ala Leu Ile Ser Arg Gln
65                  70                  75                  80

Glu Ala Leu Glu Leu Met Asn Gln Asn Leu Asp Ile Tyr Glu Gln Gln
                85                  90                  95

Val Met Thr Ala Ala Gln Lys Asp Val Gln Ile Ile Val Phe Pro Glu
            100                 105                 110

Asp Gly Ile His Gly Phe Asn Phe Thr Arg Thr Ser Ile Tyr Pro Phe
        115                 120                 125

Leu Asp Phe Met Pro Ser Pro Gln Val Val Arg Trp Asn Pro Cys Leu
    130                 135                 140

Glu Pro His Arg Phe Asn Asp Thr Glu Val Leu Gln Arg Leu Ser Cys
145                 150                 155                 160

Met Ala Ile Arg Gly Asp Met Phe Leu Val Ala Asn Leu Gly Thr Lys
                165                 170                 175

Glu Pro Cys His Ser Ser Asp Pro Arg Cys Pro Lys Asp Gly Arg Tyr
            180                 185                 190

Gln Phe Asn Thr Asn Val Val Phe Ser Asn Asn Gly Thr Leu Val Asp
        195                 200                 205

Arg Tyr Arg Lys His Asn Leu Tyr Phe Glu Ala Ala Phe Asp Val Pro
    210                 215                 220

Leu Lys Val Asp Leu Ile Thr Phe Asp Thr Pro Phe Ala Gly Arg Phe
225                 230                 235                 240

Gly Ile Phe Thr Cys Phe Asp Ile Leu Phe Phe Asp Pro Ala Ile Arg
```

```
                245                 250                 255
Val Leu Arg Asp Tyr Lys Val Lys His Val Val Tyr Pro Thr Ala Trp
            260                 265                 270

Met Asn Gln Leu Pro Leu Leu Ala Ala Ile Glu Ile Gln Lys Ala Phe
        275                 280                 285

Ala Val Ala Phe Gly Ile Asn Val Leu Ala Ala Asn Val His His Pro
    290                 295                 300

Val Leu Gly Met Thr Gly Ser Gly Ile His Thr Pro Leu Glu Ser Phe
305                 310                 315                 320

Trp Tyr His Asp Met Glu Asn Pro Lys Ser His Leu Ile Ile Ala Gln
            325                 330                 335

Val Ala Lys Asn Pro Val Gly Leu Ile Gly Ala Glu Asn Ala Thr Gly
        340                 345                 350

Glu Thr Asp Pro Ser His Ser Lys Phe Leu Lys Ile Leu Ser Gly Asp
    355                 360                 365

Pro Tyr Cys Glu Lys Asp Ala Gln Gly Val His Cys Asp Glu Ala Thr
            370                 375                 380

Lys Trp Asn Val Asn Ala Pro Pro Thr Phe His Ser Glu Met Met Tyr
385                 390                 395                 400

Asp Asn Phe Thr Leu Val Pro Val Trp Gly Lys Glu Gly Tyr Leu His
            405                 410                 415

Val Cys Ser Asn Gly Leu Cys Cys Tyr Leu Leu Tyr Glu Arg Pro Thr
        420                 425                 430

Leu Ser Lys Glu Leu Tyr Ala Leu Gly Val Phe Asp Gly Leu His Thr
    435                 440                 445

Val His Gly Thr Tyr Tyr Ile Gln Val Cys Ala Leu Val Arg Cys Gly
        450                 455                 460

Gly Leu Gly Phe Asp Thr Cys Gly Gln Glu Ile Thr Glu Ala Thr Gly
465                 470                 475                 480

Ile Phe Glu Phe His Leu Trp Gly Asn Phe Ser Thr Ser Tyr Ile Phe
            485                 490                 495

Pro Leu Phe Leu Thr Ser Gly Met Thr Leu Glu Val Pro Asp Gln Leu
        500                 505                 510

Gly Trp Glu Asn Asp His Tyr Phe Leu Arg Lys Ser Arg Leu Ser Ser
    515                 520                 525

Gly Leu Val Thr Ala Ala Leu Tyr Gly Arg Leu Tyr Glu Arg Asp
        530                 535                 540

<210> SEQ ID NO 282
<211> LENGTH: 261
<212> TYPE: PRT
<213> ORGANISM: Homo sapiens

<400> SEQUENCE: 282

Met Ala Ser Pro Asp Trp Gly Tyr Asp Asp Lys Asn Gly Pro Glu Gln
1               5                  10                  15

Trp Ser Lys Leu Tyr Pro Ile Ala Asn Gly Asn Asn Gln Ser Pro Val
            20                  25                  30

Asp Ile Lys Thr Ser Glu Thr Lys His Asp Thr Ser Leu Lys Pro Ile
        35                  40                  45

Ser Val Ser Tyr Asn Pro Ala Thr Ala Lys Glu Ile Ile Asn Val Gly
    50                  55                  60

His Ser Phe His Val Asn Phe Glu Asp Asn Asp Asn Arg Ser Val Leu
65                  70                  75                  80
```

```
Lys Gly Gly Pro Phe Ser Asp Ser Tyr Arg Leu Phe Gln Phe His Phe
                85                  90                  95

His Trp Gly Ser Thr Asn Glu His Gly Ser Glu His Thr Val Asp Gly
            100                 105                 110

Val Lys Tyr Ser Ala Glu Leu His Val Ala His Trp Asn Ser Ala Lys
        115                 120                 125

Tyr Ser Ser Leu Ala Glu Ala Ser Lys Ala Asp Gly Leu Ala Val
    130                 135                 140

Ile Gly Val Leu Met Lys Val Gly Glu Ala Asn Pro Lys Leu Gln Lys
145                 150                 155                 160

Val Leu Asp Ala Leu Gln Ala Ile Lys Thr Lys Gly Lys Arg Ala Pro
                165                 170                 175

Phe Thr Asn Phe Asp Pro Ser Thr Leu Leu Pro Ser Ser Leu Asp Phe
            180                 185                 190

Trp Thr Tyr Pro Gly Ser Leu Thr His Pro Pro Leu Tyr Glu Ser Val
        195                 200                 205

Thr Trp Ile Ile Cys Lys Glu Ser Ile Ser Val Ser Glu Gln Leu
    210                 215                 220

Ala Gln Phe Arg Ser Leu Leu Ser Asn Val Glu Gly Asp Asn Ala Val
225                 230                 235                 240

Pro Met Gln His Asn Asn Arg Pro Thr Gln Pro Leu Lys Gly Arg Thr
                245                 250                 255

Val Arg Ala Ser Phe
            260

<210> SEQ ID NO 283
<211> LENGTH: 458
<212> TYPE: PRT
<213> ORGANISM: Homo sapiens

<400> SEQUENCE: 283

Met Ser Asp Leu Leu Ser Val Phe Leu His Leu Leu Leu Phe Lys
1               5                   10                  15

Leu Val Ala Pro Val Thr Phe Arg His His Arg Tyr Asp Asp Leu Val
            20                  25                  30

Arg Thr Leu Tyr Lys Val Gln Asn Glu Cys Pro Gly Ile Thr Arg Val
        35                  40                  45

Tyr Ser Ile Gly Arg Ser Val Glu Gly Arg His Leu Tyr Val Leu Glu
    50                  55                  60

Phe Ser Asp His Pro Gly Ile His Glu Pro Leu Glu Pro Glu Val Lys
65                  70                  75                  80

Tyr Val Gly Asn Met His Gly Asn Glu Ala Leu Gly Arg Glu Leu Met
                85                  90                  95

Leu Gln Leu Ser Glu Phe Leu Cys Glu Glu Phe Arg Asn Arg Asn Gln
            100                 105                 110

Arg Ile Val Gln Leu Ile Gln Asp Thr Arg Ile His Ile Leu Pro Ser
        115                 120                 125

Met Asn Pro Asp Gly Tyr Glu Val Ala Ala Gln Gly Pro Asn Lys
    130                 135                 140

Pro Gly Tyr Leu Val Gly Arg Asn Asn Ala Asn Gly Val Asp Leu Asn
145                 150                 155                 160

Arg Asn Phe Pro Asp Leu Asn Thr Tyr Ile Tyr Tyr Asn Glu Lys Tyr
                165                 170                 175

Gly Gly Pro Asn His His Leu Pro Leu Pro Asp Asn Trp Lys Ser Gln
            180                 185                 190
```

Val Glu Pro Glu Thr Arg Ala Val Ile Arg Trp Met His Ser Phe Asn
            195                 200                 205

Phe Val Leu Ser Ala Asn Leu His Gly Gly Ala Val Val Ala Asn Tyr
        210                 215                 220

Pro Tyr Asp Lys Ser Phe Glu His Arg Val Arg Gly Val Arg Arg Thr
225                 230                 235                 240

Ala Ser Thr Pro Thr Pro Asp Asp Lys Leu Phe Gln Lys Leu Ala Lys
                245                 250                 255

Val Tyr Ser Tyr Ala His Gly Trp Met Phe Gln Gly Trp Asn Cys Gly
        260                 265                 270

Asp Tyr Phe Pro Asp Gly Ile Thr Asn Gly Ala Ser Trp Tyr Ser Leu
            275                 280                 285

Ser Lys Gly Met Gln Asp Phe Asn Tyr Leu His Thr Asn Cys Phe Glu
        290                 295                 300

Ile Thr Leu Glu Leu Ser Cys Asp Lys Phe Pro Pro Glu Glu Glu Leu
305                 310                 315                 320

Gln Arg Glu Trp Leu Gly Asn Arg Glu Ala Leu Ile Gln Phe Leu Glu
                325                 330                 335

Gln Val His Gln Gly Ile Lys Gly Met Val Leu Asp Glu Asn Tyr Asn
        340                 345                 350

Asn Leu Ala Asn Ala Val Ile Ser Val Ser Gly Ile Asn His Asp Val
            355                 360                 365

Thr Ser Gly Asp His Gly Asp Tyr Phe Arg Leu Leu Leu Pro Gly Ile
        370                 375                 380

Tyr Thr Val Ser Ala Thr Ala Pro Gly Tyr Asp Pro Glu Thr Val Thr
385                 390                 395                 400

Val Thr Val Gly Pro Ala Glu Pro Thr Leu Val Asn Phe His Leu Lys
                405                 410                 415

Arg Ser Ile Pro Gln Val Ser Pro Val Arg Arg Ala Pro Ser Arg Arg
        420                 425                 430

His Gly Val Arg Ala Lys Val Gln Pro Gln Ala Arg Lys Lys Glu Met
            435                 440                 445

Glu Met Arg Gln Leu Gln Arg Gly Pro Ala
        450                 455

<210> SEQ ID NO 284
<211> LENGTH: 1065
<212> TYPE: PRT
<213> ORGANISM: Homo sapiens

<400> SEQUENCE: 284

Met Lys Ile Leu Ile Leu Gly Ile Phe Leu Phe Leu Cys Ser Thr Pro
1               5                   10                  15

Ala Trp Ala Lys Glu Lys His Tyr Tyr Ile Gly Ile Ile Glu Thr Thr
                20                  25                  30

Trp Asp Tyr Ala Ser Asp His Gly Glu Lys Lys Leu Ile Ser Val Asp
            35                  40                  45

Thr Glu His Ser Asn Ile Tyr Leu Gln Asn Gly Pro Asp Arg Ile Gly
        50                  55                  60

Arg Leu Tyr Lys Lys Ala Leu Tyr Leu Gln Tyr Thr Asp Glu Thr Phe
65                  70                  75                  80

Arg Thr Thr Ile Glu Lys Pro Val Trp Leu Gly Phe Leu Gly Pro Ile
                85                  90                  95

Ile Lys Ala Glu Thr Gly Asp Lys Val Tyr Val His Leu Lys Asn Leu

-continued

```
                100                 105                 110
Ala Ser Arg Pro Tyr Thr Phe His Ser His Gly Ile Thr Tyr Tyr Lys
        115                 120                 125

Glu His Glu Gly Ala Ile Tyr Pro Asp Asn Thr Thr Asp Phe Gln Arg
        130                 135                 140

Ala Asp Asp Lys Val Tyr Pro Gly Glu Gln Tyr Thr Tyr Met Leu Leu
145                 150                 155                 160

Ala Thr Glu Glu Gln Ser Pro Gly Glu Gly Asp Gly Asn Cys Val Thr
                165                 170                 175

Arg Ile Tyr His Ser His Ile Asp Ala Pro Lys Asp Ile Ala Ser Gly
                180                 185                 190

Leu Ile Gly Pro Leu Ile Ile Cys Lys Lys Asp Ser Leu Asp Lys Glu
        195                 200                 205

Lys Glu Lys His Ile Asp Arg Glu Phe Val Val Met Phe Ser Val Val
        210                 215                 220

Asp Glu Asn Phe Ser Trp Tyr Leu Glu Asp Asn Ile Lys Thr Tyr Cys
225                 230                 235                 240

Ser Glu Pro Glu Lys Val Asp Lys Asp Asn Glu Asp Phe Gln Glu Ser
                245                 250                 255

Asn Arg Met Tyr Ser Val Asn Gly Tyr Thr Phe Gly Ser Leu Pro Gly
        260                 265                 270

Leu Ser Met Cys Ala Glu Asp Arg Val Lys Trp Tyr Leu Phe Gly Met
        275                 280                 285

Gly Asn Glu Val Asp Val His Ala Ala Phe Phe His Gly Gln Ala Leu
        290                 295                 300

Thr Asn Lys Asn Tyr Arg Ile Asp Thr Ile Asn Leu Phe Pro Ala Thr
305                 310                 315                 320

Leu Phe Asp Ala Tyr Met Val Ala Gln Asn Pro Gly Glu Trp Met Leu
                325                 330                 335

Ser Cys Gln Asn Leu Asn His Leu Lys Ala Gly Leu Gln Ala Phe Phe
                340                 345                 350

Gln Val Gln Glu Cys Asn Lys Ser Ser Ser Lys Asp Asn Ile Arg Gly
        355                 360                 365

Lys His Val Arg His Tyr Tyr Ile Ala Ala Glu Glu Ile Ile Trp Asn
        370                 375                 380

Tyr Ala Pro Ser Gly Ile Asp Ile Phe Thr Lys Glu Asn Leu Thr Ala
385                 390                 395                 400

Pro Gly Ser Asp Ser Ala Val Phe Phe Glu Gln Gly Thr Thr Arg Ile
                405                 410                 415

Gly Gly Ser Tyr Lys Lys Leu Val Tyr Arg Glu Tyr Thr Asp Ala Ser
                420                 425                 430

Phe Thr Asn Arg Lys Glu Arg Gly Pro Glu Glu Glu His Leu Gly Ile
        435                 440                 445

Leu Gly Pro Val Ile Trp Ala Glu Val Gly Asp Thr Ile Arg Val Thr
        450                 455                 460

Phe His Asn Lys Gly Ala Tyr Pro Leu Ser Ile Glu Pro Ile Gly Val
465                 470                 475                 480

Arg Phe Asn Lys Asn Asn Glu Gly Thr Tyr Tyr Ser Pro Asn Tyr Asn
                485                 490                 495

Pro Gln Ser Arg Ser Val Pro Pro Ser Ala Ser His Val Ala Pro Thr
                500                 505                 510

Glu Thr Phe Thr Tyr Glu Trp Thr Val Pro Lys Glu Val Gly Pro Thr
        515                 520                 525
```

```
Asn Ala Asp Pro Val Cys Leu Ala Lys Met Tyr Tyr Ser Ala Val Asp
            530                 535                 540

Pro Thr Lys Asp Ile Phe Thr Gly Leu Ile Gly Pro Met Lys Ile Cys
545                 550                 555                 560

Lys Lys Gly Ser Leu His Ala Asn Gly Arg Gln Lys Asp Val Asp Lys
                565                 570                 575

Glu Phe Tyr Leu Phe Pro Thr Val Phe Asp Glu Asn Glu Ser Leu Leu
            580                 585                 590

Leu Glu Asp Asn Ile Arg Met Phe Thr Thr Ala Pro Asp Gln Val Asp
            595                 600                 605

Lys Glu Asp Glu Asp Phe Gln Glu Ser Asn Lys Met His Ser Met Asn
610                 615                 620

Gly Phe Met Tyr Gly Asn Gln Pro Gly Leu Thr Met Cys Lys Gly Asp
625                 630                 635                 640

Ser Val Val Trp Tyr Leu Phe Ser Ala Gly Asn Glu Ala Asp Val His
                645                 650                 655

Gly Ile Tyr Phe Ser Gly Asn Thr Tyr Leu Trp Arg Gly Glu Arg Arg
                660                 665                 670

Asp Thr Ala Asn Leu Phe Pro Gln Thr Ser Leu Thr Leu His Met Trp
                675                 680                 685

Pro Asp Thr Glu Gly Thr Phe Asn Val Glu Cys Leu Thr Thr Asp His
690                 695                 700

Tyr Thr Gly Gly Met Lys Gln Lys Tyr Thr Val Asn Gln Cys Arg Arg
705                 710                 715                 720

Gln Ser Glu Asp Ser Thr Phe Tyr Leu Gly Arg Thr Tyr Tyr Ile
                725                 730                 735

Ala Ala Val Glu Val Glu Trp Asp Tyr Ser Pro Gln Arg Glu Trp Glu
                740                 745                 750

Lys Glu Leu His His Leu Gln Glu Gln Asn Val Ser Asn Ala Phe Leu
                755                 760                 765

Asp Lys Gly Glu Phe Tyr Ile Gly Ser Lys Tyr Lys Lys Val Val Tyr
                770                 775                 780

Arg Gln Tyr Thr Asp Ser Thr Phe Arg Val Pro Val Glu Arg Lys Ala
785                 790                 795                 800

Glu Glu Glu His Leu Gly Ile Leu Gly Pro Gln Leu His Ala Asp Val
                805                 810                 815

Gly Asp Lys Val Lys Ile Ile Phe Lys Asn Met Ala Thr Arg Pro Tyr
                820                 825                 830

Ser Ile His Ala His Gly Val Gln Thr Glu Ser Ser Thr Val Thr Pro
            835                 840                 845

Thr Leu Pro Gly Glu Thr Leu Thr Tyr Val Trp Lys Ile Pro Glu Arg
850                 855                 860

Ser Gly Ala Gly Thr Glu Asp Ser Ala Cys Ile Pro Trp Ala Tyr Tyr
865                 870                 875                 880

Ser Thr Val Asp Gln Val Lys Asp Leu Tyr Ser Gly Leu Ile Gly Pro
                885                 890                 895

Leu Ile Val Cys Arg Arg Pro Tyr Leu Lys Val Phe Asn Pro Arg Arg
                900                 905                 910

Lys Leu Glu Phe Ala Leu Leu Phe Leu Val Phe Asp Glu Asn Glu Ser
                915                 920                 925

Trp Tyr Leu Asp Asp Asn Ile Lys Thr Tyr Ser Asp His Pro Glu Lys
        930                 935                 940
```

-continued

```
Val Asn Lys Asp Asp Glu Phe Ile Glu Ser Asn Lys Met His Ala
945                 950                 955                 960

Ile Asn Gly Arg Met Phe Gly Asn Leu Gln Gly Leu Thr Met His Val
                965                 970                 975

Gly Asp Glu Val Asn Trp Tyr Leu Met Gly Met Gly Asn Glu Ile Asp
            980                 985                 990

Leu His Thr Val His Phe His Gly His Ser Phe Gln Tyr Lys His Arg
        995                 1000                1005

Gly Val Tyr Ser Ser Asp Val Phe Asp Ile Phe Pro Gly Thr Tyr
    1010                1015                1020

Gln Thr Leu Glu Met Phe Pro Arg Thr Pro Gly Ile Trp Leu Leu
    1025                1030                1035

His Cys His Val Thr Asp His Ile His Ala Gly Met Glu Thr Thr
    1040                1045                1050

Tyr Thr Val Leu Gln Asn Glu Asp Thr Lys Ser Gly
    1055                1060                1065

<210> SEQ ID NO 285
<211> LENGTH: 501
<212> TYPE: PRT
<213> ORGANISM: Homo sapiens

<400> SEQUENCE: 285

Met Gln Val Cys Ser Gln Pro Gln Arg Gly Cys Val Arg Glu Gln Ser
1               5                   10                  15

Ala Ile Asn Thr Ala Pro Pro Ser Ala His Asn Ala Ala Ser Pro Gly
            20                  25                  30

Gly Ala Arg Gly His Arg Val Pro Leu Thr Glu Ala Cys Lys Asp Ser
        35                  40                  45

Arg Ile Gly Gly Met Met Lys Thr Leu Leu Leu Phe Val Gly Leu Leu
50                  55                  60

Leu Thr Trp Glu Ser Gly Gln Val Leu Gly Asp Gln Thr Val Ser Asp
65                  70                  75                  80

Asn Glu Leu Gln Glu Met Ser Asn Gln Gly Ser Lys Tyr Val Asn Lys
                85                  90                  95

Glu Ile Gln Asn Ala Val Asn Gly Val Lys Gln Ile Lys Thr Leu Ile
            100                 105                 110

Glu Lys Thr Asn Glu Glu Arg Lys Thr Leu Leu Ser Asn Leu Glu Glu
        115                 120                 125

Ala Lys Lys Lys Lys Glu Asp Ala Leu Asn Glu Thr Arg Glu Ser Glu
    130                 135                 140

Thr Lys Leu Lys Glu Leu Pro Gly Val Cys Asn Glu Thr Met Met Ala
145                 150                 155                 160

Leu Trp Glu Glu Cys Lys Pro Cys Leu Lys Gln Thr Cys Met Lys Phe
                165                 170                 175

Tyr Ala Arg Val Cys Arg Ser Gly Ser Gly Leu Val Gly Arg Gln Leu
            180                 185                 190

Glu Glu Phe Leu Asn Gln Ser Ser Pro Phe Tyr Phe Trp Met Asn Gly
        195                 200                 205

Asp Arg Ile Asp Ser Leu Leu Glu Asn Asp Arg Gln Gln Thr His Met
    210                 215                 220

Leu Asp Val Met Gln Asp His Phe Ser Arg Ala Ser Ser Ile Ile Asp
225                 230                 235                 240

Glu Leu Phe Gln Asp Arg Phe Phe Thr Arg Glu Pro Gln Asp Thr Tyr
                245                 250                 255
```

His Tyr Leu Pro Phe Ser Leu Pro His Arg Arg Pro His Phe Phe
              260                 265                 270

Pro Lys Ser Arg Ile Val Arg Ser Leu Met Pro Phe Ser Pro Tyr Glu
          275                 280                 285

Pro Leu Asn Phe His Ala Met Phe Gln Pro Phe Leu Glu Met Ile His
      290                 295                 300

Glu Ala Gln Gln Ala Met Asp Ile His Phe His Ser Pro Ala Phe Gln
305                 310                 315                 320

His Pro Pro Thr Glu Phe Ile Arg Glu Gly Asp Asp Arg Thr Val
              325                 330                 335

Cys Arg Glu Ile Arg His Asn Ser Thr Gly Cys Leu Arg Met Lys Asp
              340                 345                 350

Gln Cys Asp Lys Cys Arg Glu Ile Leu Ser Val Asp Cys Ser Thr Asn
          355                 360                 365

Asn Pro Ser Gln Ala Lys Leu Arg Arg Glu Leu Asp Glu Ser Leu Gln
      370                 375                 380

Val Ala Glu Arg Leu Thr Arg Lys Tyr Asn Glu Leu Leu Lys Ser Tyr
385                 390                 395                 400

Gln Trp Lys Met Leu Asn Thr Ser Ser Leu Glu Gln Leu Asn Glu
              405                 410                 415

Gln Phe Asn Trp Val Ser Arg Leu Ala Asn Leu Thr Gln Gly Glu Asp
          420                 425                 430

Gln Tyr Tyr Leu Arg Val Thr Thr Val Ala Ser His Thr Ser Asp Ser
      435                 440                 445

Asp Val Pro Ser Gly Val Thr Glu Val Val Lys Leu Phe Asp Ser
450                 455                 460

Asp Pro Ile Thr Val Thr Val Pro Val Glu Val Ser Arg Lys Asn Pro
465                 470                 475                 480

Lys Phe Met Glu Thr Val Ala Glu Lys Ala Leu Gln Glu Tyr Arg Lys
              485                 490                 495

Lys His Arg Glu Glu
              500

<210> SEQ ID NO 286
<211> LENGTH: 622
<212> TYPE: PRT
<213> ORGANISM: Homo sapiens

<400> SEQUENCE: 286

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
              20                  25                  30

Gln Ala Arg Ser Leu Leu Gln Arg Val Arg Arg Ala Asn Thr Phe Leu
          35                  40                  45

Glu Glu Val Arg Lys Gly Asn Leu Glu Arg Glu Cys Val Glu Glu Thr
      50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
              85                  90                  95

Arg Asp Lys Leu Ala Ala Cys Leu Glu Gly Asn Cys Ala Glu Gly Leu
          100                 105                 110

Gly Thr Asn Tyr Arg Gly His Val Asn Ile Thr Arg Ser Gly Ile Glu

```
                115                 120                 125
Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
                180                 185                 190

Val Ala Met Thr Pro Arg Ser Glu Gly Ser Ser Val Asn Leu Ser Pro
            195                 200                 205

Pro Leu Glu Gln Cys Val Pro Asp Arg Gly Gln Gln Tyr Gln Gly Arg
        210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Glu Thr Gly Asp Gly Leu Asp
    290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
        355                 360                 365

Asp Ala Glu Ile Gly Met Ser Pro Trp Gln Val Met Leu Phe Arg Lys
    370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
    450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
        515                 520                 525

Pro Ile Val Glu Arg Pro Val Cys Lys Asp Ser Thr Arg Ile Arg Ile
    530                 535                 540
```

```
Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
            595                 600                 605

Leu Lys Lys Trp Ile Gln Lys Val Ile Asp Gln Phe Gly Glu
            610                 615                 620

<210> SEQ ID NO 287
<211> LENGTH: 488
<212> TYPE: PRT
<213> ORGANISM: Homo sapiens

<400> SEQUENCE: 287

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
                20                  25                  30

Asn Ile Leu Ala Arg Val Thr Arg Ala Asn Ser Phe Leu Glu Glu Met
            35                  40                  45

Lys Lys Gly His Leu Glu Arg Glu Cys Met Glu Glu Thr Cys Ser Tyr
        50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
```

```
              290                 295                 300
Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485

<210> SEQ ID NO 288
<211> LENGTH: 500
<212> TYPE: PRT
<213> ORGANISM: Homo sapiens

<400> SEQUENCE: 288

Met Ala Ser Arg Leu Thr Leu Leu Thr Leu Leu Leu Leu Leu Leu Ala
1               5                   10                  15

Gly Asp Arg Ala Ser Ser Asn Pro Asn Ala Thr Ser Ser Ser Ser Gln
            20                  25                  30

Asp Pro Glu Ser Leu Gln Asp Arg Gly Glu Gly Lys Val Ala Thr Thr
        35                  40                  45

Val Ile Ser Lys Met Leu Phe Val Glu Pro Ile Leu Glu Val Ser Ser
50                  55                  60

Leu Pro Thr Thr Asn Ser Thr Thr Asn Ser Ala Thr Lys Ile Thr Ala
65                  70                  75                  80

Asn Thr Thr Asp Glu Pro Thr Thr Gln Pro Thr Thr Glu Pro Thr Thr
                85                  90                  95

Gln Pro Thr Ile Gln Pro Thr Gln Pro Thr Thr Gln Leu Pro Thr Asp
            100                 105                 110

Ser Pro Thr Gln Pro Thr Thr Gly Ser Phe Cys Pro Gly Pro Val Thr
        115                 120                 125

Leu Cys Ser Asp Leu Glu Ser His Ser Thr Glu Ala Val Leu Gly Asp
    130                 135                 140

Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175
```

```
Leu Leu Thr Gln Val Leu Gly Ala Gly Gln Asn Thr Lys Thr Asn
            180                 185                 190

Leu Glu Ser Ile Leu Ser Tyr Pro Lys Asp Phe Thr Cys Val His Gln
        195                 200                 205

Ala Leu Lys Gly Phe Thr Thr Lys Gly Val Thr Ser Val Ser Gln Ile
    210                 215                 220

Phe His Ser Pro Asp Leu Ala Ile Arg Asp Thr Phe Val Asn Ala Ser
225                 230                 235                 240

Arg Thr Leu Tyr Ser Ser Pro Arg Val Leu Ser Asn Asn Ser Asp
            245                 250                 255

Ala Asn Leu Glu Leu Ile Asn Thr Trp Val Ala Lys Asn Thr Asn Asn
        260                 265                 270

Lys Ile Ser Arg Leu Leu Asp Ser Leu Pro Ser Asp Thr Arg Leu Val
        275                 280                 285

Leu Leu Asn Ala Ile Tyr Leu Ser Ala Lys Trp Lys Thr Thr Phe Asp
        290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335

Asp Gln Thr Leu Lys Ala Lys Val Gly Gln Leu Gln Leu Ser His Asn
            340                 345                 350

Leu Ser Leu Val Ile Leu Val Pro Gln Asn Leu Lys His Arg Leu Glu
        355                 360                 365

Asp Met Glu Gln Ala Leu Ser Pro Ser Val Phe Lys Ala Ile Met Glu
    370                 375                 380

Lys Leu Glu Met Ser Lys Phe Gln Pro Thr Leu Leu Thr Leu Pro Arg
385                 390                 395                 400

Ile Lys Val Thr Thr Ser Gln Asp Met Leu Ser Ile Met Glu Lys Leu
                405                 410                 415

Glu Phe Phe Asp Phe Ser Tyr Asp Leu Asn Leu Cys Gly Leu Thr Glu
            420                 425                 430

Asp Pro Asp Leu Gln Val Ser Ala Met Gln His Gln Thr Val Leu Glu
        435                 440                 445

Leu Thr Glu Thr Gly Val Glu Ala Ala Ala Ser Ala Ile Ser Val
    450                 455                 460

Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
                485                 490                 495

Asp Pro Arg Ala
            500

<210> SEQ ID NO 289
<211> LENGTH: 705
<212> TYPE: PRT
<213> ORGANISM: Homo sapiens

<400> SEQUENCE: 289

Met Trp Leu Leu Tyr Leu Leu Val Pro Ala Leu Phe Cys Arg Ala Gly
1               5                   10                  15

Gly Ser Ile Pro Ile Pro Gln Lys Leu Phe Gly Glu Val Thr Ser Pro
            20                  25                  30

Leu Phe Pro Lys Pro Tyr Pro Asn Asn Phe Glu Thr Thr Thr Val Ile
        35                  40                  45
```

```
Thr Val Pro Thr Gly Tyr Arg Val Lys Leu Val Phe Gln Gln Phe Asp
    50                  55                  60
Leu Glu Pro Ser Glu Gly Cys Phe Tyr Asp Tyr Val Lys Ile Ser Ala
65                  70                  75                  80
Asp Lys Lys Ser Leu Gly Arg Phe Cys Gly Gln Leu Gly Ser Pro Leu
                85                  90                  95
Gly Asn Pro Pro Gly Lys Lys Glu Phe Met Ser Gln Gly Asn Lys Met
                100                 105                 110
Leu Leu Thr Phe His Thr Asp Phe Ser Asn Glu Glu Asn Gly Thr Ile
            115                 120                 125
Met Phe Tyr Lys Gly Phe Leu Ala Tyr Gln Ala Val Asp Leu Asp
        130                 135                 140
Glu Cys Ala Ser Arg Ser Lys Leu Gly Glu Glu Asp Pro Gln Pro Gln
145                 150                 155                 160
Cys Gln His Leu Cys His Asn Tyr Val Gly Gly Tyr Phe Cys Ser Cys
                165                 170                 175
Arg Pro Gly Tyr Glu Leu Gln Glu Asp Arg His Ser Cys Gln Ala Glu
                180                 185                 190
Cys Ser Ser Glu Leu Tyr Thr Glu Ala Ser Gly Tyr Ile Ser Ser Leu
                195                 200                 205
Glu Tyr Pro Arg Ser Tyr Pro Pro Asp Leu Arg Cys Asn Tyr Ser Ile
    210                 215                 220
Arg Val Glu Arg Gly Leu Thr Leu His Leu Lys Phe Leu Glu Pro Phe
225                 230                 235                 240
Asp Ile Asp Asp His Gln Gln Val His Cys Pro Tyr Asp Gln Leu Gln
                245                 250                 255
Ile Tyr Ala Asn Gly Lys Asn Ile Gly Glu Phe Cys Gly Lys Gln Arg
                260                 265                 270
Pro Pro Asp Leu Asp Thr Ser Ser Asn Ala Val Asp Leu Leu Phe Phe
                275                 280                 285
Thr Asp Glu Ser Gly Asp Ser Arg Gly Trp Lys Leu Arg Tyr Thr Thr
    290                 295                 300
Glu Ile Ile Lys Cys Pro Gln Pro Lys Thr Leu Asp Glu Phe Thr Ile
305                 310                 315                 320
Ile Gln Asn Leu Gln Pro Gln Tyr Gln Phe Arg Asp Tyr Phe Ile Ala
                325                 330                 335
Thr Cys Lys Gln Gly Tyr Gln Leu Ile Glu Gly Asn Gln Val Leu His
                340                 345                 350
Ser Phe Thr Ala Val Cys Gln Asp Asp Gly Thr Trp His Arg Ala Met
            355                 360                 365
Pro Arg Cys Lys Ile Lys Asp Cys Gly Gln Pro Arg Asn Leu Pro Asn
    370                 375                 380
Gly Asp Phe Arg Tyr Thr Thr Thr Met Gly Val Asn Thr Tyr Lys Ala
385                 390                 395                 400
Arg Ile Gln Tyr Tyr Cys His Glu Pro Tyr Tyr Lys Met Gln Thr Arg
                405                 410                 415
Ala Gly Ser Arg Glu Ser Glu Gln Gly Val Tyr Thr Cys Thr Ala Gln
                420                 425                 430
Gly Ile Trp Lys Asn Glu Gln Lys Gly Glu Lys Ile Pro Arg Cys Leu
            435                 440                 445
Pro Val Cys Gly Lys Pro Val Asn Pro Val Glu Gln Arg Gln Arg Ile
    450                 455                 460
```

Ile Gly Gly Gln Lys Ala Lys Met Gly Asn Phe Pro Trp Gln Val Phe
465                 470                 475                 480

Thr Asn Ile His Gly Arg Gly Gly Ala Leu Leu Gly Asp Arg Trp
            485                 490                 495

Ile Leu Thr Ala Ala His Thr Leu Tyr Pro Lys Glu His Glu Ala Gln
                500                 505                 510

Ser Asn Ala Ser Leu Asp Val Phe Leu Gly His Thr Asn Val Glu Glu
            515                 520                 525

Leu Met Lys Leu Gly Asn His Pro Ile Arg Arg Val Ser Val His Pro
    530                 535                 540

Asp Tyr Arg Gln Asp Glu Ser Tyr Asn Phe Glu Gly Asp Ile Ala Leu
545                 550                 555                 560

Leu Glu Leu Glu Asn Ser Val Thr Leu Gly Pro Asn Leu Leu Pro Ile
                565                 570                 575

Cys Leu Pro Asp Asn Asp Thr Phe Tyr Asp Leu Gly Leu Met Gly Tyr
            580                 585                 590

Val Ser Gly Phe Gly Val Met Glu Glu Lys Ile Ala His Asp Leu Arg
    595                 600                 605

Phe Val Arg Leu Pro Val Ala Asn Pro Gln Ala Cys Glu Asn Trp Leu
610                 615                 620

Arg Gly Lys Asn Arg Met Asp Val Phe Ser Gln Asn Met Phe Cys Ala
625                 630                 635                 640

Gly His Pro Ser Leu Lys Gln Asp Ala Cys Gln Gly Asp Ser Gly Gly
                645                 650                 655

Val Phe Ala Val Arg Asp Pro Asn Thr Asp Arg Trp Val Ala Thr Gly
            660                 665                 670

Ile Val Ser Trp Gly Ile Gly Cys Ser Arg Gly Tyr Gly Phe Tyr Thr
    675                 680                 685

Lys Val Leu Asn Tyr Val Asp Trp Ile Lys Lys Glu Met Glu Glu Glu
690                 695                 700

Asp
705

<210> SEQ ID NO 290
<211> LENGTH: 487
<212> TYPE: PRT
<213> ORGANISM: Homo sapiens

<400> SEQUENCE: 290

Met Pro Gly Pro Arg Val Trp Gly Lys Tyr Leu Trp Arg Ser Pro His
1               5                   10                  15

Ser Lys Gly Cys Pro Gly Ala Met Trp Trp Leu Leu Leu Trp Gly Val
            20                  25                  30

Leu Gln Ala Cys Pro Thr Arg Gly Ser Val Leu Leu Ala Gln Glu Leu
        35                  40                  45

Pro Gln Gln Leu Thr Ser Pro Gly Tyr Pro Glu Pro Tyr Gly Lys Gly
    50                  55                  60

Gln Glu Ser Ser Thr Asp Ile Lys Ala Pro Glu Gly Phe Ala Val Arg
65                  70                  75                  80

Leu Val Phe Gln Asp Phe Asp Leu Glu Pro Ser Gln Asp Cys Ala Gly
                85                  90                  95

Asp Ser Val Thr Ile Ser Phe Val Gly Ser Asp Pro Ser Gln Phe Cys
            100                 105                 110

Gly Gln Gln Gly Ser Pro Leu Gly Arg Pro Pro Gly Gln Arg Glu Phe
        115                 120                 125

Val Ser Ser Gly Arg Ser Leu Arg Leu Thr Phe Arg Thr Gln Pro Ser
    130                 135                 140

Ser Glu Asn Lys Thr Ala His Leu His Lys Gly Phe Leu Ala Leu Tyr
145                 150                 155                 160

Gln Thr Val Ala Val Asn Tyr Ser Gln Pro Ile Ser Glu Ala Ser Arg
                165                 170                 175

Gly Ser Glu Ala Ile Asn Ala Pro Gly Asp Asn Pro Ala Lys Val Gln
            180                 185                 190

Asn His Cys Gln Glu Pro Tyr Tyr Gln Ala Ala Ala Gly Ala Leu
        195                 200                 205

Thr Cys Ala Thr Pro Gly Thr Trp Lys Asp Arg Gln Asp Gly Glu Glu
    210                 215                 220

Val Leu Gln Cys Met Pro Val Cys Gly Arg Pro Val Thr Pro Ile Ala
225                 230                 235                 240

Gln Asn Gln Thr Thr Leu Gly Ser Ser Arg Ala Lys Leu Gly Asn Phe
                245                 250                 255

Pro Trp Gln Ala Phe Thr Ser Ile His Gly Arg Gly Gly Gly Ala Leu
            260                 265                 270

Leu Gly Asp Arg Trp Ile Leu Thr Ala Ala His Thr Val Tyr Pro Lys
        275                 280                 285

Asp Ser Val Ser Leu Arg Lys Asn Gln Ser Val Asn Val Phe Leu Gly
    290                 295                 300

His Thr Ala Ile Asp Glu Met Leu Lys Leu Gly Asn His Pro Val His
305                 310                 315                 320

Arg Val Val Val His Pro Asp Tyr Arg Gln Asn Glu Ser His Asn Phe
                325                 330                 335

Ser Gly Asp Ile Ala Leu Leu Glu Leu Gln His Ser Ile Pro Leu Gly
            340                 345                 350

Pro Asn Val Leu Pro Val Cys Leu Pro Asp Asn Glu Thr Leu Tyr Arg
        355                 360                 365

Ser Gly Leu Leu Gly Tyr Val Ser Gly Phe Gly Met Glu Met Gly Trp
    370                 375                 380

Leu Thr Thr Glu Leu Lys Tyr Ser Arg Leu Pro Val Ala Pro Arg Glu
385                 390                 395                 400

Ala Cys Asn Ala Trp Leu Gln Lys Arg Gln Arg Pro Glu Val Phe Ser
                405                 410                 415

Asp Asn Met Phe Cys Val Gly Asp Glu Thr Gln Arg His Ser Val Cys
            420                 425                 430

Gln Gly Asp Ser Gly Ser Val Tyr Val Val Trp Asp Asn His Ala His
        435                 440                 445

His Trp Val Ala Thr Gly Ile Val Ser Trp Gly Ile Gly Cys Gly Glu
    450                 455                 460

Gly Tyr Asp Phe Tyr Thr Lys Val Leu Ser Tyr Val Asp Trp Ile Lys
465                 470                 475                 480

Gly Val Met Asn Gly Lys Asn
                485

<210> SEQ ID NO 291
<211> LENGTH: 688
<212> TYPE: PRT
<213> ORGANISM: Homo sapiens

<400> SEQUENCE: 291

Met Trp Cys Ile Val Leu Phe Ser Leu Leu Ala Trp Val Tyr Ala Glu

```
  1               5                  10                 15
Pro Thr Met Tyr Gly Glu Ile Leu Ser Pro Asn Tyr Pro Gln Ala Tyr
                 20                 25                 30

Pro Ser Glu Val Glu Lys Ser Trp Asp Ile Glu Val Pro Glu Gly Tyr
                 35                 40                 45

Gly Ile His Leu Tyr Phe Thr His Leu Asp Ile Glu Leu Ser Glu Asn
                 50                 55                 60

Cys Ala Tyr Asp Ser Val Gln Ile Ile Ser Gly Asp Thr Glu Glu Gly
 65              70                 75                 80

Arg Leu Cys Gly Gln Arg Ser Ser Asn Asn Pro His Ser Pro Ile Val
                 85                 90                 95

Glu Glu Phe Gln Val Pro Tyr Asn Lys Leu Gln Val Ile Phe Lys Ser
                100                105                110

Asp Phe Ser Asn Glu Glu Arg Phe Thr Gly Phe Ala Ala Tyr Tyr Val
                115                120                125

Ala Thr Asp Ile Asn Glu Cys Thr Asp Phe Val Asp Val Pro Cys Ser
                130                135                140

His Phe Cys Asn Asn Phe Ile Gly Gly Tyr Phe Cys Ser Cys Pro Pro
145             150                 155                160

Glu Tyr Phe Leu His Asp Asp Met Lys Asn Cys Gly Val Asn Cys Ser
                165                170                175

Gly Asp Val Phe Thr Ala Leu Ile Gly Glu Ile Ala Ser Pro Asn Tyr
                180                185                190

Pro Lys Pro Tyr Pro Glu Asn Ser Arg Cys Glu Tyr Gln Ile Arg Leu
                195                200                205

Glu Lys Gly Phe Gln Val Val Thr Leu Arg Arg Glu Asp Phe Asp
210                 215                220

Val Glu Ala Ala Asp Ser Ala Gly Asn Cys Leu Asp Ser Leu Val Phe
225                 230                235                240

Val Ala Gly Asp Arg Gln Phe Gly Pro Tyr Cys Gly His Gly Phe Pro
                245                250                255

Gly Pro Leu Asn Ile Glu Thr Lys Ser Asn Ala Leu Asp Ile Ile Phe
                260                265                270

Gln Thr Asp Leu Thr Gly Gln Lys Lys Gly Trp Lys Leu Arg Tyr His
                275                280                285

Gly Asp Pro Met Pro Cys Pro Lys Glu Asp Thr Pro Asn Ser Val Trp
                290                295                300

Glu Pro Ala Lys Ala Lys Tyr Val Phe Arg Asp Val Val Gln Ile Thr
305                 310                315                320

Cys Leu Asp Gly Phe Glu Val Val Glu Gly Arg Val Gly Ala Thr Ser
                325                330                335

Phe Tyr Ser Thr Cys Gln Ser Asn Gly Lys Trp Ser Asn Ser Lys Leu
                340                345                350

Lys Cys Gln Pro Val Asp Cys Gly Ile Pro Glu Ser Ile Glu Asn Gly
                355                360                365

Lys Val Glu Asp Pro Glu Ser Thr Leu Phe Gly Ser Val Ile Arg Tyr
                370                375                380

Thr Cys Glu Glu Pro Tyr Tyr Tyr Met Glu Asn Gly Gly Gly Gly Glu
385                 390                395                400

Tyr His Cys Ala Gly Asn Gly Ser Trp Val Asn Glu Val Leu Gly Pro
                405                410                415

Glu Leu Pro Lys Cys Val Pro Val Cys Gly Val Pro Arg Glu Pro Phe
                420                425                430
```

Glu Glu Lys Gln Arg Ile Ile Gly Gly Ser Asp Ala Asp Ile Lys Asn
            435                 440                 445

Phe Pro Trp Gln Val Phe Phe Asp Asn Pro Trp Ala Gly Gly Ala Leu
        450                 455                 460

Ile Asn Glu Tyr Trp Val Leu Thr Ala Ala His Val Val Glu Gly Asn
465                 470                 475                 480

Arg Glu Pro Thr Met Tyr Val Gly Ser Thr Ser Val Gln Thr Ser Arg
                485                 490                 495

Leu Ala Lys Ser Lys Met Leu Thr Pro Glu His Val Phe Ile His Pro
            500                 505                 510

Gly Trp Lys Leu Leu Glu Val Pro Glu Gly Arg Thr Asn Phe Asp Asn
        515                 520                 525

Asp Ile Ala Leu Val Arg Leu Lys Asp Pro Val Lys Met Gly Pro Thr
    530                 535                 540

Val Ser Pro Ile Cys Leu Pro Gly Thr Ser Ser Asp Tyr Asn Leu Met
545                 550                 555                 560

Asp Gly Asp Leu Gly Leu Ile Ser Gly Trp Gly Arg Thr Glu Lys Arg
                565                 570                 575

Asp Arg Ala Val Arg Leu Lys Ala Ala Arg Leu Pro Val Ala Pro Leu
            580                 585                 590

Arg Lys Cys Lys Glu Val Lys Val Glu Lys Pro Thr Ala Asp Ala Glu
        595                 600                 605

Ala Tyr Val Phe Thr Pro Asn Met Ile Cys Ala Gly Gly Glu Lys Gly
    610                 615                 620

Met Asp Ser Cys Lys Gly Asp Ser Gly Gly Ala Phe Ala Val Gln Asp
625                 630                 635                 640

Pro Asn Asp Lys Thr Lys Phe Tyr Ala Ala Gly Leu Val Ser Trp Gly
                645                 650                 655

Pro Gln Cys Gly Thr Tyr Gly Leu Tyr Thr Arg Val Lys Asn Tyr Val
            660                 665                 670

Asp Trp Ile Met Lys Thr Met Gln Glu Asn Ser Thr Pro Arg Glu Asp
        675                 680                 685

<210> SEQ ID NO 292
<211> LENGTH: 752
<212> TYPE: PRT
<213> ORGANISM: Homo sapiens

<400> SEQUENCE: 292

Met Gly Pro Leu Met Val Leu Phe Cys Leu Leu Phe Leu Tyr Pro Gly
1               5                   10                  15

Leu Ala Asp Ser Ala Pro Ser Cys Pro Gln Asn Val Asn Ile Ser Gly
            20                  25                  30

Gly Thr Phe Thr Leu Ser His Gly Trp Ala Pro Gly Ser Leu Leu Thr
        35                  40                  45

Tyr Ser Cys Pro Gln Gly Leu Tyr Pro Ser Pro Ala Ser Arg Leu Cys
    50                  55                  60

Lys Ser Ser Gly Gln Trp Gln Thr Pro Gly Ala Thr Arg Ser Leu Ser
65                  70                  75                  80

Lys Ala Val Cys Lys Pro Val Arg Cys Pro Ala Pro Val Ser Phe Glu
                85                  90                  95

Asn Gly Ile Tyr Thr Pro Arg Leu Gly Ser Tyr Pro Val Gly Gly Asn
            100                 105                 110

Val Ser Phe Glu Cys Glu Asp Gly Phe Ile Leu Arg Gly Ser Pro Val

-continued

```
                115                 120                 125
Arg Gln Cys Arg Pro Asn Gly Met Trp Asp Gly Glu Thr Ala Val Cys
    130                 135                 140

Asp Asn Gly Ala Gly His Cys Pro Asn Pro Gly Ile Ser Leu Gly Ala
145                 150                 155                 160

Val Arg Thr Gly Phe Arg Phe Gly His Gly Asp Lys Val Arg Tyr Arg
                165                 170                 175

Cys Ser Ser Asn Leu Val Leu Thr Gly Ser Ser Glu Arg Glu Cys Gln
            180                 185                 190

Gly Asn Gly Val Trp Ser Gly Thr Glu Pro Ile Cys Arg Gln Pro Tyr
        195                 200                 205

Ser Tyr Asp Phe Pro Glu Asp Val Ala Pro Ala Leu Gly Thr Ser Phe
    210                 215                 220

Ser His Met Leu Gly Ala Thr Asn Pro Thr Gln Lys Thr Lys Glu Ser
225                 230                 235                 240

Leu Gly Arg Lys Ile Gln Ile Gln Arg Ser Gly His Leu Asn Leu Tyr
                245                 250                 255

Leu Leu Leu Asp Cys Ser Gln Ser Val Ser Glu Asn Asp Phe Leu Ile
            260                 265                 270

Phe Lys Glu Ser Ala Ser Leu Met Val Asp Arg Ile Phe Ser Phe Glu
        275                 280                 285

Ile Asn Val Ser Val Ala Ile Ile Thr Phe Ala Ser Glu Pro Lys Val
    290                 295                 300

Leu Met Ser Val Leu Asn Asp Asn Ser Arg Asp Met Thr Glu Val Ile
305                 310                 315                 320

Ser Ser Leu Glu Asn Ala Asn Tyr Lys Asp His Glu Asn Gly Thr Gly
                325                 330                 335

Thr Asn Thr Tyr Ala Ala Leu Asn Ser Val Tyr Leu Met Met Asn Asn
            340                 345                 350

Gln Met Arg Leu Leu Gly Met Glu Thr Met Ala Trp Gln Glu Ile Arg
        355                 360                 365

His Ala Ile Ile Leu Leu Thr Asp Gly Lys Ser Asn Met Gly Gly Ser
    370                 375                 380

Pro Lys Thr Ala Val Asp His Ile Arg Glu Ile Leu Asn Ile Asn Gln
385                 390                 395                 400

Lys Arg Asn Asp Tyr Leu Asp Ile Tyr Ala Ile Gly Val Gly Lys Leu
                405                 410                 415

Asp Val Asp Trp Arg Glu Leu Asn Glu Leu Gly Ser Lys Lys Asp Gly
            420                 425                 430

Glu Arg His Ala Phe Ile Leu Gln Asp Thr Lys Ala Leu His Gln Val
        435                 440                 445

Phe Glu His Met Leu Asp Val Ser Lys Leu Thr Asp Thr Ile Cys Gly
    450                 455                 460

Val Gly Asn Met Ser Ala Asn Ala Ser Asp Gln Glu Arg Thr Pro Trp
465                 470                 475                 480

His Val Thr Ile Lys Pro Lys Ser Gln Glu Thr Cys Arg Gly Ala Leu
                485                 490                 495

Ile Ser Asp Gln Trp Val Leu Thr Ala Ala His Cys Phe Arg Asp Gly
            500                 505                 510

Asn Asp His Ser Leu Trp Arg Val Asn Val Gly Asp Pro Lys Ser Gln
        515                 520                 525

Trp Gly Lys Glu Phe Leu Ile Glu Lys Ala Val Ile Ser Pro Gly Phe
    530                 535                 540
```

```
Asp Val Phe Ala Lys Lys Asn Gln Gly Ile Leu Glu Phe Tyr Gly Asp
545                 550                 555                 560

Asp Ile Ala Leu Leu Lys Leu Ala Gln Lys Val Lys Met Ser Thr His
                565                 570                 575

Ala Arg Pro Ile Cys Leu Pro Cys Thr Met Glu Ala Asn Leu Ala Leu
                580                 585                 590

Arg Arg Pro Gln Gly Ser Thr Cys Arg Asp His Glu Asn Glu Leu Leu
            595                 600                 605

Asn Lys Gln Ser Val Pro Ala His Phe Val Ala Leu Asn Gly Ser Lys
        610                 615                 620

Leu Asn Ile Asn Leu Lys Met Gly Val Glu Trp Thr Ser Cys Ala Glu
625                 630                 635                 640

Val Val Ser Gln Glu Lys Thr Met Phe Pro Asn Leu Thr Asp Val Arg
                645                 650                 655

Glu Val Val Thr Asp Gln Phe Leu Cys Ser Gly Thr Gln Glu Asp Glu
                660                 665                 670

Ser Pro Cys Lys Gly Glu Ser Gly Gly Ala Val Phe Leu Glu Arg Arg
            675                 680                 685

Phe Arg Phe Phe Gln Val Gly Leu Val Ser Trp Gly Leu Tyr Asn Pro
        690                 695                 700

Cys Leu Gly Ser Ala Asp Lys Asn Ser Arg Lys Arg Ala Pro Arg Ser
705                 710                 715                 720

Lys Val Pro Pro Arg Asp Phe His Ile Asn Leu Phe Arg Met Gln
                725                 730                 735

Pro Trp Leu Arg Gln His Leu Gly Asp Val Leu Asn Phe Leu Pro Leu
            740                 745                 750

<210> SEQ ID NO 293
<211> LENGTH: 1663
<212> TYPE: PRT
<213> ORGANISM: Homo sapiens

<400> SEQUENCE: 293

Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
                20                  25                  30

Ile Leu Arg Leu Glu Ser Glu Glu Thr Met Val Leu Glu Ala His Asp
            35                  40                  45

Ala Gln Gly Asp Val Pro Val Thr Val Thr Val His Asp Phe Pro Gly
        50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
                100                 105                 110

Gly Thr Gln Val Val Glu Lys Val Val Leu Val Ser Leu Gln Ser Gly
            115                 120                 125

Tyr Leu Phe Ile Gln Thr Asp Lys Thr Ile Tyr Thr Pro Gly Ser Thr
        130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
```

-continued

```
            165                 170                 175
Gln Asp Ser Leu Ser Gln Asn Gln Leu Gly Val Leu Pro Leu Ser
            180                 185                 190

Trp Asp Ile Pro Glu Leu Val Asn Met Gly Gln Trp Lys Ile Arg Ala
            195                 200                 205

Tyr Tyr Glu Asn Ser Pro Gln Gln Val Phe Ser Thr Glu Phe Glu Val
            210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                    245                 250                 255

Ala Arg Phe Leu Tyr Gly Lys Lys Val Glu Gly Thr Ala Phe Val Ile
                    260                 265                 270

Phe Gly Ile Gln Asp Gly Glu Gln Arg Ile Ser Leu Pro Glu Ser Leu
                    275                 280                 285

Lys Arg Ile Pro Ile Glu Asp Gly Ser Gly Glu Val Val Leu Ser Arg
                    290                 295                 300

Lys Val Leu Leu Asp Gly Val Gln Asn Leu Arg Ala Glu Asp Leu Val
305                 310                 315                 320

Gly Lys Ser Leu Tyr Val Ser Ala Thr Val Ile Leu His Ser Gly Ser
                    325                 330                 335

Asp Met Val Gln Ala Glu Arg Ser Gly Ile Pro Ile Val Thr Ser Pro
                    340                 345                 350

Tyr Gln Ile His Phe Thr Lys Thr Pro Lys Tyr Phe Lys Pro Gly Met
                    355                 360                 365

Pro Phe Asp Leu Met Val Phe Val Thr Asn Pro Asp Gly Ser Pro Ala
                    370                 375                 380

Tyr Arg Val Pro Val Ala Val Gln Gly Glu Asp Thr Val Gln Ser Leu
385                 390                 395                 400

Thr Gln Gly Asp Gly Val Ala Lys Leu Ser Ile Asn Thr His Pro Ser
                    405                 410                 415

Gln Lys Pro Leu Ser Ile Thr Val Arg Thr Lys Lys Gln Glu Leu Ser
                    420                 425                 430

Glu Ala Glu Gln Ala Thr Arg Thr Met Gln Ala Leu Pro Tyr Ser Thr
                    435                 440                 445

Val Gly Asn Ser Asn Asn Tyr Leu His Leu Ser Val Leu Arg Thr Glu
                    450                 455                 460

Leu Arg Pro Gly Glu Thr Leu Asn Val Asn Phe Leu Leu Arg Met Asp
465                 470                 475                 480

Arg Ala His Glu Ala Lys Ile Arg Tyr Tyr Thr Tyr Leu Ile Met Asn
                    485                 490                 495

Lys Gly Arg Leu Leu Lys Ala Gly Arg Gln Val Arg Glu Pro Gly Gln
                    500                 505                 510

Asp Leu Val Val Leu Pro Leu Ser Ile Thr Thr Asp Phe Ile Pro Ser
                    515                 520                 525

Phe Arg Leu Val Ala Tyr Tyr Thr Leu Ile Gly Ala Ser Gly Gln Arg
                    530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                    565                 570                 575

Pro Gly Gln Gln Met Thr Leu Lys Ile Glu Gly Asp His Gly Ala Arg
                    580                 585                 590
```

```
Val Val Leu Val Ala Val Asp Lys Gly Val Phe Val Leu Asn Lys Lys
            595                 600                 605

Asn Lys Leu Thr Gln Ser Lys Ile Trp Asp Val Val Glu Lys Ala Asp
        610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Gly Gln Gln Thr Ala Gln
                645                 650                 655

Arg Ala Glu Leu Gln Cys Pro Gln Pro Ala Arg Arg Arg Ser
        660                 665                 670

Val Gln Leu Thr Glu Lys Arg Met Asp Lys Val Gly Lys Tyr Pro Lys
            675                 680                 685

Glu Leu Arg Lys Cys Cys Glu Asp Gly Met Arg Glu Asn Pro Met Arg
        690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
            740                 745                 750

Glu Asp Ile Ile Ala Glu Glu Asn Ile Val Ser Arg Ser Glu Phe Pro
                755                 760                 765

Glu Ser Trp Leu Trp Asn Val Glu Asp Leu Lys Glu Pro Pro Lys Asn
        770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
            805                 810                 815

Val Ala Asp Pro Phe Glu Val Thr Val Met Gln Asp Phe Phe Ile Asp
                820                 825                 830

Leu Arg Leu Pro Tyr Ser Val Arg Asn Glu Gln Val Glu Ile Arg
        835                 840                 845

Ala Val Leu Tyr Asn Tyr Arg Gln Asn Gln Glu Leu Lys Val Arg Val
            850                 855                 860

Glu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
                885                 890                 895

Pro Tyr Val Ile Val Pro Leu Lys Thr Gly Leu Gln Glu Val Glu Val
            900                 905                 910

Lys Ala Ala Val Tyr His His Phe Ile Ser Asp Gly Val Arg Lys Ser
        915                 920                 925

Leu Lys Val Val Pro Glu Gly Ile Arg Met Asn Lys Thr Val Ala Val
        930                 935                 940

Arg Thr Leu Asp Pro Glu Arg Leu Gly Arg Glu Gly Val Gln Lys Glu
945                 950                 955                 960

Asp Ile Pro Pro Ala Asp Leu Ser Asp Gln Val Pro Asp Thr Glu Ser
                965                 970                 975

Glu Thr Arg Ile Leu Leu Gln Gly Thr Pro Val Ala Gln Met Thr Glu
            980                 985                 990

Asp Ala Val Asp Ala Glu Arg Leu  Lys His Leu Ile Val  Thr Pro Ser
            995                 1000                1005
```

```
Gly Cys Gly Glu Gln Asn Met Ile Gly Met Thr Pro Thr Val Ile
    1010                1015                1020

Ala Val His Tyr Leu Asp Glu Thr Glu Gln Trp Glu Lys Phe Gly
    1025                1030                1035

Leu Glu Lys Arg Gln Gly Ala Leu Glu Leu Ile Lys Lys Gly Tyr
    1040                1045                1050

Thr Gln Gln Leu Ala Phe Arg Gln Pro Ser Ser Ala Phe Ala Ala
    1055                1060                1065

Phe Val Lys Arg Ala Pro Ser Thr Trp Leu Thr Ala Tyr Val Val
    1070                1075                1080

Lys Val Phe Ser Leu Ala Val Asn Leu Ile Ala Ile Asp Ser Gln
    1085                1090                1095

Val Leu Cys Gly Ala Val Lys Trp Leu Ile Leu Glu Lys Gln Lys
    1100                1105                1110

Pro Asp Gly Val Phe Gln Glu Asp Ala Pro Val Ile His Gln Glu
    1115                1120                1125

Met Ile Gly Gly Leu Arg Asn Asn Asn Glu Lys Asp Met Ala Leu
    1130                1135                1140

Thr Ala Phe Val Leu Ile Ser Leu Gln Glu Ala Lys Asp Ile Cys
    1145                1150                1155

Glu Glu Gln Val Asn Ser Leu Pro Gly Ser Ile Thr Lys Ala Gly
    1160                1165                1170

Asp Phe Leu Glu Ala Asn Tyr Met Asn Leu Gln Arg Ser Tyr Thr
    1175                1180                1185

Val Ala Ile Ala Gly Tyr Ala Leu Ala Gln Met Gly Arg Leu Lys
    1190                1195                1200

Gly Pro Leu Leu Asn Lys Phe Leu Thr Thr Ala Lys Asp Lys Asn
    1205                1210                1215

Arg Trp Glu Asp Pro Gly Lys Gln Leu Tyr Asn Val Glu Ala Thr
    1220                1225                1230

Ser Tyr Ala Leu Leu Ala Leu Leu Gln Leu Lys Asp Phe Asp Phe
    1235                1240                1245

Val Pro Pro Val Val Arg Trp Leu Asn Glu Gln Arg Tyr Tyr Gly
    1250                1255                1260

Gly Gly Tyr Gly Ser Thr Gln Ala Thr Phe Met Val Phe Gln Ala
    1265                1270                1275

Leu Ala Gln Tyr Gln Lys Asp Ala Pro Asp His Gln Glu Leu Asn
    1280                1285                1290

Leu Asp Val Ser Leu Gln Leu Pro Ser Arg Ser Ser Lys Ile Thr
    1295                1300                1305

His Arg Ile His Trp Glu Ser Ala Ser Leu Leu Arg Ser Glu Glu
    1310                1315                1320

Thr Lys Glu Asn Glu Gly Phe Thr Val Thr Ala Glu Gly Lys Gly
    1325                1330                1335

Gln Gly Thr Leu Ser Val Val Thr Met Tyr His Ala Lys Ala Lys
    1340                1345                1350

Asp Gln Leu Thr Cys Asn Lys Phe Asp Leu Lys Val Thr Ile Lys
    1355                1360                1365

Pro Ala Pro Glu Thr Glu Lys Arg Pro Gln Asp Ala Lys Asn Thr
    1370                1375                1380

Met Ile Leu Glu Ile Cys Thr Arg Tyr Arg Gly Asp Gln Asp Ala
    1385                1390                1395

Thr Met Ser Ile Leu Asp Ile Ser Met Met Thr Gly Phe Ala Pro
```

```
                  1400               1405                1410

Asp Thr  Asp Asp Leu Lys Gln  Leu Ala Asn Gly Val  Asp Arg Tyr
    1415               1420                1425

Ile Ser  Lys Tyr Glu Leu Asp  Lys Ala Phe Ser Asp  Arg Asn Thr
    1430               1435                1440

Leu Ile  Ile Tyr Leu Asp Lys  Val Ser His Ser Glu  Asp Asp Cys
    1445               1450                1455

Leu Ala  Phe Lys Val His Gln  Tyr Phe Asn Val Glu  Leu Ile Gln
    1460               1465                1470

Pro Gly  Ala Val Lys Val Tyr  Ala Tyr Tyr Asn Leu  Glu Glu Ser
    1475               1480                1485

Cys Thr  Arg Phe Tyr His Pro  Glu Lys Glu Asp Gly  Lys Leu Asn
    1490               1495                1500

Lys Leu  Cys Arg Asp Glu Leu  Cys Arg Cys Ala Glu  Glu Asn Cys
    1505               1510                1515

Phe Ile  Gln Lys Ser Asp Asp  Lys Val Thr Leu Glu  Glu Arg Leu
    1520               1525                1530

Asp Lys  Ala Cys Glu Pro Gly  Val Asp Tyr Val Tyr  Lys Thr Arg
    1535               1540                1545

Leu Val  Lys Val Gln Leu Ser  Asn Asp Phe Asp Glu  Tyr Ile Met
    1550               1555                1560

Ala Ile  Glu Gln Thr Ile Lys  Ser Gly Ser Asp Glu  Val Gln Val
    1565               1570                1575

Gly Gln  Gln Arg Thr Phe Ile  Ser Pro Ile Lys Cys  Arg Glu Ala
    1580               1585                1590

Leu Lys  Leu Glu Glu Lys Lys  His Tyr Leu Met Trp  Gly Leu Ser
    1595               1600                1605

Ser Asp  Phe Trp Gly Glu Lys  Pro Asn Leu Ser Tyr  Ile Ile Gly
    1610               1615                1620

Lys Asp  Thr Trp Val Glu His  Trp Pro Glu Glu Asp  Glu Cys Gln
    1625               1630                1635

Asp Glu  Glu Asn Gln Lys Gln  Cys Gln Asp Leu Gly  Ala Phe Thr
    1640               1645                1650

Glu Ser  Met Val Val Phe Gly  Cys Pro Asn
    1655               1660

<210> SEQ ID NO 294
<211> LENGTH: 597
<212> TYPE: PRT
<213> ORGANISM: Homo sapiens

<400> SEQUENCE: 294

Met His  Pro Pro Lys Thr Pro  Ser Gly Ala Leu His  Arg Lys Arg Lys
1                   5                    10                   15

Met Ala  Ala Trp Pro Phe Ser  Arg Leu Trp Lys Val  Ser Asp Pro Ile
                    20                   25                   30

Leu Phe  Gln Met Thr Leu Ile  Ala Ala Leu Leu Pro  Ala Val Leu Gly
              35                   40                   45

Asn Cys  Gly Pro Pro Pro Thr  Leu Ser Phe Ala Ala  Pro Met Asp Ile
         50                   55                   60

Thr Leu  Thr Glu Thr Arg Phe  Lys Thr Gly Thr Thr  Leu Lys Tyr Thr
65                   70                   75                   80

Cys Leu  Pro Gly Tyr Val Arg  Ser His Ser Thr Gln  Thr Leu Thr Cys
                    85                   90                   95
```

-continued

Asn Ser Asp Gly Glu Trp Val Tyr Asn Thr Phe Cys Ile Tyr Lys Arg
            100                 105                 110

Cys Arg His Pro Gly Glu Leu Arg Asn Gly Gln Val Glu Ile Lys Thr
        115                 120                 125

Asp Leu Ser Phe Gly Ser Gln Ile Glu Phe Ser Cys Ser Glu Gly Phe
    130                 135                 140

Phe Leu Ile Gly Ser Thr Thr Ser Arg Cys Glu Val Gln Asp Arg Gly
145                 150                 155                 160

Val Gly Trp Ser His Pro Leu Pro Gln Cys Glu Ile Val Lys Cys Lys
                165                 170                 175

Pro Pro Pro Asp Ile Arg Asn Gly Arg His Ser Gly Glu Glu Asn Phe
            180                 185                 190

Tyr Ala Tyr Gly Phe Ser Val Thr Tyr Ser Cys Asp Pro Arg Phe Ser
        195                 200                 205

Leu Leu Gly His Ala Ser Ile Ser Cys Thr Val Glu Asn Glu Thr Ile
    210                 215                 220

Gly Val Trp Arg Pro Ser Pro Pro Thr Cys Glu Lys Ile Thr Cys Arg
225                 230                 235                 240

Lys Pro Asp Val Ser His Gly Glu Met Val Ser Gly Phe Gly Pro Ile
                245                 250                 255

Tyr Asn Tyr Lys Asp Thr Ile Val Phe Lys Cys Gln Lys Gly Phe Val
            260                 265                 270

Leu Arg Gly Ser Ser Val Ile His Cys Asp Ala Asp Ser Lys Trp Asn
        275                 280                 285

Pro Ser Pro Pro Ala Cys Glu Pro Asn Ser Cys Ile Asn Leu Pro Asp
    290                 295                 300

Ile Pro His Ala Ser Trp Glu Thr Tyr Pro Arg Pro Thr Lys Glu Asp
305                 310                 315                 320

Val Tyr Val Val Gly Thr Val Leu Arg Tyr Arg Cys His Pro Gly Tyr
                325                 330                 335

Lys Pro Thr Thr Asp Glu Pro Thr Thr Val Ile Cys Gln Lys Asn Leu
            340                 345                 350

Arg Trp Thr Pro Tyr Gln Gly Cys Glu Ala Leu Cys Cys Pro Glu Pro
        355                 360                 365

Lys Leu Asn Asn Gly Glu Ile Thr Gln His Arg Lys Ser Arg Pro Ala
    370                 375                 380

Asn His Cys Val Tyr Phe Tyr Gly Asp Glu Ile Ser Phe Ser Cys His
385                 390                 395                 400

Glu Thr Ser Arg Phe Ser Ala Ile Cys Gln Gly Asp Gly Thr Trp Ser
                405                 410                 415

Pro Arg Thr Pro Ser Cys Gly Asp Ile Cys Asn Phe Pro Pro Lys Ile
            420                 425                 430

Ala His Gly His Tyr Lys Gln Ser Ser Ser Tyr Ser Phe Phe Lys Glu
        435                 440                 445

Glu Ile Ile Tyr Glu Cys Asp Lys Gly Tyr Ile Leu Val Gly Gln Ala
    450                 455                 460

Lys Leu Ser Cys Ser Tyr Ser His Trp Ser Ala Pro Ala Pro Gln Cys
465                 470                 475                 480

Lys Ala Leu Cys Arg Lys Pro Glu Leu Val Asn Gly Arg Leu Ser Val
                485                 490                 495

Asp Lys Asp Gln Tyr Val Glu Pro Glu Asn Val Thr Ile Gln Cys Asp
            500                 505                 510

Ser Gly Tyr Gly Val Val Gly Pro Gln Ser Ile Thr Cys Ser Gly Asn

```
            515                 520                 525
Arg Thr Trp Tyr Pro Glu Val Pro Lys Cys Glu Trp Glu Thr Pro Glu
            530                 535                 540

Gly Cys Glu Gln Val Leu Thr Gly Lys Arg Leu Met Gln Cys Leu Pro
545                 550                 555                 560

Asn Pro Glu Asp Val Lys Met Ala Leu Glu Val Tyr Lys Leu Ser Leu
            565                 570                 575

Glu Ile Glu Gln Leu Glu Leu Gln Arg Asp Ser Ala Arg Gln Ser Thr
            580                 585                 590

Leu Asp Lys Glu Leu
            595

<210> SEQ ID NO 295
<211> LENGTH: 1744
<212> TYPE: PRT
<213> ORGANISM: Homo sapiens

<400> SEQUENCE: 295

Met Arg Leu Leu Trp Gly Leu Ile Trp Ala Ser Ser Phe Phe Thr Leu
1               5                   10                  15

Ser Leu Gln Lys Pro Arg Leu Leu Phe Ser Pro Ser Val Val His
            20                  25                  30

Leu Gly Val Pro Leu Ser Val Gly Val Gln Leu Gln Asp Val Pro Arg
        35                  40                  45

Gly Gln Val Val Lys Gly Ser Val Phe Leu Arg Asn Pro Ser Arg Asn
    50                  55                  60

Asn Val Pro Cys Ser Pro Lys Val Asp Phe Thr Leu Ser Ser Glu Arg
65                  70                  75                  80

Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
    130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
    210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
        275                 280                 285
```

```
Glu Asp Gly Lys Lys Thr Phe Phe Arg Gly Leu Glu Ser Gln Thr Lys
    290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                    325                 330                 335

Arg Leu Tyr Val Ala Ala Ile Ile Glu Ser Pro Gly Gly Glu Met
                340                 345                 350

Glu Glu Ala Glu Leu Thr Ser Trp Tyr Phe Val Ser Ser Pro Phe Ser
                355                 360                 365

Leu Asp Leu Ser Lys Thr Lys Arg His Leu Val Pro Gly Ala Pro Phe
370                 375                 380

Leu Leu Gln Ala Leu Val Arg Glu Met Ser Gly Ser Pro Ala Ser Gly
385                 390                 395                 400

Ile Pro Val Lys Val Ser Ala Thr Val Ser Ser Pro Gly Ser Val Pro
                405                 410                 415

Glu Val Gln Asp Ile Gln Gln Asn Thr Asp Gly Ser Gly Gln Val Ser
                420                 425                 430

Ile Pro Ile Ile Ile Pro Gln Thr Ile Ser Glu Leu Gln Leu Ser Val
                435                 440                 445

Ser Ala Gly Ser Pro His Pro Ala Ile Ala Arg Leu Thr Val Ala Ala
450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
                485                 490                 495

Gly Ser Gly Ala Thr Phe Ser His Tyr Tyr Tyr Met Ile Leu Ser Arg
                500                 505                 510

Gly Gln Ile Val Phe Met Asn Arg Glu Pro Lys Arg Thr Leu Thr Ser
                515                 520                 525

Val Ser Val Phe Val Asp His His Leu Ala Pro Ser Phe Tyr Phe Val
530                 535                 540

Ala Phe Tyr Tyr His Gly Asp His Pro Val Ala Asn Ser Leu Arg Val
545                 550                 555                 560

Asp Val Gln Ala Gly Ala Cys Glu Gly Lys Leu Glu Leu Ser Val Asp
                565                 570                 575

Gly Ala Lys Gln Tyr Arg Asn Gly Glu Ser Val Lys Leu His Leu Glu
                580                 585                 590

Thr Asp Ser Leu Ala Leu Val Ala Leu Gly Ala Leu Asp Thr Ala Leu
                595                 600                 605

Tyr Ala Ala Gly Ser Lys Ser His Lys Pro Leu Asn Met Gly Lys Val
                610                 615                 620

Phe Glu Ala Met Asn Ser Tyr Asp Leu Gly Cys Gly Pro Gly Gly Gly
625                 630                 635                 640

Asp Ser Ala Leu Gln Val Phe Gln Ala Ala Gly Leu Ala Phe Ser Asp
                645                 650                 655

Gly Asp Gln Trp Thr Leu Ser Arg Lys Arg Leu Ser Cys Pro Lys Glu
                660                 665                 670

Lys Thr Thr Arg Lys Lys Arg Asn Val Asn Phe Gln Lys Ala Ile Asn
                675                 680                 685

Glu Lys Leu Gly Gln Tyr Ala Ser Pro Thr Ala Lys Arg Cys Cys Gln
690                 695                 700

Asp Gly Val Thr Arg Leu Pro Met Met Arg Ser Cys Glu Gln Arg Ala
```

```
             705                 710                 715                 720
Ala Arg Val Gln Gln Pro Asp Cys Arg Glu Pro Phe Leu Ser Cys Cys
                    725                 730                 735
Gln Phe Ala Glu Ser Leu Arg Lys Lys Ser Arg Asp Lys Gly Gln Ala
                    740                 745                 750
Gly Leu Gln Arg Ala Leu Glu Ile Leu Gln Glu Asp Leu Ile Asp
                    755                 760                 765
Glu Asp Asp Ile Pro Val Arg Ser Phe Phe Pro Glu Asn Trp Leu Trp
                    770                 775                 780
Arg Val Glu Thr Val Asp Arg Phe Gln Ile Leu Thr Leu Trp Leu Pro
785                 790                 795                 800
Asp Ser Leu Thr Thr Trp Glu Ile His Gly Leu Ser Leu Ser Lys Thr
                    805                 810                 815
Lys Gly Leu Cys Val Ala Thr Pro Val Gln Leu Arg Val Phe Arg Glu
                    820                 825                 830
Phe His Leu His Leu Arg Leu Pro Met Ser Val Arg Arg Phe Glu Gln
                    835                 840                 845
Leu Glu Leu Arg Pro Val Leu Tyr Asn Tyr Leu Asp Lys Asn Leu Thr
850                 855                 860
Val Ser Val His Val Ser Pro Val Glu Gly Leu Cys Leu Ala Gly Gly
865                 870                 875                 880
Gly Gly Leu Ala Gln Gln Val Leu Val Pro Ala Gly Ser Ala Arg Pro
                    885                 890                 895
Val Ala Phe Ser Val Val Pro Thr Ala Ala Thr Ala Val Ser Leu Lys
                    900                 905                 910
Val Val Ala Arg Gly Ser Phe Glu Phe Pro Val Gly Asp Ala Val Ser
                    915                 920                 925
Lys Val Leu Gln Ile Glu Lys Glu Gly Ala Ile His Arg Glu Glu Leu
                    930                 935                 940
Val Tyr Glu Leu Asn Pro Leu Asp His Arg Gly Arg Thr Leu Glu Ile
945                 950                 955                 960
Pro Gly Asn Ser Asp Pro Asn Met Ile Pro Asp Gly Asp Phe Asn Ser
                    965                 970                 975
Tyr Val Arg Val Thr Ala Ser Asp Pro Leu Asp Thr Leu Gly Ser Glu
                    980                 985                 990
Gly Ala Leu Ser Pro Gly Gly Val Ala Ser Leu Leu Arg Leu Pro Arg
                    995                 1000                1005
Gly Cys Gly Glu Gln Thr Met Ile Tyr Leu Ala Pro Thr Leu Ala
    1010                1015                1020
Ala Ser Arg Tyr Leu Asp Lys Thr Glu Gln Trp Ser Thr Leu Pro
    1025                1030                1035
Pro Glu Thr Lys Asp His Ala Val Asp Leu Ile Gln Lys Gly Tyr
    1040                1045                1050
Met Arg Ile Gln Gln Phe Arg Lys Ala Asp Gly Ser Tyr Ala Ala
    1055                1060                1065
Trp Leu Ser Arg Gly Ser Ser Thr Trp Leu Thr Ala Phe Val Leu
    1070                1075                1080
Lys Val Leu Ser Leu Ala Gln Glu Gln Val Gly Gly Ser Pro Glu
    1085                1090                1095
Lys Leu Gln Glu Thr Ser Asn Trp Leu Leu Ser Gln Gln Gln Ala
    1100                1105                1110
Asp Gly Ser Phe Gln Asp Leu Ser Pro Val Ile His Arg Ser Met
    1115                1120                1125
```

-continued

```
Gln Gly Gly Leu Val Gly Asn Asp Glu Thr Val Ala Leu Thr Ala
    1130            1135                1140

Phe Val Thr Ile Ala Leu His His Gly Leu Ala Val Phe Gln Asp
    1145            1150                1155

Glu Gly Ala Glu Pro Leu Lys Gln Arg Val Glu Ala Ser Ile Ser
    1160            1165                1170

Lys Ala Ser Ser Phe Leu Gly Glu Lys Ala Ser Ala Gly Leu Leu
    1175            1180                1185

Gly Ala His Ala Ala Ala Ile Thr Ala Tyr Ala Leu Thr Leu Thr
    1190            1195                1200

Lys Ala Pro Ala Asp Leu Arg Gly Val Ala His Asn Asn Leu Met
    1205            1210                1215

Ala Met Ala Gln Glu Thr Gly Asp Asn Leu Tyr Trp Gly Ser Val
    1220            1225                1230

Thr Gly Ser Gln Ser Asn Ala Val Ser Pro Thr Pro Ala Pro Arg
    1235            1240                1245

Asn Pro Ser Asp Pro Met Pro Gln Ala Pro Ala Leu Trp Ile Glu
    1250            1255                1260

Thr Thr Ala Tyr Ala Leu Leu His Leu Leu Leu His Glu Gly Lys
    1265            1270                1275

Ala Glu Met Ala Asp Gln Ala Ala Ala Trp Leu Thr Arg Gln Gly
    1280            1285                1290

Ser Phe Gln Gly Gly Phe Arg Ser Thr Gln Asp Thr Val Ile Ala
    1295            1300                1305

Leu Asp Ala Leu Ser Ala Tyr Trp Ile Ala Ser His Thr Thr Glu
    1310            1315                1320

Glu Arg Gly Leu Asn Val Thr Leu Ser Ser Thr Gly Arg Asn Gly
    1325            1330                1335

Phe Lys Ser His Ala Leu Gln Leu Asn Asn Arg Gln Ile Arg Gly
    1340            1345                1350

Leu Glu Glu Glu Leu Gln Phe Ser Leu Gly Ser Lys Ile Asn Val
    1355            1360                1365

Lys Val Gly Gly Asn Ser Lys Gly Thr Leu Lys Val Leu Arg Thr
    1370            1375                1380

Tyr Asn Val Leu Asp Met Lys Asn Thr Thr Cys Gln Asp Leu Gln
    1385            1390                1395

Ile Glu Val Thr Val Lys Gly His Val Glu Tyr Thr Met Glu Ala
    1400            1405                1410

Asn Glu Asp Tyr Glu Asp Tyr Glu Tyr Asp Glu Leu Pro Ala Lys
    1415            1420                1425

Asp Asp Pro Asp Ala Pro Leu Gln Pro Val Thr Pro Leu Gln Leu
    1430            1435                1440

Phe Glu Gly Arg Arg Asn Arg Arg Arg Arg Glu Ala Pro Lys Val
    1445            1450                1455

Val Glu Glu Gln Glu Ser Arg Val His Tyr Thr Val Cys Ile Trp
    1460            1465                1470

Arg Asn Gly Lys Val Gly Leu Ser Gly Met Ala Ile Ala Asp Val
    1475            1480                1485

Thr Leu Leu Ser Gly Phe His Ala Leu Arg Ala Asp Leu Glu Lys
    1490            1495                1500

Leu Thr Ser Leu Ser Asp Arg Tyr Val Ser His Phe Glu Thr Glu
    1505            1510                1515
```

```
Gly Pro His Val Leu Leu Tyr Phe Asp Ser Val Pro Thr Ser Arg
    1520                1525                1530

Glu Cys Val Gly Phe Glu Ala Val Gln Glu Val Pro Val Gly Leu
    1535                1540                1545

Val Gln Pro Ala Ser Ala Thr Leu Tyr Asp Tyr Tyr Asn Pro Glu
    1550                1555                1560

Arg Arg Cys Ser Val Phe Tyr Gly Ala Pro Ser Lys Ser Arg Leu
    1565                1570                1575

Leu Ala Thr Leu Cys Ser Ala Glu Val Cys Gln Cys Ala Glu Gly
    1580                1585                1590

Lys Cys Pro Arg Gln Arg Ala Leu Glu Arg Gly Leu Gln Asp
    1595                1600                1605

Glu Asp Gly Tyr Arg Met Lys Phe Ala Cys Tyr Tyr Pro Arg Val
    1610                1615                1620

Glu Tyr Gly Phe Gln Val Lys Val Leu Arg Glu Asp Ser Arg Ala
    1625                1630                1635

Ala Phe Arg Leu Phe Glu Thr Lys Ile Thr Gln Val Leu His Phe
    1640                1645                1650

Thr Lys Asp Val Lys Ala Ala Asn Gln Met Arg Asn Phe Leu
    1655                1660                1665

Val Arg Ala Ser Cys Arg Leu Arg Leu Glu Pro Gly Lys Glu Tyr
    1670                1675                1680

Leu Ile Met Gly Leu Asp Gly Ala Thr Tyr Asp Leu Glu Gly His
    1685                1690                1695

Pro Gln Tyr Leu Leu Asp Ser Asn Ser Trp Ile Glu Glu Met Pro
    1700                1705                1710

Ser Glu Arg Leu Cys Arg Ser Thr Arg Gln Arg Ala Ala Cys Ala
    1715                1720                1725

Gln Leu Asn Asp Phe Leu Gln Glu Tyr Gly Thr Gln Gly Cys Gln
    1730                1735                1740

Val

<210> SEQ ID NO 296
<211> LENGTH: 1676
<212> TYPE: PRT
<213> ORGANISM: Homo sapiens

<400> SEQUENCE: 296

Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
                20                  25                  30

Val Gly Ala Ser Glu Asn Ile Val Ile Gln Val Tyr Gly Tyr Thr Glu
            35                  40                  45

Ala Phe Asp Ala Thr Ile Ser Ile Lys Ser Tyr Pro Asp Lys Lys Phe
        50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
            100                 105                 110

Lys Ser Lys Arg Met Pro Ile Thr Tyr Asp Asn Gly Phe Leu Phe Ile
        115                 120                 125
```

His Thr Asp Lys Pro Val Tyr Thr Pro Asp Gln Ser Val Lys Val Arg
130                 135                 140

Val Tyr Ser Leu Asn Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
        195                 200                 205

Phe Ser Thr Thr Gly Thr Ala Tyr Phe Glu Val Lys Glu Tyr Val Leu
210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
            260                 265                 270

Glu Asp Leu Lys Asp Asp Gln Lys Glu Met Met Gln Thr Ala Met Gln
        275                 280                 285

Asn Thr Met Leu Ile Asn Gly Ile Ala Gln Val Thr Phe Asp Ser Glu
290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
            340                 345                 350

Lys Leu Asn Leu Val Ala Thr Pro Leu Phe Leu Lys Pro Gly Ile Pro
        355                 360                 365

Tyr Pro Ile Lys Val Gln Val Lys Asp Ser Leu Asp Gln Leu Val Gly
370                 375                 380

Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
                405                 410                 415

Val Ala Ser Phe Val Leu Asn Leu Pro Ser Gly Val Thr Val Leu Glu
            420                 425                 430

Phe Asn Val Lys Thr Asp Ala Pro Asp Leu Pro Glu Glu Asn Gln Ala
        435                 440                 445

Arg Glu Gly Tyr Arg Ala Ile Ala Tyr Ser Ser Leu Ser Gln Ser Tyr
450                 455                 460

Leu Tyr Ile Asp Trp Thr Asp Asn His Lys Ala Leu Leu Val Gly Glu
465                 470                 475                 480

His Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
            500                 505                 510

Gly Thr Arg Glu Lys Phe Ser Asp Ala Ser Tyr Gln Ser Ile Asn Ile
        515                 520                 525

Pro Val Thr Gln Asn Met Val Pro Ser Ser Arg Leu Leu Val Tyr Tyr
530                 535                 540

Ile Val Thr Gly Glu Gln Thr Ala Glu Leu Val Ser Asp Ser Val Trp

```
               545                 550                 555                 560
Leu Asn Ile Glu Glu Lys Cys Gly Asn Gln Leu Gln Val His Leu Ser
                565                 570                 575

Pro Asp Ala Asp Ala Tyr Ser Pro Gly Gln Thr Val Ser Leu Asn Met
                580                 585                 590

Ala Thr Gly Met Asp Ser Trp Val Ala Leu Ala Ala Val Asp Ser Ala
                595                 600                 605

Val Tyr Gly Val Gln Arg Gly Ala Lys Lys Pro Leu Glu Arg Val Phe
                610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
                660                 665                 670

Leu Arg Pro Arg Arg Thr Leu Gln Lys Lys Ile Glu Glu Ile Ala Ala
                675                 680                 685

Lys Tyr Lys His Ser Val Val Lys Cys Cys Tyr Asp Gly Ala Cys
                690                 695                 700

Val Asn Asn Asp Glu Thr Cys Glu Gln Arg Ala Ala Arg Ile Ser Leu
705                 710                 715                 720

Gly Pro Arg Cys Ile Lys Ala Phe Thr Glu Cys Cys Val Val Ala Ser
                725                 730                 735

Gln Leu Arg Ala Asn Ile Ser His Lys Asp Met Gln Leu Gly Arg Leu
                740                 745                 750

His Met Lys Thr Leu Leu Pro Val Ser Lys Pro Glu Ile Arg Ser Tyr
                755                 760                 765

Phe Pro Glu Ser Trp Leu Trp Glu Val His Leu Val Pro Arg Arg Lys
                770                 775                 780

Gln Leu Gln Phe Ala Leu Pro Asp Ser Leu Thr Thr Trp Glu Ile Gln
785                 790                 795                 800

Gly Val Gly Ile Ser Asn Thr Gly Ile Cys Val Ala Asp Thr Val Lys
                805                 810                 815

Ala Lys Val Phe Lys Asp Val Phe Leu Glu Met Asn Ile Pro Tyr Ser
                820                 825                 830

Val Val Arg Gly Glu Gln Ile Gln Leu Lys Gly Thr Val Tyr Asn Tyr
                835                 840                 845

Arg Thr Ser Gly Met Gln Phe Cys Val Lys Met Ser Ala Val Glu Gly
                850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser His Leu Val
                885                 890                 895

Thr Phe Thr Val Leu Pro Leu Glu Ile Gly Leu His Asn Ile Asn Phe
                900                 905                 910

Ser Leu Glu Thr Trp Phe Gly Lys Glu Ile Leu Val Lys Thr Leu Arg
                915                 920                 925

Val Val Pro Glu Gly Val Lys Arg Glu Ser Tyr Ser Gly Val Thr Leu
                930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                965                 970                 975
```

```
Leu Ser Val Lys Gly Leu Leu Val Gly Glu Ile Leu Ser Ala Val Leu
            980                 985                 990

Ser Gln Glu Gly Ile Asn Ile Leu Thr His Leu Pro Lys Gly Ser Ala
            995                 1000                1005

Glu Ala Glu Leu Met Ser Val Pro Val Phe Tyr Val Phe His
        1010                1015                1020

Tyr Leu Glu Thr Gly Asn His Trp Asn Ile Phe His Ser Asp Pro
        1025                1030                1035

Leu Ile Glu Lys Gln Lys Leu Lys Lys Lys Leu Lys Glu Gly Met
        1040                1045                1050

Leu Ser Ile Met Ser Tyr Arg Asn Ala Asp Tyr Ser Tyr Ser Val
        1055                1060                1065

Trp Lys Gly Gly Ser Ala Ser Thr Trp Leu Thr Ala Phe Ala Leu
        1070                1075                1080

Arg Val Leu Gly Gln Val Asn Lys Tyr Val Glu Gln Asn Gln Asn
        1085                1090                1095

Ser Ile Cys Asn Ser Leu Leu Trp Leu Val Glu Asn Tyr Gln Leu
        1100                1105                1110

Asp Asn Gly Ser Phe Lys Glu Asn Ser Gln Tyr Gln Pro Ile Lys
        1115                1120                1125

Leu Gln Gly Thr Leu Pro Val Glu Ala Arg Glu Asn Ser Leu Tyr
        1130                1135                1140

Leu Thr Ala Phe Thr Val Ile Gly Ile Arg Lys Ala Phe Asp Ile
        1145                1150                1155

Cys Pro Leu Val Lys Ile Asp Thr Ala Leu Ile Lys Ala Asp Asn
        1160                1165                1170

Phe Leu Leu Glu Asn Thr Leu Pro Ala Gln Ser Thr Phe Thr Leu
        1175                1180                1185

Ala Ile Ser Ala Tyr Ala Leu Ser Leu Gly Asp Lys Thr His Pro
        1190                1195                1200

Gln Phe Arg Ser Ile Val Ser Ala Leu Lys Arg Glu Ala Leu Val
        1205                1210                1215

Lys Gly Asn Pro Pro Ile Tyr Arg Phe Trp Lys Asp Asn Leu Gln
        1220                1225                1230

His Lys Asp Ser Ser Val Pro Asn Thr Gly Thr Ala Arg Met Val
        1235                1240                1245

Glu Thr Thr Ala Tyr Ala Leu Leu Thr Ser Leu Asn Leu Lys Asp
        1250                1255                1260

Ile Asn Tyr Val Asn Pro Val Ile Lys Trp Leu Ser Glu Glu Gln
        1265                1270                1275

Arg Tyr Gly Gly Gly Phe Tyr Ser Thr Gln Asp Thr Ile Asn Ala
        1280                1285                1290

Ile Glu Gly Leu Thr Glu Tyr Ser Leu Leu Val Lys Gln Leu Arg
        1295                1300                1305

Leu Ser Met Asp Ile Asp Val Ser Tyr Lys His Lys Gly Ala Leu
        1310                1315                1320

His Asn Tyr Lys Met Thr Asp Lys Asn Phe Leu Gly Arg Pro Val
        1325                1330                1335

Glu Val Leu Leu Asn Asp Asp Leu Ile Val Ser Thr Gly Phe Gly
        1340                1345                1350

Ser Gly Leu Ala Thr Val His Val Thr Thr Val Val His Lys Thr
        1355                1360                1365
```

Ser Thr Ser Glu Glu Val Cys Ser Phe Tyr Leu Lys Ile Asp Thr
    1370                1375                1380

Gln Asp Ile Glu Ala Ser His Tyr Arg Gly Tyr Gly Asn Ser Asp
    1385                1390                1395

Tyr Lys Arg Ile Val Ala Cys Ala Ser Tyr Lys Pro Ser Arg Glu
    1400                1405                1410

Glu Ser Ser Ser Gly Ser Ser His Ala Val Met Asp Ile Ser Leu
    1415                1420                1425

Pro Thr Gly Ile Ser Ala Asn Glu Glu Asp Leu Lys Ala Leu Val
    1430                1435                1440

Glu Gly Val Asp Gln Leu Phe Thr Asp Tyr Gln Ile Lys Asp Gly
    1445                1450                1455

His Val Ile Leu Gln Leu Asn Ser Ile Pro Ser Ser Asp Phe Leu
    1460                1465                1470

Cys Val Arg Phe Arg Ile Phe Glu Leu Phe Glu Val Gly Phe Leu
    1475                1480                1485

Ser Pro Ala Thr Phe Thr Val Tyr Glu Tyr His Arg Pro Asp Lys
    1490                1495                1500

Gln Cys Thr Met Phe Tyr Ser Thr Ser Asn Ile Lys Ile Gln Lys
    1505                1510                1515

Val Cys Glu Gly Ala Ala Cys Lys Cys Val Glu Ala Asp Cys Gly
    1520                1525                1530

Gln Met Gln Glu Glu Leu Asp Leu Thr Ile Ser Ala Glu Thr Arg
    1535                1540                1545

Lys Gln Thr Ala Cys Lys Pro Glu Ile Ala Tyr Ala Tyr Lys Val
    1550                1555                1560

Ser Ile Thr Ser Ile Thr Val Glu Asn Val Phe Val Lys Tyr Lys
    1565                1570                1575

Ala Thr Leu Leu Asp Ile Tyr Lys Thr Gly Glu Ala Val Ala Glu
    1580                1585                1590

Lys Asp Ser Glu Ile Thr Phe Ile Lys Lys Val Thr Cys Thr Asn
    1595                1600                1605

Ala Glu Leu Val Lys Gly Arg Gln Tyr Leu Ile Met Gly Lys Glu
    1610                1615                1620

Ala Leu Gln Ile Lys Tyr Asn Phe Ser Phe Arg Tyr Ile Tyr Pro
    1625                1630                1635

Leu Asp Ser Leu Thr Trp Ile Glu Tyr Trp Pro Arg Asp Thr Thr
    1640                1645                1650

Cys Ser Ser Cys Gln Ala Phe Leu Ala Asn Leu Asp Glu Phe Ala
    1655                1660                1665

Glu Asp Ile Phe Leu Asn Gly Cys
    1670                1675

<210> SEQ ID NO 297
<211> LENGTH: 934
<212> TYPE: PRT
<213> ORGANISM: Homo sapiens

<400> SEQUENCE: 297

Met Ala Arg Arg Ser Val Leu Tyr Phe Ile Leu Leu Asn Ala Leu Ile
1               5                   10                  15

Asn Lys Gly Gln Ala Cys Phe Cys Asp His Tyr Ala Trp Thr Gln Trp
            20                  25                  30

Thr Ser Cys Ser Lys Thr Cys Asn Ser Gly Thr Gln Ser Arg His Arg
        35                  40                  45

-continued

```
Gln Ile Val Val Asp Lys Tyr Tyr Gln Glu Asn Phe Cys Glu Gln Ile
        50                  55                  60
Cys Ser Lys Gln Glu Thr Arg Glu Cys Asn Trp Gln Arg Cys Pro Ile
 65                  70                  75                  80
Asn Cys Leu Leu Gly Asp Phe Gly Pro Trp Ser Asp Cys Asp Pro Cys
                 85                  90                  95
Ile Glu Lys Gln Ser Lys Val Arg Ser Val Leu Arg Pro Ser Gln Phe
            100                 105                 110
Gly Gly Gln Pro Cys Thr Glu Pro Leu Val Ala Phe Gln Pro Cys Ile
            115                 120                 125
Pro Ser Lys Leu Cys Lys Ile Glu Glu Ala Asp Cys Lys Asn Lys Phe
130                 135                 140
Arg Cys Asp Ser Gly Arg Cys Ile Ala Arg Lys Leu Glu Cys Asn Gly
145                 150                 155                 160
Glu Asn Asp Cys Gly Asp Asn Ser Asp Glu Arg Asp Cys Gly Arg Thr
                165                 170                 175
Lys Ala Val Cys Thr Arg Lys Tyr Asn Pro Ile Pro Ser Val Gln Leu
            180                 185                 190
Met Gly Asn Gly Phe His Phe Leu Ala Gly Glu Pro Arg Gly Glu Val
            195                 200                 205
Leu Asp Asn Ser Phe Thr Gly Gly Ile Cys Lys Thr Val Lys Ser Ser
210                 215                 220
Arg Thr Ser Asn Pro Tyr Arg Val Pro Ala Asn Leu Glu Asn Val Gly
225                 230                 235                 240
Phe Glu Val Gln Thr Ala Glu Asp Asp Leu Lys Thr Asp Phe Tyr Lys
                245                 250                 255
Asp Leu Thr Ser Leu Gly His Asn Glu Asn Gln Gln Gly Ser Phe Ser
            260                 265                 270
Ser Gln Gly Gly Ser Ser Phe Ser Val Pro Ile Phe Tyr Ser Ser Lys
            275                 280                 285
Arg Ser Glu Asn Ile Asn His Asn Ser Ala Phe Lys Gln Ala Ile Gln
290                 295                 300
Ala Ser His Lys Lys Asp Ser Ser Phe Ile Arg Ile His Lys Val Met
305                 310                 315                 320
Lys Val Leu Asn Phe Thr Thr Lys Ala Lys Asp Leu His Leu Ser Asp
                325                 330                 335
Val Phe Leu Lys Ala Leu Asn His Leu Pro Leu Glu Tyr Asn Ser Ala
            340                 345                 350
Leu Tyr Ser Arg Ile Phe Asp Asp Phe Gly Thr His Tyr Phe Thr Ser
            355                 360                 365
Gly Ser Leu Gly Gly Val Tyr Asp Leu Leu Tyr Gln Phe Ser Ser Glu
            370                 375                 380
Glu Leu Lys Asn Ser Gly Leu Thr Glu Glu Ala Lys His Cys Val
385                 390                 395                 400
Arg Ile Glu Thr Lys Lys Arg Val Leu Phe Ala Lys Lys Thr Lys Val
                405                 410                 415
Glu His Arg Cys Thr Thr Asn Lys Leu Ser Glu Lys His Glu Gly Ser
            420                 425                 430
Phe Ile Gln Gly Ala Glu Lys Ser Ile Ser Leu Ile Arg Gly Gly Arg
            435                 440                 445
Ser Glu Tyr Gly Ala Ala Leu Ala Trp Glu Lys Gly Ser Ser Gly Leu
450                 455                 460
```

-continued

```
Glu Glu Lys Thr Phe Ser Glu Trp Leu Glu Ser Val Lys Glu Asn Pro
465                 470                 475                 480

Ala Val Ile Asp Phe Glu Leu Ala Pro Ile Val Asp Leu Val Arg Asn
                485                 490                 495

Ile Pro Cys Ala Val Thr Lys Arg Asn Asn Leu Arg Lys Ala Leu Gln
            500                 505                 510

Glu Tyr Ala Ala Lys Phe Asp Pro Cys Gln Cys Ala Pro Cys Pro Asn
        515                 520                 525

Asn Gly Arg Pro Thr Leu Ser Gly Thr Glu Cys Leu Cys Val Cys Gln
    530                 535                 540

Ser Gly Thr Tyr Gly Glu Asn Cys Glu Lys Gln Ser Pro Asp Tyr Lys
545                 550                 555                 560

Ser Asn Ala Val Asp Gly Gln Trp Gly Cys Trp Ser Ser Trp Ser Thr
                565                 570                 575

Cys Asp Ala Thr Tyr Lys Arg Ser Arg Thr Arg Glu Cys Asn Asn Pro
            580                 585                 590

Ala Pro Gln Arg Gly Gly Lys Arg Cys Glu Gly Glu Lys Arg Gln Glu
        595                 600                 605

Glu Asp Cys Thr Phe Ser Ile Met Glu Asn Asn Gly Gln Pro Cys Ile
    610                 615                 620

Asn Asp Asp Glu Glu Met Lys Glu Val Asp Leu Pro Glu Ile Glu Ala
625                 630                 635                 640

Asp Ser Gly Cys Pro Gln Pro Val Pro Pro Glu Asn Gly Phe Ile Arg
                645                 650                 655

Asn Glu Lys Gln Leu Tyr Leu Val Gly Glu Asp Val Glu Ile Ser Cys
            660                 665                 670

Leu Thr Gly Phe Glu Thr Val Gly Tyr Gln Tyr Phe Arg Cys Leu Pro
        675                 680                 685

Asp Gly Thr Trp Arg Gln Gly Asp Val Glu Cys Gln Arg Thr Glu Cys
    690                 695                 700

Ile Lys Pro Val Val Gln Glu Val Leu Thr Ile Thr Pro Phe Gln Arg
705                 710                 715                 720

Leu Tyr Arg Ile Gly Glu Ser Ile Glu Leu Thr Cys Pro Lys Gly Phe
                725                 730                 735

Val Val Ala Gly Pro Ser Arg Tyr Thr Cys Gln Gly Asn Ser Trp Thr
            740                 745                 750

Pro Pro Ile Ser Asn Ser Leu Thr Cys Glu Lys Asp Thr Leu Thr Lys
        755                 760                 765

Leu Lys Gly His Cys Gln Leu Gly Gln Lys Gln Ser Gly Ser Glu Cys
    770                 775                 780

Ile Cys Met Ser Pro Glu Glu Asp Cys Ser His His Ser Glu Asp Leu
785                 790                 795                 800

Cys Val Phe Asp Thr Asp Ser Asn Asp Tyr Phe Thr Ser Pro Ala Cys
                805                 810                 815

Lys Phe Leu Ala Glu Lys Cys Leu Asn Asn Gln Gln Leu His Phe Leu
            820                 825                 830

His Ile Gly Ser Cys Gln Asp Gly Arg Gln Leu Glu Trp Gly Leu Glu
        835                 840                 845

Arg Thr Arg Leu Ser Ser Asn Ser Thr Lys Lys Glu Ser Cys Gly Tyr
    850                 855                 860

Asp Thr Cys Tyr Asp Trp Glu Lys Cys Ser Ala Ser Thr Ser Lys Cys
865                 870                 875                 880

Val Cys Leu Leu Pro Pro Gln Cys Phe Lys Gly Gly Asn Gln Leu Tyr
```

```
                        885                 890                 895
            Cys Val Lys Met Gly Ser Ser Thr Ser Glu Lys Thr Leu Asn Ile Cys
                        900                 905                 910

Glu Val Gly Thr Ile Arg Cys Ala Asn Arg Lys Met Glu Ile Leu His
                        915                 920                 925

Pro Gly Lys Cys Leu Ala
                        930

<210> SEQ ID NO 298
<211> LENGTH: 843
<212> TYPE: PRT
<213> ORGANISM: Homo sapiens

<400> SEQUENCE: 298

Met Lys Val Ile Ser Leu Phe Ile Leu Val Gly Phe Ile Gly Glu Phe
1               5                   10                  15

Gln Ser Phe Ser Ser Ala Ser Ser Pro Val Asn Cys Gln Trp Asp Phe
            20                  25                  30

Tyr Ala Pro Trp Ser Glu Cys Asn Gly Cys Thr Lys Thr Gln Thr Arg
        35                  40                  45

Arg Arg Ser Val Ala Val Tyr Gly Gln Tyr Gly Gly Gln Pro Cys Val
    50                  55                  60

Gly Asn Ala Phe Glu Thr Gln Ser Cys Glu Pro Thr Arg Gly Cys Pro
65                  70                  75                  80

Thr Glu Glu Gly Cys Gly Glu Arg Phe Arg Cys Phe Ser Gly Gln Cys
                85                  90                  95

Ile Ser Lys Ser Leu Val Cys Asn Gly Asp Ser Asp Cys Asp Glu Asp
            100                 105                 110

Ser Ala Asp Glu Asp Arg Cys Glu Asp Ser Glu Arg Arg Pro Ser Cys
        115                 120                 125

Asp Ile Asp Lys Pro Pro Pro Asn Ile Glu Leu Thr Gly Asn Gly Tyr
    130                 135                 140

Asn Glu Leu Thr Gly Gln Phe Arg Asn Arg Val Ile Asn Thr Lys Ser
145                 150                 155                 160

Phe Gly Gly Gln Cys Arg Lys Val Phe Ser Gly Asp Gly Lys Asp Phe
                165                 170                 175

Tyr Arg Leu Ser Gly Asn Val Leu Ser Tyr Thr Phe Gln Val Lys Ile
            180                 185                 190

Asn Asn Asp Phe Asn Tyr Glu Phe Tyr Asn Ser Thr Trp Ser Tyr Val
        195                 200                 205

Lys His Thr Ser Thr Glu His Thr Ser Ser Ser Arg Lys Arg Ser Phe
    210                 215                 220

Phe Arg Ser Ser Ser Ser Ser Arg Ser Tyr Thr Ser His Thr Asn
225                 230                 235                 240

Glu Ile His Lys Gly Lys Ser Tyr Gln Leu Leu Val Val Glu Asn Thr
                245                 250                 255

Val Glu Val Ala Gln Phe Ile Asn Asn Asn Pro Glu Phe Leu Gln Leu
            260                 265                 270

Ala Glu Pro Phe Trp Lys Glu Leu Ser His Leu Pro Ser Leu Tyr Asp
        275                 280                 285

Tyr Ser Ala Tyr Arg Arg Leu Ile Asp Gln Tyr Gly Thr His Tyr Leu
    290                 295                 300

Gln Ser Gly Ser Leu Gly Gly Leu Tyr Arg Val Leu Phe Tyr Val Asp
305                 310                 315                 320
```

```
Ser Glu Lys Leu Lys Gln Asn Asp Phe Asn Ser Val Glu Glu Lys Lys
            325                 330                 335

Cys Lys Ser Ser Gly Trp His Phe Val Val Lys Phe Ser His Gly
            340                 345                 350

Cys Lys Glu Leu Glu Asn Ala Leu Lys Ala Ala Ser Gly Thr Gln Asn
            355                 360                 365

Asn Val Leu Arg Gly Glu Pro Phe Ile Arg Gly Gly Ala Gly Phe
            370                 375                 380

Ile Ser Gly Leu Ser Tyr Leu Glu Leu Asp Asn Pro Ala Gly Asn Lys
385                 390                 395                 400

Arg Arg Tyr Ser Ala Trp Ala Glu Ser Val Thr Asn Leu Pro Gln Val
            405                 410                 415

Ile Lys Gln Lys Leu Thr Pro Leu Tyr Glu Leu Val Lys Glu Val Pro
            420                 425                 430

Cys Ala Ser Val Lys Lys Leu Tyr Leu Lys Trp Ala Leu Glu Glu Tyr
            435                 440                 445

Leu Asp Glu Phe Asp Pro Cys His Cys Arg Pro Cys Gln Asn Gly Gly
            450                 455                 460

Leu Ala Thr Val Glu Gly Thr His Cys Leu Cys His Cys Lys Pro Tyr
465                 470                 475                 480

Thr Phe Gly Ala Ala Cys Glu Gln Gly Val Leu Val Gly Asn Gln Ala
            485                 490                 495

Gly Gly Val Asp Gly Gly Trp Ser Cys Trp Ser Ser Trp Ser Pro Cys
            500                 505                 510

Val Gln Gly Lys Lys Thr Arg Ser Arg Glu Cys Asn Asn Pro Pro Pro
            515                 520                 525

Ser Gly Gly Gly Arg Ser Cys Val Gly Glu Thr Thr Glu Ser Thr Gln
            530                 535                 540

Cys Glu Asp Glu Glu Leu Glu His Leu Arg Leu Leu Glu Pro His Cys
545                 550                 555                 560

Phe Pro Leu Ser Leu Val Pro Thr Glu Phe Cys Pro Ser Pro Pro Ala
            565                 570                 575

Leu Lys Asp Gly Phe Val Gln Asp Glu Gly Thr Met Phe Pro Val Gly
            580                 585                 590

Lys Asn Val Val Tyr Thr Cys Asn Glu Gly Tyr Ser Leu Ile Gly Asn
            595                 600                 605

Pro Val Ala Arg Cys Gly Glu Asp Leu Arg Trp Leu Val Gly Glu Met
            610                 615                 620

His Cys Gln Lys Ile Ala Cys Val Leu Pro Val Leu Met Asp Gly Ile
625                 630                 635                 640

Gln Ser His Pro Gln Lys Pro Phe Tyr Thr Val Gly Glu Lys Val Thr
            645                 650                 655

Val Ser Cys Ser Gly Gly Met Ser Leu Glu Gly Pro Ser Ala Phe Leu
            660                 665                 670

Cys Gly Ser Ser Leu Lys Trp Ser Pro Glu Met Lys Asn Ala Arg Cys
            675                 680                 685

Val Gln Lys Glu Asn Pro Leu Thr Gln Ala Val Pro Lys Cys Gln Arg
            690                 695                 700

Trp Glu Lys Leu Gln Asn Ser Arg Cys Val Cys Lys Met Pro Tyr Glu
705                 710                 715                 720

Cys Gly Pro Ser Leu Asp Val Cys Ala Gln Asp Glu Arg Ser Lys Arg
            725                 730                 735

Ile Leu Pro Leu Thr Val Cys Lys Met His Val Leu His Cys Gln Gly
```

```
                740                 745                 750
Arg Asn Tyr Thr Leu Thr Gly Arg Asp Ser Cys Thr Leu Pro Ala Ser
            755                 760                 765

Ala Glu Lys Ala Cys Gly Ala Cys Pro Leu Trp Gly Lys Cys Asp Ala
        770                 775                 780

Glu Ser Ser Lys Cys Val Cys Arg Glu Ala Ser Glu Cys Glu Glu Glu
785                 790                 795                 800

Gly Phe Ser Ile Cys Val Glu Val Asn Gly Lys Glu Gln Thr Met Ser
                805                 810                 815

Glu Cys Glu Ala Gly Ala Leu Arg Cys Arg Gly Gln Ser Ile Ser Val
            820                 825                 830

Thr Ser Ile Arg Pro Cys Ala Ala Glu Thr Gln
        835                 840

<210> SEQ ID NO 299
<211> LENGTH: 584
<212> TYPE: PRT
<213> ORGANISM: Homo sapiens

<400> SEQUENCE: 299

Met Phe Ala Val Val Phe Phe Ile Leu Ser Leu Met Thr Cys Gln Pro
1               5                   10                  15

Gly Val Thr Ala Gln Glu Lys Val Asn Gln Arg Val Arg Arg Ala Ala
            20                  25                  30

Thr Pro Ala Ala Val Thr Cys Gln Leu Ser Asn Trp Ser Glu Trp Thr
        35                  40                  45

Asp Cys Phe Pro Cys Gln Asp Lys Lys Tyr Arg His Arg Ser Leu Leu
    50                  55                  60

Gln Pro Asn Lys Phe Gly Gly Thr Ile Cys Ser Gly Asp Ile Trp Asp
65                  70                  75                  80

Gln Ala Ser Cys Ser Ser Ser Thr Thr Cys Val Arg Gln Ala Gln Cys
                85                  90                  95

Gly Gln Asp Phe Gln Cys Lys Glu Thr Gly Arg Cys Leu Lys Arg His
            100                 105                 110

Leu Val Cys Asn Gly Asp Gln Asp Cys Leu Asp Gly Ser Asp Glu Asp
        115                 120                 125

Asp Cys Glu Asp Val Arg Ala Ile Asp Glu Asp Cys Ser Gln Tyr Glu
    130                 135                 140

Pro Ile Pro Gly Ser Gln Lys Ala Ala Leu Gly Tyr Asn Ile Leu Thr
145                 150                 155                 160

Gln Glu Asp Ala Gln Ser Val Tyr Asp Ala Ser Tyr Tyr Gly Gly Gln
                165                 170                 175

Cys Glu Thr Val Tyr Asn Gly Glu Trp Arg Glu Leu Arg Tyr Asp Ser
            180                 185                 190

Thr Cys Glu Arg Leu Tyr Tyr Gly Asp Asp Glu Lys Tyr Phe Arg Lys
        195                 200                 205

Pro Tyr Asn Phe Leu Lys Tyr His Phe Glu Ala Leu Ala Asp Thr Gly
    210                 215                 220

Ile Ser Ser Glu Phe Tyr Asp Asn Ala Asn Asp Leu Leu Ser Lys Val
225                 230                 235                 240

Lys Lys Asp Lys Ser Asp Ser Phe Gly Val Thr Ile Gly Ile Gly Pro
                245                 250                 255

Ala Gly Ser Pro Leu Leu Val Gly Val Gly Val Ser His Ser Gln Asp
            260                 265                 270
```

```
Thr Ser Phe Leu Asn Glu Leu Asn Lys Tyr Asn Glu Lys Phe Ile
        275                 280                 285

Phe Thr Arg Ile Phe Thr Lys Val Gln Thr Ala His Phe Lys Met Arg
290                 295                 300

Lys Asp Asp Ile Met Leu Asp Glu Gly Met Leu Gln Ser Leu Met Glu
305                 310                 315                 320

Leu Pro Asp Gln Tyr Asn Tyr Gly Met Tyr Ala Lys Phe Ile Asn Asp
                325                 330                 335

Tyr Gly Thr His Tyr Ile Thr Ser Ser Met Gly Gly Ile Tyr Glu
            340                 345                 350

Tyr Ile Leu Val Ile Asp Lys Ala Lys Met Glu Ser Leu Gly Ile Thr
        355                 360                 365

Ser Arg Asp Ile Thr Thr Cys Phe Gly Gly Ser Leu Gly Ile Gln Tyr
370                 375                 380

Glu Asp Lys Ile Asn Val Gly Gly Gly Leu Ser Gly Asp His Cys Lys
385                 390                 395                 400

Lys Phe Gly Gly Gly Lys Thr Glu Arg Ala Arg Lys Ala Met Ala Val
                405                 410                 415

Glu Asp Ile Ile Ser Arg Val Arg Gly Gly Ser Ser Gly Trp Ser Gly
            420                 425                 430

Gly Leu Ala Gln Asn Arg Ser Thr Ile Thr Tyr Arg Ser Trp Gly Arg
        435                 440                 445

Ser Leu Lys Tyr Asn Pro Val Val Ile Asp Phe Glu Met Gln Pro Ile
    450                 455                 460

His Glu Val Leu Arg His Thr Ser Leu Gly Pro Leu Glu Ala Lys Arg
465                 470                 475                 480

Gln Asn Leu Arg Arg Ala Leu Asp Gln Tyr Leu Met Glu Phe Asn Ala
                485                 490                 495

Cys Arg Cys Gly Pro Cys Phe Asn Asn Gly Val Pro Ile Leu Glu Gly
            500                 505                 510

Thr Ser Cys Arg Cys Gln Cys Arg Leu Gly Ser Leu Gly Ala Ala Cys
        515                 520                 525

Glu Gln Thr Gln Thr Glu Gly Ala Lys Ala Asp Gly Ser Trp Ser Cys
    530                 535                 540

Trp Ser Ser Trp Ser Val Cys Arg Ala Gly Ile Gln Glu Arg Arg Arg
545                 550                 555                 560

Glu Cys Asp Asn Pro Ala Pro Gln Asn Gly Gly Ala Ser Cys Pro Gly
                565                 570                 575

Arg Lys Val Gln Thr Gln Ala Cys
            580

<210> SEQ ID NO 300
<211> LENGTH: 559
<212> TYPE: PRT
<213> ORGANISM: Homo sapiens

<400> SEQUENCE: 300

Met Ser Ala Cys Arg Ser Phe Ala Val Ala Ile Cys Ile Leu Glu Ile
1               5                   10                  15

Ser Ile Leu Thr Ala Gln Tyr Thr Thr Ser Tyr Asp Pro Glu Leu Thr
            20                  25                  30

Glu Ser Ser Gly Ser Ala Ser His Ile Asp Cys Arg Met Ser Pro Trp
        35                  40                  45

Ser Glu Trp Ser Gln Cys Asp Pro Cys Leu Arg Gln Met Phe Arg Ser
    50                  55                  60
```

```
Arg Ser Ile Glu Val Phe Gly Gln Phe Asn Gly Lys Arg Cys Thr Asp
 65                  70                  75                  80

Ala Val Gly Asp Arg Gln Cys Val Pro Thr Glu Pro Cys Glu Asp
                 85                  90                  95

Ala Glu Asp Asp Cys Gly Asn Asp Phe Gln Cys Ser Thr Gly Arg Cys
                100                 105                 110

Ile Lys Met Arg Leu Arg Cys Asn Gly Asp Asn Asp Cys Gly Asp Phe
                115                 120                 125

Ser Asp Glu Asp Asp Cys Glu Ser Glu Pro Arg Pro Pro Cys Arg Asp
                130                 135                 140

Arg Val Val Glu Glu Ser Glu Leu Ala Arg Thr Ala Gly Tyr Gly Ile
145                 150                 155                 160

Asn Ile Leu Gly Met Asp Pro Leu Ser Thr Pro Phe Asp Asn Glu Phe
                165                 170                 175

Tyr Asn Gly Leu Cys Asn Arg Asp Arg Asp Gly Asn Thr Leu Thr Tyr
                180                 185                 190

Tyr Arg Arg Pro Trp Asn Val Ala Ser Leu Ile Tyr Glu Thr Lys Gly
                195                 200                 205

Glu Lys Asn Phe Arg Thr Glu His Tyr Glu Glu Gln Ile Glu Ala Phe
                210                 215                 220

Lys Ser Ile Ile Gln Glu Lys Thr Ser Asn Phe Asn Ala Ala Ile Ser
225                 230                 235                 240

Leu Lys Phe Thr Pro Thr Glu Thr Asn Lys Ala Glu Gln Cys Cys Glu
                245                 250                 255

Glu Thr Ala Ser Ser Ile Ser Leu His Gly Lys Gly Ser Phe Arg Phe
                260                 265                 270

Ser Tyr Ser Lys Asn Glu Thr Tyr Gln Leu Phe Leu Ser Tyr Ser Ser
                275                 280                 285

Lys Lys Glu Lys Met Phe Leu His Val Lys Gly Glu Ile His Leu Gly
                290                 295                 300

Arg Phe Val Met Arg Asn Arg Asp Val Val Leu Thr Thr Thr Phe Val
305                 310                 315                 320

Asp Asp Ile Lys Ala Leu Pro Thr Thr Tyr Glu Lys Gly Glu Tyr Phe
                325                 330                 335

Ala Phe Leu Glu Thr Tyr Gly Thr His Tyr Ser Ser Ser Gly Ser Leu
                340                 345                 350

Gly Gly Leu Tyr Glu Leu Ile Tyr Val Leu Asp Lys Ala Ser Met Lys
                355                 360                 365

Arg Lys Gly Val Glu Leu Lys Asp Ile Lys Arg Cys Leu Gly Tyr His
                370                 375                 380

Leu Asp Val Ser Leu Ala Phe Ser Glu Ile Ser Val Gly Ala Glu Phe
385                 390                 395                 400

Asn Lys Asp Asp Cys Val Lys Arg Gly Glu Gly Arg Ala Val Asn Ile
                405                 410                 415

Thr Ser Glu Asn Leu Ile Asp Asp Val Val Ser Leu Ile Arg Gly Gly
                420                 425                 430

Thr Arg Lys Tyr Ala Phe Glu Leu Lys Glu Lys Leu Leu Arg Gly Thr
                435                 440                 445

Val Ile Asp Val Thr Asp Phe Val Asn Trp Ala Ser Ser Ile Asn Asp
                450                 455                 460

Ala Pro Val Leu Ile Ser Gln Lys Leu Ser Pro Ile Tyr Asn Leu Val
465                 470                 475                 480
```

-continued

```
Pro Val Lys Met Lys Asn Ala His Leu Lys Lys Gln Asn Leu Glu Arg
            485                 490                 495

Ala Ile Glu Asp Tyr Ile Asn Glu Phe Ser Val Arg Lys Cys His Thr
        500                 505                 510

Cys Gln Asn Gly Gly Thr Val Ile Leu Met Asp Gly Lys Cys Leu Cys
        515                 520                 525

Ala Cys Pro Phe Lys Phe Glu Gly Ile Ala Cys Glu Ile Ser Lys Gln
    530                 535                 540

Lys Ile Ser Glu Gly Leu Pro Ala Leu Glu Phe Pro Asn Glu Lys
545                 550                 555

<210> SEQ ID NO 301
<211> LENGTH: 764
<212> TYPE: PRT
<213> ORGANISM: Homo sapiens

<400> SEQUENCE: 301

Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Gln
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
        195                 200                 205

Gly Ser Trp Ser Gly Thr Glu Pro Ser Cys Gln Asp Ser Phe Met Tyr
    210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Lys Arg Lys Ile Val Leu Asp Pro Ser Gly Ser Met Asn Ile Tyr
            260                 265                 270

Leu Val Leu Asp Gly Ser Asp Ser Ile Gly Ala Ser Asn Phe Thr Gly
        275                 280                 285

Ala Lys Lys Cys Leu Val Asn Leu Ile Glu Lys Val Ala Ser Tyr Gly
    290                 295                 300
```

```
Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
            325                 330                 335

Lys Gln Leu Asn Glu Ile Asn Tyr Glu Asp His Lys Leu Lys Ser Gly
        340                 345                 350

Thr Asn Thr Lys Lys Ala Leu Gln Ala Val Tyr Ser Met Met Ser Trp
    355                 360                 365

Pro Asp Asp Val Pro Pro Glu Gly Trp Asn Arg Thr Arg His Val Ile
370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn
        435                 440                 445

Glu Gln His Val Phe Lys Val Lys Asp Met Glu Asn Leu Glu Asp Val
    450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Val Ser Glu Tyr Phe Val Leu Thr Ala Ala His Cys Phe
        515                 520                 525

Thr Val Asp Asp Lys Glu His Ser Ile Lys Val Ser Val Gly Gly Glu
    530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
        595                 600                 605

Leu Pro Pro Thr Thr Thr Cys Gln Gln Gln Lys Glu Glu Leu Leu Pro
    610                 615                 620

Ala Gln Asp Ile Lys Ala Leu Phe Val Ser Glu Glu Glu Lys Lys Leu
625                 630                 635                 640

Thr Arg Lys Glu Val Tyr Ile Lys Asn Gly Asp Lys Lys Gly Ser Cys
                645                 650                 655

Glu Arg Asp Ala Gln Tyr Ala Pro Gly Tyr Asp Lys Val Lys Asp Ile
            660                 665                 670

Ser Glu Val Val Thr Pro Arg Phe Leu Cys Thr Gly Gly Val Ser Pro
        675                 680                 685

Tyr Ala Asp Pro Asn Thr Cys Arg Gly Asp Ser Gly Gly Pro Leu Ile
    690                 695                 700

Val His Lys Arg Ser Arg Phe Ile Gln Val Gly Val Ile Ser Trp Gly
705                 710                 715                 720
```

```
Val Val Asp Val Cys Lys Asn Gln Lys Arg Gln Lys Gln Val Pro Ala
                725                 730                 735

His Ala Arg Asp Phe His Ile Asn Leu Phe Gln Val Leu Pro Trp Leu
                740                 745                 750

Lys Glu Lys Leu Gln Asp Glu Asp Leu Gly Phe Leu
                755                 760

<210> SEQ ID NO 302
<211> LENGTH: 1231
<212> TYPE: PRT
<213> ORGANISM: Homo sapiens

<400> SEQUENCE: 302

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
            35                  40                  45

Ile Tyr Lys Cys Arg Pro Gly Tyr Arg Ser Leu Gly Asn Val Ile Met
        50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
                100                 105                 110

Thr Cys Asn Glu Gly Tyr Gln Leu Leu Gly Glu Ile Asn Tyr Arg Glu
                115                 120                 125

Cys Asp Thr Asp Gly Trp Thr Asn Asp Ile Pro Ile Cys Glu Val Val
            130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
                180                 185                 190

Ser Asp Asp Gly Phe Trp Ser Lys Glu Lys Pro Lys Cys Val Glu Ile
            195                 200                 205

Ser Cys Lys Ser Pro Asp Val Ile Asn Gly Ser Pro Ile Ser Gln Lys
        210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
                260                 265                 270

Pro Asn Gly Asp Tyr Ser Pro Leu Arg Ile Lys His Arg Thr Gly Asp
            275                 280                 285

Glu Ile Thr Tyr Gln Cys Arg Asn Gly Phe Tyr Pro Ala Thr Arg Gly
        290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335
```

```
His Glu Asn Met Arg Arg Pro Tyr Phe Pro Val Ala Val Gly Lys Tyr
                340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
370                 375                 380

Cys Leu Arg Lys Cys Tyr Phe Pro Tyr Leu Glu Asn Gly Tyr Asn Gln
385                 390                 395                 400

Asn His Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
                420                 425                 430

Glu Asn Gly Trp Ser Pro Thr Pro Arg Cys Ile Arg Val Lys Thr Cys
                435                 440                 445

Ser Lys Ser Ser Ile Asp Ile Glu Asn Gly Phe Ile Ser Glu Ser Gln
                450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Arg Cys Gly Lys
                485                 490                 495

Asp Gly Trp Ser Ala Gln Pro Thr Cys Ile Lys Ser Cys Asp Ile Pro
                500                 505                 510

Val Phe Met Asn Ala Arg Thr Lys Asn Asp Phe Thr Trp Phe Lys Leu
                515                 520                 525

Asn Asp Thr Leu Asp Tyr Glu Cys His Asp Gly Tyr Glu Ser Asn Thr
                530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
                580                 585                 590

Leu Lys Phe Ser Cys Lys Pro Gly Phe Thr Ile Val Gly Pro Asn Ser
                595                 600                 605

Val Gln Cys Tyr His Phe Gly Leu Ser Pro Asp Leu Pro Ile Cys Lys
                610                 615                 620

Glu Gln Val Gln Ser Cys Gly Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
                660                 665                 670

Cys Val Asp Gly Glu Trp Thr Thr Leu Pro Val Cys Ile Val Glu Glu
                675                 680                 685

Ser Thr Cys Gly Asp Ile Pro Glu Leu Glu His Gly Trp Ala Gln Leu
                690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
                740                 745                 750
```

-continued

```
Cys Lys Ser Ser Asn Leu Ile Ile Leu Glu Glu His Leu Lys Asn Lys
            755                 760                 765

Lys Glu Phe Asp His Asn Ser Asn Ile Arg Tyr Arg Cys Arg Gly Lys
        770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
            835                 840                 845

Glu Glu Ile Thr Cys Lys Asp Gly Arg Trp Gln Ser Ile Pro Leu Cys
850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
            885                 890                 895

Leu Ser Tyr Thr Cys Glu Gly Gly Phe Arg Ile Ser Glu Glu Asn Glu
                900                 905                 910

Thr Thr Cys Tyr Met Gly Lys Trp Ser Ser Pro Pro Gln Cys Glu Gly
        915                 920                 925

Leu Pro Cys Lys Ser Pro Pro Glu Ile Ser His Gly Val Val Ala His
    930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro Met Gly Glu Lys Lys Asp Val Tyr
        995                 1000                1005

Lys Ala Gly Glu Gln Val Thr Tyr Thr Cys Ala Thr Tyr Tyr Lys
    1010                1015                1020

Met Asp Gly Ala Ser Asn Val Thr Cys Ile Asn Ser Arg Trp Thr
    1025                1030                1035

Gly Arg Pro Thr Cys Arg Asp Thr Ser Cys Val Asn Pro Pro Thr
    1040                1045                1050

Val Gln Asn Ala Tyr Ile Val Ser Arg Gln Met Ser Lys Tyr Pro
    1055                1060                1065

Ser Gly Glu Arg Val Arg Tyr Gln Cys Arg Ser Pro Tyr Glu Met
    1070                1075                1080

Phe Gly Asp Glu Glu Val Met Cys Leu Asn Gly Asn Trp Thr Glu
    1085                1090                1095

Pro Pro Gln Cys Lys Asp Ser Thr Gly Lys Cys Gly Pro Pro Pro
    1100                1105                1110

Pro Ile Asp Asn Gly Asp Ile Thr Ser Phe Pro Leu Ser Val Tyr
    1115                1120                1125

Ala Pro Ala Ser Ser Val Glu Tyr Gln Cys Gln Asn Leu Tyr Gln
    1130                1135                1140

Leu Glu Gly Asn Lys Arg Ile Thr Cys Arg Asn Gly Gln Trp Ser
    1145                1150                1155

Glu Pro Pro Lys Cys Leu His Pro Cys Val Ile Ser Arg Glu Ile
```

```
              1160                1165                1170

Met Glu Asn Tyr Asn Ile Ala Leu Arg Trp Thr Ala Lys Gln Lys
         1175                1180                1185

Leu Tyr Ser Arg Thr Gly Glu Ser Val Glu Phe Val Cys Lys Arg
         1190                1195                1200

Gly Tyr Arg Leu Ser Ser Arg Ser His Thr Leu Arg Thr Thr Cys
         1205                1210                1215

Trp Asp Gly Lys Leu Glu Tyr Pro Thr Cys Ala Lys Arg
         1220                1225                1230

<210> SEQ ID NO 303
<211> LENGTH: 644
<212> TYPE: PRT
<213> ORGANISM: Homo sapiens

<400> SEQUENCE: 303

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
                20                  25                  30

Gly Val Arg Gly Pro Arg Val Val Glu Arg His Gln Ser Ala Cys Lys
            35                  40                  45

Asp Ser Asp Trp Pro Phe Cys Ser Asp Glu Asp Trp Asn Tyr Lys Cys
        50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
    210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
    290                 295                 300
```

Thr Gly Asn Arg Asn Pro Gly Ser Ser Gly Thr Gly Thr Ala Thr
305                 310                 315                 320

Trp Lys Pro Gly Ser Ser Gly Pro Gly Ser Thr Gly Ser Trp Asn Ser
            325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
            355                 360                 365

Ser Ala Gly His Trp Thr Ser Glu Ser Ser Val Ser Gly Ser Thr Gly
370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
            405                 410                 415

Ser Gly Asn Val Ser Pro Gly Thr Arg Arg Glu Tyr His Thr Glu Lys
            420                 425                 430

Leu Val Thr Ser Lys Gly Asp Lys Glu Leu Arg Thr Gly Lys Glu Lys
            435                 440                 445

Val Thr Ser Gly Ser Thr Thr Thr Arg Arg Ser Cys Ser Lys Thr
450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
            515                 520                 525

Phe Pro Gly Phe Phe Ser Pro Met Leu Gly Glu Phe Val Ser Glu Thr
            530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
            565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
            595                 600                 605

Ser Glu Ala Asp His Glu Gly Thr His Ser Thr Lys Arg Gly His Ala
610                 615                 620

Lys Ser Arg Pro Val Arg Gly Ile His Thr Ser Pro Leu Gly Lys Pro
625                 630                 635                 640

Ser Leu Ser Pro

<210> SEQ ID NO 304
<211> LENGTH: 491
<212> TYPE: PRT
<213> ORGANISM: Homo sapiens

<400> SEQUENCE: 304

Met Lys Arg Met Val Ser Trp Ser Phe His Lys Leu Lys Thr Met Lys
1               5                   10                  15

His Leu Leu Leu Leu Leu Leu Cys Val Phe Leu Val Lys Ser Gln Gly
                20                  25                  30

Val Asn Asp Asn Glu Glu Gly Phe Ser Ala Arg Gly His Arg Pro
        35                  40                  45

Leu Asp Lys Lys Arg Glu Glu Ala Pro Ser Leu Arg Pro Ala Pro Pro
 50                  55                  60

Pro Ile Ser Gly Gly Gly Tyr Arg Ala Arg Pro Ala Lys Ala Ala Ala
 65                  70                  75                  80

Thr Gln Lys Lys Val Glu Arg Lys Ala Pro Asp Ala Gly Gly Cys Leu
                 85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
            115                 120                 125

Glu Leu Asn Asn Asn Val Glu Ala Val Ser Gln Thr Ser Ser Ser Ser
    130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                165                 170                 175

Glu Lys His Gln Leu Tyr Ile Asp Glu Thr Val Asn Ser Asn Ile Ala
            180                 185                 190

Thr Asn Leu Arg Val Leu Arg Ser Ile Leu Glu Asn Leu Arg Ser Lys
            195                 200                 205

Ile Gln Lys Leu Glu Ser Asp Val Ser Ala Gln Met Glu Tyr Cys Arg
    210                 215                 220

Thr Pro Cys Thr Val Ser Cys Asn Ile Pro Val Val Ser Gly Lys Glu
225                 230                 235                 240

Cys Glu Glu Ile Ile Arg Lys Gly Gly Glu Thr Ser Glu Met Tyr Leu
                245                 250                 255

Ile Gln Pro Asp Ser Ser Val Lys Pro Tyr Arg Val Tyr Cys Asp Met
            260                 265                 270

Asn Thr Glu Asn Gly Gly Trp Thr Val Ile Gln Asn Arg Gln Asp Gly
            275                 280                 285

Ser Val Asp Phe Gly Arg Lys Trp Asp Pro Tyr Lys Gln Gly Phe Gly
290                 295                 300

Asn Val Ala Thr Asn Thr Asp Gly Lys Asn Tyr Cys Gly Leu Pro Gly
305                 310                 315                 320

Glu Tyr Trp Leu Gly Asn Asp Lys Ile Ser Gln Leu Thr Arg Met Gly
                325                 330                 335

Pro Thr Glu Leu Leu Ile Glu Met Glu Asp Trp Lys Gly Asp Lys Val
            340                 345                 350

Lys Ala His Tyr Gly Gly Phe Thr Val Gln Asn Glu Ala Asn Lys Tyr
            355                 360                 365

Gln Ile Ser Val Asn Lys Tyr Arg Gly Thr Ala Gly Asn Ala Leu Met
    370                 375                 380

Asp Gly Ala Ser Gln Leu Met Gly Glu Asn Arg Thr Met Thr Ile His
385                 390                 395                 400

Asn Gly Met Phe Phe Ser Thr Tyr Asp Arg Asp Asn Asp Gly Trp Leu
                405                 410                 415

Thr Ser Asp Pro Arg Lys Gln Cys Ser Lys Glu Asp Gly Gly Gly Trp
            420                 425                 430

Trp Tyr Asn Arg Cys His Ala Ala Asn Pro Asn Gly Arg Tyr Tyr Trp
            435                 440                 445

Gly Gly Gln Tyr Thr Trp Asp Met Ala Lys His Gly Thr Asp Asp Gly

```
                450                 455                 460
Val Val Trp Met Asn Trp Lys Gly Ser Trp Tyr Ser Met Arg Lys Met
465                 470                 475                 480

Ser Met Lys Ile Arg Pro Phe Phe Pro Gln Gln
                485                 490

<210> SEQ ID NO 305
<211> LENGTH: 437
<212> TYPE: PRT
<213> ORGANISM: Homo sapiens

<400> SEQUENCE: 305

Met Ser Trp Ser Leu His Pro Arg Asn Leu Ile Leu Tyr Phe Tyr Ala
1               5                   10                  15

Leu Leu Phe Leu Ser Ser Thr Cys Val Ala Tyr Val Ala Thr Arg Asp
            20                  25                  30

Asn Cys Cys Ile Leu Asp Glu Arg Phe Gly Ser Tyr Cys Pro Thr Thr
        35                  40                  45

Cys Gly Ile Ala Asp Phe Leu Ser Thr Tyr Gln Thr Lys Val Asp Lys
    50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
            100                 105                 110

Arg Ile Met Leu Glu Glu Ile Met Lys Tyr Glu Ala Ser Ile Leu Thr
        115                 120                 125

His Asp Ser Ser Ile Arg Tyr Leu Gln Glu Ile Tyr Asn Ser Asn Asn
    130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
        195                 200                 205

Glu Ile Asp Gly Ser Gly Asn Gly Trp Thr Val Phe Gln Lys Arg Leu
    210                 215                 220

Asp Gly Ser Val Asp Phe Lys Lys Asn Trp Ile Gln Tyr Lys Glu Gly
225                 230                 235                 240

Phe Gly His Leu Ser Pro Thr Gly Thr Thr Glu Phe Trp Leu Gly Asn
                245                 250                 255

Glu Lys Ile His Leu Ile Ser Thr Gln Ser Ala Ile Pro Tyr Ala Leu
            260                 265                 270

Arg Val Glu Leu Glu Asp Trp Asn Gly Arg Thr Ser Thr Ala Asp Tyr
        275                 280                 285

Ala Met Phe Lys Val Gly Pro Glu Ala Asp Lys Tyr Arg Leu Thr Tyr
    290                 295                 300

Ala Tyr Phe Ala Gly Gly Asp Ala Gly Asp Ala Phe Asp Gly Phe Asp
305                 310                 315                 320

Phe Gly Asp Asp Pro Ser Asp Lys Phe Phe Thr Ser His Asn Gly Met
                325                 330                 335
```

-continued

```
Gln Phe Ser Thr Trp Asp Asn Asp Asn Asp Lys Phe Glu Gly Asn Cys
                340                 345                 350

Ala Glu Gln Asp Gly Ser Gly Trp Trp Met Asn Lys Cys His Ala Gly
            355                 360                 365

His Leu Asn Gly Val Tyr Tyr Gln Gly Gly Thr Tyr Ser Lys Ala Ser
        370                 375                 380

Thr Pro Asn Gly Tyr Asp Asn Gly Ile Ile Trp Ala Thr Trp Lys Thr
385                 390                 395                 400

Arg Trp Tyr Ser Met Lys Lys Thr Thr Met Lys Ile Ile Pro Phe Asn
                405                 410                 415

Arg Leu Thr Ile Gly Glu Gly Gln His His Leu Gly Gly Ala Lys
            420                 425                 430

Gln Ala Gly Asp Val
        435

<210> SEQ ID NO 306
<211> LENGTH: 2477
<212> TYPE: PRT
<213> ORGANISM: Homo sapiens

<400> SEQUENCE: 306

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270
```

```
His Thr Ser Val Gln Thr Thr Ser Gly Ser Gly Pro Phe Thr Asp
            275                 280                 285

Val Arg Ala Ala Val Tyr Gln Pro Gln Pro His Pro Gln Pro Pro
290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
            355                 360                 365

Arg Thr Phe Tyr Ser Cys Thr Thr Glu Gly Arg Gln Asp Gly His Leu
370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
            530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
            675                 680                 685
```

-continued

His Gln Glu Val Thr Arg Phe Asp Phe Thr Thr Ser Thr Ser Thr
690                     695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
                755                 760                 765

Pro Ser Thr Ala Thr Ser Val Asn Ile Pro Asp Leu Leu Pro Gly Arg
770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
                835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
                915                 920                 925

Pro Pro Glu Ser Ala Val Thr Gly Tyr Arg Val Asp Val Ile Pro Val
930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
                995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile

-continued

|  | 1100 |  |  |  | 1105 |  |  |  | 1110 |  |
|---|---|---|---|---|---|---|---|---|---|---|
| Gly | Phe | Lys | Leu | Gly | Val | Arg | Pro | Ser | Gln | Gly | Gly | Glu | Ala | Pro |
|  | 1115 |  |  |  | 1120 |  |  |  | 1125 |  |
| Arg | Glu | Val | Thr | Ser | Asp | Ser | Gly | Ser | Ile | Val | Val | Ser | Gly | Leu |
|  | 1130 |  |  |  | 1135 |  |  |  | 1140 |  |
| Thr | Pro | Gly | Val | Glu | Tyr | Val | Tyr | Thr | Ile | Gln | Val | Leu | Arg | Asp |
|  | 1145 |  |  |  | 1150 |  |  |  | 1155 |  |
| Gly | Gln | Glu | Arg | Asp | Ala | Pro | Ile | Val | Asn | Lys | Val | Val | Thr | Pro |
|  | 1160 |  |  |  | 1165 |  |  |  | 1170 |  |
| Leu | Ser | Pro | Pro | Thr | Asn | Leu | His | Leu | Glu | Ala | Asn | Pro | Asp | Thr |
|  | 1175 |  |  |  | 1180 |  |  |  | 1185 |  |
| Gly | Val | Leu | Thr | Val | Ser | Trp | Glu | Arg | Ser | Thr | Thr | Pro | Asp | Ile |
|  | 1190 |  |  |  | 1195 |  |  |  | 1200 |  |
| Thr | Gly | Tyr | Arg | Ile | Thr | Thr | Thr | Pro | Thr | Asn | Gly | Gln | Gln | Gly |
|  | 1205 |  |  |  | 1210 |  |  |  | 1215 |  |
| Asn | Ser | Leu | Glu | Glu | Val | Val | His | Ala | Asp | Gln | Ser | Ser | Cys | Thr |
|  | 1220 |  |  |  | 1225 |  |  |  | 1230 |  |
| Phe | Asp | Asn | Leu | Ser | Pro | Gly | Leu | Glu | Tyr | Asn | Val | Ser | Val | Tyr |
|  | 1235 |  |  |  | 1240 |  |  |  | 1245 |  |
| Thr | Val | Lys | Asp | Asp | Lys | Glu | Ser | Val | Pro | Ile | Ser | Asp | Thr | Ile |
|  | 1250 |  |  |  | 1255 |  |  |  | 1260 |  |
| Ile | Pro | Glu | Val | Pro | Gln | Leu | Thr | Asp | Leu | Ser | Phe | Val | Asp | Ile |
|  | 1265 |  |  |  | 1270 |  |  |  | 1275 |  |
| Thr | Asp | Ser | Ser | Ile | Gly | Leu | Arg | Trp | Thr | Pro | Leu | Asn | Ser | Ser |
|  | 1280 |  |  |  | 1285 |  |  |  | 1290 |  |
| Thr | Ile | Ile | Gly | Tyr | Arg | Ile | Thr | Val | Val | Ala | Ala | Gly | Glu | Gly |
|  | 1295 |  |  |  | 1300 |  |  |  | 1305 |  |
| Ile | Pro | Ile | Phe | Glu | Asp | Phe | Val | Asp | Ser | Ser | Val | Gly | Tyr | Tyr |
|  | 1310 |  |  |  | 1315 |  |  |  | 1320 |  |
| Thr | Val | Thr | Gly | Leu | Glu | Pro | Gly | Ile | Asp | Tyr | Asp | Ile | Ser | Val |
|  | 1325 |  |  |  | 1330 |  |  |  | 1335 |  |
| Ile | Thr | Leu | Ile | Asn | Gly | Gly | Glu | Ser | Ala | Pro | Thr | Thr | Leu | Thr |
|  | 1340 |  |  |  | 1345 |  |  |  | 1350 |  |
| Gln | Gln | Thr | Ala | Val | Pro | Pro | Pro | Thr | Asp | Leu | Arg | Phe | Thr | Asn |
|  | 1355 |  |  |  | 1360 |  |  |  | 1365 |  |
| Ile | Gly | Pro | Asp | Thr | Met | Arg | Val | Thr | Trp | Ala | Pro | Pro | Pro | Ser |
|  | 1370 |  |  |  | 1375 |  |  |  | 1380 |  |
| Ile | Asp | Leu | Thr | Asn | Phe | Leu | Val | Arg | Tyr | Ser | Pro | Val | Lys | Asn |
|  | 1385 |  |  |  | 1390 |  |  |  | 1395 |  |
| Glu | Glu | Asp | Val | Ala | Glu | Leu | Ser | Ile | Ser | Pro | Ser | Asp | Asn | Ala |
|  | 1400 |  |  |  | 1405 |  |  |  | 1410 |  |
| Val | Val | Leu | Thr | Asn | Leu | Leu | Pro | Gly | Thr | Glu | Tyr | Val | Val | Ser |
|  | 1415 |  |  |  | 1420 |  |  |  | 1425 |  |
| Val | Ser | Ser | Val | Tyr | Glu | Gln | His | Glu | Ser | Thr | Pro | Leu | Arg | Gly |
|  | 1430 |  |  |  | 1435 |  |  |  | 1440 |  |
| Arg | Gln | Lys | Thr | Gly | Leu | Asp | Ser | Pro | Thr | Gly | Ile | Asp | Phe | Ser |
|  | 1445 |  |  |  | 1450 |  |  |  | 1455 |  |
| Asp | Ile | Thr | Ala | Asn | Ser | Phe | Thr | Val | His | Trp | Ile | Ala | Pro | Arg |
|  | 1460 |  |  |  | 1465 |  |  |  | 1470 |  |
| Ala | Thr | Ile | Thr | Gly | Tyr | Arg | Ile | Arg | His | His | Pro | Glu | His | Phe |
|  | 1475 |  |  |  | 1480 |  |  |  | 1485 |  |
| Ser | Gly | Arg | Pro | Arg | Glu | Asp | Arg | Val | Pro | His | Ser | Arg | Asn | Ser |
|  | 1490 |  |  |  | 1495 |  |  |  | 1500 |  |

```
Ile Thr Leu Thr Asn Leu Thr Pro Gly Thr Glu Tyr Val Val Ser
    1505            1510                1515

Ile Val Ala Leu Asn Gly Arg Glu Glu Ser Pro Leu Leu Ile Gly
    1520            1525                1530

Gln Gln Ser Thr Val Ser Asp Val Pro Arg Asp Leu Glu Val Val
    1535            1540                1545

Ala Ala Thr Pro Thr Ser Leu Leu Ile Ser Trp Asp Ala Pro Ala
    1550            1555                1560

Val Thr Val Arg Tyr Tyr Arg Ile Thr Tyr Gly Glu Thr Gly Gly
    1565            1570                1575

Asn Ser Pro Val Gln Glu Phe Thr Val Pro Gly Ser Lys Ser Thr
    1580            1585                1590

Ala Thr Ile Ser Gly Leu Lys Pro Gly Val Asp Tyr Thr Ile Thr
    1595            1600                1605

Val Tyr Ala Val Thr Gly Arg Gly Asp Ser Pro Ala Ser Ser Lys
    1610            1615                1620

Pro Ile Ser Ile Asn Tyr Arg Thr Glu Ile Asp Lys Pro Ser Gln
    1625            1630                1635

Met Gln Val Thr Asp Val Gln Asp Asn Ser Ile Ser Val Lys Trp
    1640            1645                1650

Leu Pro Ser Ser Ser Pro Val Thr Gly Tyr Arg Val Thr Thr Thr
    1655            1660                1665

Pro Lys Asn Gly Pro Gly Pro Thr Lys Thr Lys Thr Ala Gly Pro
    1670            1675                1680

Asp Gln Thr Glu Met Thr Ile Glu Gly Leu Gln Pro Thr Val Glu
    1685            1690                1695

Tyr Val Val Ser Val Tyr Ala Gln Asn Pro Ser Gly Glu Ser Gln
    1700            1705                1710

Pro Leu Val Gln Thr Ala Val Thr Asn Ile Asp Arg Pro Lys Gly
    1715            1720                1725

Leu Ala Phe Thr Asp Val Asp Val Asp Ser Ile Lys Ile Ala Trp
    1730            1735                1740

Glu Ser Pro Gln Gly Gln Val Ser Arg Tyr Arg Val Thr Tyr Ser
    1745            1750                1755

Ser Pro Glu Asp Gly Ile His Glu Leu Phe Pro Ala Pro Asp Gly
    1760            1765                1770

Glu Glu Asp Thr Ala Glu Leu Gln Gly Leu Arg Pro Gly Ser Glu
    1775            1780                1785

Tyr Thr Val Ser Val Val Ala Leu His Asp Asp Met Glu Ser Gln
    1790            1795                1800

Pro Leu Ile Gly Thr Gln Ser Thr Ala Ile Pro Ala Pro Thr Asp
    1805            1810                1815

Leu Lys Phe Thr Gln Val Thr Pro Thr Ser Leu Ser Ala Gln Trp
    1820            1825                1830

Thr Pro Pro Asn Val Gln Leu Thr Gly Tyr Arg Val Arg Val Thr
    1835            1840                1845

Pro Lys Glu Lys Thr Gly Pro Met Lys Glu Ile Asn Leu Ala Pro
    1850            1855                1860

Asp Ser Ser Ser Val Val Val Ser Gly Leu Met Val Ala Thr Lys
    1865            1870                1875

Tyr Glu Val Ser Val Tyr Ala Leu Lys Asp Thr Leu Thr Ser Arg
    1880            1885                1890
```

```
Pro Ala Gln Gly Val Val Thr Thr Leu Glu Asn Val Ser Pro Pro
1895                1900                1905

Arg Arg Ala Arg Val Thr Asp Ala Thr Glu Thr Thr Ile Thr Ile
1910                1915                1920

Ser Trp Arg Thr Lys Thr Glu Thr Ile Thr Gly Phe Gln Val Asp
1925                1930                1935

Ala Val Pro Ala Asn Gly Gln Thr Pro Ile Gln Arg Thr Ile Lys
1940                1945                1950

Pro Asp Val Arg Ser Tyr Thr Ile Thr Gly Leu Gln Pro Gly Thr
1955                1960                1965

Asp Tyr Lys Ile Tyr Leu Tyr Thr Leu Asn Asp Asn Ala Arg Ser
1970                1975                1980

Ser Pro Val Val Ile Asp Ala Ser Thr Ala Ile Asp Ala Pro Ser
1985                1990                1995

Asn Leu Arg Phe Leu Ala Thr Thr Pro Asn Ser Leu Leu Val Ser
2000                2005                2010

Trp Gln Pro Pro Arg Ala Arg Ile Thr Gly Tyr Ile Ile Lys Tyr
2015                2020                2025

Glu Lys Pro Gly Ser Pro Pro Arg Glu Val Val Pro Arg Pro Arg
2030                2035                2040

Pro Gly Val Thr Glu Ala Thr Ile Thr Gly Leu Glu Pro Gly Thr
2045                2050                2055

Glu Tyr Thr Ile Tyr Val Ile Ala Leu Lys Asn Asn Gln Lys Ser
2060                2065                2070

Glu Pro Leu Ile Gly Arg Lys Lys Thr Asp Glu Leu Pro Gln Leu
2075                2080                2085

Val Thr Leu Pro His Pro Asn Leu His Gly Pro Glu Ile Leu Asp
2090                2095                2100

Val Pro Ser Thr Val Gln Lys Thr Pro Phe Val Thr His Pro Gly
2105                2110                2115

Tyr Asp Thr Gly Asn Gly Ile Gln Leu Pro Gly Thr Ser Gly Gln
2120                2125                2130

Gln Pro Ser Val Gly Gln Gln Met Ile Phe Glu Glu His Gly Phe
2135                2140                2145

Arg Arg Thr Thr Pro Pro Thr Thr Ala Thr Pro Ile Arg His Arg
2150                2155                2160

Pro Arg Pro Tyr Pro Pro Asn Val Gly Glu Glu Ile Gln Ile Gly
2165                2170                2175

His Ile Pro Arg Glu Asp Val Asp Tyr His Leu Tyr Pro His Gly
2180                2185                2190

Pro Gly Leu Asn Pro Asn Ala Ser Thr Gly Gln Glu Ala Leu Ser
2195                2200                2205

Gln Thr Thr Ile Ser Trp Ala Pro Phe Gln Asp Thr Ser Glu Tyr
2210                2215                2220

Ile Ile Ser Cys His Pro Val Gly Thr Asp Glu Pro Leu Gln
2225                2230                2235

Phe Arg Val Pro Gly Thr Ser Thr Ser Ala Thr Leu Thr Gly Leu
2240                2245                2250

Thr Arg Gly Ala Thr Tyr Asn Ile Ile Val Glu Ala Leu Lys Asp
2255                2260                2265

Gln Gln Arg His Lys Val Arg Glu Glu Val Val Thr Val Gly Asn
2270                2275                2280

Ser Val Asn Glu Gly Leu Asn Gln Pro Thr Asp Asp Ser Cys Phe
```

-continued

```
            2285                2290                2295
Asp Pro Tyr Thr Val Ser His Tyr Ala Val Gly Asp Glu Trp Glu
        2300                2305                2310

Arg Met Ser Glu Ser Gly Phe Lys Leu Leu Cys Gln Cys Leu Gly
        2315                2320                2325

Phe Gly Ser Gly His Phe Arg Cys Asp Ser Ser Arg Trp Cys His
        2330                2335                2340

Asp Asn Gly Val Asn Tyr Lys Ile Gly Glu Lys Trp Asp Arg Gln
        2345                2350                2355

Gly Glu Asn Gly Gln Met Met Ser Cys Thr Cys Leu Gly Asn Gly
        2360                2365                2370

Lys Gly Glu Phe Lys Cys Asp Pro His Glu Ala Thr Cys Tyr Asp
        2375                2380                2385

Asp Gly Lys Thr Tyr His Val Gly Glu Gln Trp Gln Lys Glu Tyr
        2390                2395                2400

Leu Gly Ala Ile Cys Ser Cys Thr Cys Phe Gly Gly Gln Arg Gly
        2405                2410                2415

Trp Arg Cys Asp Asn Cys Arg Arg Pro Gly Gly Glu Pro Ser Pro
        2420                2425                2430

Glu Gly Thr Thr Gly Gln Ser Tyr Asn Gln Tyr Ser Gln Arg Tyr
        2435                2440                2445

His Gln Arg Thr Asn Thr Asn Val Asn Cys Pro Ile Glu Cys Phe
        2450                2455                2460

Met Pro Leu Asp Val Gln Ala Asp Arg Glu Asp Ser Arg Glu
        2465                2470                2475

<210> SEQ ID NO 307
<211> LENGTH: 782
<212> TYPE: PRT
<213> ORGANISM: Homo sapiens

<400> SEQUENCE: 307

Met Ala Pro His Arg Pro Ala Pro Ala Leu Leu Cys Ala Leu Ser Leu
1               5                   10                  15

Ala Leu Cys Ala Leu Ser Leu Pro Val Arg Ala Ala Thr Ala Ser Arg
            20                  25                  30

Gly Ala Ser Gln Ala Gly Ala Pro Gln Gly Arg Val Pro Glu Ala Arg
        35                  40                  45

Pro Asn Ser Met Val Val Glu His Pro Glu Phe Leu Lys Ala Gly Lys
    50                  55                  60

Glu Pro Gly Leu Gln Ile Trp Arg Val Glu Lys Phe Asp Leu Val Pro
65                  70                  75                  80

Val Pro Thr Asn Leu Tyr Gly Asp Phe Phe Thr Gly Asp Ala Tyr Val
                85                  90                  95

Ile Leu Lys Thr Val Gln Leu Arg Asn Gly Asn Leu Gln Tyr Asp Leu
            100                 105                 110

His Tyr Trp Leu Gly Asn Glu Cys Ser Gln Asp Glu Ser Gly Ala Ala
        115                 120                 125

Ala Ile Phe Thr Val Gln Leu Asp Asp Tyr Leu Asn Gly Arg Ala Val
    130                 135                 140

Gln His Arg Glu Val Gln Gly Phe Glu Ser Ala Thr Phe Leu Gly Tyr
145                 150                 155                 160

Phe Lys Ser Gly Leu Lys Tyr Lys Lys Gly Gly Val Ala Ser Gly Phe
                165                 170                 175
```

```
Lys His Val Val Pro Asn Glu Val Val Val Gln Arg Leu Phe Gln Val
                180                 185                 190

Lys Gly Arg Arg Val Val Arg Ala Thr Glu Val Pro Val Ser Trp Glu
            195                 200                 205

Ser Phe Asn Asn Gly Asp Cys Phe Ile Leu Asp Leu Gly Asn Asn Ile
210                 215                 220

His Gln Trp Cys Gly Ser Asn Ser Asn Arg Tyr Glu Arg Leu Lys Ala
225                 230                 235                 240

Thr Gln Val Ser Lys Gly Ile Arg Asp Asn Glu Arg Ser Gly Arg Ala
                245                 250                 255

Arg Val His Val Ser Glu Glu Gly Thr Glu Pro Glu Ala Met Leu Gln
            260                 265                 270

Val Leu Gly Pro Lys Pro Ala Leu Pro Ala Gly Thr Glu Asp Thr Ala
        275                 280                 285

Lys Glu Asp Ala Ala Asn Arg Lys Leu Ala Lys Leu Tyr Lys Val Ser
290                 295                 300

Asn Gly Ala Gly Thr Met Ser Val Ser Leu Val Ala Asp Glu Asn Pro
305                 310                 315                 320

Phe Ala Gln Gly Ala Leu Lys Ser Glu Asp Cys Phe Ile Leu Asp His
                325                 330                 335

Gly Lys Asp Gly Lys Ile Phe Val Trp Lys Gly Lys Gln Ala Asn Thr
            340                 345                 350

Glu Glu Arg Lys Ala Ala Leu Lys Thr Ala Ser Asp Phe Ile Thr Lys
        355                 360                 365

Met Asp Tyr Pro Lys Gln Thr Gln Val Ser Val Leu Pro Glu Gly Gly
370                 375                 380

Glu Thr Pro Leu Phe Lys Gln Phe Phe Lys Asn Trp Arg Asp Pro Asp
385                 390                 395                 400

Gln Thr Asp Gly Leu Gly Leu Ser Tyr Leu Ser Ser His Ile Ala Asn
                405                 410                 415

Val Glu Arg Val Pro Phe Asp Ala Ala Thr Leu His Thr Ser Thr Ala
            420                 425                 430

Met Ala Ala Gln His Gly Met Asp Asp Asp Gly Thr Gly Gln Lys Gln
        435                 440                 445

Ile Trp Arg Ile Glu Gly Ser Asn Lys Val Pro Val Asp Pro Ala Thr
450                 455                 460

Tyr Gly Gln Phe Tyr Gly Gly Asp Ser Tyr Ile Ile Leu Tyr Asn Tyr
465                 470                 475                 480

Arg His Gly Gly Arg Gln Gly Gln Ile Ile Tyr Asn Trp Gln Gly Ala
                485                 490                 495

Gln Ser Thr Gln Asp Glu Val Ala Ala Ser Ala Ile Leu Thr Ala Gln
            500                 505                 510

Leu Asp Glu Glu Leu Gly Gly Thr Pro Val Gln Ser Arg Val Val Gln
        515                 520                 525

Gly Lys Glu Pro Ala His Leu Met Ser Leu Phe Gly Gly Lys Pro Met
530                 535                 540

Ile Ile Tyr Lys Gly Gly Thr Ser Arg Glu Gly Gly Gln Thr Ala Pro
545                 550                 555                 560

Ala Ser Thr Arg Leu Phe Gln Val Arg Ala Asn Ser Ala Gly Ala Thr
                565                 570                 575

Arg Ala Val Glu Val Leu Pro Lys Ala Gly Ala Leu Asn Ser Asn Asp
            580                 585                 590

Ala Phe Val Leu Lys Thr Pro Ser Ala Ala Tyr Leu Trp Val Gly Thr
```

```
            595                 600                 605
Gly Ala Ser Glu Ala Glu Lys Thr Gly Ala Gln Glu Leu Leu Arg Val
610                 615                 620

Leu Arg Ala Gln Pro Val Gln Val Ala Glu Gly Ser Glu Pro Asp Gly
625                 630                 635                 640

Phe Trp Glu Ala Leu Gly Gly Lys Ala Ala Tyr Arg Thr Ser Pro Arg
                645                 650                 655

Leu Lys Asp Lys Lys Met Asp Ala His Pro Pro Arg Leu Phe Ala Cys
            660                 665                 670

Ser Asn Lys Ile Gly Arg Phe Val Ile Glu Val Pro Gly Glu Leu
        675                 680                 685

Met Gln Glu Asp Leu Ala Thr Asp Val Met Leu Leu Asp Thr Trp
    690                 695                 700

Asp Gln Val Phe Val Trp Val Gly Lys Asp Ser Gln Glu Glu Lys
705                 710                 715                 720

Thr Glu Ala Leu Thr Ser Ala Lys Arg Tyr Ile Glu Thr Asp Pro Ala
                725                 730                 735

Asn Arg Asp Arg Arg Thr Pro Ile Thr Val Val Lys Gln Gly Phe Glu
            740                 745                 750

Pro Pro Ser Phe Val Gly Trp Phe Leu Gly Trp Asp Asp Asp Tyr Trp
        755                 760                 765

Ser Val Asp Pro Leu Asp Arg Ala Met Ala Glu Leu Ala Ala
    770                 775                 780

<210> SEQ ID NO 308
<211> LENGTH: 462
<212> TYPE: PRT
<213> ORGANISM: Homo sapiens

<400> SEQUENCE: 308

Met Ala Arg Val Leu Gly Ala Pro Val Ala Leu Gly Leu Trp Ser Leu
1               5                   10                  15

Cys Trp Ser Leu Ala Ile Ala Thr Pro Leu Pro Pro Thr Ser Ala His
            20                  25                  30

Gly Asn Val Ala Glu Gly Glu Thr Lys Pro Asp Pro Asp Val Thr Glu
        35                  40                  45

Arg Cys Ser Asp Gly Trp Ser Phe Asp Ala Thr Thr Leu Asp Asp Asn
    50                  55                  60

Gly Thr Met Leu Phe Phe Lys Gly Glu Phe Val Trp Lys Ser His Lys
65                  70                  75                  80

Trp Asp Arg Glu Leu Ile Ser Glu Arg Trp Lys Asn Phe Pro Ser Pro
                85                  90                  95

Val Asp Ala Ala Phe Arg Gln Gly His Asn Ser Val Phe Leu Ile Lys
            100                 105                 110

Gly Asp Lys Val Trp Val Tyr Pro Pro Glu Lys Lys Glu Lys Gly Tyr
        115                 120                 125

Pro Lys Leu Leu Gln Asp Glu Phe Pro Gly Ile Pro Ser Pro Leu Asp
    130                 135                 140

Ala Ala Val Glu Cys His Arg Gly Glu Cys Gln Ala Glu Gly Val Leu
145                 150                 155                 160

Phe Phe Gln Gly Asp Arg Glu Trp Phe Trp Asp Leu Ala Thr Gly Thr
                165                 170                 175

Met Lys Glu Arg Ser Trp Pro Ala Val Gly Asn Cys Ser Ser Ala Leu
            180                 185                 190
```

```
Arg Trp Leu Gly Arg Tyr Tyr Cys Phe Gln Gly Asn Gln Phe Leu Arg
            195                 200                 205

Phe Asp Pro Val Arg Gly Glu Val Pro Pro Arg Tyr Pro Arg Asp Val
    210                 215                 220

Arg Asp Tyr Phe Met Pro Cys Pro Gly Arg Gly His Gly His Arg Asn
225                 230                 235                 240

Gly Thr Gly His Gly Asn Ser Thr His His Gly Pro Glu Tyr Met Arg
            245                 250                 255

Cys Ser Pro His Leu Val Leu Ser Ala Leu Thr Ser Asp Asn His Gly
            260                 265                 270

Ala Thr Tyr Ala Phe Ser Gly Thr His Tyr Trp Arg Leu Asp Thr Ser
            275                 280                 285

Arg Asp Gly Trp His Ser Trp Pro Ile Ala His Gln Trp Pro Gln Gly
    290                 295                 300

Pro Ser Ala Val Asp Ala Ala Phe Ser Trp Glu Glu Lys Leu Tyr Leu
305                 310                 315                 320

Val Gln Gly Thr Gln Val Tyr Val Phe Leu Thr Lys Gly Gly Tyr Thr
            325                 330                 335

Leu Val Ser Gly Tyr Pro Lys Arg Leu Glu Lys Glu Val Gly Thr Pro
            340                 345                 350

His Gly Ile Ile Leu Asp Ser Val Asp Ala Ala Phe Ile Cys Pro Gly
            355                 360                 365

Ser Ser Arg Leu His Ile Met Ala Gly Arg Arg Leu Trp Trp Leu Asp
    370                 375                 380

Leu Lys Ser Gly Ala Gln Ala Thr Trp Thr Glu Leu Pro Trp Pro His
385                 390                 395                 400

Glu Lys Val Asp Gly Ala Leu Cys Met Glu Lys Ser Leu Gly Pro Asn
            405                 410                 415

Ser Cys Ser Ala Asn Gly Pro Gly Leu Tyr Leu Ile His Gly Pro Asn
            420                 425                 430

Leu Tyr Cys Tyr Ser Asp Val Glu Lys Leu Asn Ala Ala Lys Ala Leu
            435                 440                 445

Pro Gln Pro Gln Asn Val Thr Ser Leu Leu Gly Cys Thr His
    450                 455                 460

<210> SEQ ID NO 309
<211> LENGTH: 499
<212> TYPE: PRT
<213> ORGANISM: Homo sapiens

<400> SEQUENCE: 309

Met Lys His Ser Leu Asn Ala Leu Leu Ile Phe Leu Ile Ile Thr Ser
1               5                   10                  15

Ala Trp Gly Gly Ser Lys Gly Pro Leu Asp Gln Leu Glu Lys Gly Gly
            20                  25                  30

Glu Thr Ala Gln Ser Ala Asp Pro Gln Trp Glu Gln Leu Asn Asn Lys
        35                  40                  45

Asn Leu Ser Met Pro Leu Leu Pro Ala Asp Phe His Lys Glu Asn Thr
    50                  55                  60

Val Thr Asn Asp Trp Ile Pro Glu Gly Glu Asp Asp Tyr Leu
65                  70                  75                  80

Asp Leu Glu Lys Ile Phe Ser Glu Asp Asp Tyr Ile Asp Ile Val
                85                  90                  95

Asp Ser Leu Ser Val Ser Pro Thr Asp Ser Asp Val Ser Ala Gly Asn
                100                 105                 110
```

Ile Leu Gln Leu Phe His Gly Lys Ser Arg Ile Gln Arg Leu Asn Ile
            115                 120                 125

Leu Asn Ala Lys Phe Ala Phe Asn Leu Tyr Arg Val Leu Lys Asp Gln
130                 135                 140

Val Asn Thr Phe Asp Asn Ile Phe Ile Ala Pro Val Gly Ile Ser Thr
145                 150                 155                 160

Ala Met Gly Met Ile Ser Leu Gly Leu Lys Gly Glu Thr His Glu Gln
                165                 170                 175

Val His Ser Ile Leu His Phe Lys Asp Phe Val Asn Ala Ser Ser Lys
                180                 185                 190

Tyr Glu Ile Thr Thr Ile His Asn Leu Phe Arg Lys Leu Thr His Arg
                195                 200                 205

Leu Phe Arg Arg Asn Phe Gly Tyr Thr Leu Arg Ser Val Asn Asp Leu
210                 215                 220

Tyr Ile Gln Lys Gln Phe Pro Ile Leu Leu Asp Phe Arg Thr Lys Val
225                 230                 235                 240

Arg Glu Tyr Tyr Phe Ala Glu Ala Gln Ile Ala Asp Phe Ser Asp Pro
                245                 250                 255

Ala Phe Ile Ser Lys Thr Asn Asn His Ile Met Lys Leu Thr Lys Gly
                260                 265                 270

Leu Ile Lys Asp Ala Leu Glu Asn Ile Asp Pro Ala Thr Gln Met Met
                275                 280                 285

Ile Leu Asn Cys Ile Tyr Phe Lys Gly Ser Trp Val Asn Lys Phe Pro
                290                 295                 300

Val Glu Met Thr His Asn His Asn Phe Arg Leu Asn Glu Arg Glu Val
305                 310                 315                 320

Val Lys Val Ser Met Met Gln Thr Lys Gly Asn Phe Leu Ala Ala Asn
                325                 330                 335

Asp Gln Glu Leu Asp Cys Asp Ile Leu Gln Leu Glu Tyr Val Gly Gly
                340                 345                 350

Ile Ser Met Leu Ile Val Val Pro His Lys Met Ser Gly Met Lys Thr
                355                 360                 365

Leu Glu Ala Gln Leu Thr Pro Arg Val Val Glu Arg Trp Gln Lys Ser
                370                 375                 380

Met Thr Asn Arg Thr Arg Glu Val Leu Leu Pro Lys Phe Lys Leu Glu
385                 390                 395                 400

Lys Asn Tyr Asn Leu Val Glu Ser Leu Lys Leu Met Gly Ile Arg Met
                405                 410                 415

Leu Phe Asp Lys Asn Gly Asn Met Ala Gly Ile Ser Asp Gln Arg Ile
                420                 425                 430

Ala Ile Asp Leu Phe Lys His Gln Gly Thr Ile Thr Val Asn Glu Glu
                435                 440                 445

Gly Thr Gln Ala Thr Thr Val Thr Thr Val Gly Phe Met Pro Leu Ser
450                 455                 460

Thr Gln Val Arg Phe Thr Val Asp Arg Pro Phe Leu Phe Leu Ile Tyr
465                 470                 475                 480

Glu His Arg Thr Ser Cys Leu Leu Phe Met Gly Arg Val Ala Asn Pro
                485                 490                 495

Ser Arg Ser

<210> SEQ ID NO 310
<211> LENGTH: 583
<212> TYPE: PRT

<213> ORGANISM: Homo sapiens

<400> SEQUENCE: 310

```
Met Lys Leu Leu His Val Phe Leu Leu Phe Leu Cys Phe His Leu Arg
1               5                   10                  15

Phe Cys Lys Val Thr Tyr Thr Ser Gln Glu Asp Leu Val Glu Lys Lys
            20                  25                  30

Cys Leu Ala Lys Lys Tyr Thr His Leu Ser Cys Asp Lys Val Phe Cys
        35                  40                  45

Gln Pro Trp Gln Arg Cys Ile Glu Gly Thr Cys Val Cys Lys Leu Pro
    50                  55                  60

Tyr Gln Cys Pro Lys Asn Gly Thr Ala Val Cys Ala Thr Asn Arg Arg
65                  70                  75                  80

Ser Phe Pro Thr Tyr Cys Gln Gln Lys Ser Leu Glu Cys Leu His Pro
                85                  90                  95

Gly Thr Lys Phe Leu Asn Asn Gly Thr Cys Thr Ala Glu Gly Lys Phe
            100                 105                 110

Ser Val Ser Leu Lys His Gly Asn Thr Asp Ser Glu Gly Ile Val Glu
        115                 120                 125

Val Lys Leu Val Asp Gln Asp Lys Thr Met Phe Ile Cys Lys Ser Ser
130                 135                 140

Trp Ser Met Arg Glu Ala Asn Val Ala Cys Leu Asp Leu Gly Phe Gln
145                 150                 155                 160

Gln Gly Ala Asp Thr Gln Arg Arg Phe Lys Leu Ser Asp Leu Ser Ile
                165                 170                 175

Asn Ser Thr Glu Cys Leu His Val His Cys Arg Gly Leu Glu Thr Ser
            180                 185                 190

Leu Ala Glu Cys Thr Phe Thr Lys Arg Arg Thr Met Gly Tyr Gln Asp
        195                 200                 205

Phe Ala Asp Val Val Cys Tyr Thr Gln Lys Ala Asp Ser Pro Met Asp
    210                 215                 220

Asp Phe Phe Gln Cys Val Asn Gly Lys Tyr Ile Ser Gln Met Lys Ala
225                 230                 235                 240

Cys Asp Gly Ile Asn Asp Cys Gly Asp Gln Ser Asp Glu Leu Cys Cys
                245                 250                 255

Lys Ala Cys Gln Gly Lys Gly Phe His Cys Lys Ser Gly Val Cys Ile
            260                 265                 270

Pro Ser Gln Tyr Gln Cys Asn Gly Glu Val Asp Cys Ile Thr Gly Glu
        275                 280                 285

Asp Glu Val Gly Cys Ala Gly Phe Ala Ser Val Ala Gln Glu Glu Thr
    290                 295                 300

Glu Ile Leu Thr Ala Asp Met Asp Ala Glu Arg Arg Ile Lys Ser
305                 310                 315                 320

Leu Leu Pro Lys Leu Ser Cys Gly Val Lys Asn Arg Met His Ile Arg
                325                 330                 335

Arg Lys Arg Ile Val Gly Gly Lys Arg Ala Gln Leu Gly Asp Leu Pro
            340                 345                 350

Trp Gln Val Ala Ile Lys Asp Ala Ser Gly Ile Thr Cys Gly Gly Ile
        355                 360                 365

Tyr Ile Gly Gly Cys Trp Ile Leu Thr Ala Ala His Cys Leu Arg Ala
    370                 375                 380

Ser Lys Thr His Arg Tyr Gln Ile Trp Thr Thr Val Val Asp Trp Ile
385                 390                 395                 400
```

```
His Pro Asp Leu Lys Arg Ile Val Ile Glu Tyr Val Asp Arg Ile Ile
            405                 410                 415

Phe His Glu Asn Tyr Asn Ala Gly Thr Tyr Gln Asn Asp Ile Ala Leu
        420                 425                 430

Ile Glu Met Lys Lys Asp Gly Asn Lys Lys Asp Cys Glu Leu Pro Arg
            435                 440                 445

Ser Ile Pro Ala Cys Val Pro Trp Ser Pro Tyr Leu Phe Gln Pro Asn
450                 455                 460

Asp Thr Cys Ile Val Ser Gly Trp Gly Arg Glu Lys Asp Asn Glu Arg
465                 470                 475                 480

Val Phe Ser Leu Gln Trp Gly Glu Val Lys Leu Ile Ser Asn Cys Ser
                485                 490                 495

Lys Phe Tyr Gly Asn Arg Phe Tyr Glu Lys Glu Met Glu Cys Ala Gly
                500                 505                 510

Thr Tyr Asp Gly Ser Ile Asp Ala Cys Lys Gly Asp Ser Gly Gly Pro
            515                 520                 525

Leu Val Cys Met Asp Ala Asn Asn Val Thr Tyr Val Trp Gly Val Val
            530                 535                 540

Ser Trp Gly Glu Asn Cys Gly Lys Pro Glu Phe Pro Gly Phe Tyr Thr
545                 550                 555                 560

Lys Val Ala Asn Tyr Phe Asp Trp Ile Ser Tyr His Val Gly Arg Pro
                565                 570                 575

Phe Ile Ser Gln Tyr Asn Val
            580

<210> SEQ ID NO 311
<211> LENGTH: 159
<212> TYPE: PRT
<213> ORGANISM: Homo sapiens

<400> SEQUENCE: 311

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
        115                 120                 125

Asn Lys Cys Tyr Thr Ala Val Val Pro Leu Val Tyr Gly Gly Glu Thr
    130                 135                 140

Lys Met Val Glu Thr Ala Leu Thr Pro Asp Ala Cys Tyr Pro Asp
145                 150                 155

<210> SEQ ID NO 312
<211> LENGTH: 911
<212> TYPE: PRT
<213> ORGANISM: Homo sapiens
```

<400> SEQUENCE: 312

Met Asp Gly Ala Met Gly Pro Arg Gly Leu Leu Leu Cys Met Tyr Leu
1               5                   10                  15

Val Ser Leu Leu Ile Leu Gln Ala Met Pro Ala Leu Gly Ser Ala Thr
            20                  25                  30

Gly Arg Ser Lys Ser Ser Glu Lys Arg Gln Ala Val Asp Thr Ala Val
        35                  40                  45

Asp Gly Val Phe Ile Arg Ser Leu Lys Val Asn Cys Lys Val Thr Ser
    50                  55                  60

Arg Phe Ala His Tyr Val Val Thr Ser Gln Val Val Asn Thr Ala Asn
65                  70                  75                  80

Glu Ala Arg Glu Val Ala Phe Asp Leu Glu Ile Pro Lys Thr Ala Phe
                85                  90                  95

Ile Ser Asp Phe Ala Val Thr Ala Asp Gly Asn Ala Phe Ile Gly Asp
            100                 105                 110

Ile Lys Asp Lys Val Thr Ala Trp Lys Gln Tyr Arg Lys Ala Ala Ile
        115                 120                 125

Ser Gly Glu Asn Ala Gly Leu Val Arg Ala Ser Gly Arg Thr Met Glu
    130                 135                 140

Gln Phe Thr Ile His Leu Thr Val Asn Pro Gln Ser Lys Val Thr Phe
145                 150                 155                 160

Gln Leu Thr Tyr Glu Glu Val Leu Lys Arg Asn His Met Gln Tyr Glu
                165                 170                 175

Ile Val Ile Lys Val Lys Pro Lys Gln Leu Val His His Phe Glu Ile
            180                 185                 190

Asp Val Asp Ile Phe Glu Pro Gln Gly Ile Ser Lys Leu Asp Ala Gln
        195                 200                 205

Ala Ser Phe Leu Pro Lys Glu Leu Ala Ala Gln Thr Ile Lys Lys Ser
    210                 215                 220

Phe Ser Gly Lys Lys Gly His Val Leu Phe Arg Pro Thr Val Ser Gln
225                 230                 235                 240

Gln Gln Ser Cys Pro Thr Cys Ser Thr Ser Leu Leu Asn Gly His Phe
                245                 250                 255

Lys Val Thr Tyr Asp Val Thr Arg Asp Glu Ile Cys Asp Leu Leu Val
            260                 265                 270

Ala Asn Asn His Phe Ala His Phe Phe Ala Pro Gln Asn Leu Thr Asn
        275                 280                 285

Met Asn Lys Asn Val Val Phe Val Ile Asp Ile Ser Gly Ser Met Arg
    290                 295                 300

Gly Gln Lys Val Lys Gln Thr Lys Glu Ala Leu Leu Lys Ile Leu Gly
305                 310                 315                 320

Asp Met Gln Pro Gly Asp Tyr Phe Asp Leu Val Leu Phe Gly Thr Arg
                325                 330                 335

Val Gln Ser Trp Lys Gly Ser Leu Val Gln Ala Ser Glu Ala Asn Leu
            340                 345                 350

Gln Ala Ala Gln Asp Phe Val Arg Gly Phe Ser Leu Asp Glu Ala Thr
        355                 360                 365

Asn Leu Asn Gly Gly Leu Leu Arg Gly Ile Glu Ile Leu Asn Gln Val
    370                 375                 380

Gln Glu Ser Leu Pro Glu Leu Ser Asn His Ala Ser Ile Leu Ile Met
385                 390                 395                 400

Leu Thr Asp Gly Asp Pro Thr Glu Gly Val Thr Asp Arg Ser Gln Ile

```
                    405                 410                 415
Leu Lys Asn Val Arg Asn Ala Ile Arg Gly Arg Phe Pro Leu Tyr Asn
                420                 425                 430

Leu Gly Phe Gly His Asn Val Asp Phe Asn Phe Leu Glu Val Met Ser
            435                 440                 445

Met Glu Asn Asn Gly Arg Ala Gln Arg Ile Tyr Glu Asp His Asp Ala
        450                 455                 460

Thr Gln Gln Leu Gln Gly Phe Tyr Ser Gln Val Ala Lys Pro Leu Leu
465                 470                 475                 480

Val Asp Val Asp Leu Gln Tyr Pro Gln Asp Ala Val Leu Ala Leu Thr
                485                 490                 495

Gln Asn His His Lys Gln Tyr Tyr Glu Gly Ser Glu Ile Val Val Ala
            500                 505                 510

Gly Arg Ile Ala Asp Asn Lys Gln Ser Ser Phe Lys Ala Asp Val Gln
        515                 520                 525

Ala His Gly Glu Gly Gln Glu Phe Ser Ile Thr Cys Leu Val Asp Glu
    530                 535                 540

Glu Glu Met Lys Lys Leu Leu Arg Glu Arg Gly His Met Leu Glu Asn
545                 550                 555                 560

His Val Glu Arg Leu Trp Ala Tyr Leu Thr Ile Gln Glu Leu Leu Ala
                565                 570                 575

Lys Arg Met Lys Val Asp Arg Glu Val Arg Ala Asn Leu Ser Ser Gln
            580                 585                 590

Ala Leu Arg Met Ser Leu Asp Tyr Gly Phe Val Thr Pro Leu Thr Ser
        595                 600                 605

Met Ser Ile Arg Gly Met Ala Asp Gln Asp Gly Leu Lys Pro Thr Ile
    610                 615                 620

Asp Lys Pro Ser Glu Asp Ser Pro Pro Leu Glu Met Leu Gly Pro Arg
625                 630                 635                 640

Arg Thr Phe Val Leu Ser Ala Leu Gln Pro Ser Pro Thr His Ser Ser
                645                 650                 655

Ser Asn Thr Gln Arg Leu Pro Asp Arg Val Thr Gly Val Asp Thr Asp
            660                 665                 670

Pro His Phe Ile Ile His Val Pro Gln Lys Glu Asp Thr Leu Cys Phe
        675                 680                 685

Asn Ile Asn Glu Glu Pro Gly Val Ile Leu Ser Leu Val Gln Asp Pro
    690                 695                 700

Asn Thr Gly Phe Ser Val Asn Gly Gln Leu Ile Gly Asn Lys Ala Arg
705                 710                 715                 720

Ser Pro Gly Gln His Asp Gly Thr Tyr Phe Gly Arg Leu Gly Ile Ala
                725                 730                 735

Asn Pro Ala Thr Asp Phe Gln Leu Glu Val Thr Pro Gln Asn Ile Thr
            740                 745                 750

Leu Asn Pro Gly Phe Gly Gly Pro Val Phe Ser Trp Arg Asp Gln Ala
        755                 760                 765

Val Leu Arg Gln Asp Gly Val Val Thr Ile Asn Lys Lys Arg Asn
    770                 775                 780

Leu Val Val Ser Val Asp Asp Gly Gly Thr Phe Glu Val Leu His
785                 790                 795                 800

Arg Val Trp Lys Gly Ser Ser Val His Gln Asp Phe Leu Gly Phe Tyr
                805                 810                 815

Val Leu Asp Ser His Arg Met Ser Ala Arg Thr His Gly Leu Leu Gly
            820                 825                 830
```

```
Gln Phe Phe His Pro Ile Gly Phe Glu Val Ser Asp Ile His Pro Gly
        835                 840                 845

Ser Asp Pro Thr Lys Pro Asp Ala Thr Met Val Val Arg Asn Arg Arg
850                 855                 860

Leu Thr Val Thr Arg Gly Leu Gln Lys Asp Tyr Ser Lys Asp Pro Trp
865                 870                 875                 880

His Gly Ala Glu Val Ser Cys Trp Phe Ile His Asn Asn Gly Ala Gly
                885                 890                 895

Leu Ile Asp Gly Ala Tyr Thr Asp Tyr Ile Val Pro Asp Ile Phe
                900                 905                 910

<210> SEQ ID NO 313
<211> LENGTH: 946
<212> TYPE: PRT
<213> ORGANISM: Homo sapiens

<400> SEQUENCE: 313

Met Lys Arg Leu Thr Cys Phe Phe Ile Cys Phe Phe Leu Ser Glu Val
1               5                   10                  15

Ser Gly Phe Glu Ile Pro Ile Asn Gly Leu Ser Glu Phe Val Asp Tyr
                20                  25                  30

Glu Asp Leu Val Glu Leu Ala Pro Gly Lys Phe Gln Leu Val Ala Glu
            35                  40                  45

Asn Arg Arg Tyr Gln Arg Ser Leu Pro Gly Glu Ser Glu Glu Met Met
        50                  55                  60

Glu Glu Val Asp Gln Val Thr Leu Tyr Ser Tyr Lys Val Gln Ser Thr
65                  70                  75                  80

Ile Thr Ser Arg Met Ala Thr Thr Met Ile Gln Ser Lys Val Val Asn
                85                  90                  95

Asn Ser Pro Gln Pro Gln Asn Val Val Phe Asp Val Gln Ile Pro Lys
                100                 105                 110

Gly Ala Phe Ile Ser Asn Phe Ser Met Thr Val Asp Gly Lys Thr Phe
            115                 120                 125

Arg Ser Ser Ile Lys Glu Lys Thr Val Gly Arg Ala Leu Tyr Ala Gln
        130                 135                 140

Ala Arg Ala Lys Gly Lys Thr Ala Gly Leu Val Arg Ser Ser Ala Leu
145                 150                 155                 160

Asp Met Glu Asn Phe Arg Thr Glu Val Asn Val Leu Pro Gly Ala Lys
                165                 170                 175

Val Gln Phe Glu Leu His Tyr Gln Glu Val Lys Trp Arg Lys Leu Gly
            180                 185                 190

Ser Tyr Glu His Arg Ile Tyr Leu Gln Pro Gly Arg Leu Ala Lys His
        195                 200                 205

Leu Glu Val Asp Val Trp Val Ile Glu Pro Gln Gly Leu Arg Phe Leu
    210                 215                 220

His Val Pro Asp Thr Phe Glu Gly His Phe Asp Gly Val Pro Val Ile
225                 230                 235                 240

Ser Lys Gly Gln Gln Lys Ala His Val Ser Phe Lys Pro Thr Val Ala
                245                 250                 255

Gln Gln Arg Ile Cys Pro Ser Cys Arg Glu Thr Ala Val Asp Gly Glu
            260                 265                 270

Leu Val Val Leu Tyr Asp Val Lys Arg Glu Lys Ala Gly Glu Leu
        275                 280                 285

Glu Val Phe Asn Gly Tyr Phe Val His Phe Phe Ala Pro Asp Asn Leu
```

```
              290                 295                 300
Asp Pro Ile Pro Lys Asn Ile Leu Phe Val Ile Asp Val Ser Gly Ser
305                 310                 315                 320

Met Trp Gly Val Lys Met Lys Gln Thr Val Glu Ala Met Lys Thr Ile
                325                 330                 335

Leu Asp Asp Leu Arg Ala Glu Asp His Phe Ser Val Ile Asp Phe Asn
                340                 345                 350

Gln Asn Ile Arg Thr Trp Arg Asn Asp Leu Phe Gln Leu Gln Lys His
            355                 360                 365

Arg Leu Gln Ile Ala Lys Arg Tyr Ile Glu Lys Ile Gln Pro Ser Gly
            370                 375                 380

Gly Thr Asn Ile Asn Glu Ala Leu Leu Arg Ala Ile Phe Ile Leu Asn
385                 390                 395                 400

Glu Ala Asn Asn Leu Gly Leu Leu Asp Pro Asn Ser Val Ser Leu Ile
                405                 410                 415

Ile Leu Val Ser Asp Gly Asp Pro Thr Val Gly Glu Leu Lys Leu Ser
                420                 425                 430

Lys Ile Gln Lys Asn Val Lys Glu Asn Ile Gln Asp Asn Ile Ser Leu
            435                 440                 445

Phe Ser Leu Gly Met Gly Phe Asp Val Asp Tyr Asp Phe Leu Lys Arg
            450                 455                 460

Leu Ser Asn Glu Asn His Gly Ile Ala Gln Arg Ile Tyr Gly Asn Gln
465                 470                 475                 480

Asp Thr Ser Ser Gln Leu Lys Lys Phe Tyr Asn Gln Val Ser Thr Pro
                485                 490                 495

Leu Leu Arg Asn Val Gln Phe Asn Tyr Pro His Thr Ser Val Thr Asp
                500                 505                 510

Val Thr Gln Asn Asn Phe His Asn Tyr Phe Gly Gly Ser Glu Ile Val
            515                 520                 525

Val Ala Gly Lys Phe Asp Pro Ala Lys Leu Asp Gln Ile Glu Ser Val
            530                 535                 540

Ile Thr Ala Thr Ser Ala Asn Thr Gln Leu Val Leu Glu Thr Leu Ala
545                 550                 555                 560

Gln Met Asp Asp Leu Gln Asp Phe Leu Ser Lys Asp Lys His Ala Asp
                565                 570                 575

Pro Asp Phe Thr Arg Lys Leu Trp Ala Tyr Leu Thr Ile Asn Gln Leu
                580                 585                 590

Leu Ala Glu Arg Ser Leu Ala Pro Thr Ala Ala Lys Arg Arg Ile
            595                 600                 605

Thr Arg Ser Ile Leu Gln Met Ser Leu Asp His His Ile Val Thr Pro
610                 615                 620

Leu Thr Ser Leu Val Ile Glu Asn Glu Ala Gly Asp Glu Arg Met Leu
625                 630                 635                 640

Ala Asp Ala Pro Pro Gln Asp Pro Ser Cys Cys Ser Gly Ala Leu Tyr
                645                 650                 655

Tyr Gly Ser Lys Val Val Pro Asp Ser Thr Pro Ser Trp Ala Asn Pro
                660                 665                 670

Ser Pro Thr Pro Val Ile Ser Met Leu Ala Gln Gly Ser Gln Val Leu
                675                 680                 685

Glu Ser Thr Pro Pro His Val Met Arg Val Glu Asn Asp Pro His
            690                 695                 700

Phe Ile Ile Tyr Leu Pro Lys Ser Gln Lys Asn Ile Cys Phe Asn Ile
705                 710                 715                 720
```

```
Asp Ser Glu Pro Gly Lys Ile Leu Asn Leu Val Ser Asp Pro Glu Ser
            725                 730                 735

Gly Ile Val Val Asn Gly Gln Leu Val Gly Ala Lys Lys Pro Asn Asn
            740                 745                 750

Gly Lys Leu Ser Thr Tyr Phe Gly Lys Leu Gly Phe Tyr Phe Gln Ser
            755                 760                 765

Glu Asp Ile Lys Ile Glu Ile Ser Thr Glu Thr Ile Thr Leu Ser His
            770                 775                 780

Gly Ser Ser Thr Phe Ser Leu Ser Trp Ser Asp Thr Ala Gln Val Thr
785                 790                 795                 800

Asn Gln Arg Val Gln Ile Ser Val Lys Lys Glu Lys Val Val Thr Ile
            805                 810                 815

Thr Leu Asp Lys Glu Met Ser Phe Ser Val Leu Leu His Arg Val Trp
            820                 825                 830

Lys Lys His Pro Val Asn Val Asp Phe Leu Gly Ile Tyr Ile Pro Pro
            835                 840                 845

Thr Asn Lys Phe Ser Pro Lys Ala His Gly Leu Ile Gly Gln Phe Met
            850                 855                 860

Gln Glu Pro Lys Ile His Ile Phe Asn Glu Arg Pro Gly Lys Asp Pro
865                 870                 875                 880

Glu Lys Pro Glu Ala Ser Met Glu Val Lys Gly Gln Lys Leu Ile Ile
            885                 890                 895

Thr Arg Gly Leu Gln Lys Asp Tyr Arg Thr Asp Leu Val Phe Gly Thr
            900                 905                 910

Asp Val Thr Cys Trp Phe Val His Asn Ser Gly Lys Gly Phe Ile Asp
            915                 920                 925

Gly His Tyr Lys Asp Tyr Phe Val Pro Gln Leu Tyr Ser Phe Leu Lys
            930                 935                 940

Arg Pro
945

<210> SEQ ID NO 314
<211> LENGTH: 885
<212> TYPE: PRT
<213> ORGANISM: Homo sapiens

<400> SEQUENCE: 314

Met Val Ala Leu Ser His Leu Gly Ser Ala Leu Gln Leu Gly Ser Leu
1               5                   10                  15

Cys Phe Pro Arg Ser Pro Phe Arg Leu Leu Gly Lys Arg Ser Leu Pro
            20                  25                  30

Glu Gly Val Ala Asn Gly Ile Glu Val Tyr Ser Thr Lys Ile Asn Ser
            35                  40                  45

Lys Val Thr Ser Arg Phe Ala His Asn Val Val Thr Met Arg Ala Val
        50                  55                  60

Asn Arg Ala Asp Thr Ala Lys Glu Val Ser Phe Asp Val Glu Leu Pro
65                  70                  75                  80

Lys Thr Ala Phe Ile Thr Asn Phe Thr Leu Thr Ile Asp Gly Val Thr
            85                  90                  95

Tyr Pro Gly Asn Val Lys Glu Lys Glu Val Ala Lys Lys Gln Tyr Glu
            100                 105                 110

Lys Ala Val Ser Gln Gly Lys Thr Ala Gly Leu Val Lys Ala Ser Gly
            115                 120                 125

Arg Lys Leu Glu Lys Phe Thr Val Ser Val Asn Val Ala Ala Gly Ser
```

```
            130             135             140
Lys Val Thr Phe Glu Leu Thr Tyr Glu Glu Leu Leu Lys Arg His Lys
145                 150                 155                 160

Gly Lys Tyr Glu Met Tyr Leu Lys Val Gln Pro Lys Gln Leu Val Lys
                165                 170                 175

His Phe Glu Ile Glu Val Asp Ile Phe Glu Pro Gln Gly Ile Ser Met
            180                 185                 190

Leu Asp Ala Glu Ala Ser Phe Ile Thr Asn Asp Leu Leu Gly Ser Ala
                195                 200                 205

Leu Thr Lys Ser Phe Ser Gly Lys Lys Gly His Val Ser Phe Lys Pro
210                 215                 220

Ser Leu Asp Gln Gln Arg Ser Cys Pro Thr Cys Thr Asp Ser Leu Leu
225                 230                 235                 240

Asn Gly Asp Phe Thr Ile Thr Tyr Asp Val Asn Arg Glu Ser Pro Gly
                245                 250                 255

Asn Val Gln Ile Val Asn Gly Tyr Phe Val His Phe Phe Ala Pro Gln
                260                 265                 270

Gly Leu Pro Val Val Pro Lys Asn Val Ala Phe Val Ile Asp Ile Ser
                275                 280                 285

Gly Ser Met Ala Gly Arg Lys Leu Glu Gln Thr Lys Glu Ala Leu Leu
290                 295                 300

Arg Ile Leu Glu Asp Met Lys Glu Asp Tyr Leu Asn Phe Ile Leu
305                 310                 315                 320

Phe Ser Gly Asp Val Ser Thr Trp Lys Glu His Leu Val Gln Ala Thr
                325                 330                 335

Pro Glu Asn Leu Gln Glu Ala Arg Thr Phe Val Lys Ser Met Glu Asp
                340                 345                 350

Lys Gly Met Thr Asn Ile Asn Asp Gly Leu Leu Arg Gly Ile Ser Met
                355                 360                 365

Leu Asn Lys Ala Arg Glu Glu His Arg Ile Pro Glu Arg Ser Thr Ser
                370                 375                 380

Ile Val Ile Met Leu Thr Asp Gly Asp Ala Asn Val Gly Glu Ser Arg
385                 390                 395                 400

Pro Glu Lys Ile Gln Glu Asn Val Arg Asn Ala Ile Gly Gly Lys Phe
                405                 410                 415

Pro Leu Tyr Asn Leu Gly Phe Gly Asn Asn Leu Asn Tyr Asn Phe Leu
                420                 425                 430

Glu Asn Met Ala Leu Glu Asn His Gly Phe Ala Arg Arg Ile Tyr Glu
                435                 440                 445

Asp Ser Asp Ala Asp Leu Gln Leu Gln Gly Phe Tyr Glu Glu Val Ala
                450                 455                 460

Asn Pro Leu Leu Thr Gly Val Glu Met Glu Tyr Pro Glu Asn Ala Ile
465                 470                 475                 480

Leu Asp Leu Thr Gln Asn Thr Tyr Gln His Phe Tyr Asp Gly Ser Glu
                485                 490                 495

Ile Val Val Ala Gly Arg Leu Val Asp Glu Asp Met Asn Ser Phe Lys
                500                 505                 510

Ala Asp Val Lys Gly His Gly Ala Thr Asn Asp Leu Thr Phe Thr Glu
                515                 520                 525

Glu Val Asp Met Lys Glu Met Glu Lys Ala Leu Gln Glu Arg Asp Tyr
530                 535                 540

Ile Phe Gly Asn Tyr Ile Glu Arg Leu Trp Ala Tyr Leu Thr Ile Glu
545                 550                 555                 560
```

Gln Leu Leu Glu Lys Arg Lys Asn Ala His Gly Glu Lys Glu Asn
                565                 570                 575

Leu Thr Ala Arg Ala Leu Asp Leu Ser Leu Lys Tyr His Phe Val Thr
            580                 585                 590

Pro Leu Thr Ser Met Val Val Thr Lys Pro Glu Asp Asn Glu Asp Glu
            595                 600                 605

Arg Ala Ile Ala Asp Lys Pro Gly Glu Asp Ala Glu Ala Thr Pro Val
            610                 615                 620

Ser Pro Ala Met Ser Tyr Leu Thr Ser Tyr Gln Pro Gln Asn Pro
625                 630                 635                 640

Tyr Tyr Tyr Val Asp Gly Asp Pro His Phe Ile Ile Gln Ile Pro Glu
            645                 650                 655

Lys Asp Asp Ala Leu Cys Phe Asn Ile Asp Glu Ala Pro Gly Thr Val
            660                 665                 670

Leu Arg Leu Ile Gln Asp Ala Val Thr Gly Leu Thr Val Asn Gly Gln
            675                 680                 685

Ile Thr Gly Asp Lys Arg Gly Ser Pro Asp Ser Lys Thr Arg Lys Thr
            690                 695                 700

Tyr Phe Gly Lys Leu Gly Ile Arg Asn Ala Gln Met Asp Phe Gln Val
705                 710                 715                 720

Glu Val Thr Thr Glu Lys Ile Thr Cys Gly Thr Gly Arg Ala Ser Thr
            725                 730                 735

Phe Ser Trp Leu Asp Thr Val Thr Val Thr Gln Asp Gly Leu Ser Met
            740                 745                 750

Met Ile Asn Arg Lys Asn Met Val Ser Phe Gly Asp Gly Val Thr
            755                 760                 765

Phe Val Val Leu His Gln Val Trp Lys Lys His Pro Val His Arg
            770                 775                 780

Asp Phe Leu Gly Phe Tyr Val Val Asp Ser His Arg Met Ser Ala Gln
785                 790                 795                 800

Thr His Gly Leu Leu Gly Gln Phe Phe Gln Pro Phe Asp Phe Lys Val
            805                 810                 815

Ser Asp Ile Arg Pro Gly Ser Asp Pro Thr Lys Pro Asp Ala Thr Leu
            820                 825                 830

Val Val Lys Asn His Gln Leu Ile Val Thr Arg Gly Ser Gln Lys Asp
            835                 840                 845

Tyr Arg Lys Asp Ala Ser Ile Gly Thr Lys Val Val Cys Trp Phe Val
850                 855                 860

His Asn Asn Gly Glu Gly Leu Ile Asp Gly Val His Thr Asp Tyr Ile
865                 870                 875                 880

Val Pro Asn Leu Phe
            885

<210> SEQ ID NO 315
<211> LENGTH: 930
<212> TYPE: PRT
<213> ORGANISM: Homo sapiens

<400> SEQUENCE: 315

Met Lys Pro Pro Arg Pro Val Arg Thr Cys Ser Lys Val Leu Val Leu
1               5                   10                  15

Leu Ser Leu Leu Ala Ile His Gln Thr Thr Thr Ala Glu Lys Asn Gly
            20                  25                  30

Ile Asp Ile Tyr Ser Leu Thr Val Asp Ser Arg Val Ser Ser Arg Phe

```
            35                  40                  45
Ala His Thr Val Val Thr Ser Arg Val Asn Arg Ala Asn Thr Val
 50                  55                  60

Gln Glu Ala Thr Phe Gln Met Glu Leu Pro Lys Lys Ala Phe Ile Thr
 65                  70                  75                  80

Asn Phe Ser Met Ile Ile Asp Gly Met Thr Tyr Pro Gly Ile Ile Lys
                 85                  90                  95

Glu Lys Ala Glu Ala Gln Ala Gln Tyr Ser Ala Ala Val Ala Lys Gly
                100                 105                 110

Lys Ser Ala Gly Leu Val Lys Ala Thr Gly Arg Asn Met Glu Gln Phe
                115                 120                 125

Gln Val Ser Val Ser Val Ala Pro Asn Ala Lys Ile Thr Phe Glu Leu
130                 135                 140

Val Tyr Glu Glu Leu Leu Lys Arg Arg Leu Gly Val Tyr Glu Leu Leu
145                 150                 155                 160

Leu Lys Val Arg Pro Gln Gln Leu Val Lys His Leu Gln Met Asp Ile
                165                 170                 175

His Ile Phe Glu Pro Gln Gly Ile Ser Phe Leu Glu Thr Glu Ser Thr
                180                 185                 190

Phe Met Thr Asn Gln Leu Val Asp Ala Leu Thr Thr Trp Gln Asn Lys
                195                 200                 205

Thr Lys Ala His Ile Arg Phe Lys Pro Thr Leu Ser Gln Gln Gln Lys
210                 215                 220

Ser Pro Glu Gln Gln Glu Thr Val Leu Asp Gly Asn Leu Ile Ile Arg
225                 230                 235                 240

Tyr Asp Val Asp Arg Ala Ile Ser Gly Gly Ser Ile Gln Ile Glu Asn
                245                 250                 255

Gly Tyr Phe Val His Tyr Phe Ala Pro Glu Gly Leu Thr Thr Met Pro
                260                 265                 270

Lys Asn Val Val Phe Val Ile Asp Lys Ser Gly Ser Met Ser Gly Arg
                275                 280                 285

Lys Ile Gln Gln Thr Arg Glu Ala Leu Ile Lys Ile Leu Asp Asp Leu
                290                 295                 300

Ser Pro Arg Asp Gln Phe Asn Leu Ile Val Phe Ser Thr Glu Ala Thr
305                 310                 315                 320

Gln Trp Arg Pro Ser Leu Val Pro Ala Ser Ala Glu Asn Val Asn Lys
                325                 330                 335

Ala Arg Ser Phe Ala Ala Gly Ile Gln Ala Leu Gly Gly Thr Asn Ile
                340                 345                 350

Asn Asp Ala Met Leu Met Ala Val Gln Leu Leu Asp Ser Ser Asn Gln
                355                 360                 365

Glu Glu Arg Leu Pro Glu Gly Ser Val Ser Leu Ile Ile Leu Leu Thr
                370                 375                 380

Asp Gly Asp Pro Thr Val Gly Glu Thr Asn Pro Arg Ser Ile Gln Asn
385                 390                 395                 400

Asn Val Arg Glu Ala Val Ser Gly Arg Tyr Ser Leu Phe Cys Leu Gly
                405                 410                 415

Phe Gly Phe Asp Val Ser Tyr Ala Phe Leu Glu Lys Leu Ala Leu Asp
                420                 425                 430

Asn Gly Gly Leu Ala Arg Arg Ile His Glu Asp Ser Asp Ser Ala Leu
                435                 440                 445

Gln Leu Gln Asp Phe Tyr Gln Glu Val Ala Asn Pro Leu Leu Thr Ala
                450                 455                 460
```

```
Val Thr Phe Glu Tyr Pro Ser Asn Ala Val Glu Val Thr Gln Asn
465                 470                 475                 480

Asn Phe Arg Leu Leu Phe Lys Gly Ser Glu Met Val Val Ala Gly Lys
                485                 490                 495

Leu Gln Asp Arg Gly Pro Asp Val Leu Thr Ala Thr Val Ser Gly Lys
            500                 505                 510

Leu Pro Thr Gln Asn Ile Thr Phe Gln Thr Glu Ser Ser Val Ala Glu
            515                 520                 525

Gln Glu Ala Glu Phe Gln Ser Pro Lys Tyr Ile Phe His Asn Phe Met
530                 535                 540

Glu Arg Leu Trp Ala Tyr Leu Thr Ile Gln Gln Leu Leu Glu Gln Thr
545                 550                 555                 560

Val Ser Ala Ser Asp Ala Asp Gln Gln Ala Leu Arg Asn Gln Ala Leu
                565                 570                 575

Asn Leu Ser Leu Ala Tyr Ser Phe Val Thr Pro Leu Thr Ser Met Val
            580                 585                 590

Val Thr Lys Pro Asp Asp Gln Glu Gln Ser Gln Val Ala Glu Lys Pro
            595                 600                 605

Met Glu Gly Glu Ser Arg Asn Arg Asn Val His Ser Gly Ser Thr Phe
610                 615                 620

Phe Lys Tyr Tyr Leu Gln Gly Ala Lys Ile Pro Lys Pro Glu Ala Ser
625                 630                 635                 640

Phe Ser Pro Arg Arg Gly Trp Asn Arg Gln Ala Gly Ala Ala Gly Ser
                645                 650                 655

Arg Met Asn Phe Arg Pro Gly Val Leu Ser Ser Arg Gln Leu Gly Leu
                660                 665                 670

Pro Gly Pro Pro Asp Val Pro Asp His Ala Ala Tyr His Pro Phe Arg
            675                 680                 685

Arg Leu Ala Ile Leu Pro Ala Ser Ala Pro Ala Thr Ser Asn Pro
690                 695                 700

Asp Pro Ala Val Ser Arg Val Met Asn Met Lys Ile Glu Glu Thr Thr
705                 710                 715                 720

Met Thr Thr Gln Thr Pro Ala Pro Ile Gln Ala Pro Ser Ala Ile Leu
                725                 730                 735

Pro Leu Pro Gly Gln Ser Val Glu Arg Leu Cys Val Asp Pro Arg His
            740                 745                 750

Arg Gln Gly Pro Val Asn Leu Leu Ser Asp Pro Glu Gln Gly Val Glu
            755                 760                 765

Val Thr Gly Gln Tyr Glu Arg Glu Lys Ala Gly Phe Ser Trp Ile Glu
            770                 775                 780

Val Thr Phe Lys Asn Pro Leu Val Trp Val His Ala Ser Pro Glu His
785                 790                 795                 800

Val Val Val Thr Arg Asn Arg Arg Ser Ser Ala Tyr Lys Trp Lys Glu
                805                 810                 815

Thr Leu Phe Ser Val Met Pro Gly Leu Lys Met Thr Met Asp Lys Thr
                820                 825                 830

Gly Leu Leu Leu Leu Ser Asp Pro Asp Lys Val Thr Ile Gly Leu Leu
                835                 840                 845

Phe Trp Asp Gly Arg Gly Glu Gly Leu Arg Leu Leu Leu Arg Asp Thr
            850                 855                 860

Asp Arg Phe Ser Ser His Val Gly Gly Thr Leu Gly Gln Phe Tyr Gln
865                 870                 875                 880
```

```
Glu Val Leu Trp Gly Ser Pro Ala Ala Ser Asp Asp Gly Arg Arg Thr
                885                 890                 895

Leu Arg Val Gln Gly Asn Asp His Ser Ala Thr Arg Gly Arg Arg Leu
            900                 905                 910

Asp Tyr Gln Glu Gly Pro Pro Gly Val Glu Ile Ser Cys Trp Ser Val
        915                 920                 925

Glu Leu
    930

<210> SEQ ID NO 316
<211> LENGTH: 178
<212> TYPE: PRT
<213> ORGANISM: Homo sapiens

<400> SEQUENCE: 316

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 317
<211> LENGTH: 427
<212> TYPE: PRT
<213> ORGANISM: Homo sapiens

<400> SEQUENCE: 317

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Cys Asn Asp Lys Asp
            20                  25                  30

Leu Phe Lys Ala Val Asp Ala Ala Leu Lys Lys Tyr Asn Ser Gln Asn
        35                  40                  45

Gln Ser Asn Asn Gln Phe Val Leu Tyr Arg Ile Thr Glu Ala Thr Lys
    50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
```

```
                85                  90                  95
Lys Asp Ala Ala Lys Ala Thr Gly Glu Cys Thr Ala Thr Val Gly
            100                 105                 110
Lys Arg Ser Ser Thr Lys Phe Ser Val Ala Thr Gln Thr Cys Gln Ile
            115                 120                 125
Thr Pro Ala Glu Gly Pro Val Thr Ala Gln Tyr Asp Cys Leu Gly
        130                 135                 140
Cys Val His Pro Ile Ser Thr Gln Ser Pro Asp Leu Glu Pro Ile Leu
145                 150                 155                 160
Arg His Gly Ile Gln Tyr Phe Asn Asn Thr Gln His Ser Ser Leu
            165                 170                 175
Phe Met Leu Asn Glu Val Lys Arg Ala Gln Arg Gln Val Val Ala Gly
            180                 185                 190
Leu Asn Phe Arg Ile Thr Tyr Ser Ile Val Gln Thr Asn Cys Ser Lys
        195                 200                 205
Glu Asn Phe Leu Phe Leu Thr Pro Asp Cys Lys Ser Leu Trp Asn Gly
210                 215                 220
Asp Thr Gly Glu Cys Thr Asp Asn Ala Tyr Ile Asp Ile Gln Leu Arg
225                 230                 235                 240
Ile Ala Ser Phe Ser Gln Asn Cys Asp Ile Tyr Pro Gly Lys Asp Phe
            245                 250                 255
Val Gln Pro Pro Thr Lys Ile Cys Val Gly Cys Pro Arg Asp Ile Pro
        260                 265                 270
Thr Asn Ser Pro Glu Leu Glu Glu Thr Leu Thr His Thr Ile Thr Lys
        275                 280                 285
Leu Asn Ala Glu Asn Asn Ala Thr Phe Tyr Phe Lys Ile Asp Asn Val
        290                 295                 300
Lys Lys Ala Arg Val Gln Val Val Ala Gly Lys Lys Tyr Phe Ile Asp
305                 310                 315                 320
Phe Val Ala Arg Glu Thr Thr Cys Ser Lys Glu Ser Asn Glu Glu Leu
            325                 330                 335
Thr Glu Ser Cys Glu Thr Lys Lys Leu Gly Gln Ser Leu Asp Cys Asn
            340                 345                 350
Ala Glu Val Tyr Val Pro Trp Glu Lys Lys Ile Tyr Pro Thr Val
        355                 360                 365
Asn Cys Gln Pro Leu Gly Met Ile Ser Leu Met Lys Arg Pro Gly
        370                 375                 380
Phe Ser Pro Phe Arg Ser Arg Ile Gly Glu Ile Lys Glu Thr
385                 390                 395                 400
Thr Ser His Leu Arg Ser Cys Glu Tyr Lys Gly Arg Pro Pro Lys Ala
            405                 410                 415
Gly Ala Glu Pro Ala Ser Glu Arg Glu Val Ser
            420                 425

<210> SEQ ID NO 318
<211> LENGTH: 338
<212> TYPE: PRT
<213> ORGANISM: Homo sapiens

<400> SEQUENCE: 318

Met Ser Leu Ser Ala Phe Thr Leu Phe Leu Ala Leu Ile Gly Gly Thr
1               5                   10                  15
Ser Gly Tyr Tyr Asp Tyr Asp Phe Pro Leu Ser Ile Tyr Gly Gln
            20                  25                  30
```

Ser Ser Pro Asn Cys Ala Pro Glu Cys Asn Cys Pro Glu Ser Tyr Pro
        35                  40                  45

Ser Ala Met Tyr Cys Asp Glu Leu Lys Leu Lys Ser Val Pro Met Val
 50                  55                  60

Pro Pro Gly Ile Lys Tyr Leu Tyr Leu Arg Asn Asn Gln Ile Asp His
 65              70                  75                  80

Ile Asp Glu Lys Ala Phe Glu Asn Val Thr Asp Leu Gln Trp Leu Ile
                85                  90                  95

Leu Asp His Asn Leu Leu Glu Asn Ser Lys Ile Lys Gly Arg Val Phe
            100                 105                 110

Ser Lys Leu Lys Gln Leu Lys Lys Leu His Ile Asn His Asn Asn Leu
        115                 120                 125

Thr Glu Ser Val Gly Pro Leu Pro Lys Ser Leu Glu Asp Leu Gln Leu
    130                 135                 140

Thr His Asn Lys Ile Thr Lys Leu Gly Ser Phe Glu Gly Leu Val Asn
145                 150                 155                 160

Leu Thr Phe Ile His Leu Gln His Asn Arg Leu Lys Glu Asp Ala Val
                165                 170                 175

Ser Ala Ala Phe Lys Gly Leu Lys Ser Leu Glu Tyr Leu Asp Leu Ser
            180                 185                 190

Phe Asn Gln Ile Ala Arg Leu Pro Ser Gly Leu Pro Val Ser Leu Leu
        195                 200                 205

Thr Leu Tyr Leu Asp Asn Asn Lys Ile Ser Asn Ile Pro Asp Glu Tyr
    210                 215                 220

Phe Lys Arg Phe Asn Ala Leu Gln Tyr Leu Arg Leu Ser His Asn Glu
225                 230                 235                 240

Leu Ala Asp Ser Gly Ile Pro Gly Asn Ser Phe Asn Val Ser Ser Leu
                245                 250                 255

Val Glu Leu Asp Leu Ser Tyr Asn Lys Leu Lys Asn Ile Pro Thr Val
            260                 265                 270

Asn Glu Asn Leu Glu Asn Tyr Tyr Leu Glu Val Asn Gln Leu Glu Lys
        275                 280                 285

Phe Asp Ile Lys Ser Phe Cys Lys Ile Leu Gly Pro Leu Ser Tyr Ser
    290                 295                 300

Lys Ile Lys His Leu Arg Leu Asp Gly Asn Arg Ile Ser Glu Thr Ser
305                 310                 315                 320

Leu Pro Pro Asp Met Tyr Glu Cys Leu Arg Val Ala Asn Glu Val Thr
                325                 330                 335

Leu Asn

<210> SEQ ID NO 319
<211> LENGTH: 5430
<212> TYPE: PRT
<213> ORGANISM: Homo sapiens

<400> SEQUENCE: 319

Met Ser Ser Ser Asp Glu Glu Thr Leu Ser Glu Arg Ser Cys Arg Ser
1               5                   10                  15

Glu Arg Ser Cys Arg Ser Glu Arg Ser Tyr Arg Ser Glu Arg Ser Gly
            20                  25                  30

Ser Leu Ser Pro Cys Pro Pro Gly Asp Thr Leu Pro Trp Asn Leu Pro
        35                  40                  45

Leu His Glu Gln Lys Lys Arg Lys Ser Gln Asp Ser Val Leu Asp Pro
    50                  55                  60

-continued

Ala Glu Arg Ala Val Val Arg Val Ala Asp Glu Asp Arg Val Gln
 65                  70                  75                  80

Lys Lys Thr Phe Thr Lys Trp Val Asn Lys His Leu Met Lys Val Arg
                 85                  90                  95

Lys His Ile Asn Asp Leu Tyr Glu Asp Leu Arg Asp Gly His Asn Leu
            100                 105                 110

Ile Ser Leu Leu Glu Val Leu Ser Gly Ile Lys Leu Pro Arg Glu Lys
        115                 120                 125

Gly Arg Met Arg Phe His Arg Leu Gln Asn Val Gln Ile Ala Leu Asp
    130                 135                 140

Phe Leu Lys Gln Arg Gln Val Lys Leu Val Asn Ile Arg Asn Asp Asp
145                 150                 155                 160

Ile Thr Asp Gly Asn Pro Lys Leu Thr Leu Gly Leu Ile Trp Thr Ile
                165                 170                 175

Ile Leu His Phe Gln Ile Ser Asp Ile Tyr Ile Ser Gly Glu Ser Gly
            180                 185                 190

Asp Met Ser Ala Lys Glu Lys Leu Leu Leu Trp Thr Gln Lys Val Thr
        195                 200                 205

Ala Gly Tyr Thr Gly Ile Lys Cys Thr Asn Phe Ser Ser Cys Trp Ser
    210                 215                 220

Asp Gly Lys Met Phe Asn Ala Leu Ile His Arg Tyr Arg Pro Asp Leu
225                 230                 235                 240

Val Asp Met Glu Arg Val Gln Ile Gln Ser Asn Arg Glu Asn Leu Glu
                245                 250                 255

Gln Ala Phe Glu Val Ala Glu Arg Leu Gly Val Thr Arg Leu Leu Asp
            260                 265                 270

Ala Glu Asp Val Asp Val Pro Ser Pro Asp Glu Lys Ser Val Ile Thr
        275                 280                 285

Tyr Val Ser Ser Ile Tyr Asp Ala Phe Pro Lys Val Pro Glu Gly Gly
    290                 295                 300

Glu Gly Ile Ser Ala Thr Glu Val Asp Ser Arg Trp Gln Glu Tyr Gln
305                 310                 315                 320

Ser Arg Val Asp Ser Leu Ile Pro Trp Ile Lys Gln His Thr Ile Leu
                325                 330                 335

Met Ser Asp Lys Thr Phe Pro Gln Asn Pro Val Glu Leu Lys Ala Leu
            340                 345                 350

Tyr Asn Gln Tyr Ile His Phe Lys Glu Thr Glu Ile Leu Ala Lys Glu
        355                 360                 365

Arg Glu Lys Gly Arg Ile Glu Glu Leu Tyr Lys Leu Leu Glu Val Trp
    370                 375                 380

Ile Glu Phe Gly Arg Ile Lys Leu Pro Gln Gly Tyr His Pro Asn Asp
385                 390                 395                 400

Val Glu Glu Glu Trp Gly Lys Leu Ile Ile Glu Met Leu Glu Arg Glu
                405                 410                 415

Lys Ser Leu Arg Pro Ala Val Glu Arg Leu Glu Leu Leu Leu Gln Ile
            420                 425                 430

Ala Asn Lys Ile Gln Asn Gly Ala Leu Asn Cys Glu Glu Lys Leu Thr
        435                 440                 445

Leu Ala Lys Asn Thr Leu Gln Ala Asp Ala Ala His Leu Glu Ser Gly
    450                 455                 460

Gln Pro Val Gln Cys Glu Ser Asp Val Ile Met Tyr Ile Gln Glu Cys
465                 470                 475                 480

Glu Gly Leu Ile Arg Gln Leu Gln Val Asp Leu Gln Ile Leu Arg Asp

-continued

```
                485                 490                 495
Glu Asn Tyr Tyr Gln Leu Glu Glu Leu Ala Phe Arg Val Met Arg Leu
            500                 505                 510
Gln Asp Glu Leu Val Thr Leu Arg Leu Glu Cys Thr Asn Leu Tyr Arg
            515                 520                 525
Lys Gly His Phe Thr Ser Leu Glu Leu Val Pro Pro Ser Thr Leu Thr
            530                 535                 540
Thr Thr His Leu Lys Ala Glu Pro Leu Thr Lys Ala Thr His Ser Ser
545                 550                 555                 560
Ser Thr Ser Trp Phe Arg Lys Pro Met Thr Arg Ala Glu Leu Val Ala
                565                 570                 575
Ile Ser Ser Ser Glu Asp Gly Asn Leu Arg Phe Val Tyr Glu Leu
            580                 585                 590
Leu Ser Trp Val Glu Glu Met Gln Met Lys Leu Glu Arg Ala Glu Trp
                595                 600                 605
Gly Asn Asp Leu Pro Ser Val Glu Leu Gln Leu Glu Thr Gln Gln His
            610                 615                 620
Ile His Thr Ser Val Glu Leu Gly Ser Ser Val Lys Glu Ala Arg
625                 630                 635                 640
Leu Tyr Glu Gly Lys Met Ser Gln Asn Phe His Thr Ser Tyr Ala Glu
                645                 650                 655
Thr Leu Gly Lys Leu Glu Thr Gln Tyr Cys Lys Leu Lys Glu Thr Ser
            660                 665                 670
Ser Phe Arg Met Arg His Leu Gln Ser Leu His Lys Phe Val Ser Arg
            675                 680                 685
Ala Thr Ala Glu Leu Ile Trp Leu Asn Glu Lys Glu Glu Glu Leu
690                 695                 700
Ala Tyr Asp Trp Ser Asp Asn Ser Asn Ile Ser Ala Lys Arg Asn
705                 710                 715                 720
Tyr Phe Ser Glu Leu Thr Met Glu Leu Glu Glu Lys Gln Asp Val Phe
                725                 730                 735
Arg Ser Leu Gln Asp Thr Ala Glu Leu Leu Ser Leu Glu Asn His Pro
            740                 745                 750
Ala Lys Gln Thr Val Glu Ala Tyr Ser Ala Val Gln Ser Gln Leu
            755                 760                 765
Gln Trp Met Lys Gln Leu Cys Leu Cys Val Gln His Val Lys Glu
            770                 775                 780
Asn Thr Ala Tyr Phe Gln Phe Ser Asp Ala Arg Glu Leu Glu Ser
785                 790                 795                 800
Phe Leu Arg Asn Leu Gln Asp Ser Ile Lys Arg Lys Tyr Ser Cys Asp
            805                 810                 815
His Asn Thr Ser Leu Ser Arg Leu Glu Asp Leu Leu Gln Asp Ser Met
            820                 825                 830
Asp Glu Lys Glu Gln Leu Ile Gln Ser Lys Ser Ser Val Ala Ser Leu
            835                 840                 845
Val Gly Arg Ser Lys Thr Ile Val Gln Leu Lys Pro Arg Ser Pro Asp
            850                 855                 860
His Val Leu Lys Asn Thr Ile Ser Val Lys Ala Val Cys Asp Tyr Arg
865                 870                 875                 880
Gln Ile Glu Ile Thr Ile Cys Lys Asn Asp Glu Cys Val Leu Glu Asp
                885                 890                 895
Asn Ser Gln Arg Thr Lys Trp Lys Val Ile Ser Pro Thr Gly Asn Glu
            900                 905                 910
```

```
Ala Met Val Pro Ser Val Cys Phe Leu Ile Pro Pro Asn Lys Asp
        915                 920                 925

Ala Ile Glu Met Ala Ser Arg Val Glu Gln Ser Tyr Gln Lys Val Met
930                 935                 940

Ala Leu Trp His Gln Leu His Val Asn Thr Lys Ser Leu Ile Ser Trp
945                 950                 955                 960

Asn Tyr Leu Arg Lys Asp Leu Asp Leu Val Gln Thr Trp Asn Leu Glu
                965                 970                 975

Lys Leu Arg Ser Ser Ala Pro Gly Glu Cys His Gln Ile Met Lys Asn
            980                 985                 990

Leu Gln Ala His Tyr Glu Asp Phe Leu Gln Asp Ser Arg Asp Ser Val
            995                 1000                1005

Leu Phe Ser Val Ala Asp Arg Leu Arg Leu Glu Glu Glu Val Glu
        1010                1015                1020

Ala Cys Lys Ala Arg Phe Gln His Leu Met Lys Ser Met Glu Asn
        1025                1030                1035

Glu Asp Lys Glu Glu Thr Val Ala Lys Met Tyr Ile Ser Glu Leu
        1040                1045                1050

Lys Asn Ile Arg Leu Arg Leu Glu Glu Tyr Glu Gln Arg Val Val
        1055                1060                1065

Lys Arg Ile Gln Ser Leu Ala Ser Ser Arg Thr Asp Arg Asp Ala
        1070                1075                1080

Trp Gln Asp Asn Ala Leu Arg Ile Ala Glu Gln Glu His Thr Gln
        1085                1090                1095

Glu Asp Leu Gln Gln Leu Arg Ser Asp Leu Asp Ala Val Ser Met
        1100                1105                1110

Lys Cys Asp Ser Phe Leu His Gln Ser Pro Ser Ser Ser Val
        1115                1120                1125

Pro Thr Leu Arg Ser Glu Leu Asn Leu Leu Val Glu Lys Met Asp
        1130                1135                1140

His Val Tyr Gly Leu Ser Thr Val Tyr Leu Asn Lys Leu Lys Thr
        1145                1150                1155

Val Asp Val Ile Val Arg Ser Ile Gln Asp Ala Glu Leu Leu Val
        1160                1165                1170

Lys Gly Tyr Glu Ile Lys Leu Ser Gln Glu Glu Val Val Leu Ala
        1175                1180                1185

Asp Leu Ser Ala Leu Glu Ala His Trp Ser Thr Leu Arg His Trp
        1190                1195                1200

Leu Ser Asp Val Lys Asp Lys Asn Ser Val Phe Ser Val Leu Asp
        1205                1210                1215

Glu Glu Ile Ala Lys Ala Lys Val Val Ala Glu Gln Met Ser Arg
        1220                1225                1230

Leu Thr Pro Glu Arg Asn Leu Asp Leu Glu Arg Tyr Gln Glu Lys
        1235                1240                1245

Gly Ser Gln Leu Gln Glu Arg Trp His Arg Val Ile Ala Gln Leu
        1250                1255                1260

Glu Ile Arg Gln Ser Glu Leu Glu Ser Ile Gln Glu Val Leu Gly
        1265                1270                1275

Asp Tyr Arg Ala Cys His Gly Thr Leu Ile Lys Trp Ile Glu Glu
        1280                1285                1290

Thr Thr Ala Gln Gln Glu Met Met Lys Pro Gly Gln Ala Glu Asp
        1295                1300                1305
```

-continued

Ser Arg Val Leu Ser Glu Gln Leu Ser Gln Gln Thr Ala Leu Phe
1310              1315                1320

Ala Glu Ile Glu Arg Asn Gln Thr Lys Leu Asp Gln Cys Gln Lys
1325              1330                1335

Phe Ser Gln Gln Tyr Ser Thr Ile Val Lys Asp Tyr Glu Leu Gln
1340              1345                1350

Leu Met Thr Tyr Lys Ala Phe Val Glu Ser Gln Gln Lys Ser Pro
1355              1360                1365

Gly Lys Arg Arg Arg Met Leu Ser Ser Ser Asp Ala Ile Thr Gln
1370              1375                1380

Glu Phe Met Asp Leu Arg Thr Arg Tyr Thr Ala Leu Val Thr Leu
1385              1390                1395

Thr Thr Gln His Val Lys Tyr Ile Ser Asp Ala Leu Arg Arg Leu
1400              1405                1410

Glu Glu Glu Glu Lys Val Val Glu Glu Glu Lys Gln Glu His Val
1415              1420                1425

Glu Lys Val Lys Glu Leu Leu Gly Trp Val Ser Thr Leu Ala Arg
1430              1435                1440

Asn Thr Gln Gly Lys Ala Thr Ser Ser Glu Thr Lys Glu Ser Thr
1445              1450                1455

Asp Ile Glu Lys Ala Ile Leu Glu Gln Gln Val Leu Ser Glu Glu
1460              1465                1470

Leu Thr Thr Lys Lys Glu Gln Val Ser Glu Ala Ile Lys Thr Ser
1475              1480                1485

Gln Ile Phe Leu Ala Lys His Gly His Lys Leu Ser Glu Lys Glu
1490              1495                1500

Lys Lys Gln Ile Ser Glu Gln Leu Asn Ala Leu Asn Lys Ala Tyr
1505              1510                1515

His Asp Leu Cys Asp Gly Ser Ala Asn Gln Leu Gln Gln Leu Gln
1520              1525                1530

Ser Gln Leu Ala His Gln Thr Glu Gln Lys Thr Leu Gln Lys Gln
1535              1540                1545

Gln Asn Thr Cys His Gln Gln Leu Glu Asp Leu Cys Ser Trp Val
1550              1555                1560

Gly Gln Ala Glu Arg Ala Leu Ala Gly His Gly Arg Thr Thr
1565              1570                1575

Gln Gln Asp Leu Ser Ala Leu Gln Lys Asn Gln Ser Asp Leu Lys
1580              1585                1590

Asp Leu Gln Asp Asp Ile Gln Asn Arg Ala Thr Ser Phe Ala Thr
1595              1600                1605

Val Val Lys Asp Ile Glu Gly Phe Met Glu Glu Asn Gln Thr Lys
1610              1615                1620

Leu Ser Pro Arg Glu Leu Thr Ala Leu Arg Glu Lys Leu His Gln
1625              1630                1635

Ala Lys Glu Gln Tyr Glu Ala Leu Gln Glu Glu Thr Arg Val Ala
1640              1645                1650

Gln Lys Glu Leu Glu Glu Ala Val Thr Ser Ala Leu Gln Gln Glu
1655              1660                1665

Thr Glu Lys Ser Lys Ala Ala Lys Glu Leu Ala Glu Asn Lys Lys
1670              1675                1680

Lys Ile Asp Ala Leu Leu Asp Trp Val Thr Ser Val Gly Ser Ser
1685              1690                1695

Gly Gly Gln Leu Leu Thr Asn Leu Pro Gly Met Glu Gln Leu Ser

-continued

```
            1700                1705                1710
Gly Ala Ser Leu Glu Lys Gly Ala Leu Asp Thr Thr Asp Gly Tyr
            1715                1720                1725
Met Gly Val Asn Gln Ala Pro Glu Lys Leu Asp Lys Gln Cys Glu
            1730                1735                1740
Met Met Lys Ala Arg His Gln Glu Leu Leu Ser Gln Gln Gln Asn
            1745                1750                1755
Phe Ile Leu Ala Thr Gln Ser Ala Gln Ala Phe Leu Asp Gln His
            1760                1765                1770
Gly His Asn Leu Thr Pro Glu Glu Gln Gln Met Leu Gln Gln Lys
            1775                1780                1785
Leu Gly Glu Leu Lys Glu Gln Tyr Ser Thr Ser Leu Ala Gln Ser
            1790                1795                1800
Glu Ala Glu Leu Lys Gln Val Gln Thr Leu Gln Asp Glu Leu Gln
            1805                1810                1815
Lys Phe Leu Gln Asp His Lys Glu Phe Glu Ser Trp Leu Glu Arg
            1820                1825                1830
Ser Glu Lys Glu Leu Glu Asn Met His Lys Gly Gly Ser Ser Pro
            1835                1840                1845
Glu Thr Leu Pro Ser Leu Leu Lys Arg Gln Gly Ser Phe Ser Glu
            1850                1855                1860
Asp Val Ile Ser His Lys Gly Asp Leu Arg Phe Val Thr Ile Ser
            1865                1870                1875
Gly Gln Lys Val Leu Asp Met Glu Asn Ser Phe Lys Glu Gly Lys
            1880                1885                1890
Glu Pro Ser Glu Ile Gly Asn Leu Val Lys Asp Lys Leu Lys Asp
            1895                1900                1905
Ala Thr Glu Arg Tyr Thr Ala Leu His Ser Lys Cys Thr Arg Leu
            1910                1915                1920
Gly Ser His Leu Asn Met Leu Leu Gly Gln Tyr His Gln Phe Gln
            1925                1930                1935
Asn Ser Ala Asp Ser Leu Gln Ala Trp Met Gln Ala Cys Glu Ala
            1940                1945                1950
Asn Val Glu Lys Leu Leu Ser Asp Thr Val Ala Ser Asp Pro Gly
            1955                1960                1965
Val Leu Gln Glu Gln Leu Ala Thr Thr Lys Gln Leu Gln Glu Glu
            1970                1975                1980
Leu Ala Glu His Gln Val Pro Val Glu Lys Leu Gln Lys Val Ala
            1985                1990                1995
Arg Asp Ile Met Glu Ile Glu Gly Glu Pro Ala Pro Asp His Arg
            2000                2005                2010
His Val Gln Glu Thr Thr Asp Ser Ile Leu Ser His Phe Gln Ser
            2015                2020                2025
Leu Ser Tyr Ser Leu Ala Glu Arg Ser Ser Leu Leu Gln Lys Ala
            2030                2035                2040
Ile Ala Gln Ser Gln Ser Val Gln Glu Ser Leu Glu Ser Leu Leu
            2045                2050                2055
Gln Ser Ile Gly Glu Val Gln Asn Leu Glu Gly Lys Gln Val
            2060                2065                2070
Ser Ser Leu Ser Ser Gly Val Ile Gln Glu Ala Leu Ala Thr Asn
            2075                2080                2085
Met Lys Leu Lys Gln Asp Ile Ala Arg Gln Lys Ser Ser Leu Glu
            2090                2095                2100
```

-continued

```
Ala Thr Arg Glu Met Val Thr Arg Phe Met Glu Thr Ala Asp Ser
    2105                2110                2115

Thr Thr Ala Ala Val Leu Gln Gly Lys Leu Ala Glu Val Ser Gln
    2120                2125                2130

Arg Phe Glu Gln Leu Cys Leu Gln Gln Gln Glu Lys Glu Ser Ser
    2135                2140                2145

Leu Lys Lys Leu Leu Pro Gln Ala Glu Met Phe Glu His Leu Ser
    2150                2155                2160

Gly Lys Leu Gln Gln Phe Met Glu Asn Lys Ser Arg Met Leu Ala
    2165                2170                2175

Ser Gly Asn Gln Pro Asp Gln Asp Ile Thr His Phe Phe Gln Gln
    2180                2185                2190

Ile Gln Glu Leu Asn Leu Glu Met Glu Asp Gln Glu Asn Leu
    2195                2200                2205

Asp Thr Leu Glu His Leu Val Thr Glu Leu Ser Ser Cys Gly Phe
    2210                2215                2220

Ala Leu Asp Leu Cys Gln His Gln Asp Arg Val Gln Asn Leu Arg
    2225                2230                2235

Lys Asp Phe Thr Glu Leu Gln Lys Thr Val Lys Glu Arg Glu Lys
    2240                2245                2250

Asp Ala Ser Ser Cys Gln Glu Gln Leu Asp Glu Phe Arg Lys Leu
    2255                2260                2265

Val Arg Thr Phe Gln Lys Trp Leu Lys Glu Thr Glu Gly Ser Ile
    2270                2275                2280

Pro Pro Thr Glu Thr Ser Met Ser Ala Lys Glu Leu Glu Lys Gln
    2285                2290                2295

Ile Glu His Leu Lys Ser Leu Leu Asp Asp Trp Ala Ser Lys Gly
    2300                2305                2310

Thr Leu Val Glu Glu Ile Asn Cys Lys Gly Thr Ser Leu Glu Asn
    2315                2320                2325

Leu Ile Met Glu Ile Thr Ala Pro Asp Ser Gln Gly Lys Thr Gly
    2330                2335                2340

Ser Ile Leu Pro Ser Val Gly Ser Ser Val Gly Ser Val Asn Gly
    2345                2350                2355

Tyr His Thr Cys Lys Asp Leu Thr Glu Ile Gln Cys Asp Met Ser
    2360                2365                2370

Asp Val Asn Leu Lys Tyr Glu Lys Leu Gly Gly Val Leu His Glu
    2375                2380                2385

Arg Gln Glu Ser Leu Gln Ala Ile Leu Asn Arg Met Glu Glu Val
    2390                2395                2400

His Lys Glu Ala Asn Ser Val Leu Gln Trp Leu Glu Ser Lys Glu
    2405                2410                2415

Glu Val Leu Lys Ser Met Asp Ala Met Ser Ser Pro Thr Lys Thr
    2420                2425                2430

Glu Thr Val Lys Ala Gln Ala Glu Ser Asn Lys Ala Phe Leu Ala
    2435                2440                2445

Glu Leu Glu Gln Asn Ser Pro Lys Ile Gln Lys Val Lys Glu Ala
    2450                2455                2460

Leu Ala Gly Leu Leu Val Thr Tyr Pro Asn Ser Gln Glu Ala Glu
    2465                2470                2475

Asn Trp Lys Lys Ile Gln Glu Glu Leu Asn Ser Arg Trp Glu Arg
    2480                2485                2490
```

| | | | | | | | | | | | |
|---|---|---|---|---|---|---|---|---|---|---|---|
| Ala | Thr | Glu | Val | Thr | Val | Ala | Arg | Gln | Arg | Gln | Leu | Glu | Glu | Ser |
| | 2495 | | | | 2500 | | | | | 2505 | | | |

Ala Thr Glu Val Thr Val Ala Arg Gln Arg Gln Leu Glu Glu Ser
    2495                2500                2505

Ala Ser His Leu Ala Cys Phe Gln Ala Ala Glu Ser Gln Leu Arg
    2510                2515                2520

Pro Trp Leu Met Glu Lys Glu Leu Met Met Gly Val Leu Gly Pro
    2525                2530                2535

Leu Ser Ile Asp Pro Asn Met Leu Asn Ala Gln Lys Gln Gln Val
    2540                2545                2550

Gln Phe Met Leu Lys Glu Phe Glu Ala Arg Arg Gln Gln His Glu
    2555                2560                2565

Gln Leu Asn Glu Ala Ala Gln Gly Ile Leu Thr Gly Pro Gly Asp
    2570                2575                2580

Val Ser Leu Ser Thr Ser Gln Val Gln Lys Glu Leu Gln Ser Ile
    2585                2590                2595

Asn Gln Lys Trp Val Glu Leu Thr Asp Lys Leu Asn Ser Arg Ser
    2600                2605                2610

Ser Gln Ile Asp Gln Ala Ile Val Lys Ser Thr Gln Tyr Gln Glu
    2615                2620                2625

Leu Leu Gln Asp Leu Ser Glu Lys Val Arg Ala Val Gly Gln Arg
    2630                2635                2640

Leu Ser Val Gln Ser Ala Ile Ser Thr Gln Pro Glu Ala Val Lys
    2645                2650                2655

Gln Gln Leu Glu Glu Thr Ser Glu Ile Arg Ser Asp Leu Glu Gln
    2660                2665                2670

Leu Asp His Glu Val Lys Glu Ala Gln Thr Leu Cys Asp Glu Leu
    2675                2680                2685

Ser Val Leu Ile Gly Glu Gln Tyr Leu Lys Asp Glu Leu Lys Lys
    2690                2695                2700

Arg Leu Glu Thr Val Ala Leu Pro Leu Gln Gly Leu Glu Asp Leu
    2705                2710                2715

Ala Ala Asp Arg Ile Asn Arg Leu Gln Ala Ala Leu Ala Ser Thr
    2720                2725                2730

Gln Gln Phe Gln Gln Met Phe Asp Glu Leu Arg Thr Trp Leu Asp
    2735                2740                2745

Asp Lys Gln Ser Gln Gln Ala Lys Asn Cys Pro Ile Ser Ala Lys
    2750                2755                2760

Leu Glu Arg Leu Gln Ser Gln Leu Gln Glu Asn Glu Glu Phe Gln
    2765                2770                2775

Lys Ser Leu Asn Gln His Ser Gly Ser Tyr Glu Val Ile Val Ala
    2780                2785                2790

Glu Gly Glu Ser Leu Leu Leu Ser Val Pro Pro Gly Glu Glu Lys
    2795                2800                2805

Arg Thr Leu Gln Asn Gln Leu Val Glu Leu Lys Asn His Trp Glu
    2810                2815                2820

Glu Leu Ser Lys Lys Thr Ala Asp Arg Gln Ser Arg Leu Lys Asp
    2825                2830                2835

Cys Met Gln Lys Ala Gln Lys Tyr Gln Trp His Val Glu Asp Leu
    2840                2845                2850

Val Pro Trp Ile Glu Asp Cys Lys Ala Lys Met Ser Glu Leu Arg
    2855                2860                2865

Val Thr Leu Asp Pro Val Gln Leu Glu Ser Ser Leu Leu Arg Ser
    2870                2875                2880

Lys Ala Met Leu Asn Glu Val Glu Lys Arg Arg Ser Leu Leu Glu

```
                  2885                2890                2895
Ile Leu Asn Ser Ala Ala Asp Ile Leu Ile Asn Ser Ser Glu Ala
    2900                2905                2910

Asp Glu Asp Gly Ile Arg Asp Glu Lys Ala Gly Ile Asn Gln Asn
    2915                2920                2925

Met Asp Ala Val Thr Glu Glu Leu Gln Ala Lys Thr Gly Ser Leu
    2930                2935                2940

Glu Glu Met Thr Gln Arg Leu Arg Glu Phe Gln Glu Ser Phe Lys
    2945                2950                2955

Asn Ile Glu Lys Lys Val Glu Gly Ala Lys His Gln Leu Glu Ile
    2960                2965                2970

Phe Asp Ala Leu Gly Ser Gln Ala Cys Ser Asn Lys Asn Leu Glu
    2975                2980                2985

Lys Leu Arg Ala Gln Gln Glu Val Leu Gln Ala Leu Glu Pro Gln
    2990                2995                3000

Val Asp Tyr Leu Arg Asn Phe Thr Gln Gly Leu Val Glu Asp Ala
    3005                3010                3015

Pro Asp Gly Ser Asp Ala Ser Gln Leu Leu His Gln Ala Glu Val
    3020                3025                3030

Ala Gln Gln Glu Phe Leu Glu Val Lys Gln Arg Val Asn Ser Gly
    3035                3040                3045

Cys Val Met Met Glu Asn Lys Leu Glu Gly Ile Gly Gln Phe His
    3050                3055                3060

Cys Arg Val Arg Glu Met Phe Ser Gln Leu Ala Asp Leu Asp Asp
    3065                3070                3075

Glu Leu Asp Gly Met Gly Ala Ile Gly Arg Asp Thr Asp Ser Leu
    3080                3085                3090

Gln Ser Gln Ile Glu Asp Val Arg Leu Phe Leu Asn Lys Ile His
    3095                3100                3105

Val Leu Lys Leu Asp Ile Glu Ala Ser Glu Ala Glu Cys Arg His
    3110                3115                3120

Met Leu Glu Glu Glu Gly Thr Leu Asp Leu Leu Gly Leu Lys Arg
    3125                3130                3135

Glu Leu Glu Ala Leu Asn Lys Gln Cys Gly Lys Leu Thr Glu Arg
    3140                3145                3150

Gly Lys Ala Arg Gln Glu Gln Leu Glu Leu Thr Leu Gly Arg Val
    3155                3160                3165

Glu Asp Phe Tyr Arg Lys Leu Lys Gly Leu Asn Asp Ala Thr Thr
    3170                3175                3180

Ala Ala Glu Glu Ala Glu Ala Leu Gln Trp Val Val Gly Thr Glu
    3185                3190                3195

Val Glu Ile Ile Asn Gln Gln Leu Ala Asp Phe Lys Met Phe Gln
    3200                3205                3210

Lys Glu Gln Val Asp Pro Leu Gln Met Lys Leu Gln Gln Val Asn
    3215                3220                3225

Gly Leu Gly Gln Gly Leu Ile Gln Ser Ala Gly Lys Asp Cys Asp
    3230                3235                3240

Val Gln Gly Leu Glu His Asp Met Glu Glu Ile Asn Ala Arg Trp
    3245                3250                3255

Asn Thr Leu Asn Lys Lys Val Ala Gln Arg Ile Ala Gln Leu Gln
    3260                3265                3270

Glu Ala Leu Leu His Cys Gly Lys Phe Gln Asp Ala Leu Glu Pro
    3275                3280                3285
```

-continued

```
Leu Leu Ser Trp Leu Ala Asp Thr Glu Glu Leu Ile Ala Asn Gln
3290                3295                3300

Lys Pro Pro Ser Ala Glu Tyr Lys Val Val Lys Ala Gln Ile Gln
3305                3310                3315

Glu Gln Lys Leu Leu Gln Arg Leu Leu Asp Asp Arg Lys Ala Thr
3320                3325                3330

Val Asp Met Leu Gln Ala Glu Gly Gly Arg Ile Ala Gln Ser Ala
3335                3340                3345

Glu Leu Ala Asp Arg Glu Lys Ile Thr Gly Gln Leu Glu Ser Leu
3350                3355                3360

Glu Ser Arg Trp Thr Glu Leu Leu Ser Lys Ala Ala Ala Arg Gln
3365                3370                3375

Lys Gln Leu Glu Asp Ile Leu Val Leu Ala Lys Gln Phe His Glu
3380                3385                3390

Thr Ala Glu Pro Ile Ser Asp Phe Leu Ser Val Thr Glu Lys Lys
3395                3400                3405

Leu Ala Asn Ser Glu Pro Val Gly Thr Gln Thr Ala Lys Ile Gln
3410                3415                3420

Gln Gln Ile Ile Arg His Lys Ala Leu Glu Glu Asp Ile Glu Asn
3425                3430                3435

His Ala Thr Asp Val His Gln Ala Val Lys Ile Gly Gln Ser Leu
3440                3445                3450

Ser Ser Leu Thr Ser Pro Ala Glu Gln Gly Val Leu Ser Glu Lys
3455                3460                3465

Ile Asp Ser Leu Gln Ala Arg Tyr Ser Glu Ile Gln Asp Arg Cys
3470                3475                3480

Cys Arg Lys Ala Ala Leu Leu Asp Gln Ala Leu Ser Asn Ala Arg
3485                3490                3495

Leu Phe Gly Glu Asp Glu Val Glu Val Leu Asn Trp Leu Ala Glu
3500                3505                3510

Val Glu Asp Lys Leu Ser Ser Val Phe Val Lys Asp Phe Lys Gln
3515                3520                3525

Asp Val Leu His Arg Gln His Ala Asp His Leu Ala Leu Asn Glu
3530                3535                3540

Glu Ile Val Asn Arg Lys Lys Asn Val Asp Gln Ala Ile Lys Asn
3545                3550                3555

Gly Gln Ala Leu Leu Lys Gln Thr Thr Gly Glu Glu Val Leu Leu
3560                3565                3570

Ile Gln Glu Lys Leu Asp Gly Ile Lys Thr Arg Tyr Ala Asp Ile
3575                3580                3585

Thr Val Thr Ser Ser Lys Ala Leu Arg Thr Leu Glu Gln Ala Arg
3590                3595                3600

Gln Leu Ala Thr Lys Phe Gln Ser Thr Tyr Glu Glu Leu Thr Gly
3605                3610                3615

Trp Leu Arg Glu Val Glu Glu Leu Ala Thr Ser Gly Gly Gln
3620                3625                3630

Ser Pro Thr Gly Glu Gln Ile Pro Gln Phe Gln Gln Arg Gln Lys
3635                3640                3645

Glu Leu Lys Lys Glu Val Met Glu His Arg Leu Val Leu Asp Thr
3650                3655                3660

Val Asn Glu Val Ser Arg Ala Leu Leu Glu Leu Val Pro Trp Arg
3665                3670                3675
```

```
Ala Arg Glu Gly Leu Asp Lys Leu Val Ser Asp Ala Asn Glu Gln
3680              3685              3690

Tyr Lys Leu Val Ser Asp Thr Ile Gly Gln Arg Val Asp Glu Ile
3695              3700              3705

Asp Ala Ala Ile Gln Arg Ser Gln Gln Tyr Gln Ala Ala Asp
3710              3715              3720

Ala Glu Leu Ala Trp Val Ala Glu Thr Lys Arg Lys Leu Met Ala
3725              3730              3735

Leu Gly Pro Ile Arg Leu Glu Gln Asp Gln Thr Thr Ala Gln Leu
3740              3745              3750

Gln Val Gln Lys Ala Phe Ser Ile Asp Ile Ile Arg His Lys Asp
3755              3760              3765

Ser Met Asp Glu Leu Phe Ser His Arg Ser Glu Ile Phe Gly Thr
3770              3775              3780

Cys Gly Glu Glu Gln Lys Thr Val Leu Gln Glu Lys Thr Glu Ser
3785              3790              3795

Leu Ile Gln Gln Tyr Glu Ala Ile Ser Leu Leu Asn Ser Glu Arg
3800              3805              3810

Tyr Ala Arg Leu Glu Arg Ala Gln Val Leu Val Asn Gln Phe Trp
3815              3820              3825

Glu Thr Tyr Glu Glu Leu Ser Pro Trp Ile Glu Glu Thr Arg Ala
3830              3835              3840

Leu Ile Ala Gln Leu Pro Ser Pro Ala Ile Asp His Glu Gln Leu
3845              3850              3855

Arg Gln Gln Gln Glu Glu Met Arg Gln Leu Arg Glu Ser Ile Ala
3860              3865              3870

Glu His Lys Pro His Ile Asp Lys Leu Leu Lys Ile Gly Pro Gln
3875              3880              3885

Leu Lys Glu Leu Asn Pro Glu Glu Gly Glu Met Val Glu Glu Lys
3890              3895              3900

Tyr Gln Lys Ala Glu Asn Met Tyr Ala Gln Ile Lys Glu Glu Val
3905              3910              3915

Arg Gln Arg Ala Leu Ala Leu Asp Glu Ala Val Ser Gln Ser Thr
3920              3925              3930

Gln Ile Thr Glu Phe His Asp Lys Ile Glu Pro Met Leu Glu Thr
3935              3940              3945

Leu Glu Asn Leu Ser Ser Arg Leu Arg Met Pro Pro Leu Ile Pro
3950              3955              3960

Ala Glu Val Asp Lys Ile Arg Glu Cys Ile Ser Asp Asn Lys Ser
3965              3970              3975

Ala Thr Val Glu Leu Glu Lys Leu Gln Pro Ser Phe Glu Ala Leu
3980              3985              3990

Lys Arg Arg Gly Glu Glu Leu Ile Gly Arg Ser Gln Gly Ala Asp
3995              4000              4005

Lys Asp Leu Ala Ala Lys Glu Ile Gln Asp Lys Leu Asp Gln Met
4010              4015              4020

Val Phe Phe Trp Glu Asp Ile Lys Ala Arg Ala Glu Glu Arg Glu
4025              4030              4035

Ile Lys Phe Leu Asp Val Leu Glu Leu Ala Glu Lys Phe Trp Tyr
4040              4045              4050

Asp Met Ala Ala Leu Leu Thr Thr Ile Lys Asp Thr Gln Asp Ile
4055              4060              4065

Val His Asp Leu Glu Ser Pro Gly Ile Asp Pro Ser Ile Ile Lys
```

-continued

```
            4070              4075              4080
Gln Gln Val Glu Ala Ala Glu Thr Ile Lys Glu Thr Asp Gly
        4085              4090              4095
Leu His Glu Glu Leu Glu Phe Ile Arg Ile Leu Gly Ala Asp Leu
    4100              4105              4110
Ile Phe Ala Cys Gly Glu Thr Glu Lys Pro Glu Val Arg Lys Ser
    4115              4120              4125
Ile Asp Glu Met Asn Asn Ala Trp Glu Asn Leu Asn Lys Thr Trp
    4130              4135              4140
Lys Glu Arg Leu Glu Lys Leu Glu Asp Ala Met Gln Ala Ala Val
    4145              4150              4155
Gln Tyr Gln Asp Thr Leu Gln Ala Met Phe Asp Trp Leu Asp Asn
    4160              4165              4170
Thr Val Ile Lys Leu Cys Thr Met Pro Pro Val Gly Thr Asp Leu
    4175              4180              4185
Asn Thr Val Lys Asp Gln Leu Asn Glu Met Lys Glu Phe Lys Val
    4190              4195              4200
Glu Val Tyr Gln Gln Gln Ile Glu Met Glu Lys Leu Asn His Gln
    4205              4210              4215
Gly Glu Leu Met Leu Lys Lys Ala Thr Asp Glu Thr Asp Arg Asp
    4220              4225              4230
Ile Ile Arg Glu Pro Leu Thr Glu Leu Lys His Leu Trp Glu Asn
    4235              4240              4245
Leu Gly Glu Lys Ile Ala His Arg Gln His Lys Leu Glu Gly Ala
    4250              4255              4260
Leu Leu Ala Leu Gly Gln Phe Gln His Ala Leu Glu Glu Leu Met
    4265              4270              4275
Ser Trp Leu Thr His Thr Glu Glu Leu Leu Asp Ala Gln Arg Pro
    4280              4285              4290
Ile Ser Gly Asp Pro Lys Val Ile Glu Val Glu Leu Ala Lys His
    4295              4300              4305
His Val Leu Lys Asn Asp Val Leu Ala His Gln Ala Thr Val Glu
    4310              4315              4320
Thr Val Asn Lys Ala Gly Asn Glu Leu Leu Glu Ser Ser Ala Gly
    4325              4330              4335
Asp Asp Ala Ser Ser Leu Arg Ser Arg Leu Glu Ala Met Asn Gln
    4340              4345              4350
Cys Trp Glu Ser Val Leu Gln Lys Thr Glu Glu Arg Glu Gln Gln
    4355              4360              4365
Leu Gln Ser Thr Leu Gln Gln Ala Gln Gly Phe His Ser Glu Ile
    4370              4375              4380
Glu Asp Phe Leu Leu Glu Leu Thr Arg Met Glu Ser Gln Leu Ser
    4385              4390              4395
Ala Ser Lys Pro Thr Gly Gly Leu Pro Glu Thr Ala Arg Glu Gln
    4400              4405              4410
Leu Asp Thr His Met Glu Leu Tyr Ser Gln Leu Lys Ala Lys Glu
    4415              4420              4425
Glu Thr Tyr Asn Gln Leu Leu Asp Lys Gly Arg Leu Met Leu Leu
    4430              4435              4440
Ser Arg Asp Asp Ser Gly Ser Gly Ser Lys Thr Glu Gln Ser Val
    4445              4450              4455
Ala Leu Leu Glu Gln Lys Trp His Val Val Ser Ser Lys Met Glu
    4460              4465              4470
```

```
Glu Arg Lys Ser Lys Leu Glu Glu Ala Leu Asn Leu Ala Thr Glu
    4475            4480                4485
Phe Gln Asn Ser Leu Gln Glu Phe Ile Asn Trp Leu Thr Leu Ala
    4490            4495                4500
Glu Gln Ser Leu Asn Ile Ala Ser Pro Pro Ser Leu Ile Leu Asn
    4505            4510                4515
Thr Val Leu Ser Gln Ile Glu His Lys Val Phe Ala Asn Glu
    4520            4525                4530
Val Asn Ala His Arg Asp Gln Ile Ile Glu Leu Asp Gln Thr Gly
    4535            4540                4545
Asn Gln Leu Lys Phe Leu Ser Gln Lys Gln Asp Val Val Leu Ile
    4550            4555                4560
Lys Asn Leu Leu Val Ser Val Gln Ser Arg Trp Glu Lys Val Val
    4565            4570                4575
Gln Arg Ser Ile Glu Arg Gly Arg Ser Leu Asp Asp Ala Arg Lys
    4580            4585                4590
Arg Ala Lys Gln Phe His Glu Ala Trp Lys Lys Leu Ile Asp Trp
    4595            4600                4605
Leu Glu Asp Ala Glu Ser His Leu Asp Ser Glu Leu Glu Ile Ser
    4610            4615                4620
Asn Asp Pro Asp Lys Ile Lys Leu Gln Leu Ser Lys His Lys Glu
    4625            4630                4635
Phe Gln Lys Thr Leu Gly Gly Lys Gln Pro Val Tyr Asp Thr Thr
    4640            4645                4650
Ile Arg Thr Gly Arg Ala Leu Lys Glu Lys Thr Leu Leu Pro Glu
    4655            4660                4665
Asp Ser Gln Lys Leu Asp Asn Phe Leu Gly Glu Val Arg Asp Lys
    4670            4675                4680
Trp Asp Thr Val Cys Gly Lys Ser Val Glu Arg Gln His Lys Leu
    4685            4690                4695
Glu Glu Ala Leu Leu Phe Ser Gly Gln Phe Met Asp Ala Leu Gln
    4700            4705                4710
Ala Leu Val Asp Trp Leu Tyr Lys Val Glu Pro Gln Leu Ala Glu
    4715            4720                4725
Asp Gln Pro Val His Gly Asp Leu Asp Leu Val Met Asn Leu Met
    4730            4735                4740
Asp Ala His Lys Val Phe Gln Lys Glu Leu Gly Lys Arg Thr Gly
    4745            4750                4755
Thr Val Gln Val Leu Lys Arg Ser Gly Arg Glu Leu Ile Glu Asn
    4760            4765                4770
Ser Arg Asp Asp Thr Thr Trp Val Lys Gly Gln Leu Gln Glu Leu
    4775            4780                4785
Ser Thr Arg Trp Asp Thr Val Cys Lys Leu Ser Val Ser Lys Gln
    4790            4795                4800
Ser Arg Leu Glu Gln Ala Leu Lys Gln Ala Glu Val Phe Arg Asp
    4805            4810                4815
Thr Val His Met Leu Leu Glu Trp Leu Ser Glu Ala Glu Gln Thr
    4820            4825                4830
Leu Arg Phe Arg Gly Ala Leu Pro Asp Asp Thr Glu Ala Leu Gln
    4835            4840                4845
Ser Leu Ile Asp Thr His Lys Glu Phe Met Lys Lys Val Glu Glu
    4850            4855                4860
```

```
Lys Arg Val Asp Val Asn Ser Ala Val Ala Met Gly Glu Val Ile
    4865             4870                4875

Leu Ala Val Cys His Pro Asp Cys Ile Thr Thr Ile Lys His Trp
    4880             4885                4890

Ile Thr Ile Ile Arg Ala Arg Phe Glu Glu Val Leu Thr Trp Ala
    4895             4900                4905

Lys Gln His Gln Gln Arg Leu Glu Thr Ala Leu Ser Glu Leu Val
    4910             4915                4920

Ala Asn Ala Glu Leu Leu Glu Glu Leu Leu Ala Trp Ile Gln Trp
    4925             4930                4935

Ala Glu Thr Thr Leu Ile Gln Arg Asp Gln Glu Pro Ile Pro Gln
    4940             4945                4950

Asn Ile Asp Arg Val Lys Ala Leu Ile Ala Glu His Gln Thr Phe
    4955             4960                4965

Met Glu Glu Met Thr Arg Lys Gln Pro Asp Val Asp Arg Val Thr
    4970             4975                4980

Lys Thr Tyr Lys Arg Lys Asn Ile Glu Pro Thr His Ala Pro Phe
    4985             4990                4995

Ile Glu Lys Ser Arg Ser Gly Gly Arg Lys Ser Leu Ser Gln Pro
    5000             5005                5010

Thr Pro Pro Pro Met Pro Ile Leu Ser Gln Ser Glu Ala Lys Asn
    5015             5020                5025

Pro Arg Ile Asn Gln Leu Ser Ala Arg Trp Gln Gln Val Trp Leu
    5030             5035                5040

Leu Ala Leu Glu Arg Gln Arg Lys Leu Asn Asp Ala Leu Asp Arg
    5045             5050                5055

Leu Glu Glu Leu Lys Glu Phe Ala Asn Phe Asp Phe Asp Val Trp
    5060             5065                5070

Arg Lys Lys Tyr Met Arg Trp Met Asn His Lys Lys Ser Arg Val
    5075             5080                5085

Met Asp Phe Phe Arg Arg Ile Asp Lys Asp Gln Asp Gly Lys Ile
    5090             5095                5100

Thr Arg Gln Glu Phe Ile Asp Gly Ile Leu Ala Ser Lys Phe Pro
    5105             5110                5115

Thr Thr Lys Leu Glu Met Thr Ala Val Ala Asp Ile Phe Asp Arg
    5120             5125                5130

Asp Gly Asp Gly Tyr Ile Asp Tyr Tyr Glu Phe Val Ala Ala Leu
    5135             5140                5145

His Pro Asn Lys Asp Ala Tyr Arg Pro Thr Thr Asp Ala Asp Lys
    5150             5155                5160

Ile Glu Asp Glu Val Thr Arg Gln Val Ala Gln Cys Lys Cys Ala
    5165             5170                5175

Lys Arg Phe Gln Val Glu Gln Ile Gly Glu Asn Lys Tyr Arg Phe
    5180             5185                5190

Gly Asp Ser Gln Gln Leu Arg Leu Val Arg Ile Leu Arg Ser Thr
    5195             5200                5205

Val Met Val Arg Val Gly Gly Gly Trp Met Ala Leu Asp Glu Phe
    5210             5215                5220

Leu Val Lys Asn Asp Pro Cys Arg Ala Arg Gly Arg Thr Asn Ile
    5225             5230                5235

Glu Leu Arg Glu Lys Phe Ile Leu Pro Glu Gly Ala Ser Gln Gly
    5240             5245                5250

Met Thr Pro Phe Arg Ser Arg Gly Arg Arg Ser Lys Pro Ser Ser
```

```
                5255                5260                5265
Arg Ala Ala Ser Pro Thr Arg Ser Ser Ser Ala Ser Gln Ser
    5270                5275                5280

Asn His Ser Cys Thr Ser Met Pro Ser Ser Pro Ala Thr Pro Ala
    5285                5290                5295

Ser Gly Thr Lys Val Ile Pro Ser Ser Gly Ser Lys Leu Lys Arg
    5300                5305                5310

Pro Thr Pro Thr Phe His Ser Ser Arg Thr Ser Leu Ala Gly Asp
    5315                5320                5325

Thr Ser Asn Ser Ser Ser Pro Ala Ser Thr Gly Ala Lys Thr Asn
    5330                5335                5340

Arg Ala Asp Pro Lys Lys Ser Ala Ser Arg Pro Gly Ser Arg Ala
    5345                5350                5355

Gly Ser Arg Ala Gly Ser Arg Ala Ser Ser Arg Arg Gly Ser Asp
    5360                5365                5370

Ala Ser Asp Phe Asp Leu Leu Glu Thr Gln Ser Ala Cys Ser Asp
    5375                5380                5385

Thr Ser Glu Ser Ser Ala Ala Gly Gly Gln Gly Asn Ser Arg Arg
    5390                5395                5400

Gly Leu Asn Lys Pro Ser Lys Ile Pro Thr Met Ser Lys Lys Thr
    5405                5410                5415

Thr Thr Ala Ser Pro Arg Thr Pro Gly Pro Lys Arg
    5420                5425                5430

<210> SEQ ID NO 320
<211> LENGTH: 355
<212> TYPE: PRT
<213> ORGANISM: Homo sapiens

<400> SEQUENCE: 320

Met Ala Lys Leu Ile Ala Leu Thr Leu Leu Gly Met Gly Leu Ala Leu
1               5                   10                  15

Phe Arg Asn His Gln Ser Ser Tyr Gln Thr Arg Leu Asn Ala Leu Arg
                20                  25                  30

Glu Val Gln Pro Val Glu Leu Pro Asn Cys Asn Leu Val Lys Gly Ile
            35                  40                  45

Glu Thr Gly Ser Glu Asp Leu Glu Ile Leu Pro Asn Gly Leu Ala Phe
        50                  55                  60

Ile Ser Ser Gly Leu Lys Tyr Pro Gly Ile Lys Ser Phe Asn Pro Asn
65                  70                  75                  80

Ser Pro Gly Lys Ile Leu Leu Met Asp Leu Asn Glu Glu Asp Pro Thr
                85                  90                  95

Val Leu Glu Leu Gly Ile Thr Gly Ser Lys Phe Asp Val Ser Ser Phe
            100                 105                 110

Asn Pro His Gly Ile Ser Thr Phe Thr Asp Glu Asp Asn Ala Met Tyr
        115                 120                 125

Leu Leu Val Val Asn His Pro Asp Ala Lys Ser Thr Val Glu Leu Phe
    130                 135                 140

Lys Phe Gln Glu Glu Glu Lys Ser Leu Leu His Leu Lys Thr Ile Arg
145                 150                 155                 160

His Lys Leu Leu Pro Asn Leu Asn Asp Ile Val Ala Val Gly Pro Glu
                165                 170                 175

His Phe Tyr Gly Thr Asn Asp His Tyr Phe Leu Asp Pro Tyr Leu Gln
            180                 185                 190
```

```
Ser Trp Glu Met Tyr Leu Gly Leu Ala Trp Ser Tyr Val Tyr Tyr
            195                 200                 205

Ser Pro Ser Glu Val Arg Val Ala Glu Gly Phe Asp Phe Ala Asn
        210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
                260                 265                 270

Val Asp Pro Glu Thr Gly Asp Leu Trp Val Gly Cys His Pro Asn Gly
            275                 280                 285

Met Lys Ile Phe Phe Tyr Asp Ser Glu Asn Pro Pro Ala Ser Glu Val
            290                 295                 300

Leu Arg Ile Gln Asn Ile Leu Thr Glu Glu Pro Lys Val Thr Gln Val
305                 310                 315                 320

Tyr Ala Glu Asn Gly Thr Val Leu Gln Gly Ser Thr Val Ala Ser Val
                325                 330                 335

Tyr Lys Gly Lys Leu Leu Ile Gly Thr Val Phe His Lys Ala Leu Tyr
                340                 345                 350

Cys Glu Leu
        355

<210> SEQ ID NO 321
<211> LENGTH: 634
<212> TYPE: PRT
<213> ORGANISM: Homo sapiens

<400> SEQUENCE: 321

Met Ala Gln Gly Val Leu Trp Ile Leu Leu Gly Leu Leu Leu Trp Ser
1               5                   10                  15

Asp Pro Gly Thr Ala Ser Leu Pro Leu Leu Met Asp Ser Val Ile Gln
            20                  25                  30

Ala Leu Ala Glu Leu Glu Gln Lys Val Pro Ala Ala Lys Thr Arg His
        35                  40                  45

Thr Ala Ser Ala Trp Leu Met Ser Ala Pro Asn Ser Gly Pro His Asn
    50                  55                  60

Arg Leu Tyr His Phe Leu Leu Gly Ala Trp Ser Leu Asn Ala Thr Glu
65                  70                  75                  80

Leu Asp Pro Cys Pro Leu Ser Pro Glu Leu Leu Gly Leu Thr Lys Glu
                85                  90                  95

Val Ala Arg His Asp Val Arg Glu Gly Lys Glu Tyr Gly Val Val Leu
            100                 105                 110

Ala Pro Asp Gly Ser Thr Val Ala Val Glu Pro Leu Leu Ala Gly Leu
        115                 120                 125

Glu Ala Gly Leu Gln Gly Arg Arg Val Ile Asn Leu Pro Leu Asp Ser
    130                 135                 140

Met Ala Ala Pro Trp Glu Thr Gly Asp Thr Phe Pro Asp Val Val Ala
145                 150                 155                 160

Ile Ala Pro Asp Val Arg Ala Thr Ser Ser Pro Gly Leu Arg Asp Gly
                165                 170                 175

Ser Pro Asp Val Thr Thr Ala Asp Ile Gly Ala Asn Thr Pro Asp Ala
            180                 185                 190

Thr Lys Gly Cys Pro Asp Val Gln Ala Ser Leu Pro Asp Ala Lys Ala
        195                 200                 205
```

```
Lys Ser Pro Pro Thr Met Val Asp Ser Leu Leu Ala Val Thr Leu Ala
    210                 215                 220
Gly Asn Leu Gly Leu Thr Phe Leu Arg Gly Ser Gln Thr Gln Ser His
225                 230                 235                 240
Pro Asp Leu Gly Thr Glu Gly Cys Trp Asp Gln Leu Ser Ala Pro Arg
                245                 250                 255
Thr Phe Thr Leu Leu Asp Pro Lys Ala Ser Leu Leu Thr Met Ala Phe
                260                 265                 270
Leu Asn Gly Ala Leu Asp Gly Val Ile Leu Gly Asp Tyr Leu Ser Arg
            275                 280                 285
Thr Pro Glu Pro Arg Pro Ser Leu Ser His Leu Leu Ser Gln Tyr Tyr
        290                 295                 300
Gly Ala Gly Val Ala Arg Asp Pro Gly Phe Arg Ser Asn Phe Arg Arg
305                 310                 315                 320
Gln Asn Gly Ala Ala Leu Thr Ser Ala Ser Ile Leu Ala Gln Gln Val
                325                 330                 335
Trp Gly Thr Leu Val Leu Leu Gln Arg Leu Glu Pro Val His Leu Gln
            340                 345                 350
Leu Gln Cys Met Ser Gln Glu Gln Leu Ala Gln Val Ala Ala Asn Ala
        355                 360                 365
Thr Lys Glu Phe Thr Glu Ala Phe Leu Gly Cys Pro Ala Ile His Pro
370                 375                 380
Arg Cys Arg Trp Gly Ala Ala Pro Tyr Arg Gly Arg Pro Lys Leu Leu
385                 390                 395                 400
Gln Leu Pro Leu Gly Phe Leu Tyr Val His His Thr Tyr Val Pro Ala
                405                 410                 415
Pro Pro Cys Thr Asp Phe Thr Arg Cys Ala Ala Asn Met Arg Ser Met
            420                 425                 430
Gln Arg Tyr His Gln Asp Thr Gln Gly Trp Gly Asp Ile Gly Tyr Gly
        435                 440                 445
Phe Val Val Gly Ser Asp Gly Tyr Val Tyr Glu Gly Arg Gly Trp His
450                 455                 460
Trp Val Gly Ala His Thr Leu Gly His Asn Ser Arg Gly Phe Gly Val
465                 470                 475                 480
Ala Ile Val Gly Asn Tyr Thr Ala Ala Leu Pro Thr Glu Ala Ala Leu
                485                 490                 495
Arg Thr Val Arg Asp Thr Leu Pro Ser Cys Ala Val Arg Ala Gly Leu
            500                 505                 510
Leu Arg Pro Asp Tyr Ala Leu Leu Gly His Arg Gln Leu Val Arg Thr
        515                 520                 525
Asp Cys Pro Gly Asp Ala Leu Phe Asp Leu Leu Arg Thr Trp Pro His
530                 535                 540
Phe Thr Ala Val Ser Leu Arg Ser Leu His Tyr Thr Ala Arg Arg Pro
545                 550                 555                 560
Ser Val Tyr Thr Ser Ser Thr Arg Pro Leu Pro Pro Ala Cys Asn Ser
                565                 570                 575
Cys Ala Arg Thr Ala Ser Ala Arg Pro Pro Thr Ser Arg Arg His Val
            580                 585                 590
Tyr Ser Gly Asn Leu Gly Pro Ala Phe Ala Gly His Ser Ala Gly Asn
        595                 600                 605
Ile Pro Asp Pro Val Thr Ser Ala Tyr Ala Ala Ser Ala Gln Pro Gln
610                 615                 620
```

```
Thr Gln Pro Ala Cys Pro Phe Pro Ser Ser
625                 630
```

<210> SEQ ID NO 322
<211> LENGTH: 638
<212> TYPE: PRT
<213> ORGANISM: Homo sapiens

<400> SEQUENCE: 322

```
Met Ile Leu Phe Lys Gln Ala Thr Tyr Phe Ile Ser Leu Phe Ala Thr
1               5                   10                  15

Val Ser Cys Gly Cys Leu Thr Gln Leu Tyr Glu Asn Ala Phe Phe Arg
            20                  25                  30

Gly Gly Asp Val Ala Ser Met Tyr Thr Pro Asn Ala Gln Tyr Cys Gln
            35                  40                  45

Met Arg Cys Thr Phe His Pro Arg Cys Leu Leu Phe Ser Phe Leu Pro
    50                  55                  60

Ala Ser Ser Ile Asn Asp Met Glu Lys Arg Phe Gly Cys Phe Leu Lys
65                  70                  75                  80

Asp Ser Val Thr Gly Thr Leu Pro Lys Val His Arg Thr Gly Ala Val
                85                  90                  95

Ser Gly His Ser Leu Lys Gln Cys Gly His Gln Ile Ser Ala Cys His
            100                 105                 110

Arg Asp Ile Tyr Lys Gly Val Asp Met Arg Gly Val Asn Phe Asn Val
            115                 120                 125

Ser Lys Val Ser Val Glu Glu Cys Gln Lys Arg Cys Thr Asn Asn
            130                 135                 140

Ile Arg Cys Gln Phe Phe Ser Tyr Ala Thr Gln Thr Phe His Lys Ala
145                 150                 155                 160

Glu Tyr Arg Asn Asn Cys Leu Leu Lys Tyr Ser Pro Gly Gly Thr Pro
                165                 170                 175

Thr Ala Ile Lys Val Leu Ser Asn Val Glu Ser Gly Phe Ser Leu Lys
            180                 185                 190

Pro Cys Ala Leu Ser Glu Ile Gly Cys His Met Asn Ile Phe Gln His
            195                 200                 205

Leu Ala Phe Ser Asp Val Asp Val Ala Arg Val Leu Thr Pro Asp Ala
210                 215                 220

Phe Val Cys Arg Thr Ile Cys Thr Tyr His Pro Asn Cys Leu Phe Phe
225                 230                 235                 240

Thr Phe Tyr Thr Asn Val Trp Lys Ile Glu Ser Gln Arg Asn Val Cys
                245                 250                 255

Leu Leu Lys Thr Ser Glu Ser Gly Thr Pro Ser Ser Ser Thr Pro Gln
            260                 265                 270

Glu Asn Thr Ile Ser Gly Tyr Ser Leu Leu Thr Cys Lys Arg Thr Leu
            275                 280                 285

Pro Glu Pro Cys His Ser Lys Ile Tyr Pro Gly Val Asp Phe Gly Gly
            290                 295                 300

Glu Glu Leu Asn Val Thr Phe Val Lys Gly Val Asn Val Cys Gln Glu
305                 310                 315                 320

Thr Cys Thr Lys Met Ile Arg Cys Gln Phe Phe Thr Tyr Ser Leu Leu
                325                 330                 335

Pro Glu Asp Cys Lys Glu Glu Lys Cys Lys Cys Phe Leu Arg Leu Ser
            340                 345                 350

Met Asp Gly Ser Pro Thr Arg Ile Ala Tyr Gly Thr Gln Gly Ser Ser
            355                 360                 365
```

Gly Tyr Ser Leu Arg Leu Cys Asn Thr Gly Asp Asn Ser Val Cys Thr
370                 375                 380

Thr Lys Thr Ser Thr Arg Ile Val Gly Gly Thr Asn Ser Ser Trp Gly
385                 390                 395                 400

Glu Trp Pro Trp Gln Val Ser Leu Gln Val Lys Leu Thr Ala Gln Arg
            405                 410                 415

His Leu Cys Gly Gly Ser Leu Ile Gly His Gln Trp Val Leu Thr Ala
            420                 425                 430

Ala His Cys Phe Asp Gly Leu Pro Leu Gln Asp Val Trp Arg Ile Tyr
        435                 440                 445

Ser Gly Ile Leu Asn Leu Ser Asp Ile Thr Lys Asp Thr Pro Phe Ser
450                 455                 460

Gln Ile Lys Glu Ile Ile Ile His Gln Asn Tyr Lys Val Ser Glu Gly
465                 470                 475                 480

Asn His Asp Ile Ala Leu Ile Lys Leu Gln Ala Pro Leu Asn Tyr Thr
            485                 490                 495

Glu Phe Gln Lys Pro Ile Cys Leu Pro Ser Lys Gly Asp Thr Ser Thr
            500                 505                 510

Ile Tyr Thr Asn Cys Trp Val Thr Gly Trp Gly Phe Ser Lys Glu Lys
        515                 520                 525

Gly Glu Ile Gln Asn Ile Leu Gln Lys Val Asn Ile Pro Leu Val Thr
530                 535                 540

Asn Glu Glu Cys Gln Lys Arg Tyr Gln Asp Tyr Lys Ile Thr Gln Arg
545                 550                 555                 560

Met Val Cys Ala Gly Tyr Lys Glu Gly Lys Asp Ala Cys Lys Gly
            565                 570                 575

Asp Ser Gly Gly Pro Leu Val Cys Lys His Asn Gly Met Trp Arg Leu
            580                 585                 590

Val Gly Ile Thr Ser Trp Gly Glu Gly Cys Ala Arg Arg Glu Gln Pro
        595                 600                 605

Gly Val Tyr Thr Lys Val Ala Glu Tyr Met Asp Trp Ile Leu Glu Lys
        610                 615                 620

Thr Gln Ser Ser Asp Gly Lys Ala Gln Met Gln Ser Pro Ala
625                 630                 635

<210> SEQ ID NO 323
<211> LENGTH: 810
<212> TYPE: PRT
<213> ORGANISM: Homo sapiens

<400> SEQUENCE: 323

Met Glu His Lys Glu Val Val Leu Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg

```
                100                 105                 110
Gly Thr Met Ser Lys Thr Lys Asn Gly Ile Thr Cys Gln Lys Trp Ser
            115                 120                 125
Ser Thr Ser Pro His Arg Pro Arg Phe Ser Pro Ala Thr His Pro Ser
        130                 135                 140
Glu Gly Leu Glu Glu Asn Tyr Cys Arg Asn Pro Asp Asn Asp Pro Gln
145                 150                 155                 160
Gly Pro Trp Cys Tyr Thr Thr Asp Pro Glu Lys Arg Tyr Asp Tyr Cys
                165                 170                 175
Asp Ile Leu Glu Cys Glu Glu Cys Met His Cys Ser Gly Glu Asn
            180                 185                 190
Tyr Asp Gly Lys Ile Ser Lys Thr Met Ser Gly Leu Glu Cys Gln Ala
        195                 200                 205
Trp Asp Ser Gln Ser Pro His Ala His Gly Tyr Ile Pro Ser Lys Phe
    210                 215                 220
Pro Asn Lys Asn Leu Lys Lys Asn Tyr Cys Arg Asn Pro Asp Arg Glu
225                 230                 235                 240
Leu Arg Pro Trp Cys Phe Thr Thr Asp Pro Asn Lys Arg Trp Glu Leu
                245                 250                 255
Cys Asp Ile Pro Arg Cys Thr Thr Pro Pro Ser Ser Gly Pro Thr
            260                 265                 270
Tyr Gln Cys Leu Lys Gly Thr Gly Glu Asn Tyr Arg Gly Asn Val Ala
        275                 280                 285
Val Thr Val Ser Gly His Thr Cys Gln His Trp Ser Ala Gln Thr Pro
    290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
                325                 330                 335
Thr Thr Asn Ser Gln Val Arg Trp Glu Tyr Cys Lys Ile Pro Ser Cys
            340                 345                 350
Asp Ser Ser Pro Val Ser Thr Glu Gln Leu Ala Pro Thr Ala Pro Pro
        355                 360                 365
Glu Leu Thr Pro Val Val Gln Asp Cys Tyr His Gly Asp Gly Gln Ser
    370                 375                 380
Tyr Arg Gly Thr Ser Ser Thr Thr Thr Thr Gly Lys Lys Cys Gln Ser
385                 390                 395                 400
Trp Ser Ser Met Thr Pro His Arg His Gln Lys Thr Pro Glu Asn Tyr
                405                 410                 415
Pro Asn Ala Gly Leu Thr Met Asn Tyr Cys Arg Asn Pro Asp Ala Asp
            420                 425                 430
Lys Gly Pro Trp Cys Phe Thr Thr Asp Pro Ser Val Arg Trp Glu Tyr
        435                 440                 445
Cys Asn Leu Lys Lys Cys Ser Gly Thr Glu Ala Ser Val Val Ala Pro
    450                 455                 460
Pro Pro Val Val Leu Leu Pro Asp Val Glu Thr Pro Ser Glu Glu Asp
465                 470                 475                 480
Cys Met Phe Gly Asn Gly Lys Gly Tyr Arg Gly Lys Arg Ala Thr Thr
                485                 490                 495
Val Thr Gly Thr Pro Cys Gln Asp Trp Ala Ala Gln Glu Pro His Arg
            500                 505                 510
His Ser Ile Phe Thr Pro Glu Thr Asn Pro Arg Ala Gly Leu Glu Lys
        515                 520                 525
```

Asn Tyr Cys Arg Asn Pro Asp Gly Asp Val Gly Pro Trp Cys Tyr
        530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
                580                 585                 590

Pro Trp Gln Val Ser Leu Arg Thr Arg Phe Gly Met His Phe Cys Gly
                595                 600                 605

Gly Thr Leu Ile Ser Pro Glu Trp Val Leu Thr Ala Ala His Cys Leu
                610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
                660                 665                 670

Ser Pro Ala Val Ile Thr Asp Lys Val Ile Pro Ala Cys Leu Pro Ser
                675                 680                 685

Pro Asn Tyr Val Val Ala Asp Arg Thr Glu Cys Phe Ile Thr Gly Trp
                690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
                740                 745                 750

Thr Asp Ser Cys Gln Gly Asp Ser Gly Gly Pro Leu Val Cys Phe Glu
                755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 324
<211> LENGTH: 722
<212> TYPE: PRT
<213> ORGANISM: Homo sapiens

<400> SEQUENCE: 324

Met Ser Gln Gln Asp Ala Val Ala Ala Leu Ser Glu Arg Leu Leu Val
1               5                   10                  15

Ala Ala Tyr Lys Gly Gln Thr Glu Asn Val Val Gln Leu Ile Asn Lys
                20                  25                  30

Gly Ala Arg Val Ala Val Thr Lys His Gly Arg Thr Pro Leu His Leu
            35                  40                  45

Ala Ala Asn Lys Gly His Leu Pro Val Val Gln Ile Leu Leu Lys Ala
        50                  55                  60

Gly Cys Asp Leu Asp Val Gln Asp Asp Gly Asp Gln Thr Ala Leu His
65                  70                  75                  80

Arg Ala Thr Val Val Gly Asn Thr Glu Ile Ile Ala Ala Leu Ile His

```
                            85                  90                  95
Glu Gly Cys Ala Leu Asp Arg Gln Asp Lys Asp Gly Asn Thr Ala Leu
            100                 105                 110

His Glu Ala Ser Trp His Gly Phe Ser Gln Ser Ala Lys Leu Leu Ile
            115                 120                 125

Lys Ala Gly Ala Asn Val Leu Ala Lys Asn Lys Ala Gly Asn Thr Ala
            130                 135                 140

Leu His Leu Ala Cys Gln Asn Ser His Ser Gln Ser Thr Arg Val Leu
145                 150                 155                 160

Leu Leu Ala Gly Ser Arg Ala Asp Leu Lys Asn Asn Ala Gly Asp Thr
                165                 170                 175

Cys Leu His Val Ala Ala Arg Tyr Asn His Leu Ser Ile Ile Arg Leu
                180                 185                 190

Leu Leu Thr Ala Phe Cys Ser Val His Glu Lys Asn Gln Ala Gly Asp
                195                 200                 205

Thr Ala Leu His Val Ala Ala Leu Asn His Lys Lys Val Ala Lys
            210                 215                 220

Ile Leu Leu Glu Ala Gly Ala Asp Thr Thr Ile Val Asn Asn Ala Gly
225                 230                 235                 240

Gln Thr Pro Leu Glu Thr Ala Arg Tyr His Asn Asn Pro Glu Val Ala
                245                 250                 255

Leu Leu Leu Thr Lys Ala Pro Gln Val Leu Arg Phe Ser Arg Gly Arg
                260                 265                 270

Ser Leu Arg Lys Lys Arg Glu Arg Leu Lys Glu Glu Arg Arg Ala Gln
            275                 280                 285

Ser Val Pro Arg Asp Glu Val Ala Gln Ser Lys Gly Ser Val Ser Ala
            290                 295                 300

Gly Asp Thr Pro Ser Ser Glu Gln Ala Val Ala Arg Lys Glu Glu Ala
305                 310                 315                 320

Arg Glu Glu Phe Leu Ser Ala Ser Pro Glu Pro Arg Ala Lys Asp Asp
                325                 330                 335

Arg Arg Arg Lys Ser Arg Pro Lys Val Ser Ala Phe Ser Asp Pro Thr
            340                 345                 350

Pro Pro Ala Asp Gln Gln Pro Gly His Gln Lys Asn Leu His Ala His
            355                 360                 365

Asn His Pro Lys Lys Arg Asn Arg His Arg Cys Ser Ser Pro Pro Pro
370                 375                 380

Pro His Glu Phe Arg Ala Tyr Gln Leu Tyr Thr Leu Tyr Arg Gly Lys
385                 390                 395                 400

Asp Gly Lys Val Met Gln Ala Pro Ile Asn Gly Cys Arg Cys Glu Pro
                405                 410                 415

Leu Ile Asn Lys Leu Glu Asn Gln Leu Glu Ala Thr Val Glu Glu Ile
            420                 425                 430

Lys Ala Glu Leu Gly Ser Val Gln Asp Lys Met Asn Thr Lys Leu Gly
            435                 440                 445

Gln Met Glu Asn Lys Thr Gln His Gln Met Arg Val Leu Asp Lys Leu
            450                 455                 460

Met Val Glu Arg Leu Ser Ala Glu Arg Thr Glu Cys Leu Asn Arg Leu
465                 470                 475                 480

Gln Gln His Ser Asp Thr Glu Lys His Glu Gly Glu Lys Arg Gln Ile
                485                 490                 495

Ser Leu Val Asp Glu Leu Lys Thr Trp Cys Met Leu Lys Ile Gln Asn
            500                 505                 510
```

```
Leu Glu Gln Lys Leu Ser Gly Asp Ser Arg Ala Cys Arg Ala Lys Ser
            515                 520                 525

Thr Pro Ser Thr Cys Val Asp Gln Leu Val Val Thr Ala Gly Pro Ala
530                 535                 540

Ala Ala Ser Asp Ser Ser Pro Pro Val Val Arg Pro Lys Glu Lys Ala
545                 550                 555                 560

Leu Asn Ser Thr Ala Thr Gln Arg Leu Gln Gln Glu Leu Ser Ser Ser
            565                 570                 575

Asp Cys Thr Gly Ser Arg Leu Arg Asn Val Lys Val Gln Thr Ala Leu
        580                 585                 590

Leu Pro Met Asn Glu Ala Ala Arg Ser Asp Gln Ala Gly Pro Cys
    595                 600                 605

Val Asn Arg Gly Thr Gln Thr Lys Lys Ser Gly Lys Ser Gly Pro Thr
    610                 615                 620

Arg His Arg Ala Gln Gln Pro Ala Ala Ser Ser Thr Cys Gly Gln Pro
625                 630                 635                 640

Pro Pro Ala Thr Gly Ser Glu Gln Thr Gly Pro His Ile Arg Asp Thr
            645                 650                 655

Ser Gln Ala Leu Glu Leu Thr Gln Tyr Phe Phe Glu Ala Val Ser Thr
        660                 665                 670

Gln Met Glu Lys Trp Tyr Glu Arg Lys Ile Glu Glu Ala Arg Ser Gln
    675                 680                 685

Ala Asn Gln Lys Ala Gln Gln Asp Lys Ala Thr Leu Lys Glu His Ile
690                 695                 700

Lys Ser Leu Glu Glu Leu Ala Lys Leu Arg Thr Arg Val Gln Lys
705                 710                 715                 720

Glu Asn

<210> SEQ ID NO 325
<211> LENGTH: 94
<212> TYPE: PRT
<213> ORGANISM: Homo sapiens

<400> SEQUENCE: 325

Met Glu Lys Glu Ser Leu Pro Arg Ser Leu Asn Phe Asp His His Gly
1               5                   10                  15

Ile Tyr Met Asn Trp Gln Thr Lys Phe Met Leu Leu Leu Lys Thr Val
            20                  25                  30

Ser Ile Pro Arg Ser Gln Ala Ile Phe Thr Gln Pro Gly Leu Gly Ser
        35                  40                  45

Gly Thr Pro Gln Gly Tyr Lys Gln Ser His Ser Ala Leu Gly Trp Ala
    50                  55                  60

Ala Thr Leu Ser Cys Trp Gly Lys Asp Gly Arg Gln Leu Ser Trp
65                  70                  75                  80

Val Thr Ala Gly Ser Ser Phe His Lys Ser Asp Leu Ile Ser
            85                  90

<210> SEQ ID NO 326
<211> LENGTH: 790
<212> TYPE: PRT
<213> ORGANISM: Homo sapiens

<400> SEQUENCE: 326

Met Asn Ile Met Asn Thr Glu Gln Ser Gln Asn Ser Ile Val Ser Arg
1               5                   10                  15
```

```
Ile Lys Val Phe Glu Gly Gln Thr Asn Ile Glu Thr Ser Gly Leu Pro
             20                  25                  30

Lys Lys Pro Glu Ile Thr Pro Arg Ser Leu Pro Pro Lys Pro Thr Val
             35                  40                  45

Ser Ser Gly Lys Pro Ser Val Ala Pro Lys Pro Ala Ala Asn Arg Ala
 50                  55                  60

Ser Gly Glu Trp Asp Ser Gly Thr Glu Asn Arg Leu Lys Val Thr Ser
 65                  70                  75                  80

Lys Glu Gly Leu Thr Pro Tyr Pro Pro Leu Gln Glu Ala Gly Ser Ile
             85                  90                  95

Pro Val Thr Lys Pro Glu Leu Pro Lys Lys Pro Asn Pro Gly Leu Ile
            100                 105                 110

Arg Ser Val Asn Pro Glu Ile Pro Gly Arg Gly Pro Leu Ala Glu Ser
            115                 120                 125

Ser Asp Ser Gly Lys Lys Val Pro Thr Pro Ala Pro Arg Pro Leu Leu
130                 135                 140

Leu Lys Lys Ser Val Ser Ser Glu Asn Pro Thr Tyr Pro Ser Ala Pro
145                 150                 155                 160

Leu Lys Pro Val Thr Val Pro Pro Arg Leu Ala Gly Ala Ser Gln Ala
            165                 170                 175

Lys Ala Tyr Lys Ser Leu Gly Glu Gly Pro Pro Ala Asn Pro Pro Val
            180                 185                 190

Pro Val Leu Gln Ser Lys Pro Leu Val Asp Ile Asp Leu Ile Ser Phe
            195                 200                 205

Asp Asp Asp Val Leu Pro Thr Pro Ser Gly Asn Leu Ala Glu Glu Ser
210                 215                 220

Val Gly Ser Glu Met Val Leu Asp Pro Phe Gln Leu Pro Ala Lys Thr
225                 230                 235                 240

Glu Pro Ile Lys Glu Arg Ala Val Gln Pro Ala Pro Thr Arg Lys Pro
            245                 250                 255

Thr Val Ile Arg Ile Pro Ala Lys Pro Gly Lys Cys Leu His Glu Asp
            260                 265                 270

Pro Gln Ser Pro Pro Leu Pro Ala Glu Lys Pro Ile Gly Asn Thr
            275                 280                 285

Phe Ser Thr Val Ser Gly Lys Leu Ser Asn Val Glu Arg Thr Arg Asn
290                 295                 300

Leu Glu Ser Asn His Pro Gly Gln Thr Gly Gly Phe Val Arg Val Pro
305                 310                 315                 320

Pro Arg Leu Pro Arg Pro Val Asn Gly Lys Thr Ile Pro Thr Gln
            325                 330                 335

Gln Pro Pro Thr Lys Val Pro Pro Glu Arg Pro Pro Pro Lys Leu
            340                 345                 350

Ser Ala Thr Arg Arg Ser Asn Lys Lys Leu Pro Phe Asn Arg Ser Ser
            355                 360                 365

Ser Asp Met Asp Leu Gln Lys Lys Gln Ser Asn Leu Ala Thr Gly Leu
            370                 375                 380

Ser Lys Ala Lys Ser Gln Val Phe Lys Asn Gln Asp Pro Val Leu Pro
385                 390                 395                 400

Pro Arg Pro Lys Pro Gly His Pro Leu Tyr Ser Lys Tyr Met Leu Ser
            405                 410                 415

Val Pro His Gly Ile Ala Asn Glu Asp Ile Val Ser Gln Asn Pro Gly
            420                 425                 430

Glu Leu Ser Cys Lys Arg Gly Asp Val Leu Val Met Leu Lys Gln Thr
```

```
                        435                 440                 445
Glu Asn Asn Tyr Leu Glu Cys Gln Lys Gly Glu Asp Thr Gly Arg Val
    450                 455                 460

His Leu Ser Gln Met Lys Ile Ile Thr Pro Leu Asp Glu His Leu Arg
465                 470                 475                 480

Ser Arg Pro Asn Asp Pro Ser His Ala Gln Lys Pro Val Asp Ser Gly
                485                 490                 495

Ala Pro His Ala Val Val Leu His Asp Phe Pro Ala Glu Gln Val Asp
            500                 505                 510

Asp Leu Asn Leu Thr Ser Gly Glu Ile Val Tyr Leu Leu Glu Lys Ile
        515                 520                 525

Asp Thr Asp Trp Tyr Arg Gly Asn Cys Arg Asn Gln Ile Gly Ile Phe
    530                 535                 540

Pro Ala Asn Tyr Val Lys Val Ile Ile Asp Ile Pro Glu Gly Gly Asn
545                 550                 555                 560

Gly Lys Arg Glu Cys Val Ser Ser His Cys Val Lys Gly Ser Arg Cys
                565                 570                 575

Val Ala Arg Phe Glu Tyr Ile Gly Glu Gln Lys Asp Glu Leu Ser Phe
            580                 585                 590

Ser Glu Gly Glu Ile Ile Ile Leu Lys Glu Tyr Val Asn Glu Glu Trp
        595                 600                 605

Ala Arg Gly Glu Val Arg Gly Arg Thr Gly Ile Phe Pro Leu Asn Phe
    610                 615                 620

Val Glu Pro Val Glu Asp Tyr Pro Thr Ser Gly Ala Asn Val Leu Ser
625                 630                 635                 640

Thr Lys Val Pro Leu Lys Thr Lys Lys Glu Asp Ser Gly Ser Asn Ser
                645                 650                 655

Gln Val Asn Ser Leu Pro Ala Glu Trp Cys Glu Ala Leu His Ser Phe
            660                 665                 670

Thr Ala Glu Thr Ser Asp Asp Leu Ser Phe Lys Arg Gly Asp Arg Ile
        675                 680                 685

Gln Ile Leu Glu Arg Leu Asp Ser Asp Trp Cys Arg Gly Arg Leu Gln
    690                 695                 700

Asp Arg Glu Gly Ile Phe Pro Ala Val Phe Val Arg Pro Cys Pro Ala
705                 710                 715                 720

Glu Ala Lys Ser Met Leu Ala Ile Val Pro Lys Gly Arg Lys Ala Lys
                725                 730                 735

Ala Leu Tyr Asp Phe Arg Gly Glu Asn Glu Asp Glu Leu Ser Phe Lys
            740                 745                 750

Ala Gly Asp Ile Ile Thr Glu Leu Glu Ser Val Asp Asp Trp Met
        755                 760                 765

Ser Gly Glu Leu Met Gly Lys Ser Gly Ile Phe Pro Lys Asn Tyr Ile
770                 775                 780

Gln Phe Leu Gln Ile Ser
785                 790

<210> SEQ ID NO 327
<211> LENGTH: 593
<212> TYPE: PRT
<213> ORGANISM: Homo sapiens

<400> SEQUENCE: 327

Met Gly Gly Val Gln Gly His Phe Val Ile Phe Arg Gly Leu Ala Lys
1               5                   10                  15
```

```
Ala Leu Ser Arg Pro Val Thr Leu Ala Thr Pro Asp Ser Ser Leu Leu
             20                  25                  30

Leu Arg Lys Thr Gly Gln Pro Gly Ala Thr Arg Ser Ala Leu Thr Lys
         35                  40                  45

Met Leu Pro Gly Ala Trp Leu Leu Trp Thr Ser Leu Leu Leu Leu Ala
 50                  55                  60

Arg Pro Ala Gln Pro Cys Pro Met Gly Cys Asp Cys Phe Val Gln Glu
 65                  70                  75                  80

Val Phe Cys Ser Asp Glu Glu Leu Ala Thr Val Pro Leu Asp Ile Pro
             85                  90                  95

Pro Tyr Thr Lys Asn Ile Ile Phe Val Glu Thr Ser Phe Thr Thr Leu
             100                 105                 110

Glu Thr Arg Ala Phe Gly Ser Asn Pro Asn Leu Thr Lys Val Val Phe
         115                 120                 125

Leu Asn Thr Gln Leu Cys Gln Phe Arg Pro Asp Ala Phe Gly Gly Leu
 130                 135                 140

Pro Arg Leu Glu Asp Leu Glu Val Thr Gly Ser Ser Phe Leu Asn Leu
145                 150                 155                 160

Ser Thr Asn Ile Phe Ser Asn Leu Thr Ser Leu Gly Lys Leu Thr Leu
             165                 170                 175

Asn Phe Asn Met Leu Glu Ala Leu Pro Glu Gly Leu Phe Gln His Leu
         180                 185                 190

Ala Ala Leu Glu Ser Leu His Leu Gln Gly Asn Gln Leu Gln Ala Leu
         195                 200                 205

Pro Arg Arg Leu Phe Gln Pro Leu Thr His Leu Lys Thr Leu Asn Leu
210                 215                 220

Ala Gln Asn Leu Leu Ala Gln Leu Pro Glu Glu Leu Phe His Pro Leu
225                 230                 235                 240

Thr Ser Leu Gln Thr Leu Lys Leu Ser Asn Asn Ala Leu Ser Gly Leu
             245                 250                 255

Pro Gln Gly Val Phe Gly Lys Leu Gly Ser Leu Gln Glu Leu Phe Leu
         260                 265                 270

Asp Ser Asn Asn Ile Ser Glu Leu Pro Pro Gln Val Phe Ser Gln Leu
         275                 280                 285

Phe Cys Leu Glu Arg Leu Trp Leu Gln Arg Asn Ala Ile Thr His Leu
 290                 295                 300

Pro Leu Ser Ile Phe Ala Ser Leu Gly Asn Leu Thr Phe Leu Ser Leu
305                 310                 315                 320

Gln Trp Asn Met Leu Arg Val Leu Pro Ala Gly Leu Phe Ala His Thr
             325                 330                 335

Pro Cys Leu Val Gly Leu Ser Leu Thr His Asn Gln Leu Glu Thr Val
         340                 345                 350

Ala Glu Gly Thr Phe Ala His Leu Ser Asn Leu Arg Ser Leu Met Leu
         355                 360                 365

Ser Tyr Asn Ala Ile Thr His Leu Pro Ala Gly Ile Phe Arg Asp Leu
 370                 375                 380

Glu Glu Leu Val Lys Leu Tyr Leu Gly Ser Asn Asn Leu Thr Ala Leu
385                 390                 395                 400

His Pro Ala Leu Phe Gln Asn Leu Ser Lys Leu Glu Leu Leu Ser Leu
             405                 410                 415

Ser Lys Asn Gln Leu Thr Thr Leu Pro Glu Gly Ile Phe Asp Thr Asn
         420                 425                 430

Tyr Asn Leu Phe Asn Leu Ala Leu His Gly Asn Pro Trp Gln Cys Asp
```

```
            435                 440                 445
Cys His Leu Ala Tyr Leu Phe Asn Trp Leu Gln Gln Tyr Thr Asp Arg
    450                 455                 460

Leu Leu Asn Ile Gln Thr Tyr Cys Ala Gly Pro Ala Tyr Leu Lys Gly
465                 470                 475                 480

Gln Val Val Pro Ala Leu Asn Glu Lys Gln Leu Val Cys Pro Val Thr
                485                 490                 495

Arg Asp His Leu Gly Phe Gln Val Thr Trp Pro Asp Glu Ser Lys Ala
            500                 505                 510

Gly Gly Ser Trp Asp Leu Ala Val Gln Glu Arg Ala Ala Arg Ser Gln
        515                 520                 525

Cys Thr Tyr Ser Asn Pro Glu Gly Thr Val Val Leu Ala Cys Asp Gln
        530                 535                 540

Ala Gln Cys Arg Trp Leu Asn Val Gln Leu Ser Pro Trp Gln Gly Ser
545                 550                 555                 560

Leu Gly Leu Gln Tyr Asn Ala Ser Gln Glu Trp Asp Leu Arg Ser Ser
                565                 570                 575

Cys Gly Ser Leu Arg Leu Thr Val Ser Ile Glu Ala Arg Ala Ala Gly
            580                 585                 590

Pro

<210> SEQ ID NO 328
<211> LENGTH: 210
<212> TYPE: PRT
<213> ORGANISM: Homo sapiens
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid

<400> SEQUENCE: 328

Met Asp Asp Asp Asn Lys Asp Asn Ala Ile Leu Glu Asn Asp Ser
1               5                   10                  15

Arg Thr Trp Ser Lys Asp Leu Gln Asn Val Asn Ile Thr Leu His Ile
                20                  25                  30

Pro Phe Gln Pro Val Ala Ser Gln Leu Pro Arg Ile Phe Thr Ser Ile
            35                  40                  45

Gly Glu Asp Tyr Asp Glu Pro Val Leu Pro Ser Ile Thr Thr Glu Met
        50                  55                  60

Leu Lys Ser Val Val Cys Phe Asp Ala Gly Glu Leu Ile Thr Gln
65                  70                  75                  80

Arg Glu Leu Val Ser Arg Gln Val Ser Asp Asn Leu Thr Glu Xaa Ala
                85                  90                  95

Ala Thr Phe Arg Leu Ile Leu Asp Asp Val Ser Leu Thr Tyr Leu Thr
            100                 105                 110

Phe Arg Lys Asp Phe Thr Glu Ala Val Gly Ala Lys Gln Val Ala Gln
        115                 120                 125

Gln Glu Ala Glu Arg Ala Arg Phe Val Met Glu Lys Ala Lys Gln Gln
    130                 135                 140

Lys Lys Ala Ala Ile Ile Ser Ala Glu Gly Asp Ser Lys Ala Ala Glu
145                 150                 155                 160

Leu Ile Ala Asn Ser Leu Ala Thr Ala Gly Asp Gly Leu Ile Glu Leu
                165                 170                 175
```

```
Arg Lys Leu Xaa Ala Ala Glu Asp Ile Ala Tyr Gln Leu Ser Arg Ser
            180                 185                 190

Gln Asn Ile Thr Tyr Leu Pro Ala Gly Gln Ser Val Leu Leu Gln Leu
        195                 200                 205

Pro Gln
    210

<210> SEQ ID NO 329
<211> LENGTH: 374
<212> TYPE: PRT
<213> ORGANISM: Homo sapiens

<400> SEQUENCE: 329

Met Ala Pro Ala Lys Asn Ser Gly Lys Lys Met Asp His Ser Ala
1               5                   10                  15

Ile Asn Glu Val Met Thr Gln Glu Tyr Thr Asn Ile His Lys His Ile
            20                  25                  30

His Arg Val Gly Phe Lys His Val Pro Gln Ala Leu Lys Glu Ile
        35                  40                  45

Arg Lys Phe Cys Asn Glu Gly Asp Gly Asn Ser Arg Ser Thr Glu Gln
50                  55                  60

Val Leu Leu Gln Gly Ala Thr Met Ala Asp Lys Ser Lys Phe Ile Glu
65                  70                  75                  80

Tyr Ile Asp Glu Ala Leu Glu Lys Ser Lys Glu Thr Ala Leu Ser His
                85                  90                  95

Leu Phe Phe Thr Tyr Gln Gly Ile Pro Tyr Pro Ile Thr Met Cys Thr
            100                 105                 110

Ser Glu Thr Phe Gln Ala Leu Asp Thr Phe Glu Ala Arg His Asp Asp
        115                 120                 125

Ile Val Leu Ala Ser Tyr Pro Lys Cys Gly Ser Asn Trp Ile Leu His
    130                 135                 140

Ile Val Ser Glu Leu Ile Tyr Ala Val Ser Lys Lys Tyr Lys Tyr
145                 150                 155                 160

Pro Glu Phe Pro Val Leu Glu Cys Gly Asp Ser Glu Lys Tyr Gln Arg
                165                 170                 175

Met Lys Gly Phe Pro Ser Pro Arg Ile Leu Ala Thr His Leu His Tyr
            180                 185                 190

Asp Lys Leu Pro Gly Ser Ile Phe Glu Asn Lys Ala Lys Ile Leu Val
        195                 200                 205

Ile Phe Arg Asn Pro Lys Asp Thr Ala Val Ser Phe Leu His Phe His
    210                 215                 220

Asn Asp Val Pro Asp Ile Pro Ser Tyr Gly Ser Trp Asp Glu Phe Phe
225                 230                 235                 240

Arg Gln Phe Met Lys Gly Gln Val Ser Trp Gly Arg Tyr Phe Asp Phe
                245                 250                 255

Ala Ile Asn Trp Asn Lys His Leu Asp Gly Asp Asn Val Lys Phe Ile
            260                 265                 270

Leu Tyr Glu Asp Leu Lys Glu Asn Leu Ala Ala Gly Ile Lys Gln Ile
        275                 280                 285

Ala Glu Phe Leu Gly Phe Phe Leu Thr Gly Glu Ile Gln Thr Ile
    290                 295                 300

Ser Val Gln Ser Thr Phe Gln Ala Met Arg Ala Lys Ser Gln Asp Thr
305                 310                 315                 320

His Gly Ala Val Gly Pro Phe Leu Phe Arg Lys Gly Glu Val Gly Asp
```

```
            325                 330                 335
Trp Lys Asn Leu Phe Ser Glu Ile Gln Asn Gln Glu Met Asp Glu Lys
        340                 345                 350

Phe Lys Glu Cys Leu Ala Gly Thr Ser Leu Gly Ala Lys Leu Lys Tyr
        355                 360                 365

Glu Ser Tyr Cys Gln Gly
        370

<210> SEQ ID NO 330
<211> LENGTH: 676
<212> TYPE: PRT
<213> ORGANISM: Homo sapiens

<400> SEQUENCE: 330

Met Arg Val Leu Gly Gly Arg Cys Gly Ala Pro Leu Ala Cys Leu Leu
1               5                   10                  15

Leu Val Leu Pro Val Ser Glu Ala Asn Leu Leu Ser Lys Gln Gln Ala
            20                  25                  30

Ser Gln Val Leu Val Arg Lys Arg Ala Asn Ser Leu Leu Glu Glu
        35                  40                  45

Thr Lys Gln Gly Asn Leu Glu Arg Glu Cys Ile Glu Glu Leu Cys Asn
50                  55                  60

Lys Glu Glu Ala Arg Glu Val Phe Glu Asn Asp Pro Glu Thr Asp Tyr
65                  70                  75                  80

Phe Tyr Pro Lys Tyr Leu Val Cys Leu Arg Ser Phe Gln Thr Gly Leu
                85                  90                  95

Phe Thr Ala Ala Arg Gln Ser Thr Asn Ala Tyr Pro Asp Leu Arg Ser
            100                 105                 110

Cys Val Asn Ala Ile Pro Asp Gln Cys Ser Pro Leu Pro Cys Asn Glu
        115                 120                 125

Asp Gly Tyr Met Ser Cys Lys Asp Gly Lys Ala Ser Phe Thr Cys Thr
130                 135                 140

Cys Lys Pro Gly Trp Gln Gly Glu Lys Cys Glu Phe Asp Ile Asn Glu
145                 150                 155                 160

Cys Lys Asp Pro Ser Asn Ile Asn Gly Gly Cys Ser Gln Ile Cys Asp
                165                 170                 175

Asn Thr Pro Gly Ser Tyr His Cys Ser Cys Lys Asn Gly Phe Val Met
            180                 185                 190

Leu Ser Asn Lys Lys Asp Cys Lys Asp Val Asp Glu Cys Ser Leu Lys
        195                 200                 205

Pro Ser Ile Cys Gly Thr Ala Val Cys Lys Asn Ile Pro Gly Asp Phe
210                 215                 220

Glu Cys Glu Cys Pro Glu Gly Tyr Arg Tyr Asn Leu Lys Ser Lys Ser
225                 230                 235                 240

Cys Glu Asp Ile Asp Glu Cys Ser Glu Asn Met Cys Ala Gln Leu Cys
                245                 250                 255

Val Asn Tyr Pro Gly Gly Tyr Thr Cys Tyr Cys Asp Gly Lys Lys Gly
            260                 265                 270

Phe Lys Leu Ala Gln Asp Gln Lys Ser Cys Glu Val Val Ser Val Cys
        275                 280                 285

Leu Pro Leu Asn Leu Asp Thr Lys Tyr Glu Leu Leu Tyr Leu Ala Glu
        290                 295                 300

Gln Phe Ala Gly Val Val Leu Tyr Leu Lys Phe Arg Leu Pro Glu Ile
305                 310                 315                 320
```

```
Ser Arg Phe Ser Ala Glu Phe Asp Phe Arg Thr Tyr Asp Ser Glu Gly
                325                 330                 335

Val Ile Leu Tyr Ala Glu Ser Ile Asp His Ser Ala Trp Leu Leu Ile
            340                 345                 350

Ala Leu Arg Gly Gly Lys Ile Glu Val Gln Leu Lys Asn Glu His Thr
        355                 360                 365

Ser Lys Ile Thr Thr Gly Gly Asp Val Ile Asn Asn Gly Leu Trp Asn
    370                 375                 380

Met Val Ser Val Glu Glu Leu Glu His Ser Ile Ser Ile Lys Ile Ala
385                 390                 395                 400

Lys Glu Ala Val Met Asp Ile Asn Lys Pro Gly Pro Leu Phe Lys Pro
                405                 410                 415

Glu Asn Gly Leu Leu Glu Thr Lys Val Tyr Phe Ala Gly Phe Pro Arg
            420                 425                 430

Lys Val Glu Ser Glu Leu Ile Lys Pro Ile Asn Pro Arg Leu Asp Gly
        435                 440                 445

Cys Ile Arg Ser Trp Asn Leu Met Lys Gln Gly Ala Ser Gly Ile Lys
    450                 455                 460

Glu Ile Ile Gln Glu Lys Gln Asn Lys His Cys Leu Val Thr Val Glu
465                 470                 475                 480

Lys Gly Ser Tyr Tyr Pro Gly Ser Gly Ile Ala Gln Phe His Ile Asp
                485                 490                 495

Tyr Asn Asn Val Ser Ser Ala Glu Gly Trp His Val Asn Val Thr Leu
            500                 505                 510

Asn Ile Arg Pro Ser Thr Gly Thr Gly Val Met Leu Ala Leu Val Ser
        515                 520                 525

Gly Asn Asn Thr Val Pro Phe Ala Val Ser Leu Val Asp Ser Thr Ser
    530                 535                 540

Glu Lys Ser Gln Asp Ile Leu Leu Ser Val Glu Asn Thr Val Ile Tyr
545                 550                 555                 560

Arg Ile Gln Ala Leu Ser Leu Cys Ser Asp Gln Ser His Leu Glu
                565                 570                 575

Phe Arg Val Asn Arg Asn Asn Leu Glu Leu Ser Thr Pro Leu Lys Ile
            580                 585                 590

Glu Thr Ile Ser His Glu Asp Leu Gln Arg Gln Leu Ala Val Leu Asp
        595                 600                 605

Lys Ala Met Lys Ala Lys Val Ala Thr Tyr Leu Gly Gly Leu Pro Asp
    610                 615                 620

Val Pro Phe Ser Ala Thr Pro Val Asn Ala Phe Tyr Asn Gly Cys Met
625                 630                 635                 640

Glu Val Asn Ile Asn Gly Val Gln Leu Asp Leu Asp Glu Ala Ile Ser
                645                 650                 655

Lys His Asn Asp Ile Arg Ala His Ser Cys Pro Ser Val Trp Lys Lys
            660                 665                 670

Thr Lys Asn Ser
        675

<210> SEQ ID NO 331
<211> LENGTH: 747
<212> TYPE: PRT
<213> ORGANISM: Homo sapiens

<400> SEQUENCE: 331

Met Arg Arg Cys Asn Ser Gly Ser Gly Pro Pro Pro Ser Leu Leu Leu
1               5                   10                  15
```

```
Leu Leu Leu Trp Leu Leu Ala Val Pro Gly Ala Asn Ala Ala Pro Arg
            20                  25                  30

Ser Ala Leu Tyr Ser Pro Ser Asp Pro Leu Thr Leu Gln Ala Asp
        35                  40                  45

Thr Val Arg Gly Ala Val Leu Gly Ser Arg Ser Ala Trp Ala Val Glu
50                  55                  60

Phe Phe Ala Ser Trp Cys Gly His Cys Ile Ala Phe Ala Pro Thr Trp
65                  70                  75                  80

Lys Ala Leu Ala Glu Asp Val Lys Ala Trp Arg Pro Ala Leu Tyr Leu
                85                  90                  95

Ala Ala Leu Asp Cys Ala Glu Glu Thr Asn Ser Ala Val Cys Arg Asp
            100                 105                 110

Phe Asn Ile Pro Gly Phe Pro Thr Val Arg Phe Phe Lys Ala Phe Thr
            115                 120                 125

Lys Asn Gly Ser Gly Ala Val Phe Pro Val Ala Gly Ala Asp Val Gln
130                 135                 140

Thr Leu Arg Glu Arg Leu Ile Asp Ala Leu Glu Ser His His Asp Thr
145                 150                 155                 160

Trp Pro Pro Ala Cys Pro Pro Leu Glu Pro Ala Lys Leu Glu Glu Ile
                165                 170                 175

Asp Gly Phe Phe Ala Arg Asn Asn Glu Glu Tyr Leu Ala Leu Ile Phe
            180                 185                 190

Glu Lys Gly Gly Ser Tyr Leu Gly Arg Glu Val Ala Leu Asp Leu Ser
            195                 200                 205

Gln His Lys Gly Val Ala Val Arg Arg Val Leu Asn Thr Glu Ala Asn
        210                 215                 220

Val Val Arg Lys Phe Gly Val Thr Asp Phe Pro Ser Cys Tyr Leu Leu
225                 230                 235                 240

Phe Arg Asn Gly Ser Val Ser Arg Val Pro Val Leu Met Glu Ser Arg
            245                 250                 255

Ser Phe Tyr Thr Ala Tyr Leu Gln Arg Leu Ser Gly Leu Thr Arg Glu
            260                 265                 270

Ala Ala Gln Thr Thr Val Ala Pro Thr Thr Ala Asn Lys Ile Ala Pro
        275                 280                 285

Thr Val Trp Lys Leu Ala Asp Arg Ser Lys Ile Tyr Met Ala Asp Leu
290                 295                 300

Glu Ser Ala Leu His Tyr Ile Leu Arg Ile Glu Val Gly Arg Phe Pro
305                 310                 315                 320

Val Leu Glu Gly Gln Arg Leu Val Ala Leu Lys Lys Phe Val Ala Val
            325                 330                 335

Leu Ala Lys Tyr Phe Pro Gly Arg Pro Leu Val Gln Asn Phe Leu His
            340                 345                 350

Ser Val Asn Glu Trp Leu Lys Arg Gln Lys Arg Asn Lys Ile Pro Tyr
        355                 360                 365

Ser Phe Phe Lys Thr Ala Leu Asp Asp Arg Lys Glu Gly Ala Val Leu
        370                 375                 380

Ala Lys Lys Val Asn Trp Ile Gly Cys Gln Gly Ser Glu Pro His Phe
385                 390                 395                 400

Arg Gly Phe Pro Cys Ser Leu Trp Val Leu Phe His Phe Leu Thr Val
            405                 410                 415

Gln Ala Ala Arg Gln Asn Val Asp His Ser Gln Glu Ala Ala Lys Ala
            420                 425                 430
```

```
Lys Glu Val Leu Pro Ala Ile Arg Gly Tyr Val His Tyr Phe Phe Gly
            435                 440                 445

Cys Arg Asp Cys Ala Ser His Phe Glu Gln Met Ala Ala Ala Ser Met
450                 455                 460

His Arg Val Gly Ser Pro Asn Ala Ala Val Leu Trp Leu Trp Ser Ser
465                 470                 475                 480

His Asn Arg Val Asn Ala Arg Leu Ala Gly Ala Pro Ser Glu Asp Pro
                485                 490                 495

Gln Phe Pro Lys Val Gln Trp Pro Arg Glu Leu Cys Ser Ala Cys
            500                 505                 510

His Asn Glu Arg Leu Asp Val Pro Val Trp Asp Val Glu Ala Thr Leu
            515                 520                 525

Asn Phe Leu Lys Ala His Phe Ser Pro Ser Asn Ile Ile Leu Asp Phe
530                 535                 540

Pro Ala Gly Ser Ala Ala Arg Arg Asp Val Gln Asn Val Ala Ala
545                 550                 555                 560

Ala Pro Glu Leu Ala Met Gly Ala Leu Glu Leu Glu Ser Arg Asn Ser
                565                 570                 575

Thr Leu Asp Pro Gly Lys Pro Glu Met Met Lys Ser Pro Thr Asn Thr
            580                 585                 590

Thr Pro His Val Pro Ala Glu Gly Pro Glu Ala Ser Arg Pro Pro Lys
            595                 600                 605

Leu His Pro Gly Leu Arg Ala Ala Pro Gly Gln Glu Pro Pro Glu His
            610                 615                 620

Met Ala Glu Leu Gln Arg Asn Glu Gln Glu Gln Pro Leu Gly Gln Trp
625                 630                 635                 640

His Leu Ser Lys Arg Asp Thr Gly Ala Ala Leu Leu Ala Glu Ser Arg
                645                 650                 655

Ala Glu Lys Asn Arg Leu Trp Gly Pro Leu Glu Val Arg Arg Val Gly
                660                 665                 670

Arg Ser Ser Lys Gln Leu Val Asp Ile Pro Glu Gly Gln Leu Glu Ala
            675                 680                 685

Arg Ala Gly Arg Gly Arg Gly Gln Trp Leu Gln Val Leu Gly Gly Gly
690                 695                 700

Phe Ser Tyr Leu Asp Ile Ser Leu Cys Val Gly Leu Tyr Ser Leu Ser
705                 710                 715                 720

Phe Met Gly Leu Leu Ala Met Tyr Thr Tyr Phe Gln Ala Lys Ile Arg
                725                 730                 735

Ala Leu Lys Gly His Ala Gly His Pro Ala Ala
            740                 745

<210> SEQ ID NO 332
<211> LENGTH: 199
<212> TYPE: PRT
<213> ORGANISM: Homo sapiens

<400> SEQUENCE: 332

Met Lys Trp Val Trp Ala Leu Leu Leu Leu Ala Ala Trp Ala Ala Ala
1               5                   10                  15

Glu Arg Asp Cys Arg Val Ser Ser Phe Arg Val Lys Glu Asn Phe Asp
            20                  25                  30

Lys Ala Arg Phe Ser Gly Thr Trp Tyr Ala Met Ala Lys Lys Asp Pro
        35                  40                  45

Glu Gly Leu Phe Leu Gln Asp Asn Ile Val Ala Glu Phe Ser Val Asp
50                  55                  60
```

```
Glu Thr Gly Gln Met Ser Ala Thr Ala Lys Gly Arg Val Arg Leu Leu
 65                  70                  75                  80

Asn Asn Trp Asp Val Cys Ala Asp Met Val Gly Thr Phe Thr Asp Thr
                 85                  90                  95

Glu Asp Pro Ala Lys Phe Lys Met Lys Tyr Trp Gly Val Ala Ser Phe
            100                 105                 110

Leu Gln Lys Gly Asn Asp Asp His Trp Ile Val Asp Thr Asp Tyr Asp
        115                 120                 125

Thr Tyr Ala Val Gln Tyr Ser Cys Arg Leu Leu Asn Leu Asp Gly Thr
    130                 135                 140

Cys Ala Asp Ser Tyr Ser Phe Val Phe Ser Arg Asp Pro Asn Gly Leu
145                 150                 155                 160

Pro Pro Glu Ala Gln Lys Ile Val Arg Gln Arg Gln Glu Leu Cys
                165                 170                 175

Leu Ala Arg Gln Tyr Arg Leu Ile Val His Asn Gly Tyr Cys Asp Gly
            180                 185                 190

Arg Ser Glu Arg Asn Leu Leu
        195

<210> SEQ ID NO 333
<211> LENGTH: 418
<212> TYPE: PRT
<213> ORGANISM: Homo sapiens

<400> SEQUENCE: 333

Met Pro Ser Ser Val Ser Trp Gly Ile Leu Leu Leu Ala Gly Leu Cys
  1               5                  10                  15

Cys Leu Val Pro Val Ser Leu Ala Glu Asp Pro Gln Gly Asp Ala Ala
                 20                  25                  30

Gln Lys Thr Asp Thr Ser His His Asp Gln Asp His Pro Thr Phe Asn
             35                  40                  45

Lys Ile Thr Pro Asn Leu Ala Glu Phe Ala Phe Ser Leu Tyr Arg Gln
     50                  55                  60

Leu Ala His Gln Ser Asn Ser Thr Asn Ile Phe Phe Ser Pro Val Ser
 65                  70                  75                  80

Ile Ala Thr Ala Phe Ala Met Leu Ser Leu Gly Thr Lys Ala Asp Thr
                 85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
```

```
                225                 230                 235                 240
Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
                260                 265                 270

Thr Ala Ile Phe Phe Leu Pro Asp Glu Gly Lys Leu Gln His Leu Glu
                275                 280                 285

Asn Glu Leu Thr His Asp Ile Ile Thr Lys Phe Leu Glu Asn Glu Asp
                290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
                340                 345                 350

Leu Ser Lys Ala Val His Lys Ala Val Leu Thr Ile Asp Glu Lys Gly
                355                 360                 365

Thr Glu Ala Ala Gly Ala Met Phe Leu Glu Ala Ile Pro Met Ser Ile
                370                 375                 380

Pro Pro Glu Val Lys Phe Asn Lys Pro Phe Val Phe Leu Met Ile Asp
385                 390                 395                 400

Gln Asn Thr Lys Ser Pro Leu Phe Met Gly Lys Val Val Asn Pro Thr
                405                 410                 415

Gln Lys

<210> SEQ ID NO 334
<211> LENGTH: 415
<212> TYPE: PRT
<213> ORGANISM: Homo sapiens

<400> SEQUENCE: 334

Met Ser Pro Phe Leu Tyr Leu Val Leu Leu Val Leu Gly Leu His Ala
1               5                   10                  15

Thr Ile His Cys Ala Ser Pro Glu Gly Lys Val Thr Ala Cys His Ser
                20                  25                  30

Ser Gln Pro Asn Ala Thr Leu Tyr Lys Met Ser Ser Ile Asn Ala Asp
                35                  40                  45

Phe Ala Phe Asn Leu Tyr Arg Arg Phe Thr Val Glu Thr Pro Asp Lys
            50                  55                  60

Asn Ile Phe Phe Ser Pro Val Ser Ile Ser Ala Ala Leu Val Met Leu
65                  70                  75                  80

Ser Phe Gly Ala Cys Cys Ser Thr Gln Thr Glu Ile Val Glu Thr Leu
                85                  90                  95

Gly Phe Asn Leu Thr Asp Thr Pro Met Val Glu Ile Gln His Gly Phe
                100                 105                 110

Gln His Leu Ile Cys Ser Leu Asn Phe Pro Lys Lys Glu Leu Glu Leu
                115                 120                 125

Gln Ile Gly Asn Ala Leu Phe Ile Gly Lys His Leu Lys Pro Leu Ala
                130                 135                 140

Lys Phe Leu Asn Asp Val Lys Thr Leu Tyr Glu Thr Glu Val Phe Ser
145                 150                 155                 160

Thr Asp Phe Ser Asn Ile Ser Ala Ala Lys Gln Glu Ile Asn Ser His
                165                 170                 175

Val Glu Met Gln Thr Lys Gly Lys Val Val Gly Leu Ile Gln Asp Leu
```

```
                180                 185                 190
Lys Pro Asn Thr Thr Met Val Leu Val Asn Tyr Ile His Phe Lys Ala
            195                 200                 205

Gln Trp Ala Asn Pro Phe Asp Pro Ser Lys Thr Glu Asp Ser Ser Ser
        210                 215                 220

Phe Leu Ile Asp Lys Thr Thr Thr Val Gln Val Pro Met Met His Gln
225                 230                 235                 240

Met Glu Gln Tyr Tyr His Leu Val Asp Met Glu Leu Asn Cys Thr Val
                245                 250                 255

Leu Gln Met Asp Tyr Ser Lys Asn Ala Leu Ala Leu Phe Val Leu Pro
            260                 265                 270

Lys Glu Gly Gln Met Glu Ser Val Glu Ala Ala Met Ser Ser Lys Thr
        275                 280                 285

Leu Lys Lys Trp Asn Arg Leu Leu Gln Lys Gly Trp Val Asp Leu Phe
290                 295                 300

Val Pro Lys Phe Ser Ile Ser Ala Thr Tyr Asp Leu Gly Ala Thr Leu
305                 310                 315                 320

Leu Lys Met Gly Ile Gln His Ala Tyr Ser Glu Asn Ala Asp Phe Ser
                325                 330                 335

Gly Leu Thr Glu Asp Asn Gly Leu Lys Leu Ser Asn Ala Ala His Lys
            340                 345                 350

Ala Val Leu His Ile Gly Glu Lys Gly Thr Glu Ala Ala Val Pro
        355                 360                 365

Glu Val Glu Leu Ser Asp Gln Pro Glu Asn Thr Phe Leu His Pro Ile
    370                 375                 380

Ile Gln Ile Asp Arg Ser Phe Met Leu Leu Ile Leu Glu Arg Ser Thr
385                 390                 395                 400

Arg Ser Ile Leu Phe Leu Gly Lys Val Val Asn Pro Thr Glu Ala
                405                 410                 415

<210> SEQ ID NO 335
<211> LENGTH: 464
<212> TYPE: PRT
<213> ORGANISM: Homo sapiens

<400> SEQUENCE: 335

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140
```

Glu Lys Thr Ser Asp Gln Ile His Phe Phe Ala Lys Leu Asn Cys
145                 150                 155                 160

Arg Leu Tyr Arg Lys Ala Asn Lys Ser Ser Lys Leu Val Ser Ala Asn
            165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Arg Ser Leu Asn Pro Asn Arg Val
            420                 425                 430

Thr Phe Lys Ala Asn Arg Pro Phe Leu Val Phe Ile Arg Glu Val Pro
        435                 440                 445

Leu Asn Thr Ile Ile Phe Met Gly Arg Val Ala Asn Pro Cys Val Lys
    450                 455                 460

<210> SEQ ID NO 336
<211> LENGTH: 418
<212> TYPE: PRT
<213> ORGANISM: Homo sapiens

<400> SEQUENCE: 336

Met Gln Ala Leu Val Leu Leu Cys Ile Gly Ala Leu Leu Gly His
1               5                   10                  15

Ser Ser Cys Gln Asn Pro Ala Ser Pro Pro Glu Glu Gly Ser Pro Asp
                20                  25                  30

Pro Asp Ser Thr Gly Ala Leu Val Glu Glu Glu Asp Pro Phe Phe Lys
            35                  40                  45

Val Pro Val Asn Lys Leu Ala Ala Ala Val Ser Asn Phe Gly Tyr Asp
        50                  55                  60

Leu Tyr Arg Val Arg Ser Ser Thr Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 337
<211> LENGTH: 223
<212> TYPE: PRT
<213> ORGANISM: Homo sapiens

<400> SEQUENCE: 337

Met Asn Lys Pro Leu Leu Trp Ile Ser Val Leu Thr Ser Leu Leu Glu
1               5                   10                  15

Ala Phe Ala His Thr Asp Leu Ser Gly Lys Val Phe Val Phe Pro Arg
            20                  25                  30

Glu Ser Val Thr Asp His Val Asn Leu Ile Thr Pro Leu Glu Lys Pro
            35                  40                  45

Leu Gln Asn Phe Thr Leu Cys Phe Arg Ala Tyr Ser Asp Leu Ser Arg
 50                  55                  60

Ala Tyr Ser Leu Phe Ser Tyr Asn Thr Gln Gly Arg Asp Asn Glu Leu
 65                  70                  75                  80

Leu Val Tyr Lys Glu Arg Val Gly Glu Tyr Ser Leu Tyr Ile Gly Arg
                85                  90                  95

His Lys Val Thr Ser Lys Val Ile Glu Lys Phe Pro Ala Pro Val His
            100                 105                 110

Ile Cys Val Ser Trp Glu Ser Ser Gly Ile Ala Glu Phe Trp Ile
            115                 120                 125

Asn Gly Thr Pro Leu Val Lys Lys Gly Leu Arg Gln Gly Tyr Phe Val
 130                 135                 140

Glu Ala Gln Pro Lys Ile Val Leu Gly Gln Glu Gln Asp Ser Tyr Gly
145                 150                 155                 160

Gly Lys Phe Asp Arg Ser Gln Ser Phe Val Gly Glu Ile Gly Asp Leu
                165                 170                 175

Tyr Met Trp Asp Ser Val Leu Pro Pro Glu Asn Ile Leu Ser Ala Tyr
            180                 185                 190

Gln Gly Thr Pro Leu Pro Ala Asn Ile Leu Asp Trp Gln Ala Leu Asn
            195                 200                 205

Tyr Glu Ile Arg Gly Tyr Val Ile Ile Lys Pro Leu Val Trp Val
210                 215                 220

<210> SEQ ID NO 338
<211> LENGTH: 402
<212> TYPE: PRT
<213> ORGANISM: Homo sapiens

<400> SEQUENCE: 338

Met Glu Ser Arg Gly Pro Leu Ala Thr Ser Arg Leu Leu Leu Leu
1               5                   10                  15

Leu Leu Leu Leu Arg His Thr Arg Gln Gly Trp Ala Leu Arg Pro
            20                  25                  30

Val Leu Pro Thr Gln Ser Ala His Asp Pro Ala Val His Leu Ser
            35                  40                  45

Asn Gly Pro Gly Gln Glu Pro Ile Ala Val Met Thr Phe Asp Leu Thr
 50                  55                  60

Lys Ile Thr Lys Thr Ser Ser Ser Phe Glu Val Arg Thr Trp Asp Pro
65                  70                  75                  80

Glu Gly Val Ile Phe Tyr Gly Asp Thr Asn Pro Lys Asp Asp Trp Phe
                85                  90                  95

Met Leu Gly Leu Arg Asp Gly Arg Pro Glu Ile Gln Leu His Asn His
            100                 105                 110

Trp Ala Gln Leu Thr Val Gly Ala Gly Pro Arg Leu Asp Asp Gly Arg
            115                 120                 125

Trp His Gln Val Glu Val Lys Met Glu Gly Asp Ser Val Leu Leu Glu
 130                 135                 140

Val Asp Gly Glu Glu Val Leu Arg Leu Arg Gln Val Ser Gly Pro Leu
145                 150                 155                 160

Thr Ser Lys Arg His Pro Ile Met Arg Ile Ala Leu Gly Gly Leu Leu

-continued

```
                165                 170                 175
Phe Pro Ala Ser Asn Leu Arg Leu Pro Leu Val Pro Ala Leu Asp Gly
            180                 185                 190

Cys Leu Arg Arg Asp Ser Trp Leu Asp Lys Gln Ala Glu Ile Ser Ala
            195                 200                 205

Ser Ala Pro Thr Ser Leu Arg Ser Cys Asp Val Glu Ser Asn Pro Gly
210                 215                 220

Ile Phe Leu Pro Pro Gly Thr Gln Ala Glu Phe Asn Leu Arg Asp Ile
225                 230                 235                 240

Pro Gln Pro His Ala Glu Pro Trp Ala Phe Ser Leu Asp Leu Gly Leu
            245                 250                 255

Lys Gln Ala Ala Gly Ser Gly His Leu Leu Ala Leu Gly Thr Pro Glu
            260                 265                 270

Asn Pro Ser Trp Leu Ser Leu His Leu Gln Asp Gln Lys Val Val Leu
            275                 280                 285

Ser Ser Gly Ser Gly Pro Gly Leu Asp Leu Pro Leu Val Leu Gly Leu
        290                 295                 300

Pro Leu Gln Leu Lys Leu Ser Met Ser Arg Val Val Leu Ser Gln Gly
305                 310                 315                 320

Ser Lys Met Lys Ala Leu Ala Leu Pro Pro Leu Gly Leu Ala Pro Leu
            325                 330                 335

Leu Asn Leu Trp Ala Lys Pro Gln Gly Arg Leu Phe Leu Gly Ala Leu
            340                 345                 350

Pro Gly Glu Asp Ser Ser Thr Ser Phe Cys Leu Asn Gly Leu Trp Ala
        355                 360                 365

Gln Gly Gln Arg Leu Asp Val Asp Gln Ala Leu Asn Arg Ser His Glu
    370                 375                 380

Ile Trp Thr His Ser Cys Pro Gln Ser Pro Gly Asn Gly Thr Asp Ala
385                 390                 395                 400

Ser His

<210> SEQ ID NO 339
<211> LENGTH: 248
<212> TYPE: PRT
<213> ORGANISM: Homo sapiens

<400> SEQUENCE: 339

Met Ser Leu Phe Pro Ser Leu Pro Leu Leu Leu Ser Met Val Ala
1               5                  10                  15

Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
            35                  40                  45

Lys Asp Gly Arg Asp Gly Thr Lys Gly Glu Lys Gly Glu Pro Gly Gln
50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
            85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
            115                 120                 125

Ser Leu Gly Lys Gln Val Gly Asn Lys Phe Phe Leu Thr Asn Gly Glu
```

```
                130                 135                 140
Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
            195                 200                 205

Asn Glu Gly Glu Pro Asn Asn Ala Gly Ser Asp Glu Asp Cys Val Leu
            210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245

<210> SEQ ID NO 340
<211> LENGTH: 2349
<212> TYPE: PRT
<213> ORGANISM: Homo sapiens

<400> SEQUENCE: 340

Met Ala Ala Val Leu Gln Gln Val Leu Glu Arg Thr Glu Leu Asn Lys
1               5                   10                  15

Leu Pro Lys Ser Val Gln Asn Lys Leu Glu Lys Phe Leu Ala Asp Gln
                20                  25                  30

Gln Ser Glu Ile Asp Gly Leu Lys Gly Arg His Glu Lys Phe Lys Val
            35                  40                  45

Glu Ser Glu Gln Gln Tyr Phe Glu Ile Glu Lys Arg Leu Ser His Ser
        50                  55                  60

Gln Glu Arg Leu Val Asn Glu Thr Arg Glu Cys Gln Ser Leu Arg Leu
65                  70                  75                  80

Glu Leu Glu Lys Leu Asn Asn Gln Leu Lys Ala Leu Thr Glu Lys Asn
                85                  90                  95

Lys Glu Leu Glu Ile Ala Gln Asp Arg Asn Ile Ala Ile Gln Ser Gln
                100                 105                 110

Phe Thr Arg Thr Lys Glu Glu Leu Glu Ala Glu Lys Arg Asp Leu Ile
            115                 120                 125

Arg Thr Asn Glu Arg Leu Ser Gln Glu Leu Glu Tyr Leu Thr Glu Asp
        130                 135                 140

Val Lys Arg Leu Asn Glu Lys Leu Lys Glu Ser Asn Thr Thr Lys Gly
145                 150                 155                 160

Glu Leu Gln Leu Lys Leu Asp Glu Leu Gln Ala Ser Asp Val Ser Val
                165                 170                 175

Lys Tyr Arg Glu Lys Arg Leu Glu Gln Glu Lys Glu Leu Leu His Ser
                180                 185                 190

Gln Asn Thr Trp Leu Asn Thr Glu Leu Lys Thr Lys Thr Asp Glu Leu
            195                 200                 205

Leu Ala Leu Gly Arg Glu Lys Gly Asn Glu Ile Leu Glu Leu Lys Cys
            210                 215                 220

Asn Leu Glu Asn Lys Lys Glu Glu Val Ser Arg Leu Glu Glu Gln Met
225                 230                 235                 240

Asn Gly Leu Lys Thr Ser Asn Glu His Leu Gln Lys His Val Glu Asp
                245                 250                 255
```

```
Leu Leu Thr Lys Leu Lys Glu Ala Lys Glu Gln Gln Ala Ser Met Glu
            260                 265                 270

Glu Lys Phe His Asn Glu Leu Asn Ala His Ile Lys Leu Ser Asn Leu
        275                 280                 285

Tyr Lys Ser Ala Ala Asp Asp Ser Glu Ala Lys Ser Asn Glu Leu Thr
    290                 295                 300

Arg Ala Val Glu Glu Leu His Lys Leu Leu Lys Glu Ala Gly Glu Ala
305                 310                 315                 320

Asn Lys Ala Ile Gln Asp His Leu Leu Val Glu Gln Ser Lys Asp
                325                 330                 335

Gln Met Glu Lys Glu Met Leu Glu Lys Ile Gly Arg Leu Glu Lys Glu
            340                 345                 350

Leu Glu Asn Ala Asn Asp Leu Leu Ser Ala Thr Lys Arg Lys Gly Ala
                355                 360                 365

Ile Leu Ser Glu Glu Glu Leu Ala Ala Met Ser Pro Thr Ala Ala Ala
        370                 375                 380

Val Ala Lys Ile Val Lys Pro Gly Met Lys Leu Thr Glu Leu Tyr Asn
385                 390                 395                 400

Ala Tyr Val Glu Thr Gln Asp Gln Leu Leu Leu Glu Lys Leu Glu Asn
                405                 410                 415

Lys Arg Ile Asn Lys Tyr Leu Asp Glu Ile Val Lys Glu Val Glu Ala
                420                 425                 430

Lys Ala Pro Ile Leu Lys Arg Gln Arg Glu Glu Tyr Glu Arg Ala Gln
            435                 440                 445

Lys Ala Val Ala Ser Leu Ser Val Lys Leu Glu Gln Ala Met Lys Glu
        450                 455                 460

Ile Gln Arg Leu Gln Glu Asp Thr Asp Lys Ala Asn Lys Gln Ser Ser
465                 470                 475                 480

Val Leu Glu Arg Asp Asn Arg Arg Met Glu Ile Gln Val Lys Asp Leu
                485                 490                 495

Ser Gln Gln Ile Arg Val Leu Leu Met Glu Leu Glu Glu Ala Arg Gly
            500                 505                 510

Asn His Val Ile Arg Asp Glu Glu Val Ser Ser Ala Asp Ile Ser Ser
        515                 520                 525

Ser Ser Glu Val Ile Ser Gln His Leu Val Ser Tyr Arg Asn Ile Glu
530                 535                 540

Glu Leu Gln Gln Gln Asn Gln Arg Leu Leu Val Ala Leu Arg Glu Leu
545                 550                 555                 560

Gly Glu Thr Arg Glu Arg Glu Gln Glu Thr Thr Ser Ser Lys Ile
            565                 570                 575

Thr Glu Leu Gln Leu Lys Leu Glu Ser Ala Leu Thr Glu Leu Glu Gln
            580                 585                 590

Leu Arg Lys Ser Arg Gln His Gln Met Gln Leu Val Asp Ser Ile Val
        595                 600                 605

Arg Gln Arg Asp Met Tyr Arg Ile Leu Leu Ser Gln Thr Thr Gly Val
    610                 615                 620

Ala Ile Pro Leu His Ala Ser Ser Leu Asp Asp Val Ser Leu Ala Ser
625                 630                 635                 640

Thr Pro Lys Arg Pro Ser Thr Ser Gln Thr Val Ser Thr Pro Ala Pro
                645                 650                 655

Val Pro Val Ile Glu Ser Thr Glu Ala Ile Glu Ala Lys Ala Ala Leu
                660                 665                 670

Lys Gln Leu Gln Glu Ile Phe Glu Asn Tyr Lys Lys Glu Lys Ala Glu
```

-continued

|   | 675 |   |   |   | 680 |   |   |   | 685 |   |   |
|---|---|---|---|---|---|---|---|---|---|---|---|

Asn Glu Lys Ile Gln Asn Glu Gln Leu Glu Lys Leu Gln Glu Gln Val
    690                    695                    700

Thr Asp Leu Arg Ser Gln Asn Thr Lys Ile Ser Thr Gln Leu Asp Phe
705                    710                    715                    720

Ala Ser Lys Arg Tyr Glu Met Leu Gln Asp Asn Val Glu Gly Tyr Arg
                725                    730                    735

Arg Glu Ile Thr Ser Leu His Glu Arg Asn Gln Lys Leu Thr Ala Thr
            740                    745                    750

Thr Gln Lys Gln Glu Gln Ile Ile Asn Thr Met Thr Gln Asp Leu Arg
        755                    760                    765

Gly Ala Asn Glu Lys Leu Ala Val Ala Glu Val Arg Ala Glu Asn Leu
    770                    775                    780

Lys Lys Glu Lys Glu Met Leu Lys Leu Ser Glu Val Arg Leu Ser Gln
785                    790                    795                    800

Gln Arg Glu Ser Leu Leu Ala Glu Gln Arg Gly Gln Asn Leu Leu Leu
                805                    810                    815

Thr Asn Leu Gln Thr Ile Gln Gly Ile Leu Glu Arg Ser Glu Thr Glu
        820                    825                    830

Thr Lys Gln Arg Leu Ser Ser Gln Ile Glu Lys Leu Glu His Glu Ile
        835                    840                    845

Ser His Leu Lys Lys Leu Glu Asn Glu Val Glu Gln Arg His Thr
850                    855                    860

Leu Thr Arg Asn Leu Asp Val Gln Leu Leu Asp Thr Lys Arg Gln Leu
865                    870                    875                  880

Asp Thr Glu Thr Asn Leu His Leu Asn Thr Lys Glu Leu Leu Lys Asn
                885                    890                    895

Ala Gln Lys Glu Ile Ala Thr Leu Lys Gln His Leu Ser Asn Met Glu
                900                    905                    910

Val Gln Val Ala Ser Gln Ser Ser Gln Arg Thr Gly Lys Gly Gln Pro
        915                    920                    925

Ser Asn Lys Glu Asp Val Asp Asp Leu Val Ser Gln Leu Arg Gln Thr
    930                    935                    940

Glu Glu Gln Val Asn Asp Leu Lys Glu Arg Leu Lys Thr Ser Thr Ser
945                    950                    955                    960

Asn Val Glu Gln Tyr Gln Ala Met Val Thr Ser Leu Glu Glu Ser Leu
                965                    970                    975

Asn Lys Glu Lys Gln Val Thr Glu Glu Val Arg Lys Asn Ile Glu Val
        980                    985                    990

Arg Leu Lys Glu Ser Ala Glu Phe Gln Thr Gln Leu Glu Lys Lys Leu
        995                  1000                  1005

Met Glu Val Glu Lys Glu Lys Gln Glu Leu Gln Asp Asp Lys Arg
    1010                    1015                  1020

Arg Ala Ile Glu Ser Met Glu Gln Gln Leu Ser Glu Leu Lys Lys
    1025                    1030                  1035

Thr Leu Ser Ser Val Gln Asn Glu Val Gln Glu Ala Leu Gln Arg
    1040                    1045                  1050

Ala Ser Thr Ala Leu Ser Asn Glu Gln Gln Ala Arg Arg Asp Cys
    1055                    1060                  1065

Gln Glu Gln Ala Lys Ile Ala Val Glu Ala Gln Asn Lys Tyr Glu
    1070                    1075                  1080

Arg Glu Leu Met Leu His Ala Ala Asp Val Glu Ala Leu Gln Ala
    1085                    1090                  1095

-continued

```
Ala Lys Glu Gln Val Ser Lys Met Ala Ser Val Arg Gln His Leu
1100            1105            1110

Glu Glu Thr Thr Gln Lys Ala Glu Ser Gln Leu Leu Glu Cys Lys
1115            1120            1125

Ala Ser Trp Glu Glu Arg Glu Arg Met Leu Lys Asp Glu Val Ser
1130            1135            1140

Lys Cys Val Cys Arg Cys Glu Asp Leu Glu Lys Gln Asn Arg Leu
1145            1150            1155

Leu His Asp Gln Ile Glu Lys Leu Ser Asp Lys Val Val Ala Ser
1160            1165            1170

Val Lys Glu Gly Val Gln Gly Pro Leu Asn Val Ser Leu Ser Glu
1175            1180            1185

Glu Gly Lys Ser Gln Glu Gln Ile Leu Glu Ile Leu Arg Phe Ile
1190            1195            1200

Arg Arg Glu Lys Glu Ile Ala Glu Thr Arg Phe Glu Val Ala Gln
1205            1210            1215

Val Glu Ser Leu Arg Tyr Arg Gln Arg Val Glu Leu Leu Glu Arg
1220            1225            1230

Glu Leu Gln Glu Leu Glu Asp Ser Leu Asn Ala Glu Arg Glu Lys
1235            1240            1245

Val Gln Val Thr Ala Lys Thr Met Ala Gln His Glu Glu Leu Met
1250            1255            1260

Lys Lys Thr Glu Thr Met Asn Val Val Met Glu Thr Asn Lys Met
1265            1270            1275

Leu Arg Glu Glu Lys Glu Arg Leu Glu Gln Asp Leu Gln Gln Met
1280            1285            1290

Gln Ala Lys Val Arg Lys Leu Glu Leu Asp Ile Leu Pro Leu Gln
1295            1300            1305

Glu Ala Asn Ala Glu Leu Ser Glu Lys Ser Gly Met Leu Gln Ala
1310            1315            1320

Glu Lys Lys Leu Leu Glu Glu Asp Val Lys Arg Trp Lys Ala Arg
1325            1330            1335

Asn Gln His Leu Val Ser Gln Gln Lys Asp Pro Asp Thr Glu Glu
1340            1345            1350

Tyr Arg Lys Leu Leu Ser Glu Lys Glu Val His Thr Lys Arg Ile
1355            1360            1365

Gln Gln Leu Thr Glu Glu Ile Gly Arg Leu Lys Ala Glu Ile Ala
1370            1375            1380

Arg Ser Asn Ala Ser Leu Thr Asn Asn Gln Asn Leu Ile Gln Ser
1385            1390            1395

Leu Lys Glu Asp Leu Asn Lys Val Arg Thr Glu Lys Glu Thr Ile
1400            1405            1410

Gln Lys Asp Leu Asp Ala Lys Ile Ile Asp Ile Gln Glu Lys Val
1415            1420            1425

Lys Thr Ile Thr Gln Val Lys Lys Ile Gly Arg Arg Tyr Lys Thr
1430            1435            1440

Gln Tyr Glu Glu Leu Lys Ala Gln Gln Asp Lys Val Met Glu Thr
1445            1450            1455

Ser Ala Gln Ser Ser Gly Asp His Gln Glu Gln His Val Ser Val
1460            1465            1470

Gln Glu Met Gln Glu Leu Lys Glu Thr Leu Asn Gln Ala Glu Thr
1475            1480            1485
```

```
Lys Ser Lys Ser Leu Glu Ser Gln Val Glu Asn Leu Gln Lys Thr
    1490            1495                1500

Leu Ser Glu Lys Glu Thr Glu Ala Arg Asn Leu Gln Glu Gln Thr
    1505            1510                1515

Val Gln Leu Gln Ser Glu Leu Ser Arg Leu Arg Gln Asp Leu Gln
    1520            1525                1530

Asp Arg Thr Thr Gln Glu Glu Gln Leu Arg Gln Gln Ile Thr Glu
    1535            1540                1545

Lys Glu Glu Lys Thr Arg Lys Ala Ile Val Ala Ala Lys Ser Lys
    1550            1555                1560

Ile Ala His Leu Ala Gly Val Lys Asp Gln Leu Thr Lys Glu Asn
    1565            1570                1575

Glu Glu Leu Lys Gln Arg Asn Gly Ala Leu Asp Gln Gln Lys Asp
    1580            1585                1590

Glu Leu Asp Val Arg Ile Thr Ala Leu Lys Ser Gln Tyr Glu Gly
    1595            1600                1605

Arg Ile Ser Arg Leu Glu Arg Glu Leu Arg Glu His Gln Glu Arg
    1610            1615                1620

His Leu Glu Gln Arg Asp Glu Pro Gln Glu Pro Ser Asn Lys Val
    1625            1630                1635

Pro Glu Gln Gln Arg Gln Ile Thr Leu Lys Thr Thr Pro Ala Ser
    1640            1645                1650

Gly Glu Arg Gly Ile Ala Ser Thr Ser Asp Pro Pro Thr Ala Asn
    1655            1660                1665

Ile Lys Pro Thr Pro Val Val Ser Thr Pro Ser Lys Val Thr Ala
    1670            1675                1680

Ala Ala Met Ala Gly Asn Lys Ser Thr Pro Arg Ala Ser Ile Arg
    1685            1690                1695

Pro Met Val Thr Pro Ala Thr Val Thr Asn Pro Thr Thr Thr Pro
    1700            1705                1710

Thr Ala Thr Val Met Pro Thr Thr Gln Val Glu Ser Gln Glu Ala
    1715            1720                1725

Met Gln Ser Glu Gly Pro Val Glu His Val Pro Val Phe Gly Ser
    1730            1735                1740

Thr Ser Gly Ser Val Arg Ser Thr Ser Pro Asn Val Gln Pro Ser
    1745            1750                1755

Ile Ser Gln Pro Ile Leu Thr Val Gln Gln Thr Gln Ala Thr
    1760            1765                1770

Ala Phe Val Gln Pro Thr Gln Gln Ser His Pro Gln Ile Glu Pro
    1775            1780                1785

Ala Asn Gln Glu Leu Ser Ser Asn Ile Val Glu Val Val Gln Ser
    1790            1795                1800

Ser Pro Val Glu Arg Pro Ser Thr Ser Thr Ala Val Phe Gly Thr
    1805            1810                1815

Val Ser Ala Thr Pro Ser Ser Ser Leu Pro Lys Arg Thr Arg Glu
    1820            1825                1830

Glu Glu Glu Asp Ser Thr Ile Glu Ala Ser Asp Gln Val Ser Asp
    1835            1840                1845

Asp Thr Val Glu Met Pro Leu Pro Lys Lys Leu Lys Ser Val Thr
    1850            1855                1860

Pro Val Gly Thr Glu Glu Val Met Ala Glu Glu Ser Thr Asp
    1865            1870                1875

Gly Glu Val Glu Thr Gln Val Tyr Asn Gln Asp Ser Gln Asp Ser
```

```
                1880                1885                1890
Ile Gly Glu Gly Val Thr Gln Gly Asp Tyr Thr Pro Met Glu Asp
                1895                1900                1905

Ser Glu Glu Thr Ser Gln Ser Leu Gln Ile Asp Leu Gly Pro Leu
                1910                1915                1920

Gln Ser Asp Gln Gln Thr Thr Thr Ser Ser Gln Asp Gly Gln Gly
                1925                1930                1935

Lys Gly Asp Asp Val Ile Val Ile Asp Ser Asp Asp Glu Glu Glu
                1940                1945                1950

Asp Glu Glu Asp Asp Asp Asp Glu Asp Asp Thr Gly Met Gly
                1955                1960                1965

Asp Glu Gly Glu Asp Ser Asn Glu Gly Thr Gly Ser Ala Asp Gly
                1970                1975                1980

Asn Asp Gly Tyr Glu Ala Asp Asp Ala Glu Gly Asp Gly Thr
                1985                1990                1995

Asp Pro Gly Thr Glu Thr Glu Glu Ser Met Gly Gly Glu Gly
                2000                2005                2010

Asn His Arg Ala Ala Asp Ser Gln Asn Ser Gly Glu Gly Asn Thr
                2015                2020                2025

Gly Ala Ala Glu Ser Ser Phe Ser Gln Glu Val Ser Arg Glu Gln
                2030                2035                2040

Gln Pro Ser Ser Ala Ser Glu Arg Gln Ala Pro Arg Ala Pro Gln
                2045                2050                2055

Ser Pro Arg Arg Pro Pro His Pro Leu Pro Pro Arg Leu Thr Ile
                2060                2065                2070

His Ala Pro Pro Gln Glu Leu Gly Pro Pro Val Gln Arg Ile Gln
                2075                2080                2085

Met Thr Arg Arg Gln Ser Val Gly Arg Gly Leu Gln Leu Thr Pro
                2090                2095                2100

Gly Ile Gly Gly Met Gln Gln His Phe Phe Asp Asp Glu Asp Arg
                2105                2110                2115

Thr Val Pro Ser Thr Pro Thr Leu Val Val Pro His Arg Thr Asp
                2120                2125                2130

Gly Phe Ala Glu Ala Ile His Ser Pro Gln Val Ala Gly Val Pro
                2135                2140                2145

Arg Phe Arg Phe Gly Pro Pro Glu Asp Met Pro Gln Thr Ser Ser
                2150                2155                2160

Ser His Ser Asp Leu Gly Gln Leu Ala Ser Gln Gly Gly Leu Gly
                2165                2170                2175

Met Tyr Glu Thr Pro Leu Phe Leu Ala His Glu Glu Glu Ser Gly
                2180                2185                2190

Gly Arg Ser Val Pro Thr Thr Pro Leu Gln Val Ala Ala Pro Val
                2195                2200                2205

Thr Val Phe Thr Glu Ser Thr Thr Ser Asp Ala Ser Glu His Ala
                2210                2215                2220

Ser Gln Ser Val Pro Met Val Thr Thr Ser Thr Gly Thr Leu Ser
                2225                2230                2235

Thr Thr Asn Glu Thr Ala Thr Gly Asp Asp Gly Asp Glu Val Phe
                2240                2245                2250

Val Glu Ala Glu Ser Glu Gly Ile Ser Ser Glu Ala Gly Leu Glu
                2255                2260                2265

Ile Asp Ser Gln Gln Glu Glu Glu Pro Val Gln Ala Ser Asp Glu
                2270                2275                2280
```

```
Ser  Asp  Leu  Pro  Ser  Thr  Ser  Gln  Asp  Pro  Ser  Ser  Ser  Ser
         2285                2290               2295

Val  Asp  Thr  Ser  Ser  Ser  Gln  Pro  Lys  Pro  Phe  Arg  Arg  Val  Arg
         2300                2305               2310

Leu  Gln  Thr  Thr  Leu  Arg  Gln  Gly  Val  Arg  Gly  Arg  Gln  Phe  Asn
         2315                2320               2325

Arg  Gln  Arg  Gly  Val  Ser  His  Ala  Met  Gly  Gly  Arg  Gly  Gly  Ile
         2330                2335               2340

Asn  Arg  Gly  Asn  Ile  Asn
         2345

<210> SEQ ID NO 341
<211> LENGTH: 1090
<212> TYPE: PRT
<213> ORGANISM: Homo sapiens

<400> SEQUENCE: 341

Met  Ala  Thr  Leu  Leu  Ser  His  Pro  Gln  Gln  Arg  Pro  Pro  Phe  Leu  Arg
1               5                   10                  15

Gln  Ala  Ile  Lys  Ile  Arg  Arg  Arg  Val  Arg  Asp  Leu  Gln  Asp  Pro
         20                  25                  30

Pro  Pro  Gln  Met  Ala  Pro  Glu  Ile  Gln  Pro  Pro  Ser  His  His  Phe  Ser
         35                  40                  45

Pro  Glu  Gln  Arg  Ala  Leu  Leu  Tyr  Glu  Asp  Ala  Leu  Tyr  Thr  Val  Leu
         50                  55                  60

His  Arg  Leu  Gly  His  Pro  Glu  Pro  Asn  His  Val  Thr  Glu  Ala  Ser  Glu
65                  70                  75                  80

Leu  Leu  Arg  Tyr  Leu  Gln  Glu  Ala  Phe  His  Val  Glu  Pro  Glu  His
                    85                  90                  95

Gln  Gln  Thr  Leu  Gln  Arg  Val  Arg  Glu  Leu  Glu  Lys  Pro  Ile  Phe  Cys
         100                 105                 110

Leu  Lys  Ala  Thr  Val  Lys  Gln  Ala  Lys  Gly  Ile  Leu  Gly  Lys  Asp  Val
         115                 120                 125

Ser  Gly  Phe  Ser  Asp  Pro  Tyr  Cys  Leu  Leu  Gly  Ile  Glu  Gln  Gly  Val
         130                 135                 140

Gly  Val  Pro  Gly  Gly  Ser  Pro  Gly  Ser  Arg  His  Arg  Gln  Lys  Ala  Val
145                 150                 155                 160

Val  Arg  His  Thr  Ile  Pro  Glu  Glu  Glu  Thr  His  Arg  Thr  Gln  Val  Ile
                    165                 170                 175

Thr  Gln  Thr  Leu  Asn  Pro  Val  Trp  Asp  Glu  Thr  Phe  Ile  Leu  Glu  Phe
         180                 185                 190

Glu  Asp  Ile  Thr  Asn  Ala  Ser  Phe  His  Leu  Asp  Met  Trp  Asp  Leu  Asp
         195                 200                 205

Thr  Val  Glu  Ser  Val  Arg  Gln  Lys  Leu  Gly  Glu  Leu  Thr  Asp  Leu  His
         210                 215                 220

Gly  Leu  Arg  Arg  Ile  Phe  Lys  Glu  Ala  Arg  Lys  Asp  Lys  Gly  Gln  Asp
225                 230                 235                 240

Asp  Phe  Leu  Gly  Asn  Val  Val  Leu  Arg  Leu  Gln  Asp  Leu  Arg  Cys  Arg
                    245                 250                 255

Glu  Asp  Gln  Trp  Tyr  Pro  Leu  Glu  Pro  Arg  Thr  Glu  Thr  Tyr  Pro  Asp
         260                 265                 270

Arg  Gly  Gln  Cys  His  Leu  Gln  Phe  Gln  Leu  Ile  His  Lys  Arg  Arg  Ala
         275                 280                 285

Thr  Ser  Ala  Ser  Arg  Ser  Gln  Pro  Ser  Tyr  Thr  Val  His  Leu  His  Leu
```

```
              290                 295                 300
Leu Gln Gln Leu Val Ser His Glu Val Thr Gln His Glu Ala Gly Ser
305                 310                 315                 320

Thr Ser Trp Asp Gly Ser Leu Ser Pro Gln Ala Ala Thr Val Leu Phe
                325                 330                 335

Leu His Ala Thr Gln Lys Asp Leu Ser Asp Phe His Gln Ser Met Ala
                340                 345                 350

Gln Trp Leu Ala Tyr Ser Arg Leu Tyr Gln Ser Leu Glu Phe Pro Ser
                355                 360                 365

Ser Cys Leu Leu His Pro Ile Thr Ser Ile Glu Tyr Gln Trp Ile Gln
370                 375                 380

Gly Arg Leu Lys Ala Glu Gln Gln Glu Leu Ala Ala Ser Phe Ser
385                 390                 395                 400

Ser Leu Leu Thr Tyr Gly Leu Ser Leu Ile Arg Arg Phe Arg Ser Val
                405                 410                 415

Phe Pro Leu Ser Val Ser Asp Ser Pro Ala Arg Leu Gln Ser Leu Leu
                420                 425                 430

Arg Val Leu Val Gln Met Cys Lys Met Lys Ala Phe Gly Glu Leu Cys
                435                 440                 445

Pro Asn Thr Ala Pro Leu Pro Gln Leu Val Thr Glu Ala Leu Gln Thr
450                 455                 460

Gly Thr Thr Glu Trp Phe His Leu Lys Gln Gln His His Gln Pro Met
465                 470                 475                 480

Val Gln Gly Ile Pro Glu Ala Gly Lys Ala Leu Leu Gly Leu Val Gln
                485                 490                 495

Asp Val Ile Gly Asp Leu His Gln Cys Gln Arg Thr Trp Asp Lys Ile
                500                 505                 510

Phe His Asn Thr Leu Lys Ile His Leu Phe Ser Met Ala Phe Arg Glu
                515                 520                 525

Leu Gln Trp Leu Val Ala Lys Arg Val Gln Asp His Thr Thr Val Val
530                 535                 540

Gly Asp Val Val Ser Pro Glu Met Gly Glu Ser Leu Phe Gln Leu Tyr
545                 550                 555                 560

Ile Ser Leu Lys Glu Leu Cys Gln Leu Arg Met Ser Ser Glu Arg
                565                 570                 575

Asp Gly Val Leu Ala Leu Asp Asn Phe His Arg Trp Phe Gln Pro Ala
                580                 585                 590

Ile Pro Ser Trp Leu Gln Lys Thr Tyr Asn Glu Ala Leu Ala Arg Val
                595                 600                 605

Gln Arg Ala Val Gln Met Asp Glu Leu Val Pro Leu Gly Glu Leu Thr
610                 615                 620

Lys His Ser Thr Ser Ala Val Asp Leu Ser Thr Cys Phe Ala Gln Ile
625                 630                 635                 640

Ser His Thr Ala Arg Gln Leu Asp Trp Pro Asp Pro Glu Glu Ala Phe
                645                 650                 655

Met Ile Thr Val Lys Phe Val Glu Asp Thr Cys Arg Leu Ala Leu Val
                660                 665                 670

Tyr Cys Ser Leu Ile Lys Ala Arg Ala Arg Glu Leu Ser Ser Gly Gln
                675                 680                 685

Lys Asp Gln Gly Gln Ala Ala Asn Met Leu Cys Val Val Asn Asp
690                 695                 700

Met Glu Gln Leu Arg Leu Val Ile Gly Lys Leu Pro Ala Gln Leu Ala
705                 710                 715                 720
```

-continued

```
Trp Glu Ala Leu Glu Gln Arg Val Gly Ala Val Leu Glu Gln Gly Gln
            725                 730                 735

Leu Gln Asn Thr Leu His Ala Gln Leu Gln Ser Ala Leu Ala Gly Leu
        740                 745                 750

Gly His Glu Ile Arg Thr Gly Val Arg Thr Leu Ala Gly Gln Leu Glu
    755                 760                 765

Val Gly Ile Ala Lys His Ile Gln Lys Leu Val Gly Val Arg Glu Ser
770                 775                 780

Val Leu Pro Glu Asp Ala Ile Leu Pro Leu Met Lys Phe Leu Glu Val
785                 790                 795                 800

Glu Leu Cys Tyr Met Asn Thr Asn Leu Val Gln Glu Asn Phe Ser Ser
                805                 810                 815

Leu Leu Thr Leu Leu Trp Thr His Thr Leu Thr Val Leu Val Glu Ala
            820                 825                 830

Ala Ala Ser Gln Arg Ser Ser Leu Ala Ser Asn Arg Leu Lys Ile
        835                 840                 845

Ala Leu Gln Asn Leu Glu Ile Cys Phe His Ala Glu Gly Cys Gly Leu
    850                 855                 860

Pro Pro Lys Ala Leu His Thr Ala Thr Phe Gln Ala Leu Gln Arg Asp
865                 870                 875                 880

Leu Glu Leu Gln Ala Ala Ser Ser Arg Glu Leu Ile Arg Lys Tyr Phe
                885                 890                 895

Cys Ser Arg Ile Gln Gln Gln Ala Glu Thr Thr Ser Glu Glu Leu Gly
            900                 905                 910

Ala Val Thr Val Lys Ala Ser Tyr Arg Ala Ser Glu Gln Lys Leu Arg
        915                 920                 925

Val Glu Leu Leu Ser Ala Ser Ser Leu Pro Leu Asp Ser Asn Gly
    930                 935                 940

Ser Ser Asp Pro Phe Val Gln Leu Thr Leu Glu Pro Arg His Glu Phe
945                 950                 955                 960

Pro Glu Leu Ala Ala Arg Glu Thr Gln Lys His Lys Lys Asp Leu His
                965                 970                 975

Pro Leu Phe Asp Glu Thr Phe Glu Phe Leu Val Pro Ala Glu Pro Cys
            980                 985                 990

Arg Lys Ala Gly Ala Cys Leu Leu Leu Thr Val Leu Asp Tyr Asp Thr
        995                 1000                1005

Leu Gly Ala Asp Asp Leu Glu Gly Glu Ala Phe Leu Pro Leu Arg
    1010                1015                1020

Glu Val Pro Gly Leu Ser Gly Ser Glu Pro Gly Glu Val Pro
    1025                1030                1035

Gln Thr Arg Leu Pro Leu Thr Tyr Pro Ala Pro Asn Gly Asp Pro
    1040                1045                1050

Ile Leu Gln Leu Leu Glu Gly Arg Lys Gly Asp Arg Glu Ala Gln
    1055                1060                1065

Val Phe Val Arg Leu Arg Arg His Arg Ala Lys Gln Ala Ser Gln
    1070                1075                1080

His Ala Leu Arg Pro Ala Pro
    1085                1090
```

<210> SEQ ID NO 342
<211> LENGTH: 474
<212> TYPE: PRT
<213> ORGANISM: Homo sapiens

<400> SEQUENCE: 342

```
Met Lys Arg Val Leu Val Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Leu Val
    50                  55                  60

Lys Glu Val Val Ser Leu Thr Glu Ala Cys Cys Ala Glu Gly Ala Asp
65                  70                  75                  80

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
    130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Gly Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
    210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285

Leu Ser Thr Lys Asn Ser Lys Phe Glu Asp Cys Cys Gln Glu Lys Thr
    290                 295                 300

Ala Met Asp Val Phe Val Cys Thr Tyr Phe Met Pro Ala Ala Gln Leu
305                 310                 315                 320

Pro Glu Leu Pro Asp Val Glu Leu Pro Thr Asn Lys Asp Val Cys Asp
                325                 330                 335

Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
        355                 360                 365

Leu Lys Ser Leu Gly Glu Cys Cys Asp Val Glu Asp Ser Thr Thr Cys
    370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr
                405                 410                 415
```

```
Glu Tyr Lys Lys Lys Leu Ala Glu Arg Leu Lys Ala Lys Leu Pro Asp
            420                 425                 430

Ala Thr Pro Thr Glu Leu Ala Lys Leu Val Asn Lys His Ser Asp Phe
        435                 440                 445

Ala Ser Asn Cys Cys Ser Ile Asn Ser Pro Pro Leu Tyr Cys Asp Ser
    450                 455                 460

Glu Ile Asp Ala Glu Leu Lys Asn Ile Leu
465                 470

<210> SEQ ID NO 343
<211> LENGTH: 478
<212> TYPE: PRT
<213> ORGANISM: Homo sapiens

<400> SEQUENCE: 343

Met Ala Pro Leu Arg Pro Leu Leu Ile Leu Ala Leu Leu Ala Trp Val
1               5                   10                  15

Ala Leu Ala Asp Gln Glu Ser Cys Lys Gly Arg Cys Thr Glu Gly Phe
            20                  25                  30

Asn Val Asp Lys Lys Cys Gln Cys Asp Glu Leu Cys Ser Tyr Tyr Gln
        35                  40                  45

Ser Cys Cys Thr Asp Tyr Thr Ala Glu Cys Lys Pro Gln Val Thr Arg
    50                  55                  60

Gly Asp Val Phe Thr Met Pro Glu Asp Glu Tyr Thr Val Tyr Asp Asp
65                  70                  75                  80

Gly Glu Glu Lys Asn Asn Ala Thr Val His Glu Gln Val Gly Gly Pro
                85                  90                  95

Ser Leu Thr Ser Asp Leu Gln Ala Gln Ser Lys Gly Asn Pro Glu Gln
            100                 105                 110

Thr Pro Val Leu Lys Pro Glu Glu Ala Pro Ala Pro Glu Val Gly
        115                 120                 125

Ala Ser Lys Pro Glu Gly Ile Asp Ser Arg Pro Glu Thr Leu His Pro
    130                 135                 140

Gly Arg Pro Gln Pro Pro Ala Glu Glu Glu Leu Cys Ser Gly Lys Pro
145                 150                 155                 160

Phe Asp Ala Phe Thr Asp Leu Lys Asn Gly Ser Leu Phe Ala Phe Arg
                165                 170                 175

Gly Gln Tyr Cys Tyr Glu Leu Asp Glu Lys Ala Val Arg Pro Gly Tyr
            180                 185                 190

Pro Lys Leu Ile Arg Asp Val Trp Gly Ile Glu Gly Pro Ile Asp Ala
        195                 200                 205

Ala Phe Thr Arg Ile Asn Cys Gln Gly Lys Thr Tyr Leu Phe Lys Gly
    210                 215                 220

Ser Gln Tyr Trp Arg Phe Glu Asp Gly Val Leu Asp Pro Asp Tyr Pro
225                 230                 235                 240

Arg Asn Ile Ser Asp Gly Phe Asp Gly Ile Pro Asp Asn Val Asp Ala
                245                 250                 255

Ala Leu Ala Leu Pro Ala His Ser Tyr Ser Gly Arg Glu Arg Val Tyr
            260                 265                 270

Phe Phe Lys Gly Lys Gln Tyr Trp Glu Tyr Gln Phe Gln His Gln Pro
        275                 280                 285

Ser Gln Glu Glu Cys Glu Gly Ser Ser Leu Ser Ala Val Phe Glu His
    290                 295                 300

Phe Ala Met Met Gln Arg Asp Ser Trp Glu Asp Ile Phe Glu Leu Leu
305                 310                 315                 320
```

-continued

```
Phe Trp Gly Arg Thr Ser Ala Gly Thr Arg Gln Pro Gln Phe Ile Ser
                325                 330                 335

Arg Asp Trp His Gly Val Pro Gly Gln Val Asp Ala Ala Met Ala Gly
            340                 345                 350

Arg Ile Tyr Ile Ser Gly Met Ala Pro Arg Pro Ser Leu Ala Lys Lys
        355                 360                 365

Gln Arg Phe Arg His Arg Asn Arg Lys Gly Tyr Arg Ser Gln Arg Gly
    370                 375                 380

His Ser Arg Gly Arg Asn Gln Asn Ser Arg Arg Pro Ser Arg Ala Met
385                 390                 395                 400

Trp Leu Ser Leu Phe Ser Ser Glu Glu Ser Asn Leu Gly Ala Asn Asn
                405                 410                 415

Tyr Asp Asp Tyr Arg Met Asp Trp Leu Val Pro Ala Thr Cys Glu Pro
                420                 425                 430

Ile Gln Ser Val Phe Phe Phe Ser Gly Asp Lys Tyr Tyr Arg Val Asn
            435                 440                 445

Leu Arg Thr Arg Arg Val Asp Thr Val Asp Pro Pro Tyr Pro Arg Ser
    450                 455                 460

Ile Ala Gln Tyr Trp Leu Gly Cys Pro Ala Pro Gly His Leu
465                 470                 475
```

APPARATUS, COMPOSITIONS, AND METHODS FOR ASSESSMENT OF CHRONIC OBSTRUCTIVE PULMONARY DISEASE PROGRESSION AMONG RAPID AND SLOW DECLINE CONDITIONS

RELATED APPLICATIONS

This application claims the Paris Convention Priority and fully incorporates by reference U.S. Provisional Application No. 60/817,316 entitled "Apparatus, Compositions, and Methods for Assessment of Chronic Obstructive Pulmonary Disease Progression Among Rapid and Slow Decline Conditions" filed on 28 Jun. 2006, which is hereby incorporated by reference as if fully disclosed herein.

GOVERNMENTAL INSPECTION

The present disclosure is subject to a right of inspection by the Department of Energy.

BACKGROUND

The present disclosure relates to the study of respiratory functions and conditions, specifically chronic obstructive pulmonary disease, biomarkers related to respiratory functions and conditions, specifically biomarkers related to chronic obstructive pulmonary disease, and the creation of an informative content repository of biomarkers related to chronic obstructive pulmonary disease (COPD).

SUMMARY

Methods are disclosed for generating and isolating biomarkers related to pulmonary functions and conditions, specifically biomarkers related to chronic obstructive pulmonary disease, and an informative content repository of respiratory related biomarkers to accurately determine whether an individual has normal or abnormal pulmonary function. Specifically, methods are directed to determination of whether individuals have chronic obstructive pulmonary disease, and if so, whether the affected individuals experience rapid lung decline or slow lung decline as a result of COPD. Also disclosed is an informative content repository of chronic obstructive pulmonary disease biomarkers, which when linked with other informative content provides a powerful tool for diagnosis, study, therapeutic discovery and development, condition management, health maintenance, and linking chronic obstructive pulmonary disease through pattern of life style, environmental exposure, and genetic susceptibility and inheritance. Disclosed herein are at least one biomarker related to COPD and a chronic obstructive pulmonary disease biomarker informative content repository comprising at least one COPD biomarker, apparatus and methods to diagnose, assess, address, and ameliorate related conditions.

According to a feature of the present disclosure, a respiratory condition informative content repository is disclosed comprising at least one respiratory condition-related biomarker.

According to a feature of the present disclosure, a process is disclosed comprising identification of a respiratory related condition to study, use of an informative content repository containing at least one first set of data useful in the selection of at least one individual having or predisposed to a respiratory related condition, identification of at least one biomarker from samples taken from the at least one individual; and populating a biomarker informative content repository with the at least one biomarker.

According to a feature of the present disclosure, a process is disclosed comprising, obtaining a sample from a patient, using a chronic obstructive pulmonary disease (COPD) biomarker diagnostic tool in conjunction the sample to obtain data, and using the data to decide whether the patient is a rapid decliner or a slow decliner.

According to a feature of the present disclosure, an informative content repository is disclosed comprising at least the amino acid sequences of SEQ ID NO:1 to SEQ ID NO:266.

According to a feature of the present disclosure, an informative content repository of proteins is disclosed comprising at least a set of data comprising the proteins of Table 2.

DRAWINGS

The above-mentioned features and objects of the present disclosure will become more apparent with reference to the following description taken in conjunction with the accompanying drawings wherein like reference numerals denote like elements and in which:

FIG. 2B is a graph illustrating how rapid decliner and slow decliner subjects are selected from a group of known COPD patients;

DETAILED DESCRIPTION

Figure 1:
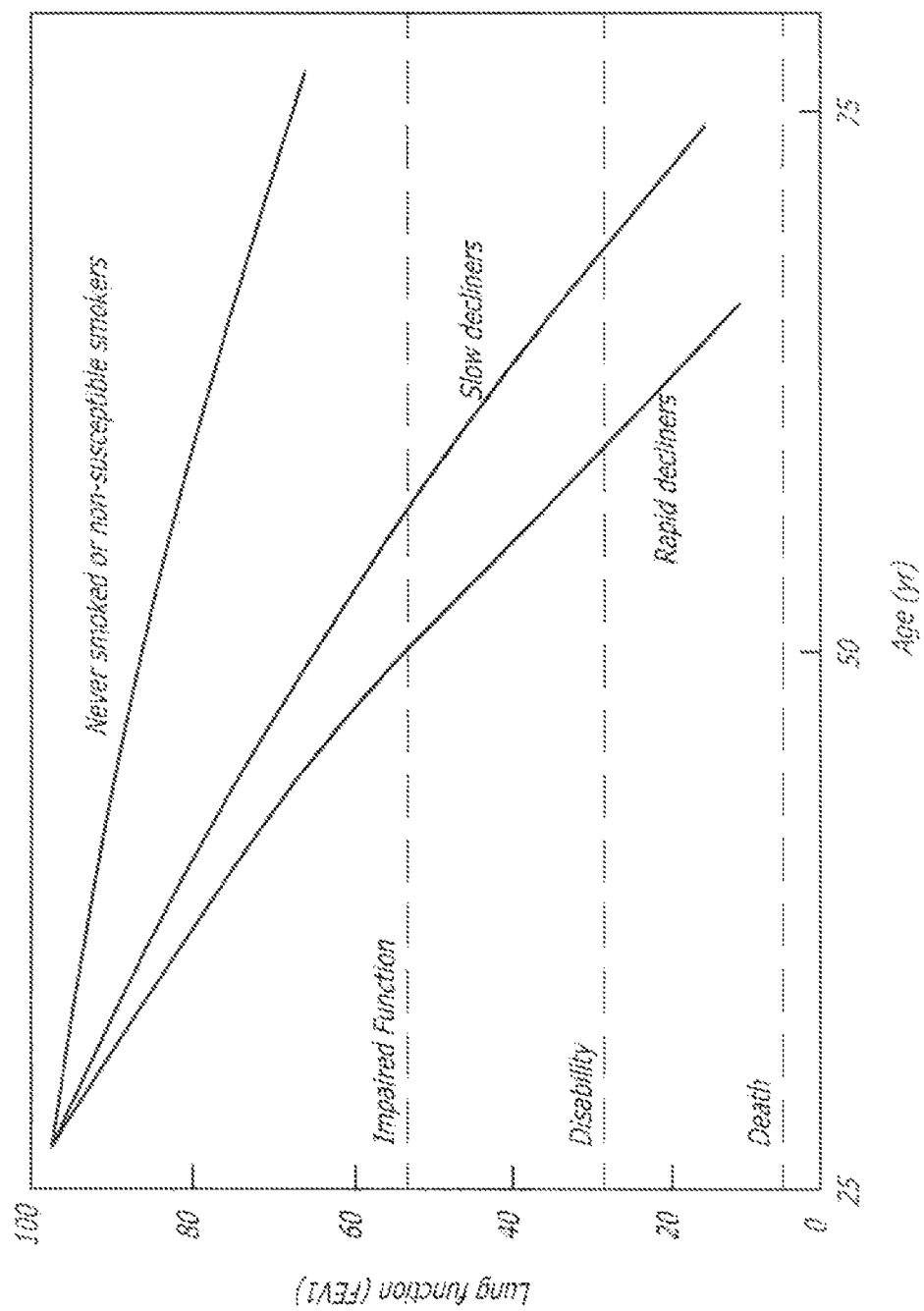
FIG. 1 is a graph illustrating the relative progression of the loss of pulmonary function between non-smokers, chronic pulmonary obstructive disorder (COPD) slow decliners, and COPD fast decliners.

In the following detailed description of embodiments of the invention, reference is made to the accompanying drawings in which like references indicate similar elements, and in which is shown by way of illustration specific embodiments in which the invention may be practiced. These embodiments are described in sufficient detail to enable those skilled in the art to practice the invention, and it is to be understood that other embodiments may be utilized and that logical, mechanical, biological, electrical, functional, and other changes may be made without departing from the scope of the present invention. The following detailed description is, therefore, not to be taken in a limiting sense, and the scope of the present invention is defined only by the appended claims. As used in the present disclosure, the term "or" shall be understood to be defined as a logical disjunction and shall not indicate an exclusive disjunction unless expressly indicated as such or notated as "xor."

As used in this application, the term "biomarker" means any characteristic that is objectively measured and evaluated as an indicator of normal biologic processes, pathogenic processes, or pharmacologic responses to a therapeutic intervention, including biological measurements that provide information regarding progression, pharmacology, or safety of conditions that can be used as a basis for decision-making in drug development and therapeutic administration decisions.

As used in this application, the term "function" and "condition" means normal physiological and pathophysiological states, including diseases and disorders. As used herein, the terms "function" and "condition" include normal physiological as well as acute and chronic pathophysiological states, such as diseases and disorders.

As used in this application, the term "disease" or "disorder" means any condition in humans or animals deemed to be abnormal as compared to the majority of humans and animals respectively.

As used in this application, the term "informative content repository" means a collection of at least one set of respiratory condition related biomarker data, optionally indexed together with other ancillary data, and stored in a suitable data structure. Examples of suitable data structures include databases, gene chips, protein chips, and filing cabinets.

As used in this application, the term "decline" refers to the rate in which a condition or conditions worsens over time, and the term "decliner" refers to an individual affected with a respiratory condition in whom the condition worsens over time.

As used in this application, the term "related" refers to causing or being associated with a function or condition.

As used in this application, the terms "COPD related biomarker(s)" or "COPD biomarker(s)" refer to one or more biomarkers that are associated with COPD.

Mapping condition indicators by use of integrated phenotypic and genotypic data from humans is a longstanding need, which only serves to underscore or highlight prior attempts to effectively do so with significant informative condition end-points.

Harnessing the power of the computer to manage large volumes of data in conjunction with the volume of information contained in the human genome, proteome, metabalome, regulome, functome, phenome, and textome proved critical for projects such as the human genome project to high-throughput devices such as DNA and protein microarrays. Naturally, the scientific community recognized the brute force power of computers for management of otherwise impossibly large volumes of information. Since then numerous bioinformatic and computational biology applications now exist. However, in most cases, the data sets are created as byproducts of experimental protocols. Other databases grew as researchers obtained experimental data and populated the databases with their findings for later reference.

Functions and conditions of the respiratory system, including lung conditions may be suitable targets for study using the instant techniques. Despite advances in practice, lung conditions continue to afflict millions of people worldwide. Many lung conditions such as emphysema, asthma, and COPD develop, at least in part, due to genetic predispositions or are directly linked with life-style choices and environmental exposure. Still others are caused by infections, such as tuberculosis.

Nonmalignant respiratory conditions are typically characterized as obstructive, restrictive, infectious, or vascular in nature. Obstructive respiratory conditions are those that impede the rate that air can flow into and out of the respiratory system, including the lungs. They include emphysema, bronchitis, asthma, and COPD. Similarly, restrictive lung conditions are characterized by a reduction of the functional volume of the lungs. Examples of restrictive lung conditions are sarcoidosis, pleural effusion, fibrosis, and alveolar effusion. Infectious lung conditions include tuberculosis, pneumonia, upper respiratory tract infections, and lower respiratory tract infections. Vascular lung conditions include pulmonary edema, pulmonary embolism, and pulmonary hypertension. Lung cancer alone causes of 3 million deaths each year.

Of the respiratory conditions, COPD is a condition especially suited to the instant techniques. COPD is a condition of the respiratory tract characterized by permanent airway obstruction. It constitutes an abnormal inflammatory response triggered by foreign particles and gasses. COPD victims experience a chronic inflammation of the bronchi, which leads to airway obstruction. Other causes of COPD may include cd-antitrypsin deficiency, byssinosis, genetic susceptibility, and idiopathic disease.

Researchers currently believe that smoking is that main risk factor associated with the development of COPD. Indeed, nearly one-fifth of all smokers will develop the condition. Nevertheless, other risk factors exist such as the prolonged breathing of dust, for example in coal-mines. Women comprise the majority of non-smoking victims. Greater susceptibility in women appears to be related to decreased estrogen levels. Additionally, it is estimated that up to 15% to 20% of all COPD cases are non-smoking related, thus highlighting the heterogeneous nature and genetic susceptibility of COPD.

COPD is a progressive condition that worsens over time and with prolonged contact to smoke or other irritants. Spirometry changes, as illustrated in FIG. 1, and decreased diffusion capacity are commonly seen prior to diagnosis of COPD. As COPD progresses, patients experience shortness of breath, coughs, and recurrent respiratory infections. Progression of COPD is marked by increased severity and duration of symptoms, until, during advanced stages, the patient experiences constant wheezing and shortness of breath, with a severe cough even while at rest. COPD advances either rapidly or slowly; rapid decliners, as shown in FIG. 1, experience a more pronounced deterioration in lung capacity compared to slow decliners.

Currently, doctors diagnose COPD by observing a patient's symptoms. Doctors evaluate life-style choices, such as smoking and occupation, perform physical examinations on patients, and conduct spirometry tests to measure patient's airflow. Generally and turning again to FIG. 1, $FEV_1$ to FVC ratio is decreased in a COPD patient. Often, the COPD patient cannot expire 80% of their vital capacity in one second, which is a measurement of normal airflow. Moreover, doctors may observe a residual volume or hyperinflation of lung capacity in COPD patients. Despite these indicia, no existing molecular factors or definitive tests currently exists to positively identify patients with COPD, nor are there existing molecular factors or definitive tests that can differentiate between affected patients that may experience rapid lung decline or slow lung decline as a result of COPD.

To that end, the present disclosure presents a novel way to discover or isolate respiratory system related biomarkers, specifically COPD related biomarkers. Once biomarkers are identified for a condition, diagnostic tools, for example genomic or protein chips, may be manufactured and used to positively determine whether a patient has developed the condition, and how a patient's condition may progress (i.e., rapid lung decline vs. slow lung decline). Moreover, isolating the biomarkers informs researchers as to the causative factors and pathways that eventually lead to COPD and how COPD progresses. Better understanding of the causes and pathways of COPD allow researchers to focus on discovering better treatments for COPD, including targeted therapeutics, combination of diagnostics and therapeutics, and holistic type treatments.

The present inventors have discovered embodiments of the present disclosure that contemplate COPD related biomarkers and repositories of biomarker content useful for diagnoses, treatment, research, and other uses suitable to such an informative content repository. Methods for the generation and use of informative content repositories are naturally contemplated as well. Specifically, the present disclosure relates to the development and use of COPD related biomarkers or an informative content repository of COPD biomarkers.

The COPD related biomarkers and the informative content repository disclosed in the present disclosure may be used for diagnosis or determination of predisposition of conditions in humans, plants, and animals or for the treatment of the condition. For example, the information contained in an informative content repository may be used to design personalized treatments. The informative content repository is also useful for basic research activities, health care decision-making, for forensic applications, or for genetic counseling.

The informative content repository contains at least one set of biomarkers. Biomarker informative content may include molecular factors comprising one or more sets of genes, proteins, or metabolites. In embodiments, the informative content is easily accessible, sortable, and indexed. Additionally, the informative content repository may be linked to other informative content repositories, which increases the correlative power of the informative content sets comprising the informative content repository.

In an embodiment, the data structure of the informative content repository is a computerized database, for example a MySQL or Oracle database. Informative content is easily accessible using MySQL or Oracle tables and may be manipulated in ways common to a person of ordinary skill in the art. Using computer databases as the data structure for the informative content repository is beneficial because it provides for easy searching, organization, and correlation to data in other informative content repositories.

Among the uses of COPD related biomarkers and the informative content repository are as diagnostic tools. An informative content repository with at least one respiratory related biomarker or at least one set of respiratory related biomarker informative content, for example, is useful in the diagnosis of respiratory related conditions. It is also useful for diagnosis of such conditions or predisposition to such conditions. As previously discussed, COPD diagnosis is accomplished by assessing symptoms because there does not exist definitive tests (blood-based or molecular-based) to diagnose COPD. Thus, COPD related biomarkers or an informative content repository of biomarkers that includes COPD biomarker informative content could be potentially used to positively diagnose whether an individual is affected with COPD and whether a COPD patient is a rapid decliner or a slow decliner. For example, for sets of protein biomarkers, protein chips may be used to screen a patient's blood (serum or plasma) for the presence of, or absence of, a pattern of proteins indicative of COPD or COPD progression.

Similarly, COPD related biomarkers or an informative content repository of respiratory related biomarkers are useful tools for prediction of predispositions to respiratory related conditions. Genes, proteins, metabolites, and other molecular or non-molecular indicia may give healthcare providers and researchers clues as to individuals or populations of individuals susceptible to specific respiratory related conditions. For example, in a subject with susceptibility to COPD, a healthcare provider (including pharmacists) could screen blood samples of each smoking subject using a diagnostic (i.e., genomic or proteomic) chip. Healthcare providers could then use the positive informative content as additional content in individualized healthcare regimens for their subjects.

COPD related biomarkers or an informative content repository of respiratory related biomarkers are also useful in the development of treatments for the conditions predicted by the biomarkers in the informative content repository. Using such an informative content repository, researchers can access sets of data useful in development of compounds for treatment of respiratory related conditions. For example, with COPD, COPD related biomarkers and informative content obtained from the informative content repository, such as proteins, genes, or metabolites can be used to target compounds against the specific proteins, genes, or metabolites. Compounds may also be used to induce or artificially introduce proteins, genes, or metabolites that characteristically are absent in rapid decline conditions. Consequently, the use of compound combinations based on clues provided by respiratory related biomarkers for a respiratory related condition gives researchers and healthcare providers the power to design optimized and personalized regimens of compounds targeted specifically towards maintaining or modulating the condition.

In addition to traditionally administered compounds, COPD related biomarkers or an informative content repository of related biomarkers are useful tools for creating or administering therapies. For example, contemplated in the present disclosure is use of an informative content repository of respiratory related biomarkers useful for the administration or development of inhaled substances including drug therapies.

An informative content repository of respiratory related biomarkers is also useful in developing more individualized or personalized drug treatments for patients. At doctor visits, patients may donate a sample to the doctor, which may then be analyzed and compared against informative content in the respiratory related informative content repository. Using the correlation between the informative content in the informative content repository and the patient's personal genetic, proteomic, and metabonomic make-up, the doctor can prescribe optimal drug regimens for each individual patient.

Naturally, the research applications of such COPD related biomarkers and informative content repositories are broader than simply for use in personalized medical applications. Researchers may also use the informative content repository of respiratory related biomarkers in the pursuit and development of compounds to treat respiratory related conditions in humans and animals. As previously discussed, COPD related biomarkers and biomarker informative content in informative content repositories gives researchers clues as to potential targets for newly developed compounds.

Moreover, the absence of healthy biomarkers in a condition may give healthcare providers clues about ways to induce resurgence of healthy proteins, genes, or metabolites that will restore normal function or eradicate a respiratory related condition. Similarly, information regarding healthy biomarkers gives healthcare providers health maintenance type tools. Healthcare providers may use these type of tools to help maintain and improve otherwise healthy states and lifestyles, in addition to helping patients prevent pathophysiological conditions. Indeed, the ability of healthcare providers to positively assert the presence of a healthy condition or an abnormal condition is a tool in the medical field that has utility in mapping lifestyles, habits, and genes that promote good health or healing.

Nevertheless, COPD related biomarkers or an informative content repository of respiratory related biomarkers are not only useful for research and development of new diagnostics, drugs, or medical devices. The COPD related biomarkers and informative content repository may also be used for more general research purposes. Using subject-specific informative content in an informative content repository, researchers can target individuals who may be susceptible to a particular condition for long-term studies before the condition develops to monitor physiological, phenotypic, and genetic changes in the subject. Similarly, COPD related biomarkers or an informative content repository gives researchers clues as to where they can find potential subjects for studies already expressing a respiratory related condition. Likewise, an informative content repository gives researchers another tool to study pathways, development, and expression of respiratory related conditions over time.

An informative content repository of respiratory related biomarkers may also be used in various decision-making processes. As previously alluded to, healthcare providers may use the correlation between informative content in the informative content repository and the biomarkers expressed in an individual to advise the patient regarding specific treatment decisions and lifestyle choices. Insurance companies, health maintenance organizations, pharmacies, pharmacy benefit managers, hospitals, and other healthcare related organizations may use such informative content to reduce costs by using information learned from correlation between patients and informative content repositories. For example, referencing a particular patient's informative content may reduce the need for expensive testing regimens by correlating with each patient profile with predispositions and other indicia useful in streamlining medical services. Moreover, informative content may be used to pre-approve patients for available treatments, visits to specialists with merely a phone call to a service center that correlates a set of symptoms, life-style choices, and predispositions with the informative content in an informative content repository.

Similarly, optimal prescriptions may be prescribed using COPD related biomarkers or an informative content repository of respiratory related biomarkers that will reduce costs for insurance companies, hospitals, pharmacy benefit managers, health management organizations, and other healthcare related organizations by accurate diagnoses, prescribing, dispensing, or administering optimal drugs for increased efficacy or for reducing the number of adverse reactions, for example. Finally, the correlation of patient information and information contained in an informative content repository of respiratory related biomarkers may be used for automated treatment decisions or insurance reimbursement decisions for both private insurance companies and for federal government insurance programs such as Medicare and Medicaid.

Furthermore, COPD related biomarkers or an informative content repository of respiratory related biomarkers may be used as a method of tracking family data over generations. In embodiments, conditions may be studied using genealogical correlations for each subject or tracked through generations to study condition evolution and inheritance in humans, plants, and animals. The informative content repository is also useful for tracking phenotypic data. Additionally, COPD related biomarkers or the informative content repository may be used for genetic analysis and counseling. The respiratory related data in an informative content repository is an invaluable tool for genetic counselors that allows them to streamline gathering, studying, and disseminating genetic information to clients. Clients could learn the consequences and risk factors for themselves and their children, now and in the foreseeable future.

According to an embodiment, an informative content repository contains data relevant to lung treatment and more broadly to the use of the respiratory system for treatment regimens, specifically inhalation-type conditions, and inhaled administration of therapeutic ingredients. The COPD related biomarkers and an informative content repository COPD related biomarkers and a set of biomarkers contained in the informative content repository would be specifically relevant to upper and lower respiratory system function and conditions. In an embodiment, the informative content repository contains biomarkers relevant to the progression of COPD. Specifically, the biomarkers would indicate differences between the progression of COPD rapid decline conditions and slow decline conditions. In another embodiment, the biomarker informative content would identify individuals with a greater or lesser degree of pulmonary function, thereby indicating or selecting individuals as candidates for inhaled drug therapy.

Example 1

Figure 2A:
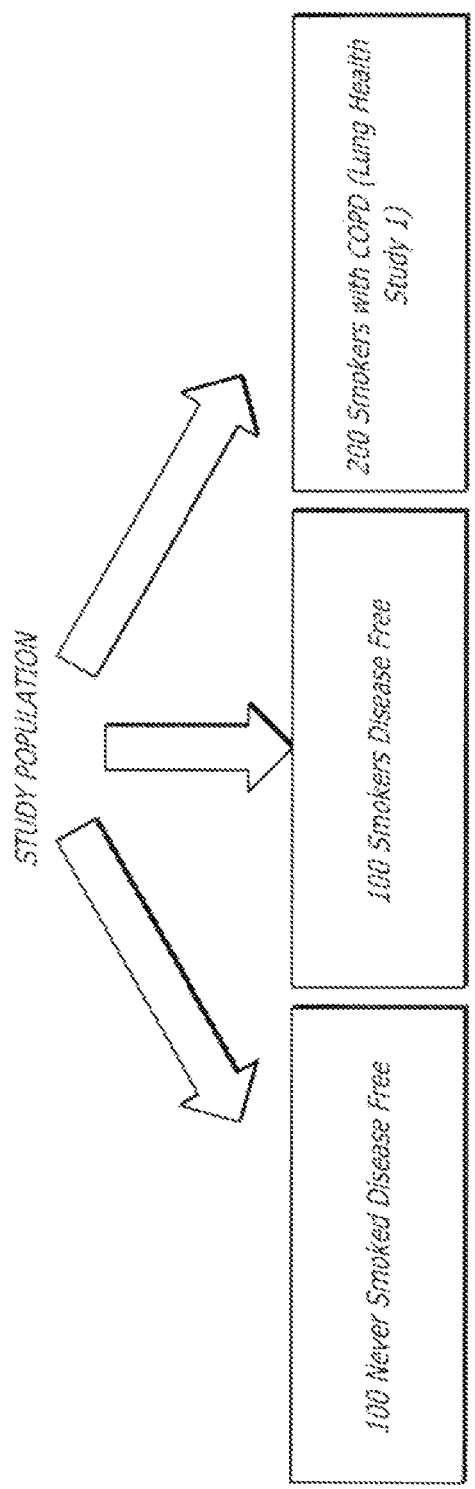
FIG. 2A is a block diagram of an embodiment of an experimental design for determination of biomarkers contributing to COPD and biomarkers distinguishing between COPD rapid and slow decliners.

An embodiment of the present disclosure describes the informative content repository of COPD markers. Clinical histories, pulmonary function tests, and related data were obtained from 100 subjects who had never smoked and unaffected with COPD, 100 smokers who were disease free, and 200 smokers with COPD, as illustrated in FIG. 2A. The COPD subjects were divided into quintiles depending on the decline rate, as shown in FIG. 2B. Subjects in the first quintile and fifth quintile representing the slowest decliners and the most rapid decliners were selected for the purposes of determining a set of biomarkers differentiating between slow and fast decliners. Plasma samples were taken from subjects and a subset of these samples were analyzed as a source of COPD biomarkers. The COPD informative content repository in an embodiment is designed to be a set of peptides or proteins. Approximately forty smokers with COPD were selected for the study herein disclosed.

The twelve top most abundant plasma proteins were depleted using GenWay Seppro 12 spin-columns (GenWay Biotech, Inc., San Diego, Calif., now ProteomeLab™ IgY-12, Beckman Coulter, Inc.). The removal of abundant proteins was monitored by SDS-PAGE.

Protein depletion has been used for some years to remove most of the albumin or IgG from biofluids such as plasma and serum prior to analysis, but it is clear that this alone is insufficient to enable progress to be made in biomarker discovery. The presence of highly abundant proteins significantly complicates the discovery process by masking the presence and limiting the detection of low abundance species. ProteomeLab IgY partitioning addresses this issue by reversibly capturing 12 of the more abundant proteins from human biofluids such as plasma and serum, yielding an enriched pool of low abundance proteins for further study. The captured proteins can also be easily recovered for investigation if required.

Figure 3:
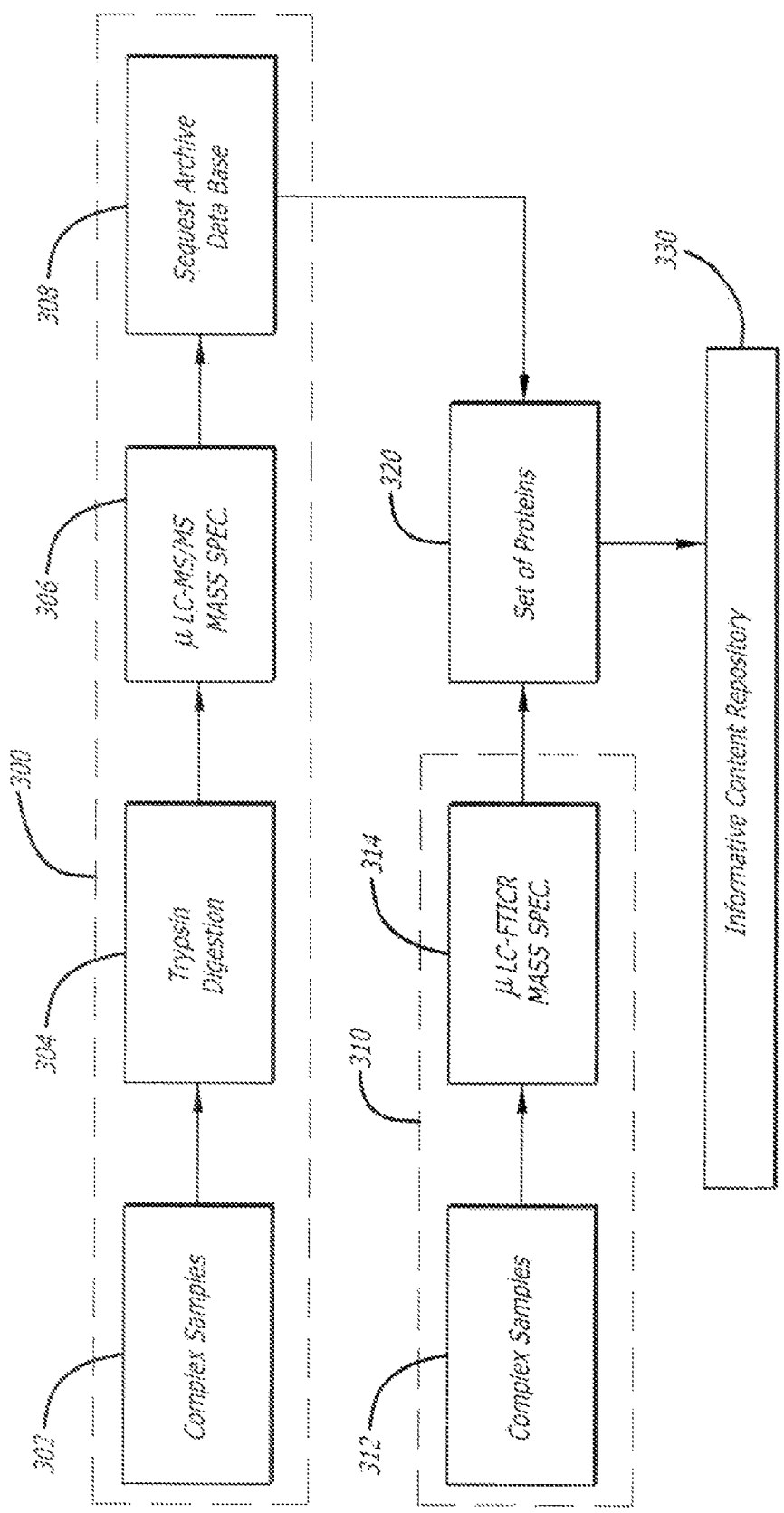
FIG. 3 is a block diagram of an embodiment of an experimental design for identification of the biomarkers of COPD using iLC-MS/MS analysis and µUL-FTICR-MS analysis to identify and correlate candidate proteins.

As shown in FIG. 3, after the abundant serum proteins were removed from the samples, the first series of mass spectrometry is μLC-MS/MS mass spectrometry in operation 300. μLC-MS-MS mass spectrometry was used to identify peptide fragments from trypsin-digested proteins. Proteins, after being run through the IgY-12 columns in operation 302 were trypsin digested in operation 304.

Trichloroacetic acid-precipitated protein from the depleted serum samples was denatured by addition of urea to 8 M, thiourea to 2 M, D11 to 5 mM, and heating to 60° C. for 30 minutes. The sample was then diluted 4-fold with 100 mM ammonium bicarbonate and $CaCl_2$ was added to a concentration 1 mM. Methylated, sequencing-grade trypsin (Promega, Madison, Wis.) was added at a substrate-to-enzyme ratio of 50:1 (mass:mass) and incubated at 37° C. for 15 hours. Sample cleanup was achieved using a 1-mL SPE C18 column (Supelco, Bellefonte, Pa.). The peptides were eluted from each column with 1 mL of methanol and concentrated via SpeedVac. The samples were reconstituted to 10 μg/μl, with 25 mM ammonium bicarbonate and frozen at −20° C. until analyzed.

Selected plasma samples (corresponding to experimental sample numbers: 54110, 54128, 54207, 54112, 54154, 54118) were depleted of abundant proteins, trypsin digested as detailed previously, and pooled. Strong cation exchange chromatography was performed on the pooled peptide sample utilizing a Synchropak S 300, 100×2 mm chromatographic column (Thermo Hypersil-Keystone, Bellefonte, Pa.). A 1 h gradient was utilized at a flow rate of 200 μl/min with fractions collected every 2 minutes. The beginning solvent system was 25% acetonitrile, 75% water containing 10 mM $HCOONH_4$, pH 3.0, adjusted with formic acid, and the ending solvent system was 25% acetonitrile, 75% water containing 200 mM $HCOONH_4$, pH 8.0. The peptide mixture was resuspended in 25% acetonitrile, 75% water containing 10 mM $HCOONH_4$, pH 3.0 with formic acid prior to injection. Fractions were lyophilized and stored at −20° C. until mass spectrometer analysis.

The fractionated peptide samples were analyzed by tandem mass spectrometry to identify the peptides for a mass and time tag database in operation 306. Peptide samples were analyzed by reversed phase microcapillary LC coupled directly with electrospray tandem mass spectrometers (Thermo Finnigan, models LCQ Duo and DecaXP). Chromatography was performed on a 60-cm, 150 μm i.d.×360 μm o.d capillary column (Polymicro Technologies, Phoenix, Ariz.) packed with Jupiter C18 5-μm-diameter particles (Phenomenex, Torrance, Calif.). A solvent gradient was used to elute the peptides using 0.1% formic acid in water (Solvent A) and 0.1% formic acid in acetonitrile (Solvent B). The gradient was linear from 0 to 5% solvent B in 20 minutes, followed by 5 to 70% solvent B in 80 minutes, and then 70-85% solvent B in 45 minutes. Solvent flow rate was 1.8 μl/min.

The capillary LC system was coupled to a LCQ ion trap mass spectrometer (Thermo Finnigan, San Jose, Calif.). The temperature of heated capillary and electrospray voltage was 200° C. and 3.0 kV, respectively. Samples were analyzed using the data-dependent MS/MS mode over the m/z range of 300-2000. The three most abundant ions detected in each MS scan were selected for collision-induced dissociation.

Figure 4:
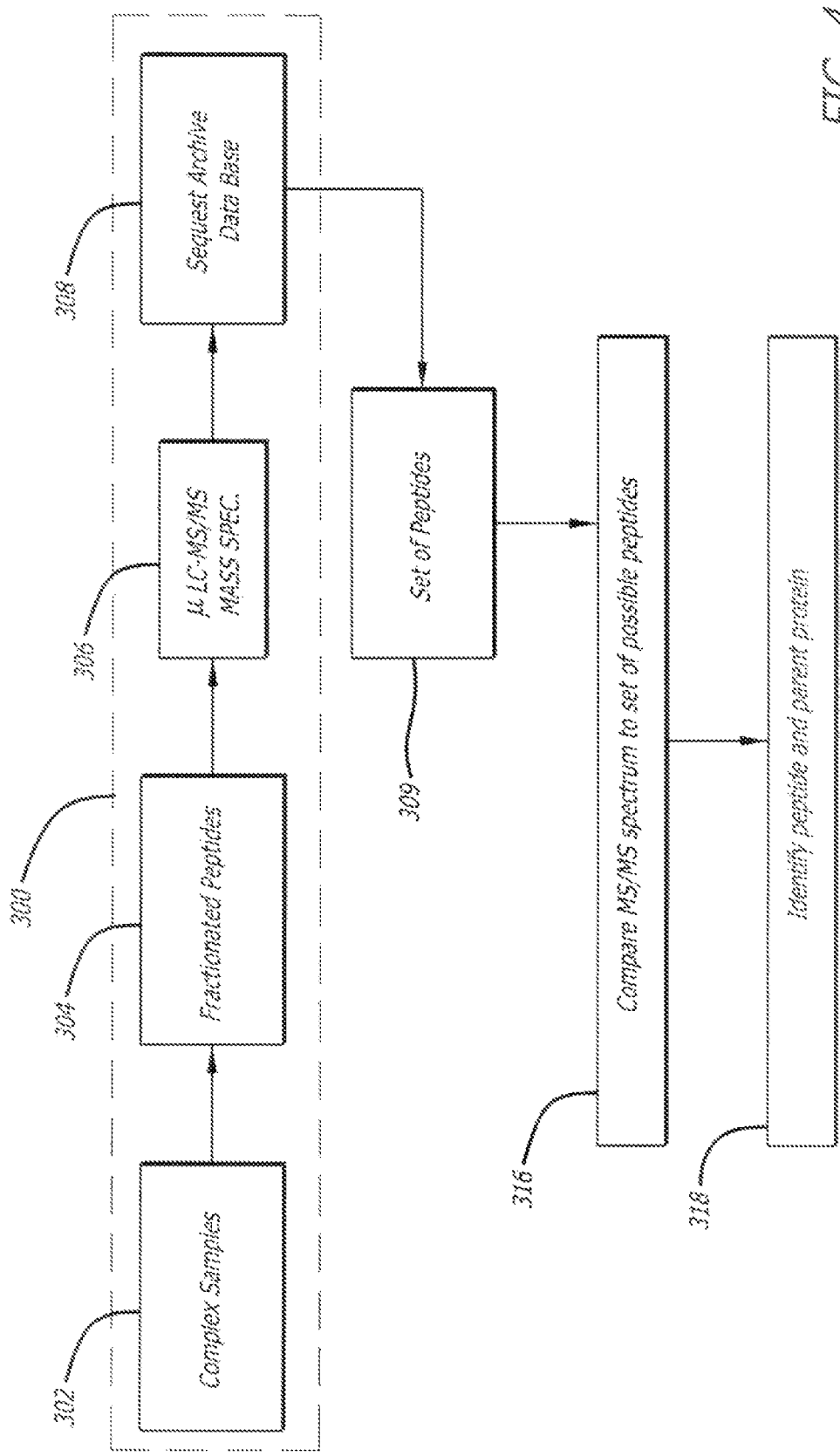
FIG. 4 is a block diagram of an embodiment of an experimental design illustrating a method for determining biomarkers from µLC-MS/MS analysis.

Peptide sequences (see operation 309 in FIG. 4) were obtained by analysis of MS/MS spectra using the SEQUEST algorithm against the human.fasta from the National Center for Biotechnology Information (RefSeq release 10, March, 2005) in operation 308 of FIG. 3. Peptide identifications were accepted using a conservative criteria set developed by Yates and coworkers (Link et al, 1999; Washburn et al, 2001) in operation 316. Briefly, all accepted SEQUEST results had a delta Cn of 0.1 or greater. Peptides with a +1 charge state were accepted if they were fully tryptic and had a cross correlation (Xcorr) of at least 1.9. Peptides with a +2 charge state were accepted if they were fully tryptic or partially tryptic and had an Xcorr of at least 2.2. Peptides with +2 or +3 charge states with an Xcorr of at least 3.0 or 3.75, respectively, were accepted regardless of their tryptic state.

The peptide identifications and elution times from analysis of the pooled samples were used to establish the mass and time tag database and combined with identifications of plasma protein peptides from previous multidimensional analyses done previously (Qian et al, 2005) in operation 318. The raw LC-MS/MS data from the pooled sample described above and from the previous multidimensional analysis were reanalyzed to populate the PMT database that was subsequently used for generating the AMT tag results. The PMT database was derived using a PMT quality score of 1.0 (requires a minimum cross correlation score of 2) and a discriminant score of 0.5 (Stritmatter et al, 2005).

Turning still to FIG. 3 and according to embodiments, the second round of mass spectrometry was done using microcapillary liquid chromatography Fourier transform ion cyclotron resonance mass spectrometry (LC-FTICR-MS) in operation 310 after sample preparation in operation 312. A modified and enhanced Bruker Daltonics 9.4 tesla FTICR mass spectrometer was employed for the high-throughput proteomics as described by Belov et al (2004). Briefly, the FTICR mass spectrometer was combined with the capillary liquid chromatography system and modified for concurrent internal mass calibration and auto-sampling in operation 314. Tryptic peptides were resuspended in mobile phase A (0.1% TFA) and analyzed using reversed phase capillary LC coupled to an electrospray ionization interface with a FTICR mass spectrometer as described by Smith et al.

Analysis of the LC-FTICR experiments was performed using in-house software tools (Kiebel et al. 2006) to identify MS features, deisotope, normalize elution times, and match features to peptides. These tools are incorporated into the Proteomics Research Information Storage and Management system (PRISM). The result yielded a set of peptides.

Figure 5A:
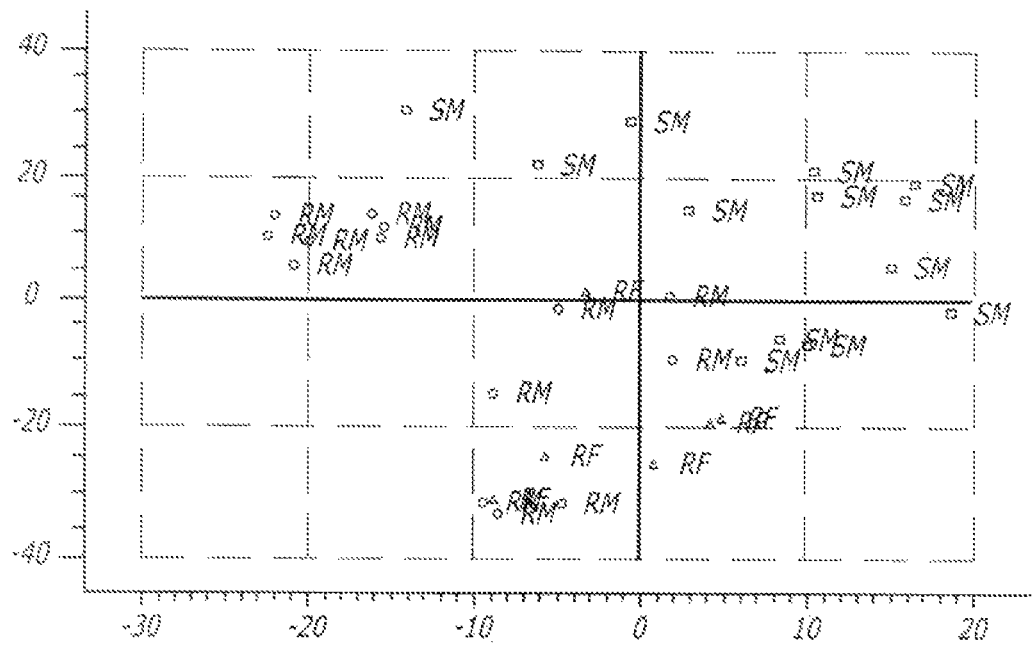
FIG. 5A and FIG. 5B are diagrams of an embodiment of an experimental design illustrating statistical analysis of identified proteins.
Figure 5B:
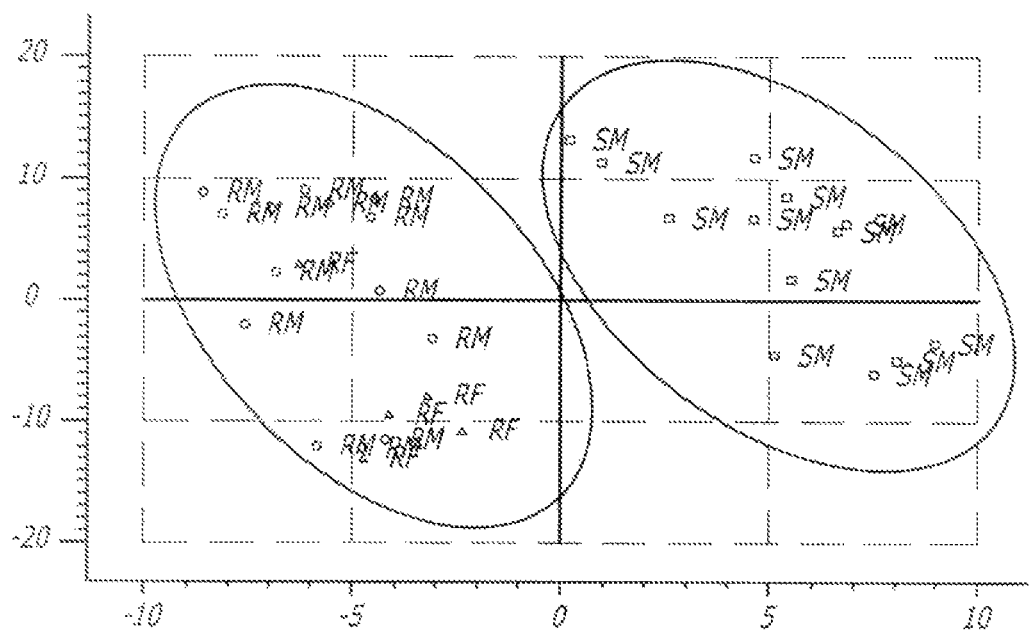

A discriminant program was used to determine peptide confidence probabilities. The results of an exemplary embodiment are shown in FIGS. 5A and 5B. The discriminant score takes advantage of elution time information and tryptic cleavage information, which enhances peptide confidence. Protein identifications from the list of peptides (see operation 318 in FIG. 4) were accomplished by using the ProteinProphet program and only peptides having a discriminant score greater than 0.5 were considered. The result was a set of proteins in operation 320.

Abundances of the individual peptides were computed by summing the intensity of the ions from a single scan or multiple scans that matched each peptide. Peptides from each protein that were in the top 66% in peak abundance for that protein were averaged to compute protein abundance. In general the integrated, averaged peptide intensities correlate with the relative protein mass.

Missing values were replaced using approximately one-half the minimum detectable peak (0.004). Data was preprocessed using a $log_{10}$ transformation and quantile normalization to make the distribution of ion currents for each mass spectrometry run in the experiment the same. Normalized technical replicates were averaged for each subject. For each of the over 525 proteins identified, a separate linear model accounting for phenotype and gender were used to assess the ion current values. A large-scale simultaneous testing approach was then used for the statistical analysis of the normalized data.

Once the proteins were identified between the sets of subjects with rapid declining pulmonary function versus slow declining pulmonary function, a statistical analysis was used to determine the relevant biomarkers. The statistical analysis compared the biomarkers of rapid decline condition subjects against the biomarkers of slow decline condition subjects to determine proteins either present or absent in rapid decline conditions versus slow decline conditions. Several statistical methods were used to determine the absence or presence of proteins in the rapid decline condition, including QC, filtering the data, transformation of the data, and normalization of the data, as would be common to a person of ordinary skill in the art.

As demonstrated in the current study of COPD biomarkers, 267 peptides leading to 78 proteins distinguished slow decline conditions from rapid decline conditions. Table 1 lists the proteins determined to distinguish slow decline conditions from rapid decline conditions:

TABLE 1

| Reference | SEQ. ID. NO. | Protein Description | Number of Unique Peptides/ Protein | Present in PLS analysis of Proteins |
|---|---|---|---|---|
| gi\|4501987\|ref\|NP_001124.1\| | 267 | afamin precursor; alpha-albumin [Homo sapeins] | 1 | |
| gi\|4502027\|ref\|NP_000468.1\| | 268 | albumin precursor; PRO0883 protein [Homo sapeins] | 8 | |
| gi\|21071030\|ref\|NP_570602.2\| | 269 | alpha 1B-glycoprotein [Homo sapiens] | 6 | |
| gi\|4501843\|ref\|NP_001076.1\| | 270 | alpha-1-antichymotrypsin, precursor; alpha-1-antichymotrypsin; antichymotrypsin [Homo sapiens] | 2 | |
| gi\|4557225\|ref\|NP_000005.1\| | 271 | alpha-2-macroglobulin precursor [Homo sapiens] | 6 | |
| gi\|11386143\|ref\|NP_000925.1\| | 272 | alpha-2-plasmin inhibitor; alpha-2-antiplasmin [Homo sapiens] | 7 | |
| gi\|4557287\|ref\|NP_000020.1\| | 273 | angiotensinogen precursor; angiotensin II precursor; pre-angiotensinogen; angiotensin I [Homo sapiens] | 1 | |
| gi\|4557321\|ref\|NP_000030.1\| | 274 | apolipoprotein A-I precursor [Homo sapiens] | 2 | |
| gi\|4502149\|ref\|NP_001634.1\| | 275 | apolipoprotein A-II precursor [Homo sapeins] | 2 | |
| gi\|4502151\|ref\|NP_000473.1\| | 276 | apolipoprotein A-IV precursor [Homo sapeins] | 7 | |
| gi\|4502153\|ref\|NP_000375.1\| | 277 | apolipoprotein B precursor; apoB-100; apoB-48 [Homo sapiens] | 25 | |
| gi\|4502157\|ref\|NP_001636.1\| | 278 | apolipoprotein C-I precursor [Homo sapiens] | 1 | |
| gi\|4557325\|ref\|NP_000032.1\| | 279 | apolipoprotein E precursor; apolipoprotein E3 [Homo sapiens] | 1 | |
| gi\|4557327\|ref\|NP_000033.1\| | 280 | beta-2-glycoprotein I precursor [Homo sapiens] | 1 | |
| gi\|4557373\|ref\|NP_000051.1\| | 281 | biotindase precursor [Homo sapiens] | 1 | |
| gi\|4502517\|ref\|NP_001729.1\| | 282 | carbonic anhydrase I; carbonic dehydrase [Homo sapiens] | 1 | |
| gi\|4503011\|ref\|NP_001299.1\| | 283 | carboxypeptidase N, polypeptide 1, 50kD precursor [Homo sapiens] | 2 | |
| gi\|4557485\|ref\|NP_000087.1\| | 284 | ceruloplasmin (ferroxidase); Ceruloplasmin [Homo sapiens] | 6 | |
| gi\|42716297\|ref\|NP_001822.2\| | 285 | clusterin isoform 1; complement-associated protein SP-40 [Homo sapiens] | 1 | |
| gi\|4503635\|ref\|NP_000497.1\| | 286 | coagulation factor II precursor; prothrombin [Homo sapiens] | 4 | |
| gi\|4503625\|ref\|NP_000495.1\| | 287 | coagulation factor X precursor; prothrombinase; factor Xa [Homo sapiens] | 1 | |
| gi\|4557379\|ref\|NP_000053.1\| | 288 | complement component 1 inhibitor precursor [Homo sapiens] | 2 | |
| gi\|4502493\|ref\|NP_001724.1\| | 289 | complement component 1, r subcomponent [Homo sapiens] | 1 | |
| gi\|7706083\|ref\|NP_057630.1\| | 290 | complement component 1, r subcomponent-like precursor; complement C1r-like proteinase; C1r-like serine protease analog [Homo sapiens] | 1 | |
| gi\|4502495\|ref\|NP_001725.1\| | 291 | complement component 1, s subcomponent [Homo sapiens] | 1 | |
| gi\|14550407\|ref\|NP_000054.2\| | 292 | complement component 2 precursor; C3/C5 convertase [Homo sapiens] | 2 | |
| gi\|4557385\|ref\|NP_000055.1\| | 293 | complement component 3 precursor; acylation-stimulating protein cleavage product [Homo sapiens] | 21 | |
| gi\|4502503\|ref\|NP_000706.1\| | 294 | complement component 4 binding protein, alpha; Complement component 4-binding protein, alpha polypeptide; complement component 4-binding, alpha [Homo sapiens] | 1 | yes |
| gi\|50345296\|ref\|NP_001002029.1\| | 295 | complement component 4B preproprotein; Chido form of C4; basic C4; C4A anaphylatoxin [Homo sapiens] | 12 | |
| gi\|38016947\|ref\|NP_001726.2\| | 296 | complement component 5 [Homo sapiens] | 4 | |
| gi\|4559406\|ref\|NP_000056.1\| | 297 | Complement component 6 precursor [Homo sapiens] | 3 | |
| gi\|45580688\|ref\|NP_000578.2\| | 298 | complement component 7 precursor [Homo sapiens] | 2 | |
| gi\|4557389\|ref\|NP_000553.1\| | 299 | complement component 8, alpha polypeptide precursor [Homo sapiens] | 1 | |
| gi\|4502511\|ref\|NP_001728.1\| | 300 | complement component 9 [Homo sapiens] | 2 | |
| gi\|4502397\|ref\|NP_001701.1\| | 301 | complement factor B preproprotein; C3 proactivator; C3 proaccelerator; glycine-rich beta-glycoprotein; C3/C5 convertase [Homo sapiens] | 7 | |
| gi\|4504375\|ref\|NP_000177.1\| | 302 | complement factor H; H factor-1 (complement); factor H-like 1; H factor 2 (complement); H factor 1 (complement) [Homo sapiens] | 3 | |
| gi\|11761629\|ref\|NP_068657.1\| | 303 | fibrinogen, alpha chain isoform alpha preproprotein [Homo sapiens] | 7 | |
| gi\|11761631\|ref\|NP_005132.1\| | 304 | fibrinogen, beta chain preproprotein [Homo sapiens] | 9 | |
| gi\|4503715\|ref\|NP_000500.1\| | 305 | fibrinogen, gamma chain isoform gamma-A precursor [Homo sapiens] | 5 | |
| gi\|47132557\|ref\|NP_997647.1\| | 306 | fibronectin 1 isoform 1 preproprotein; cold-insoluble globulin; migration-stimulating factor [Homo sapiens] | 3 | |
| gi\|4504165\|ref\|NP_000168.1 | 307 | gelsolin isoform a [Homo sapiens] | 7 | |
| gi\|11321561\|ref\|NP_000604.1\| | 308 | hemopexin [Homo sapiens] | 4 | |
| gi\|4504355\|ref\|NP_000176.1\| | 309 | heparin cofactor II [Homo sapiens] | 3 | |
| gi\|4504579\|ref\|NP_000195.1\| | 310 | I factor (complement) [Homo sapiens] | 1 | |
| gi\|21489959\|ref\|NP_653247.1\| | 311 | immunoglobulin J chain [Homo sapiens] | 1 | |
| gi\|4504781\|ref\|NP_002206.1\| | 312 | inter-alpha (globulin) inhibitor H1; inter-alpha (globulin) inhibitor, H1 polypeptide [Homo sapiens] | 6 | |
| gi\|4504783\|ref\|NP_002207.1\| | 313 | inter-alpha (globulin) inhibitor H2; inter-alpha (globulin) inhibitor, H2 polypeptide [Homo sapiens] | 10 | |

TABLE 1-continued

| Reference | SEQ. ID. NO. | Protein Description | Number of Unique Peptides/ Protein | Present in PLS analysis of Proteins |
|---|---|---|---|---|
| gi\|10092579\|ref\|NP_002208.1\| | 314 | inter-alpha (globulin) inhibitor H3; Inter-alpha (globulin) inhibitor, H3 polypeptide; pre-alpha (globulin) inhibitor, H3 polypeptide [Homo sapiens] | 2 | |
| gi\|31542984\|ref\|NP_002209.2\| | 315 | inter-alpha (globulin) inhibitor H4 (plasma Kallikrein-sensitive glycoprotein); Inter-alpha (globulin) inhibitor, H4 polypeptide; inter-alpha (globulin) inhibitor, H polypeptide-like 1 [Homo sapiens] | 11 | |
| gi\|10835141\|ref\|NP_000563.1\| | 316 | interleukin 10 precursor; cytokine synthesis inhibitory factor [Homo sapiens] | 2 | |
| gi\|4504893\|ref\|NP_000884.1\| | 317 | kininogen 1; alpha-2-thiol proteinase inhibitor; bradykinin [Homo sapiens] | 2 | |
| gi\|4505047\|ref\|NP_002336.1\| | 318 | lumican [Homo sapiens] | 2 | |
| gi\|33188445\|ref\|NP_036222.3\| | 319 | microfilament and actin filament cross-linker protein isoform a; actin cross-linking factor; 620 kDa actin binding protein; macrophin 1; trabeculin-alpha; actin cross-linking family protein 7 [Homo sapiens] | 1 | |
| gi\|19923106\|ref\|NP_000437.3\| | 320 | paraoxonase 1; Paraoxonase [Homo sapiens] | 1 | |
| gi\|21361845\|ref\|NP_443122.2\| | 321 | peptidoglycan recognition protein L precursor [Homo sapiens] | 2 | |
| gi\|4504877\|ref\|NP_000883.1\| | 322 | plasma kallikrein B1 precursor; kallikrein 3, plasma; Kallikrein, plasma; kallikrein B plasma; Fletcher factor [Homo sapiens] | 1 | |
| gi\|4505881\|ref\|NP_000292.1\| | 323 | plasminogen [Homo sapiens] | 2 | |
| gi\|51465432\|ref\|XP_376519.2\| | 324 | PREDICTED: ankyrin repeat domain 6 [Homo sapiens] | 1 | yes |
| gi\|42662334\|ref\|XP_375941.1\| | 325 | PREDICTED: FLJ45139 protein [Homo sapiens] | 1 | |
| gi\|42656986\|ref\|XP_098238.8\| | 326 | PREDICTED: SH3 domain protein D19 [Homo sapiens] | 1 | |
| gi\|51464068\|ref\|XP_209550.4\| | 327 | PREDICTED: similar to Carboxypeptidase N 83 kDa chain (Carboxypeptidase N regulatory subunit) [Homo sapiens] | 1 | |
| gi\|51458647\|ref\|XP_497680.1\| | 328 | PREDICTED: similar to prohibitin [Homo sapiens] | 1 | |
| gi\|51460685\|ref\|XP_497833.1\| | 329 | PREDICTED: similar to SULT6B1 [Homo sapiens] | 1 | |
| gi\|4506117\|ref\|NP_000304.1\| | 330 | protein S (alpha); Protein S, alpha [Homo sapiens] | 2 | |
| gi\|13325075\|ref\|NP_002817.2\| | 331 | quiescin Q6 [Homo sapiens] | 1 | |
| gi\|5803139\|ref\|NP_006735.1\| | 332 | RBP4 gene product [Homo sapiens] | 1 | |
| gi\|21361198\|ref\|NP_000286.2\| | 333 | serine (or cysteine) proteinase inhibitor, clade A (alpha-1 antiproteinase, antitrypsin), member 1; protease inhibitor 1 (anti-elastase), alpha-1-antitrypsin [Homo sapiens] | 4 | |
| gi\|4507377\|ref\|NP_000345.1\| | 334 | serine (or cysteine) proteinase inhibitor, clade A (alpha-1 antiproteinase, antitrypsin), member 7; thyroxine-binding globulin; thyroxin-binding globulin [Homo sapiens] | 1 | |
| gi\|4502261\|ref\|NP_000479.1\| | 335 | serine (or cysteine) proteinase inhibitor, clade C (antithrombin), member 1; antithrombin III [Homo sapiens] | 7 | |
| gi\|39725934\|ref\|NP_002606.3\| | 336 | serine (or cysteine) proteinase inhibitor, clade F (alpha-2 antiplasmin, pigment epithelium derived factor), member 1; pigment epithelium-derived factor [Homo sapiens] | 2 | |
| gi\|4502133\|ref\|NP_001630.1\| | 337 | serum amyloid P component precursor; pentaxin-related; 9.5S alpha-1-glycoprotein [Homo sapiens] | 2 | |
| gi\|7382460\|ref\|NP_001031.2\| | 338 | sex hormone-binding globulin; Sex hormone-binding globulin (androgen binding protein) [Homo sapiens] | 1 | yes |
| gi\|4557739\|ref\|NP_000233.1\| | 339 | soluble mannose-binding lectin precursor; Mannose-binding lectin 2, soluble (opsonic defect); mannose binding protein [Homo sapiens] | 1 | |
| gi\|4507659\|ref\|NP_003283.1\| | 340 | translocated promoter region (to activated MET oncogene); Tumor potentiating region (translocated promoter region) [Homo sapiens] | 1 | |
| gi\|46195765\|ref\|NP_954712.1\| | 341 | unc-13 homolog D [Homo sapiens] | 1 | yes |
| gi\|32483410\|ref\|NP_000574.2\| | 342 | vitamin D-binding protein precursor; vitamin D-binding alpha-globulin [Homo sapiens] | 2 | |
| gi\|18201911\|ref\|NP_000629.2\| | 343 | vitronectin precursor; serum spreading factor; somatomedin B; complement S-protein; epibolin [Homo sapiens] | 4 | |

TABLE 2

| NCB1 Reference | SEQ. ID. | Protein Description | Anti-Log (Rapid decline conditions vs. Slow decline conditions | Average Rapid decline conditions to Slow decline conditions Ratio | Standard Deviation | Number of Significant Peptides |
|---|---|---|---|---|---|---|
| 4501843 | 270 | Antichymotrypsin | 0.87 | 0.83 | 0.05 | 2 |
| 4557225 | 271 | Alpha-2-macroglobulin | 0.88 | 1.05 | 0.48 | 4 |
| 4502153 | 277 | Apolipoprotein B | 1.48 | 1.22 | 0.21 | 17 |
| 4557485 | 284 | Ceruloplasmin | 0.97 | 0.82 | 0.34 | 5 |
| 4557385 | 293 | Complement component 3 | 0.64 | 0.71 | 0.22 | 15 |

TABLE 2-continued

| NCB1 Reference | SEQ. ID. | Protein Description | Anti-Log (Rapid decline conditions vs. Slow decline conditions | Average Rapid decline conditions to Slow decline conditions Ratio | Standard Deviation | Number of Significant Peptides |
|---|---|---|---|---|---|---|
| 11761629 | 303 | Fibrogen, alpha chain isoform | 1.24 | 1.29 | 0.37 | 6 |
| 11761631 | 304 | Fibrogen, beta chain | 1.41 | 1.23 | 0.30 | 5 |
| 4503715 | 305 | Fibrogen, gamma chain isoform | 1.21 | 1.24 | 0.50 | 5 |
| 47132557 | 306 | Fibronectin I isoform 1 | 0.75 | 0.63 | 0.17 | 2 |
| 4504165 | 307 | Gelsolin isoform a | 0.76 | 0.85 | 0.30 | 4 |
| 4504893 | 317 | Kininogen 1, bradykinin | 1.20 | 1.27 | 0.10 | 2 |
| 4504877 | 322 | Plasma kallikresin B1; kallikresin 3, plasma | 0.46 | | | 1 |
| 21361108 | 333 | Serine (or cysteine) proteinase inhibitor; alpha-1-antitrypsin | 1.60 | 1.37 | 0.15 | 4 |
| 4502133 | 337 | Serum amyloid P component | 1.26 | 1.23 | 0.04 | 2 |
| 32483410 | 342 | Vitamin D-binding protein | 0.86 | | | 1 |

The results of the mass spectrometry experiments yielded an average of 1,407 peptide fragments per subject, leading to 207 identified proteins per subject. Of the proteins identified in aggregate, 532 proteins occurred in more than 10 subjects. Of those 532 proteins, 21 were proteases, 16 were cytokines and chemokines, 26 were hypothetical proteins, and one was cytochrome P450.

According to embodiments and referring again to FIG. 3, the biomarker informative content repository 330 was created using data sets generated from the COPD protein study. According to embodiments, the COPD informative content repository is a MySQL database populated with protein, peptide, and metabolite data. The COPD informative content repository database resides on a server, according to embodiments, and may be accessed using various protocols such as http, ssh, ftp, and odbc.

The COPD informative content repository MySQL tables are organized and sortable by subject, sample name, peptide sequence, demographic information, and protein. Various tables are used to link the data, as well as to link other informative content repositories with the COPD informative content repository. The COPD informative content repository is linked to other databases for correlation of clinical data, genealogical data, and demographic data. The informative content repositories are maintained independently of each other and a firewall is employed to maintain independence of each respective informative content repository.

According to embodiments, the informative content repository of the present disclosure comprises high throughput screening devices, such as gene and protein chips, for rapid determination of predisposition to rapid COPD decline or slow COPD decline.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

REFERENCES

The following references are hereby incorporated by reference as if fully disclosed herein.

Belov, M. E., Anderson, G. A., Wingerd, M. A., Udseth, H. R., Tang, K., Prior, D. C., Swanson, K. R. et al., 2004. J. Am Soc. Mass Spectrom. 15, 212-232.

Bolstad, B. M., Irizarry, R. A., Astrand, M. and Speed, T. A. (2003) A comparison of normalization methods for high density oligonucleotide array data based on variance and bias. Bioinformatics, 19(2), pp. 185-193.

Efron, B. (2004) Large-scale simultaneous hypothesis testing: The choice of a null hypothesis. J. Am. Stat. Assoc., 99(465), pp. 96-104.

Eng, J. K., McCormack, A. L., Yates, J. R. 1994. J. Am Soc. Mass Spectrom. 5: 976-989.

Gary R. Kiebel, Ken J. Auberry, Navdeep Jaitly, David A. Clark, Matthew E. Monroe, Elena S. Peterson, Nikola Toli, Gordon A. Anderson, Richard D. Smith. PROTEOMICS. 6:1783-1790. 2006.

Link, A. J., Eng, J., Schieltz, D. M., Carmack, E., Mize, G. J., Morris, D. R., Garvik, B. M., Yates III, J. R. 1999. Nat. Biotechnol. 17: 676-682.

Smith, R. D., Anderson, G. A., Lipton, M. S., Pasa-Tolic, L., Shen, Y., Conrads, T. P., Veenstra, T. D., and H. R. Udseth. 2002. Proteomics 2, 513-523.

Smith, R. D., Anderson, G. A., Lipton, M. S., Pasa-Tolic, L., Shen, Y., Conrads, T. P., Veenstra, T. D., and H. R. Udseth. 2002. Proteomics 2, 513-523.

Tang, H.; Wang, Y; Nicholson, J; and Lindon, J. "Use of relaxation-edited one-dimensional and two dimensional nuclear magnetic resonance spectroscopy to improve detection of small metabolites in blood plasma." Analytical Biochemistry 325:260-272. 2004.

Washburn, M. P., Wolters, D., Yates III, J. R. 2001. Nat. Biotechnol. 19: 242-247.

Wei-Jun Qian, Jon M. Jacob1., David G. Camp III, Matthew E. Monroe, Ronald J. Moore, Marina A. Gritsenko, Steve E. Calvano, Stephen F. Lowry, Wenzhong Xiao, Lyle L. Moldawer, Ronald W. Davis, Ronald G. Tompkins and Richard D. Smith, 2005. Proteomics 5:572-584.

The invention claimed is:

1. A diagnostic tool comprising:
a mass spectrometer, liquid chromatograph, size separation column, electrophoretic gel or protein chip; and
tryptic peptides of at least one of the respiratory condition biomarkers serum amyloid P component, apolipoprotein B, and fibronectin 1 isoform 1, wherein the respiratory condition biomarkers are indexed with their abundance;
with the proviso that the diagnostic tool does not comprise tryptic peptides of at least one of the proteins in Table 1.

2. The diagnostic tool of claim 1, wherein the diagnostic tool further comprises tryptic peptides of at least one Chronic Obstructive Pulmonary Disease (COPD) biomarker identified in Table 2, showing a two-fold or greater difference in abundance between slow and rapid decline conditions, in addition to the tryptic peptides of serum amyloid P component, apolipoprotein B and fibronectin 1 isoform 1.

3. The diagnostic tool of claim 1, wherein the diagnostic tool further comprises tryptic peptides of at least one Chronic Obstructive Pulmonary Disease (COPD) biomarker identified in Table 1 in addition to the tryptic peptides of serum amyloid P component, apolipoprotein B and fibronectin 1 isoform 1.

4. A diagnostic tool comprising: a protein chip that specifically binds the respiratory condition biomarkers serum amyloid P component, apolipoprotein B and fibronectin 1 isoform 1 indexed with their abundance;
with the proviso that the diagnostic tool does not comprise the protein of SEQ ID No. 325 and the protein of SEQ ID No. 326.

5. The diagnostic tool of claim 1, comprising tryptic peptides of substantially all of the proteins of Table 2.

6. The diagnostic tool of claim 1, comprising tryptic peptides of substantially all of the proteins of Table 1.

7. The diagnostic tool of claim 1, wherein the diagnostic tool does not contain the most abundant protein in human plasma.

8. The diagnostic tool of claim 5, wherein the diagnostic tool does not contain the most abundant protein in human plasma.

9. The diagnostic tool of claim 6, wherein the diagnostic tool does not contain the most abundant protein in human plasma.

10. A protein chip for determining three or more proteins, or peptides of three or more proteins, selected from the group consisting of:
Antichymotrypsin,
Alpha-2-macroglobulin,
Apolipoprotein B,
Ceruloplasmin,
Complement component 3,
Fibrogen, alpha chain isoform,
Fibrogen, beta chain,
Fibrogen, gamma chain isoform 1,
Fibronectin 1 isoform 1,
Gelsolin isoform a,
Kininogen 1, bradykinin,
Plasma kallikrein B1,
Serine (or cysteine) proteinase inhibitor, alpha-1-antitrypsin,
Serum amyloid P component, and
Vitamin D-binding protein;
wherein said proteins, or the peptides of the proteins, bind to the surface of the chip.

11. The protein chip of claim 10, wherein the chip determines four or more of the proteins, or peptides of four or more proteins.

12. The protein chip of claim 10, wherein the chip determines five or more of the proteins, or peptides of five or more proteins.

13. A diagnostic tool comprising:
a mass spectrometer, liquid chromatograph, size separation column, electrophoretic gel or protein chip; and
tryptic peptides of the respiratory condition biomarkers serum amyloid P component, apolipoprotein B and fibronectin 1 isoform 1;

wherein, when the diagnostic tool comprises a protein chip, the respiratory condition biomarkers bind to the surface of the chip; and wherein the diagnostic tool does not contain each of the respiratory condition biomarkers recited in Table 1.

14. A diagnostic tool comprising:

a mass spectrometer, liquid chromatograph, size separation column, electrophoretic gel or protein chip; and tryptic peptides of serum amyloid P component, apolipoprotein B and fibronectin 1 isoform 1, wherein the respiratory condition biomarkers are indexed with their abundance;

with the proviso that the diagnostic tool does not contain the protein of SEQ ID No. 325 and the protein of SEQ ID No. 326.

15. A diagnostic tool comprising:

a gene chip that specifically binds expressed nucleic acids for the respiratory condition biomarkers serum amyloid P component, apolipoprotein B and fibronectin 1 isoform 1;

wherein the expressed nucleic acids for the respiratory condition biomarkers specifically bind to the surface of the gene chip; and wherein said gene chip does not specifically bind an expressed nucleic acid for at least ten respiratory condition biomarkers set forth in Table 1.

16. The diagnostic tool of claim 15, wherein the diagnostic tool also specifically binds at least one expressed nucleic acid for a respiratory condition biomarker identified in Table 2, in addition to the expressed nucleic acids for serum amyloid P component, apolipoprotein B and fibronectin 1 isoform 1.

17. The diagnostic tool of claim 15, wherein the diagnostic tool also specifically binds expressed nucleic acids for at least two respiratory condition biomarkers identified in Table 2, in addition to the expressed nucleic acids for serum amyloid P component, apolipoprotein B and fibronectin 1 isoform 1.

18. The diagnostic tool of claim 15, wherein the diagnostic tool also specifically binds at least one expressed nucleic acid for a respiratory condition biomarker identified in Table 1, in addition to the expressed nucleic acids for serum amyloid P component, apolipoprotein B and fibronectin 1 isoform 1.

19. The diagnostic tool of claim 15, wherein the diagnostic tool also specifically binds expressed nucleic acids for at least four respiratory condition biomarkers identified in Table 1, in addition to the expressed nucleic acids for serum amyloid P component, apolipoprotein B and fibronectin 1 isoform 1.

20. A composition comprising one or more tryptic peptides of each of serum amyloid P component, apolipoprotein B, and fibronectin 1 isoform 1; wherein the composition does not comprise a tryptic peptide for each of the proteins in Table 1.

21. The composition of claim 20; wherein the composition does not comprise a tryptic peptide for alpha-albumin protein of SEQ ID NO. 267.

22. The composition of claim 20, wherein the composition does not comprise tryptic peptides for at least three of the proteins in Table 1.

23. The composition of claim 20, wherein the composition does not comprise tryptic peptides for at least three of the proteins in Table 2.

24. A diagnostic tool comprising:

a gene chip that specifically binds expressed nucleic acids for the respiratory condition biomarkers serum amyloid P component, apolipoprotein B and fibronectin 1 isoform 1;

wherein the expressed nucleic acids for the respiratory condition biomarkers specifically bind to the surface of the gene chip; and wherein said gene chip does not specifically bind an expressed nucleic acid for each of the respiratory condition biomarkers set forth in Table 1.

25. The diagnostic tool of claim 24, wherein said gene chip does not specifically bind an expressed nucleic acid for each of the respiratory condition biomarkers set forth in Table 2.

26. The diagnostic tool of claim 24, wherein said gene chip does not specifically bind an expressed nucleic acid for at least one of the respiratory condition biomarkers in Table 1.

27. The diagnostic tool of claim 24, wherein said gene chip does not specifically bind an expressed nucleic acid for at least one of the respiratory condition biomarkers in Table 2.

* * * * *